United States Patent
Adlerstein et al.

(10) Patent No.: US 9,404,149 B2
(45) Date of Patent: Aug. 2, 2016

(54) COMPOSITION, KITS AND METHODS FOR THE DETECTION OF POINT MUTATIONS AND SNPS

(75) Inventors: Daniel Adlerstein, Arese (IT); Giulia Amicarelli, Parabiago (IT); Giulia Minnucci, Milan (IT)

(73) Assignee: BIOTRIN INTERNATIONAL LIMITED, Dublin (IE)

(*) Notice: Subject to any disclaimer, the term of this patent is extended or adjusted under 35 U.S.C. 154(b) by 837 days.

(21) Appl. No.: 13/383,141

(22) PCT Filed: Jun. 8, 2010

(86) PCT No.: PCT/EP2010/058022
§ 371 (c)(1),
(2), (4) Date: Jan. 9, 2012

(87) PCT Pub. No.: WO2011/003690
PCT Pub. Date: Jan. 13, 2011

(65) Prior Publication Data
US 2012/0171676 A1    Jul. 5, 2012

(30) Foreign Application Priority Data
Jul. 10, 2009 (EP) .................... 09165252

(51) Int. Cl.
*C12Q 1/68* (2006.01)
(52) U.S. Cl.
CPC .................... *C12Q 1/6858* (2013.01)
(58) Field of Classification Search
None
See application file for complete search history.

(56) References Cited

U.S. PATENT DOCUMENTS

| 6,277,607 B1 * | 8/2001 | Tyagi et al. .......... 435/91.2 |
| 2007/0218464 A1 | 9/2007 | Nakamura et al. |

FOREIGN PATENT DOCUMENTS

| DK | WO2009049630 | * | 4/2009 | .......... C12Q 1/68 |
| EP | 1 231 281 A1 | | 8/2002 | |
| EP | 1 692 281 B2 | | 12/2007 | |
| EP | 1 975 249 A2 | | 10/2008 | |
| EP | 1 020 534 B2 | | 1/2011 | |
| JP | WO2009049630 | * | 4/2009 | .......... C12Q 1/68 |
| WO | WO 2007/011901 A2 | | 1/2007 | |
| WO | WO2007011901 | * | 1/2007 | .......... C12Q 1/68 |
| WO | WO 2009/049630 A1 | | 4/2009 | |
| WO | WO 2009/073575 A2 | | 6/2009 | |

OTHER PUBLICATIONS

Antonioli et al., "Clinical implications of the JAK2 V617F mutation in essential thrombocythemia," Leukemia, 2005, vol. 19, pp. 1847-1849, published online Aug. 4, 2005.
Baxter et al., "Acquired mutation of the tyrosine kinase JAK2 in human myeloproliferative disorders," Lancet, 2005, vol. 365, pp. 1054-1061.
De Keersmaecker et al., "Chronic myeloproliferative disorders: a tyrosine kinase tale," Leukemia, 2006, vol. 20, pp. 200-205.
(Continued)

*Primary Examiner* — Stephanie K Mummert
(74) *Attorney, Agent, or Firm* — Pearl Cohen Zedek Latzer Baratz LLP

(57) ABSTRACT

The present invention refers to a method for detecting a point mutations of a nucleotide sequence by an improvement of the LAMP (loop amplification mediated polymerization) amplification method, as well as to a set of primers and kit therefor. As a non limitative embodiment, the invention refers to the G1849T mutation of the JAK2 gene.

11 Claims, 15 Drawing Sheets

(56) References Cited

OTHER PUBLICATIONS

Figure 1:
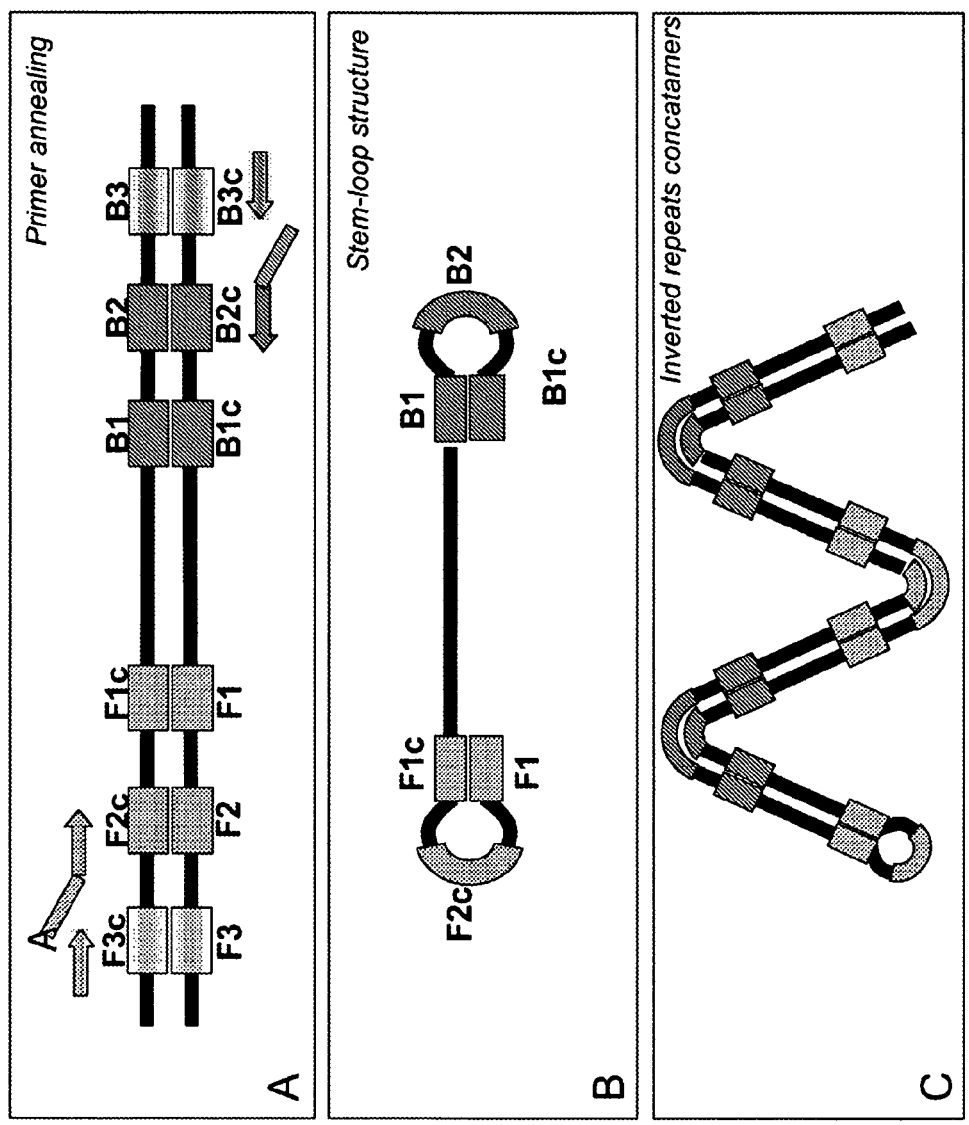

Fukuta et al., Development of loop-mediated isothermal amplification (LAMP)-based SNP markers for shelf-life in melon (*Cucumis melo* L.), J Appl Genet, 2006, vol. 47, No. 4, pp. 303-308.

Ikeda et al., "Detection of gene point mutation in paraffin sections using in situ loop-mediated isothermal amplification," Pathology International, 2007, vol. 57, pp. 594-599.

Iwasaki et al., "Validation of the Loop-Mediated Isothermal Amplification Method for Single Nucleotide Polymorphism Genotyping with Whole Blood," Genome Letters, 2003, vol. 2, No. 3, pp. 119-126.

James et al., "Letters to Nature: A unique clonal JAK2 mutation leading to constitutive signaling causes polycythaemia vera," Nature, Apr. 28, 2005, vol. 434, pp. 1144-1148.

James et al., "Letter to the Editor: Detection of JAK2 V617F as a first intention diagnostic test for erythrocytosis," Leukemia, 2006, vol. 20, pp. 350-353.

Jelinek et al., "JAK2 mutation 1849G>T is rare in acute leukemias but can be found in CMML, Philadelphia chromosome-negative CML, and megakaryocytic leukemia," Blood, 2006, vol. 106, pp. 3370-3373.

Jones et al., "Widespread occurrence of the JAK2 V617F mutation in chronic myeloproliferative disorders," Blood, 2005, vol. 106, pp. 2162-2168.

Kaushansky, "On the molecular origins of the chronic myeloproliferative disorders: it all makes sense," Blood, 2005, vol. 105, pp. 4187-4190.

Levine et al., "Activating mutation in the tyrosine kinase JAK2 in polycythemia vera, essential thrombocythemia, and myeloid metaplasia with myelofibrosis," Cancer Cell, Apr. 2005, vol. 7, pp. 387-397.

Nelson et al., "JAK2 V617F in myeloid disorders: What do we know now, and where are we headed?" Leukemia & Lymphoma, Feb. 2006, vol. 47, No. 2, pp. 177-194.

Smith et al., "Detection of Single-Base Mutations in a Mixed Population of Cells: A Comparison of SSCP and Direct Sequencing," GATA, 1992, vol. 9, Nos. 5-6, pp. 143-145.

Steensma, "JAK2 V617F in Myeloid Disorders: Molecular Diagnostic Techniques and Their Clinical Utility," Journal of Molecular Diagnostics, Sep. 2006, vol. 8, No. 4, pp. 397-411.

International Search Report and Written Opinion issued for International Application No. PCT/EP2010/058022 and mailed on Sep. 30, 2010.

Nagamine K et al., "Accelerated reaction by loop-mediated isothermal amplification using loop primers," Molecular and Cellular Probes, Jun. 2002, vol. 16, No. 3, pp. 223-229.

Murugesan Gurunathan et al., "Identification of the JAK2 V617F mutation in chronic myeloproliferative disorders using FRET probes and melting curve analysis," American Journal of Clinical Pathology, vol. 125, No. 4, pp. 625-633, Apr. 2006.

* cited by examiner

COMPOSITION, KITS AND METHODS FOR THE DETECTION OF POINT MUTATIONS AND SNPS

CROSS-REFERENCE TO RELATED APPLICATIONS

This application is a National Phase Application of PCT International Application No. PCT/EP2010/058022, International Filing Date, 8 Jun. 2010, claiming priority to European Patent Application No. 09165252.9, filed 10 Jul. 2009, both of which are hereby incorporated by reference in their entirety.

FIELD OF THE INVENTION

The present invention refers to a method for detecting a point mutation or SNP in a nucleotide sequence by means of an improved LAMP (loop amplification mediated polymerization) amplification method, as well as to a set of primers and a kit for carrying out the method of the invention. According to a non limiting embodiment, the method, the set of primers and the kit are suitable for detecting the G1849T (V617F) mutation in the JAK2 gene.

BACKGROUND OF THE INVENTION

Myeloproliferative disorders (MPD) are clonal disorders of haematopoietic progenitors, and include the classical MPD chronic myeloid leukaemia (CML), polycythaemia vera (PV), essential thrombocythaemia (ED and primary myelofibrosis (PMF), as well as chronic eosinophilic leukaemia (CEL), chronic myelomonocytic leukaemia (CMML), and systemic mastocytosis (SM) and others. In the past two decades, mutant alleles have been identified in CML, CMML, CEL and SM2-5; and in each case the causative mutation results in constitutive activation of tyrosine kinase signalling. The genetic causes of the most common MPD remained unknown until the identification of mutations that activate Janus kinase 2 (JAK2) signalling in most patients with PV, ET or PMF(1, 2, 3, 4). JAK2 is a member of the Janus family of cytoplasmic non-receptor tyrosine kinases, which also includes JAK1, JAK3 and TYK2. The mutation is a guanine-to-thymidine substitution at position 1849 in the JAK2 coding sequence (GenBank accession no. NM_004972, SEQ ID NO:1), numbering starting at the ATG start codon, corresponding to position 2343 of SEQ ID NO: 1. Such a mutation results in a substitution of valine for phenylalanine at amino acid 617 of the JAK2 protein (JAK2V617F), within the JH2 pseudokinase domain (5). Loss of JAK2 autoinhibition results in constitutive activation of the kinase, analogous to other mutations in MPDs and leukemia that aberrantly activate tyrosine kinases (6,7,8).

Direct sequencing is only sensitive down to about 20% of mutant DNA in a wild-type background (9, 10). This issue is quite relevant to chronic myeloid disorders, where blood and marrow are often composed of a mixture of neoplastic and residual normal hematopoietic elements. This is especially the case of ET and MDS, in which phenotypically apparent gene mutations may be present in tiny clones comprising less than 10% of the total marrow cell population. James et al. (11) explored this issue specifically with respect to JAK2 1849 G-T by performing a series of mixing experiments with HEL erythroleukemia cells, which bear the JAK2 mutation, admixed with TF-1 erythroleukemia cells, which do not. They failed to detect the mutated allele when it was present in <5% of the total DNA. With homozygous mutant patient DNA diluted in DNA from a healthy person, sequencing was even less sensitive (10%) than it was with the cell lines (12).

A common method used for the detection of nucleic acid mutations is the Amplification Refractory Mutation System (ARMS). It exploits the fact that oligonucleotide primers must be perfectly annealed at their 3' ends for a DNA polymerase to extend these primers during PCR (12). By designing oligonucleotide primers that match only a specific DNA point mutation, such as that encoding JAK2 V617F, ARMS can distinguish between polymorphic alleles. Therefore, these techniques go by the alternative names of "allele-specific PCR" (AS-PCR) or "sequence-specific primer PCR." The ARMS sensitivity is up to 1 to 2% (13) mutant DNA in a wild-type background.

Real-time monitoring of PCR product accumulation during thermocycling can be of value as a semiquantitative method and DNA-melting curve assays can be used in conjunction with real-time PCR. Likewise, James et al. (14) compared fluorescent dye chemistry sequencing with two different real-time PCR based mutation detection systems, one using a LightCycler instrument (Roche Diagnostics) and the other using a Taqman ABI Prism 7500 machine (Applied Biosystems). These real-time PCR techniques detected 0.5 to 1% of HEL cell line DNA diluted in TF-1 cell line DNA and 2 to 4% of homozygously mutated patient DNA diluted in DNA from a healthy person.

A Restriction Fragment Length Polymorphism (RFLP) analysis is possible since the JAK2 1849 G-T mutation abolishes a motif in the wild-type JAK2 sequence that is recognized by the restriction enzyme BsaXI. Although abolition of a restriction site is not as satisfying as creation of a new site, because a negative enzymatic cleavage reaction could be due either to absence of the mutation or to failure of the digestion procedure, it can be useful as a first pass analysis. Reported proportional sensitivity depends in part on the method used to detect the fragments and is approximately 20% mutant DNA in Wild-type background (15, 16).

Pyrosequencing is a method of rapid genotyping that depends on the liberation of pyrophosphate (PPi) whenever a dNTP is incorporated into a growing DNA chain during template-driven DNA polymerization (17). Pyrosequencing of JAK2 using the automated PSQ HS 96 system (Biotage, Uppsala, Sweden) has been attempted by several groups (17, 18) with dilution experiments similar to those described above showing a reported assay sensitivity of 5 to 10% mutant allele in a wild-type background.

Several other mutation detection techniques have been described, including single stranded conformational polymorphism (SSCP) analysis, denaturing gradient gel electrophoresis (DGGE), denaturing high-performance liquid chromatography (DHPLC), single-nucleotide primer extension assays (Pronto), and others. In fact, DHPLC can detect the genomic DNA mutation underlying JAK2 V617F reliably, and it can detect mutations at a proportionality of <1 to 2%. However, DHPLC and the other techniques are either technically challenging or labor-intensive or both. They either do not allow high throughput at a cost suitable for a clinical laboratory (SSCP and DGGE) or require a considerable initial investment for equipment (DHPLC).

Theoretically, protein-based techniques could also be used to detect the JAK2 V617F mutation, but these are generally cumbersome, and access to such resources is limited. Therefore, protein-based assays are usually not preferred if DNA- or RNA-based tests are feasible.

European patent application EP1692281A discloses a method for the detection of G1849T JAK2 mutation based on PCR amplification.

The methods of the prior art show several limitations. First of all the lower level of sensitivity, that allows detection of the mutant JAK2 sequence down to 1% of the sample in the best cases. Such a sensitivity requires the enrichment of the mutants via granulocytes-isolation before extraction. This is a time consuming and labor-intensive step resulting in about 2 additional hours to the already long procedures (from 2 to 5 hours) requested for the diagnosis. Furthermore, all the methods previously illustrated are relatively labor intensive and expensive, often requiring specialized equipment that may not always be readily available.

DESCRIPTION OF THE INVENTION

The present inventors have set up a novel LAMP method of detecting a point mutation or SNP in a nucleic acid molecule, which is particularly selective and rapid. The present inventors have also set up a novel set of primers and a kit for carrying out the method of the invention. The method for detecting a nucleic acid point mutation or SNP and the set of primers and kit therefor are characterized by the features defined in the appended claims, which form an integral part of the description.

The method of the present invention differs from the conventional LAMP technology which is disclosed in European patent application EP 1020534A and which is depicted herein in FIG. 1. The method of the invention enables the simultaneous selective amplification and detection of a single base substitution in a nucleic acid sample. Furthermore, the method of the present invention is easy to be performed, since it requires simple instrumentation and the results can be generated in a single tube reaction. For these reasons, it is also less expensive compared to the prior art methods.

The method of the invention overcomes the limitations and drawbacks of the techniques of the prior art, resulting in a higher sensitivity (down to 0.01% mutant sequences in a wild-type background); it is isothermal and rapid, completing the diagnosis in one hour reaction. In addition, the method of the invention enables to evaluate whether the amount of the mutant allele, such as for example the mutant JAK2 allele, which is present in the tested sample is higher or lower than 50%, providing as indication as to whether the tested subject is heterozygotic or homozygotic for the nucleic acid single point mutation or SNP of interest.

Therefore, a first aspect of the present invention is a method of detecting the presence of a point mutation in a target nucleic acid molecule within a background of wild-type nucleic acid molecules, the method comprising the steps of:
1) providing a nucleic acid sample;
2) contacting said nucleic acid sample, under appropriate reaction conditions, with a solution comprising a mixture of oligonucleotides and a DNA polymerase having strand displacement activity under hybridization conditions, wherein said mixture of oligonucleotides consists of primers suitable for the loop mediated isothermal amplification of the region of the target nucleic acid molecule including the nucleic acid position of the point mutation to be detected, said primers comprising:
   i. a first outer primer F3 and a second outer primer B3;
   ii. a first inner primer FIP and a second inner primer BIP, wherein FIP consists of a 3' nucleic acid sequence F2 and a 5' nucleic acid sequence F1c and BIP consists of a 3' nucleic acid sequence B2 and a 5' nucleic acid sequence B1c,
   wherein F2 is able to recognize and hybridize to a region of the target nucleic acid molecule designated as F2c and B2 is able to recognize and hybridize to a region of the target nucleic acid molecule designated as B2c,
   wherein F2c and B2c are different regions located on opposite strands of the target nucleic acid molecule,
   wherein either B2c is downstream of the point mutation or F2c is upstream of the point mutation, and wherein
   if B2c is downstream of the point mutation, then said point mutation is located in the F2c sequence or downstream of the F2c sequence and upstream of the F1c sequence, or
   if F2c is upstream of the point mutation, then said point mutation is located in the B2c sequence or upstream of the B2c sequence and downstream of the B1c sequence;
   iii. a stem-loop mutant extensible primer comprising:
   a central loop sequence able to selectively recognize and hybridize to a region of the target nucleic acid molecule comprising the point mutation, such that the central loop sequence is capable of recognizing and hybridizing to the target nucleic acid molecule only if the point mutation is present, and
   a 5' end sequence and a 3' end sequence which are complementary to each other such as to form a stem upon intramolecular hybridization, the hybridization affinity of the central loop sequence to the region of the target nucleic acid molecule comprising the point mutation being higher than the intramolecular hybridization affinity of the 5' sequence to the 3' sequence such that, if the point mutation is present, the central loop sequence will anneal to and amplify the region of the target nucleic acid molecule comprising the point mutation;
   iv. a non extensible moiety which is capable of selectively recognize and hybridize to the wild type nucleic acid molecules;
3) incubating the resulting mixture at a constant temperature;
4) detecting a signal indicative of amplification of the region of the target nucleic acid molecule comprising the point mutation.

The first step of the method implies obtaining the nucleic acid sample to be tested, such as for example from a patient suspected of bearing the point mutation of interest, either in an heterozygotic in a homozygotic form.

In a preferred embodiment, the two inner primers FIP and BIP are designed on a region of the target nucleic acid molecule comprising the nucleic acid position of the point mutation to be detected such that the point mutation is located in the region between the F2c sequence and the F1c sequence or between the B2c sequence and the B1c sequence. In an alternative embodiment, the point mutation is located in the region probed by B2 or F2, that is to say within the F2c sequence or within the B2c sequence.

In another preferred embodiment, the sequence at the 5' end and the sequence at the 3' end of the stem-loop mutant extensible primer is of at least 3 nucleotides in length. The stem-loop mutant extensible primer can alternatively be designated as a "self-annealed mutant extensible primer", or more simply as a "self-annealed extensible primer" (LB or LF).

In a further preferred embodiment of the method of the invention, the non extensible moiety is a peptide nucleic acid (PNA), which is preferably at least 10 nucleotides in length. DNAs and RNAs respectively consist a deoxyribose and a ribose sugar backbone, whereas the backbone of PNAs is made of repeating N-(2-aminoethyl)-glycine units linked by peptide bonds. Purine and pyrimidine bases are linked to the backbone by methylene carbonyl bonds. PNAs are depicted like peptides, with the N-terminus at the first (left) position and the C-terminus at the right. Since the backbone of PNA does not contain any phosphate group, the binding between PNA/DNA strands is stronger than between DNA/DNA strands due to the lack of electrostatic repulsion.

In a most preferred embodiment of the invention, the peptide nucleic acid (PNA) comprises a sequence of bases which is capable of hybridizing to the region of the nucleic acid molecule which includes the putative point mutation (that is to say, which includes the nucleic acid position of the point mutation to be detected), thereby resulting in the formation of two double strand structures, one with the wild type target nucleic acid molecule and the other with the mutated target nucleic acid molecule. The melting temperature of the double stranded structure resulting from the hybridization of the PNA with the target nucleic acid molecule in the absence of the point mutation (i.e., with the Wild-type sequence) is designated as (Tm)=X and the melting temperature of the double stranded structure resulting from the hybridization of the PNA with the target nucleic acid molecule in the presence of the point mutation (i.e., with the mutated sequence) is designated as (Tm)=Y. According to a preferred embodiment, Y<Incubation Temperature <or equal to X and X is at least 5° C. higher than Y.

In an alternative embodiment of the present invention, the non extensible moiety is a stem-loop wild type non extensible primer, which comprises:
  a central loop sequence able to selectively recognize and hybridize to a region of the wild type nucleic acid molecule comprising the nucleic acid position of the point mutation to be detected,
  a 5' end sequence and a 3' end sequence, said 5' end and said 3' end sequences being complementary to each other to form a stem, so that said central loop sequence has a higher hybridization affinity to the region comprising the wild-type sequence of the nucleic acid molecule than the hybridization affinity of the 5' end sequence to the 3' and sequence, so that it results in annealing to and blocking the amplification of the WT sequence. The skilled in the art is aware of the fact that the hybridization between the 5' end sequence and the 3' end sequence is an intramolecular hybridization.

In a preferred embodiment of the present invention, the DNA polymerase having strand displacement activity under the reaction conditions is the Bst large fragment polymerase; alternatively, it is one of or a combination of Bca (exo-), Vent, Vent (exo-), Deep Vent, Deep Vent (exo-), 029 phage, MS-2 phage, Z-Taq, KOD, Klenow fragment.

In a preferred embodiment the constant reaction temperature is comprised between 62° C. and 67° C.

In a preferred embodiment of the present invention, the signal indicative of amplification of the nucleotide molecule comprising the point mutation is detected by turbidimetry.

Alternatively, the signal indicative of amplification of the nucleotide molecule comprising the point mutation is detected by fluorescence or any other suitable means for detection.

In still another preferred embodiment of the present invention, the target nucleic acid molecule comprises the region of the human JAK2 gene (GenBank accession no. NG_009904, SEQ ID NO:2) containing the putative guanine-to-thymidine substitution at base 93526 of SEQ ID NO:2, corresponding to nucleotide position 1849 from the start codon in the JAK2 coding sequence (GenBank accession no NM_004972, SEQ ID NO:1), which in turn corresponds to position 2343 of SEQ ID NO: 1.

Preferably, the first and second outer primers F3 and B3 are located respectively in the intron regions flanking exon 14 of the human JAK2 gene (GenBank accession no NG_009904, SEQ ID NO:2) which contains the putative G→T base substitution at position 93526. More preferably, F3 consists of a nucleotide sequence spanning positions 93367-93388 of SEQ ID NO:2 and B3 consists of a nucleotide sequence which is complementary to the nucleotide region between positions 93561-93582 of SEQ ID NO:2. Preferably, the first and second inner primers FIP and BIP are designed as follows: the FIP primer consists of a F2 sequence located in the intron region upstream JAK2 exon 14 (preferably between positions 93408-93425 of SEQ ID NO:2) and of a F1c sequence which is complementary to nucleotides 93445 to 93470 of SEQ ID NO:2; the BIP primer consists of a B2 sequence complementary to a region comprising nucleotides 93538-93559 of SEQ ID NO:2, which includes the first eighteen bases of the downstream intron, and of a B1c sequence located at position 93486-93515 of SEQ ID NO:2. The central loop sequence of the stem-loop mutant extensible primer preferably consists of nucleotides 93516-93529 of SEQ ID NO:2. The PNA base sequence preferably consists of nucleotides 93518-93534 of SEQ ID NO:2.

Most preferably, primers suitable for loop mediated isothermal amplification, which are employed for carrying out the method according to the present invention, consist of the following sequences:

```
                                           (SEQ ID NO. 3)
F3       5'-GCATCTTTATTATGGCAGAGAG-3';

(SEQ ID NO. 4)
B3       5'-TGCTCTGAGAAAGGCATTA-3';

(SEQ ID NO. 5)
FIP      5'-GCTGCTTCAAAGAAAGACTAAGGAAATGG
         ACAACAGTCAAACAAC-3';

(SEQ ID NO. 6)
BIP      5'-GCTTTCTCACAAGCATTTGGTTTTAAAT
         TAGCCTGTAGTTTTACTTACTCTC-3';

Stem-loop mutant extensible primer:
                                           (SEQ ID NO: 8)
         GTCTCCACTGGAGTATGTTTCTGTGGAGAC-3'.
```

In a more preferred embodiment, the non extensible moiety is a PNA molecule, preferably having the structure: $^{NH2}GAGTATGTGTCTGTGGA^{CONH2}$. (SEQ ID NO:9).

The method of the present invention is also suitable for quantitatively assessing the amount of mutant alleles (e.g. of the present JAK2 mutant alleles) in a nucleic acid sample, e.g. for assessing whether the point mutation is in an homozygotic or heterozygotic form. This is achieved by quantitatively comparing the signal indicative of amplification of the region of the target nucleic acid molecule comprising the point mutation obtained from the sample with the said signal obtained from at least one calibrator. In a preferred embodiment, the at least one calibrator consists of a predetermined percentage (%) of mutant target nucleic acid molecules in a background of wild-type nucleic acid molecules, wherein the said predetermined percentage (%) is preferably about 10%. For example, by analyzing the amplification efficiency of undiluted and 1:5 diluted samples in comparison to 3 calibrators (e.g. 100%, 10% and 1% mutant G1849T JAK plasmid in wild-type plasmid background), it is possible to determine whether the amount of mutant alleles in the test samples is higher or lower than 50%, which is indicative of homozygosity or heterozygosity.

The method of the invention is also suitable for detecting other gene mutations responsible for different pathologies, such as kRAS, EGFR, as well as for detecting SNPs.

Another aspect of the present invention is a set of primers for detecting the presence of a point mutation in a target nucleic acid molecule in a background of wild type nucleic acid molecules by loop mediated isothermal amplification, the set of primers comprising a first outer primer F3, a second outer primer B3, a first inner primer FIP, a second inner primer BIP and a stem-loop mutant extensible primer, all as defined above with reference to the method of the invention.

According to a preferred embodiment, the set of primers comprises a first outer primer F3 consisting of SEQ ID NO:3, a second outer primer B3 consisting of SEQ ID NO:4, a first inner primer FIP consisting of SEQ ID NO:5, a second inner primer BIP consisting of SEQ ID NO:6 and a stem-loop mutant extensible primer consisting of SEQ ID NO:8.

A further preferred embodiment of the invention is a set of primers as defined above further comprising a non extensible moiety which is capable of hybridizing to the wild type nucleic acid molecules. The non extensible moiety is for example a Peptide Nucleic Acid (PNA) or a stem-loop non extensible primer, as defined in the appended claims. A PNA which is at least 10 bases in length is more preferred. The PNA illustrated in the sequence listing as SEQ ID NO:9 is the most preferred embodiment of the non extensible moiety.

A further aspect of the present invention is a kit for detecting the presence of a point mutation in a target nucleic acid molecule in a background of wild type nucleic acid molecules by loop mediated isothermal amplification, the kit comprising a set of primers as defined above as well as one or more DNA polymerases having strand displacement activity. The DNA polymerase is preferably selected from the group consisting of Bst large fragment polymerase, Bca (exo-), Vent, Vent (exo-), Deep Vent, Deep Vent (exo-), φ29 phage, MS-2 phage, Z-Taq, KOD, Klenow fragment, and any combination thereof. The most preferred DNA polymerase is the Bst large fragment polymerase.

The kit according to the present invention may contain additional conventional components such as for example one or more calibrators, means for detecting and/or quantifying amplification of the target nucleic acid molecules, as well as instructions for carrying out the assay. The selection and use of such additional components is well within the abilities of the person of average skill in the art.

The scope of the invention further comprises an isolated oligonucleotide primer selected from the group consisting of SEQ ID NO:3, SEQ ID NO:4, SEQ ID NO:5, SEQ ID NO:6 and SEQ ID NO:8, as well as a Peptide Nucleic Acid (PNA) of 6-24 bases in length, comprising a base sequence which is capable of hybridizing to a region of the JAK 2 genomic DNA (SEQ ID NO:2) including position 93526 of SEQ ID NO:2 or to a region of the JAK 2 cDNA (SEQ ID NO:1) including position 2343 of SEQ ID NO:1. A preferred embodiment of the PNA of the invention comprises the following base sequence: NH$_2$-GAGTATGTGTCTGTGGA-COOH (SEQ ID NO:9), wherein G is guanine, A is adenine, T is thymine and C is cytosine.

The invention is further described herein below by means of specific non limiting examples, with reference to the following drawings:

FIG. 1. LAMP Principle (Prior Art)

The amplification reaction is performed by employing 4 oligonucleotide primers specific for 6 different regions of the target genomic sequence. The internal primers hybridize to complementary sequences on the target nucleic acid molecule and are extended by the DNA polymerase; the amplification product is displaced in two steps by the external primers (F3, B3) and is shaped as a double stem-loop structure (starting structure) (panel A). The starting structure is simultaneously amplified from the free 3' ends and by another internal primer (panel B). DNA concatamers built by inverted repeats of the initial module are progressively synthesized in an exponential fashion (panel C).

Figure 2:
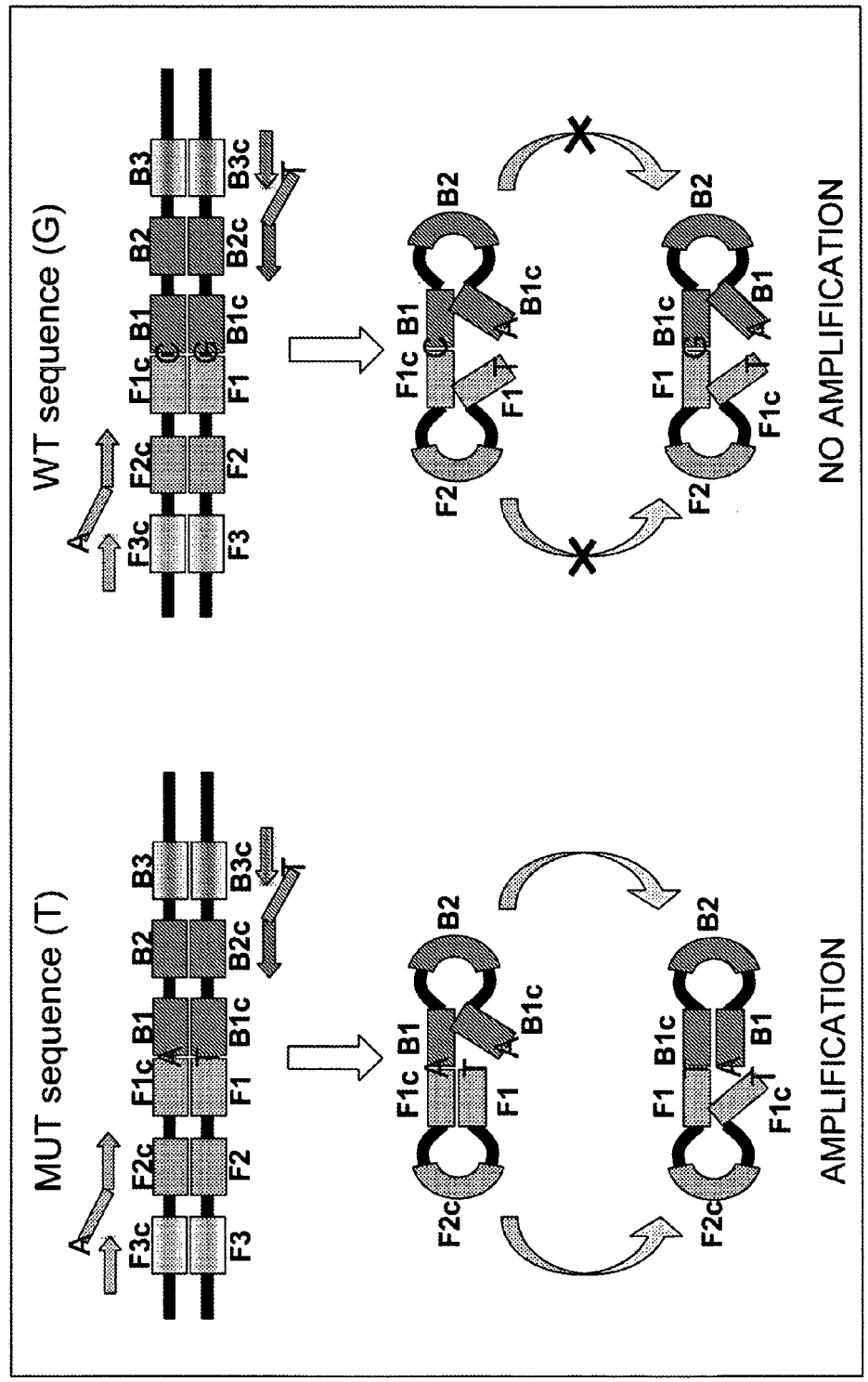

FIG. 2. LAMP "DUMB-BELL" Strategy

In the present assay set-up illustrated in FIG. 2, the F1c and B1c oligonucleotides contained in the FIP and BIP inner primers are complementary to non-overlapping regions of the JAK2 gene which ends and starts respectively one base upstream and one base downstream the nucleotide of interest at position 1849 from the start codon in the JAK2 coding sequence. Furthermore, the 5' end base of the FIP and BIP primers is specific for the mutated nucleotide in the JAK2 sequence and both inner primers have a mismatched base at the third base from the 3' end. When the reaction contains the wild-type target allele and a dumb-bell structure is formed, the mutant specific F1c and B1c sequences do not anneal at the 3' end blocking any further target amplification. Differently, if the mutant target allele is present in solution, the mutant specific F1c and B1c sequences hybridize perfectly to the complementary nucleic acid target region and are extended by the DNA polymerase.

Figure 3:
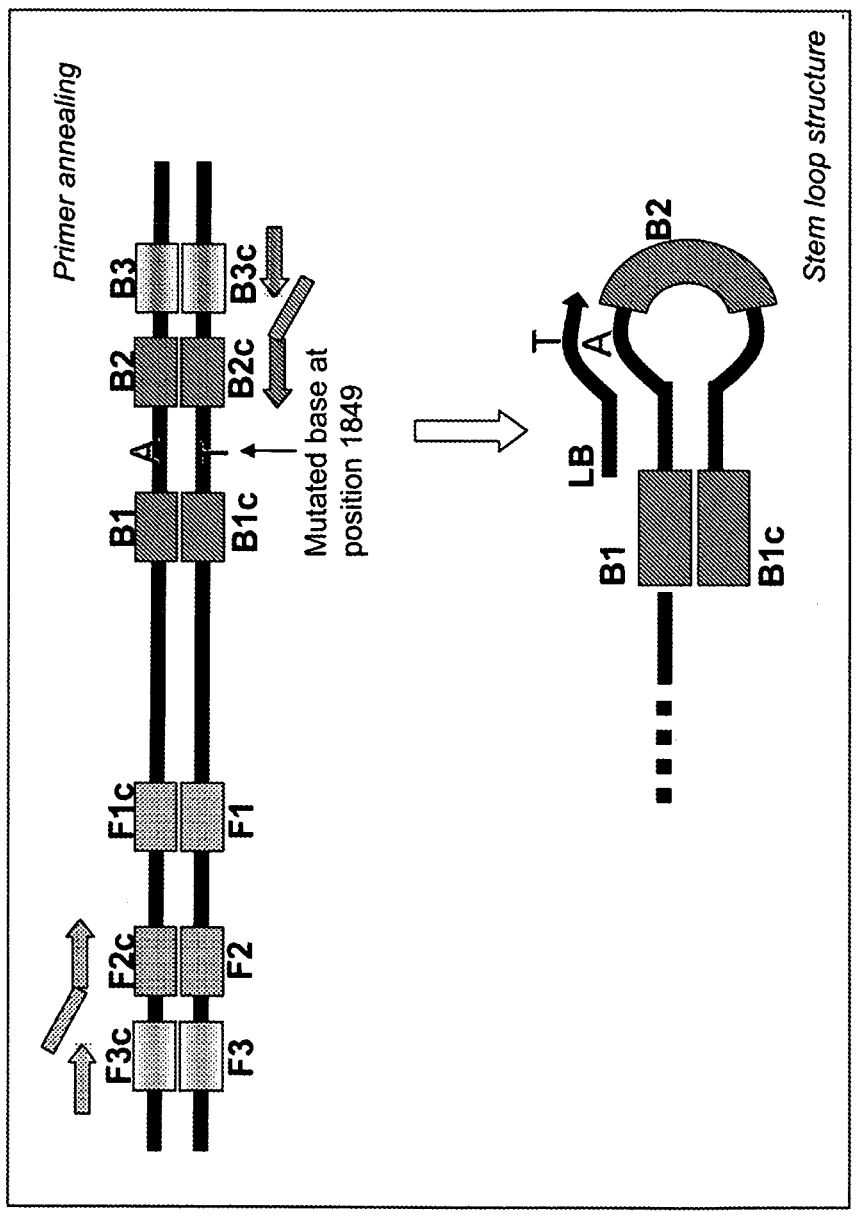

FIG. 3. LAMP "Allele Specific Loop Primer Extension" Strategy

The nucleotide at the 3' end of the mutant-specific loop primer is complementary to the mutated T nucleotide at position 1849 in the JAK2 coding sequence. In addition, this loop primer contains a mismatched base in the third base from the 3' end. If the reaction contains the WT JAK2 sequence, the 3'-end mutant-specific loop primer does not anneal to the target sequence resulting in no amplification. Differently, if mutant JAK2 sequences are present in solution, the mutant-specific loop primer hybridizes perfectly to the complementary target sequence and is extended by the DNA polymerase.

Figure 4:
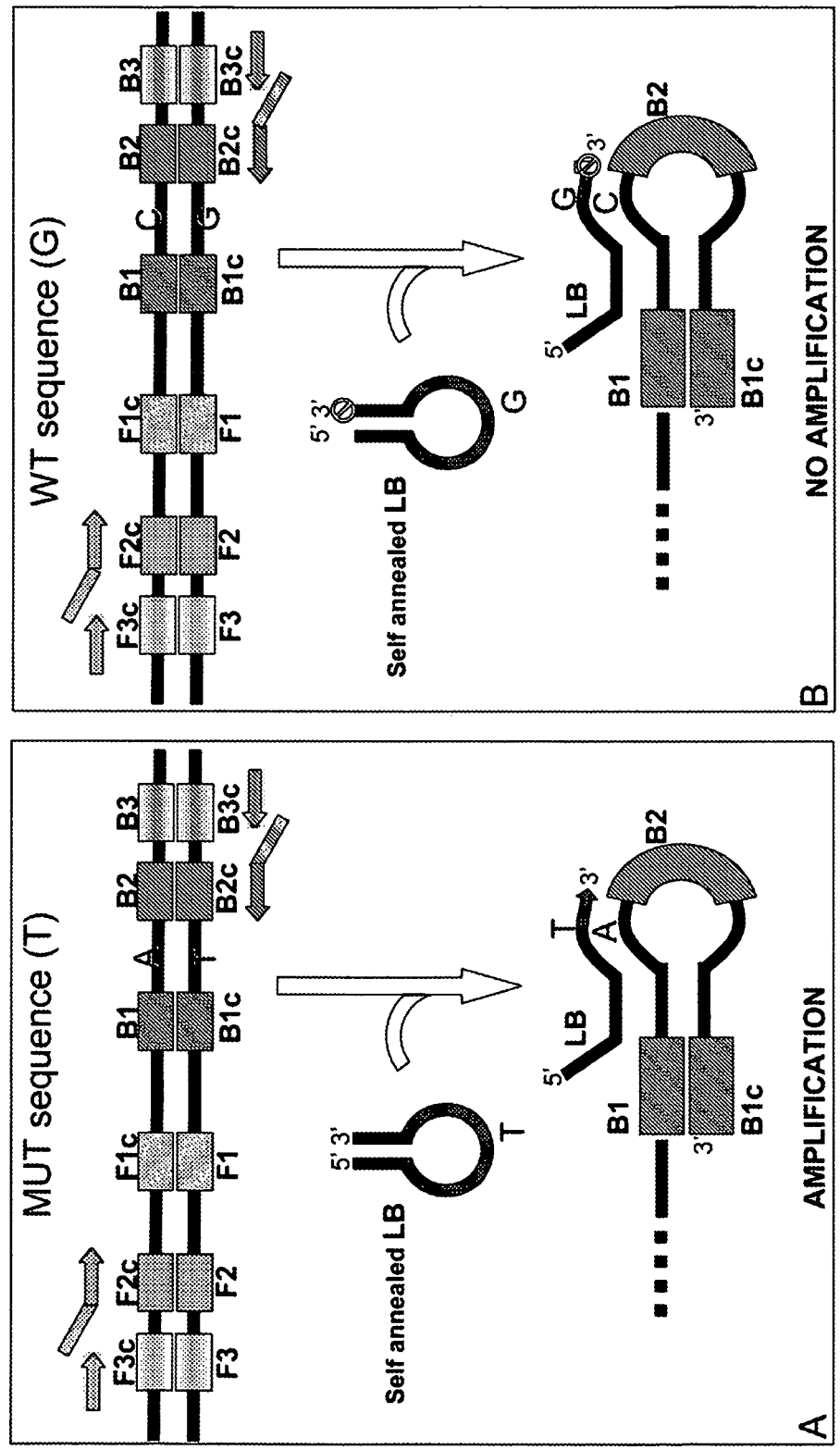

FIG. 4. LAMP "Stem-Loop Primers" Strategy

Universal (mutant insensitive) set of primers comprising the F3, B3, FIP and BIP oligonucleotides to obtain a dumb-bell presenting the putative mutated T nucleotide in the loop region. A first stem-loop primer is included designed to recognize the mutated base in the single strand dumb-bell structure, together with a second modified stem-loop primer complementary to the JAK2 wild-type sequence and containing a not extensible 3'-end. When the mutated JAK2 sequence is present in the nucleic acid sample (panel A), the mutant-specific stem-loop primer breaks its internal structure to anneal to the target sequence and is extended by the DNA polymerase. Conversely, if the WT target sequence is present in the sample (panel B), the modified not extensible stem-loop primer hybridizes to the WT target sequence blocking the amplification of this sequence ("silencing" effect).

Figure 5:
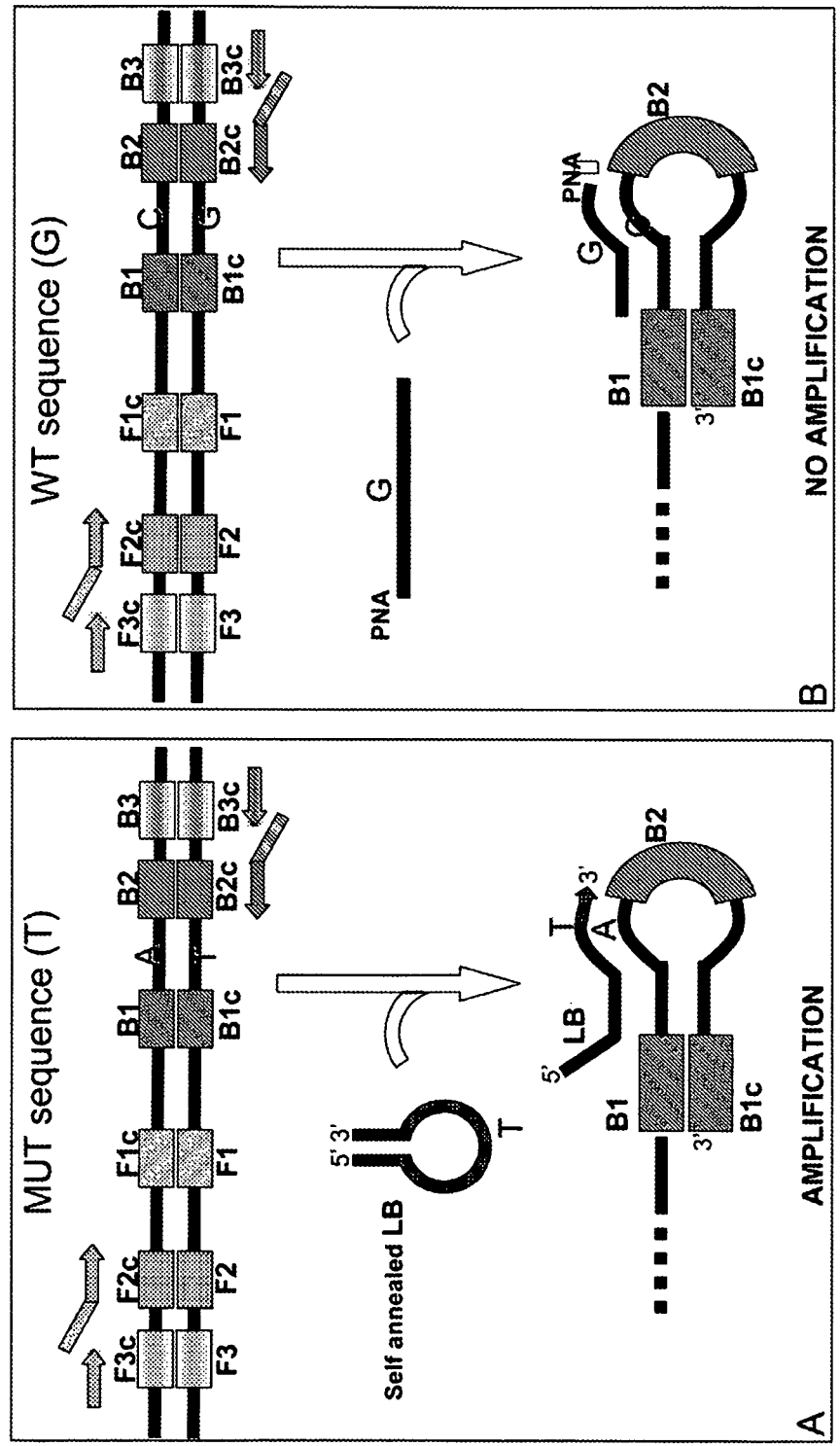

FIG. 5. LAMP "Mutant-Specific Stem-Loop Primer with PNA" Strategy

Universal (mutant insensitive) set of primers comprising the F3, B3, FIP and BIP oligonucleotides to obtain a dumb-bell presenting the putative mutated T nucleotide in the loop region. A first stem-loop primer is included designed to recognize the mutated base in the single strand dumb-bell structure, together with a PNA molecule. The PNA is designed to be complementary to the loop region comprised between B2 and B1c and encompassing the nucleic acid position of the point mutation to be detected. It forms a stable duplex with the JAK2 WT sequence, thus preventing the hybridization and extension of the mutant-specific stem-loop primer and suppressing the unspecific amplification of the wild-type sequence (panel B). The PNA does not hybridize to the mutated JAK2 sequence because of the lower affinity (panel A).

Figure 6:
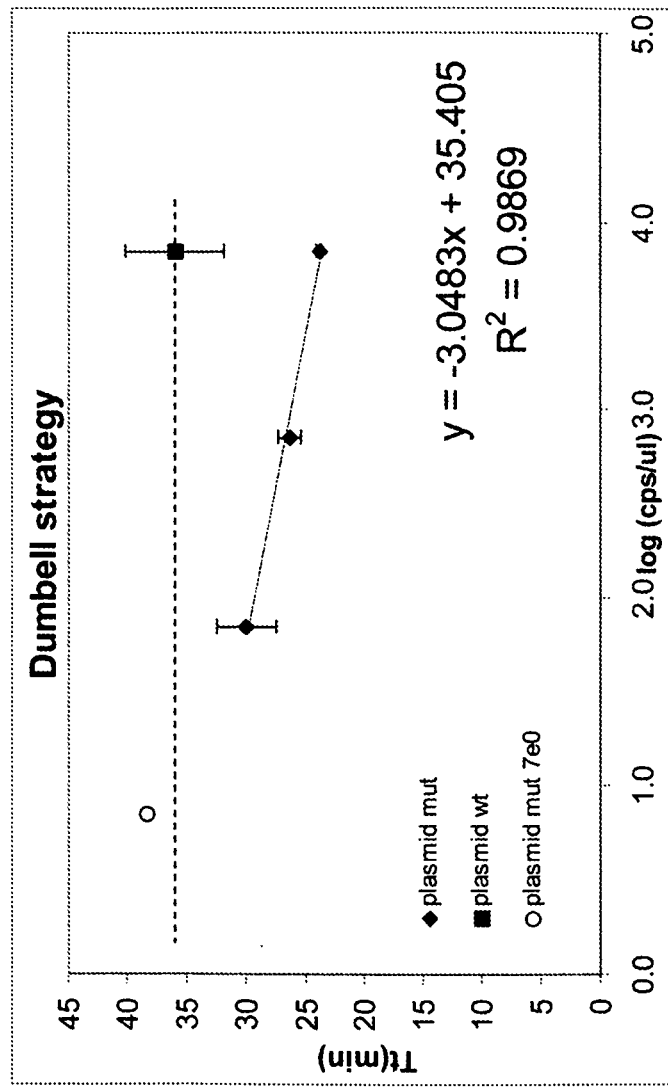

FIG. 6. Sensitivity of the LAMP "DUMB-BELL" Assay

The amplification reaction was performed on a sample containing 7 e3 cps/μl of JAK2 wild-type plasmid (square), on a no-target control and on serial dilutions of JAK2 mutant plasmid in water (from 7 e3 to 7 e1 cps/μl, rhomboidal points, and 7 e0 cps/μl, circle point). Each sample was tested in triplicate. The error bars represent one standard deviation. In comparison to the wild-type plasmid, the mutant target sequence is amplified with higher efficiency up to a sample concentration of 7 e1 cps/μl. The present assay shows linearity between 7 e3 and 7 e1 cps/μl mutant plasmid sample.

Figure 7:
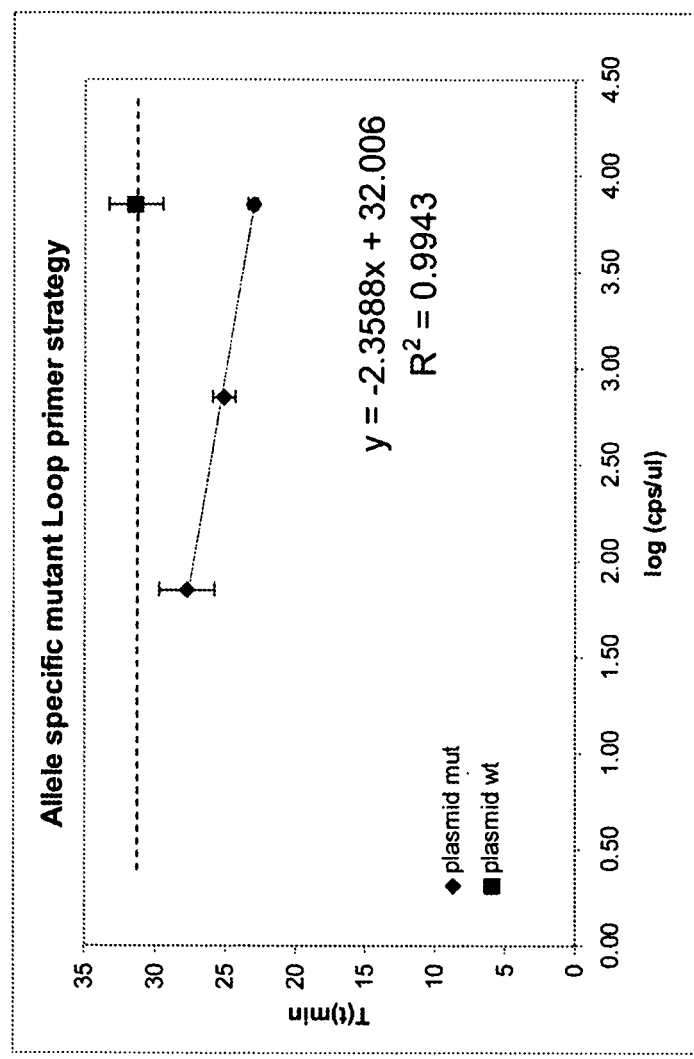

FIG. 7. Sensitivity of the LAMP "Allele Specific Mutant Loop Primer" Assay

The amplification reaction was performed on a sample containing 7 e3 cps/μl of JAK2 wild-type plasmid (square point), on a no-target control and on serial dilutions of JAK2 mutant plasmid in water (from 7 e3 to 7 e1 cps/μl, rhomboidal points). Each sample was tested in triplicate. The error bars represent one standard deviation. In comparison to the wild-type plasmid, the mutant target sequence is amplified with higher efficiency up to a sample concentration of 7 e2 cps/μl. The present assay shows linearity between 7 e3 and 7 e1 cps/μl mutant plasmid sample.

Figure 8:
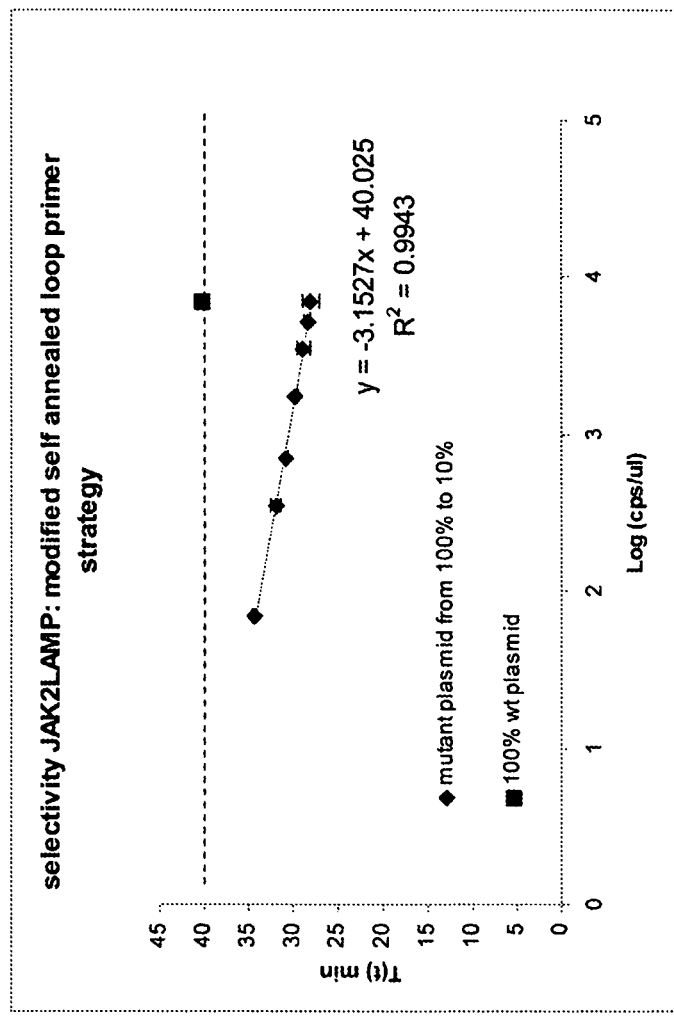

FIG. 8. Selectivity of the LAMP "Stem-Loop Primer" Assay

The amplification reaction was performed on a sample containing 7 e3 cps/μl of JAK2 wild-type plasmid (square point), on a no-target control and on serial dilutions of JAK2 mutant plasmid in wild-type plasmid, ranging from 75% to 1%, 35000 cps total amount of DNA per reaction. Each sample was tested in triplicate. The error bars represent one standard deviation. In comparison to the wild-type plasmid, the mutant target sequence is amplified with higher efficiency up to a 1% dose sample (350 copies mutant plasmid in 34650 copies original parent plasmid). The assay shows linearity between 100% and 1% mutant plasmid sample in wild-type background.

Figure 9:
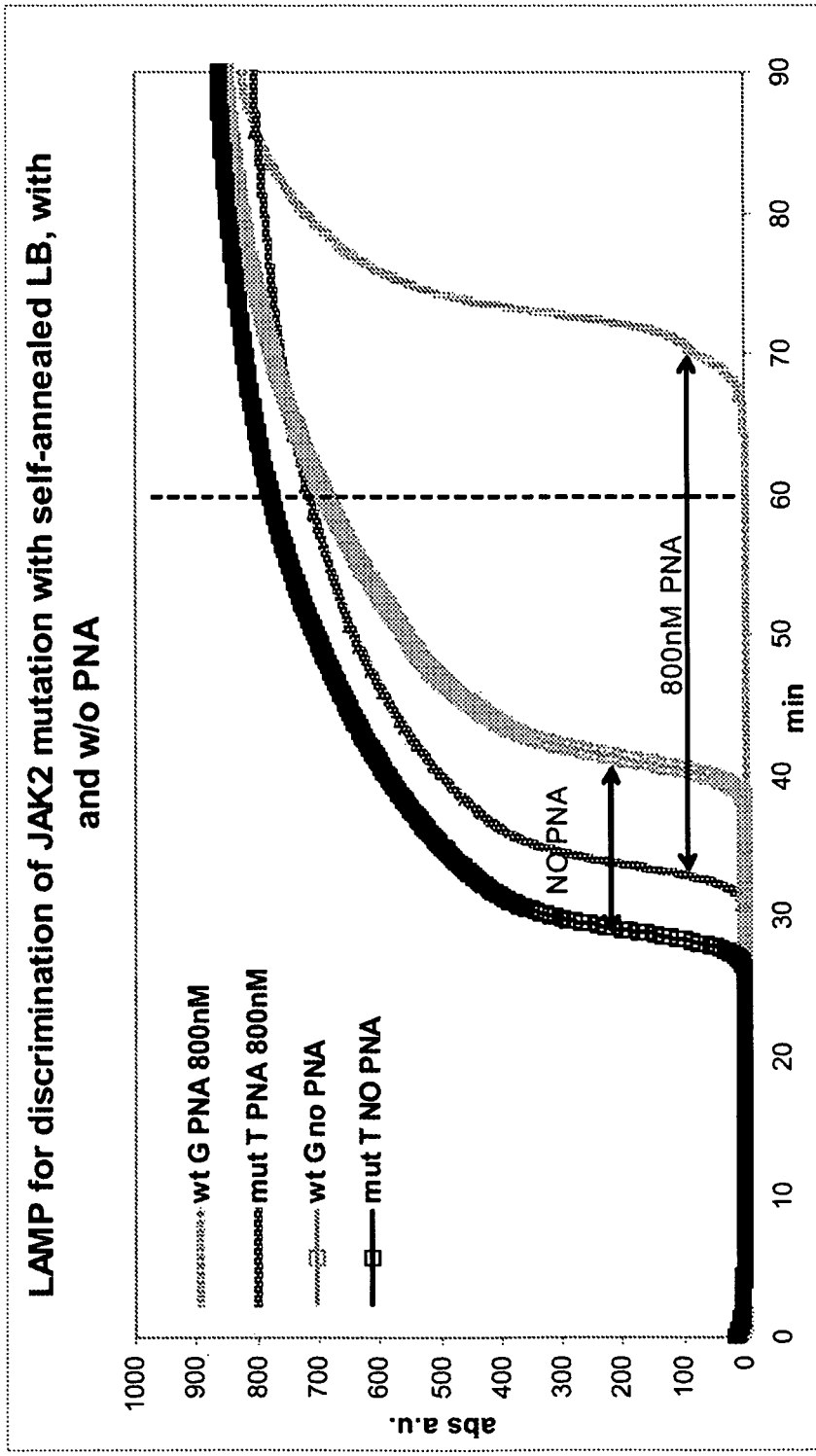

FIG. 9. LAMP "Stem-Loop Primer with PNA"

Assay performance on mutant and wild-type plasmid samples (35000 cps each) with and without PNA. In the absence of PNA, the JAK2 WT plasmid is unspecifically amplified by the mutant-specific stem-loop primer, with a delay of 5 minutes in respect to the mutated target sequence. In contrast, when the PNA is added to the reaction mixture, the WT plasmid is amplified by the mutant-specific stem-loop primer with a one hour delay and only 5 minutes delay are measured for the specific amplification of the JAK2 mutant plasmid. The PNA forms a stable duplex only with the WT complementary sequence preventing the hybridization and extension of the mutant-specific stem-loop primer thereby causing a one hour shift in the amplification time of the wild-type sequence.

Figure 10:
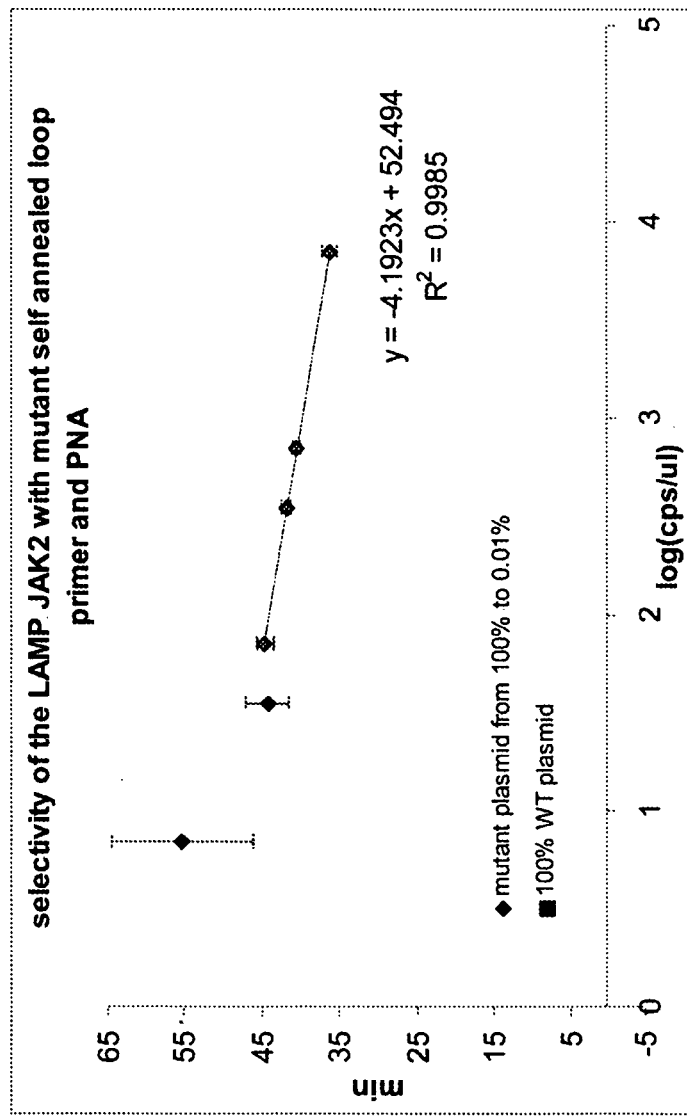

FIG. 10. Selectivity of the LAMP "Stem-Loop Primer with PNA" Assay,

Assay performance on JAK2 mutated plasmid samples (350000 cps), JAK2 wild-type plasmid samples (350000 cps) and on mutated plasmids serially diluted into wild-type background in the following proportions 1, 0.5, 0.1, 0.05 and 0.01%. Error bars correspond to 1 standard deviation. No amplification was detected for the WT sample (350000 cps WT plasmid) within one hour reaction. The specific amplification of the mutant target sequence is detected down to 0.01% mutant sequences in wild-type background (35 copies tot mutant plasmid in 349650 copies of WT plasmid). The assay is linear down to a concentration of 0.1% mutant plasmid (350 copies tot mutant plasmid in 349650 copies of WT plasmid).

Figure 11:
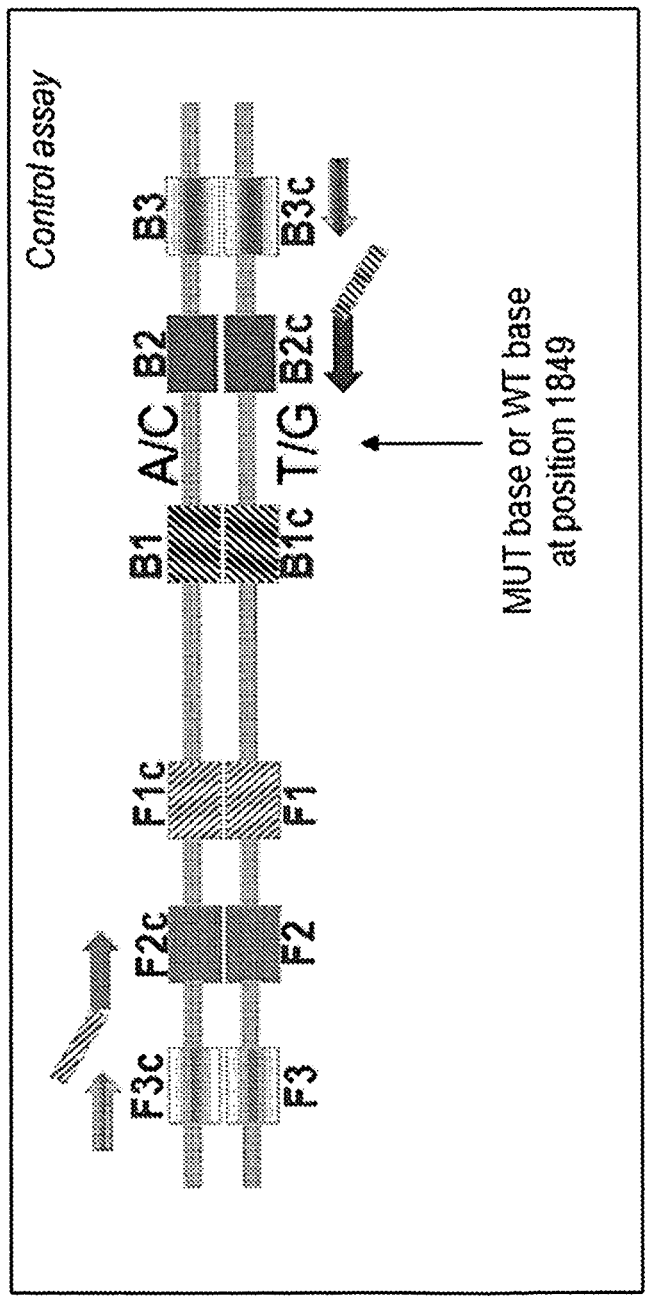

FIG. 11. LAMP Control Reaction

Universal (mutant insensitive) set of primers including the F3, B3, FIP and BIP oligonucleotides. This method is designed to amplify the genomic DNA target sequence independent of the presence of the specific mutation. Such a control assay enables to assess the amplification efficiency of the primers and the presence of inhibitors in the reaction tube.

Figure 12:
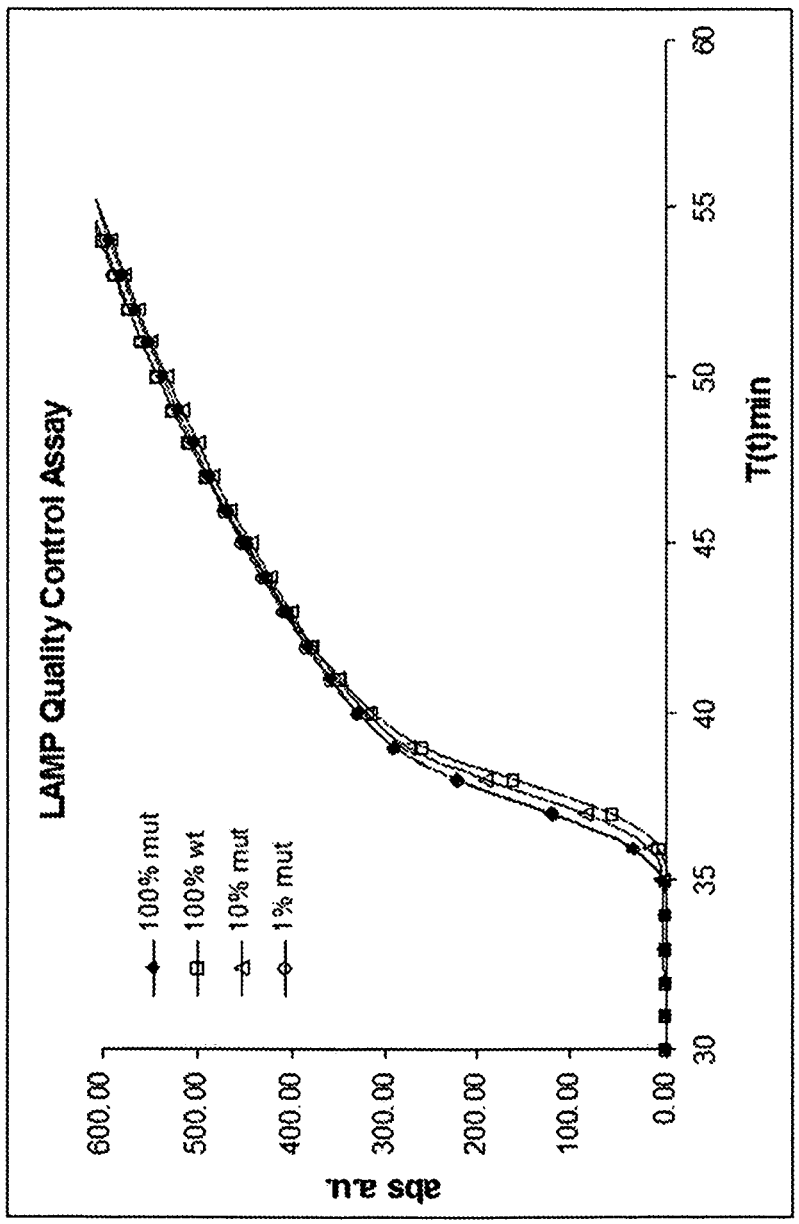

FIG. 12. LAMP Control Reaction on JAK2 Wild-Type and Mutant Nucleic Acid Samples The amplification efficiency of the universal (mutant insensitive) set of primers including the F3, B3, FIP and BIP oligonucleotides is comparable for all the analyzed samples: 100% JAK2 wild-type plasmid, 100%, 10% and 1% JAK2 mutant plasmid. A delay or absence of target sequence amplification is indicative of the presence of reaction inhibitors or problems in the reaction conditions.

Figure 13:
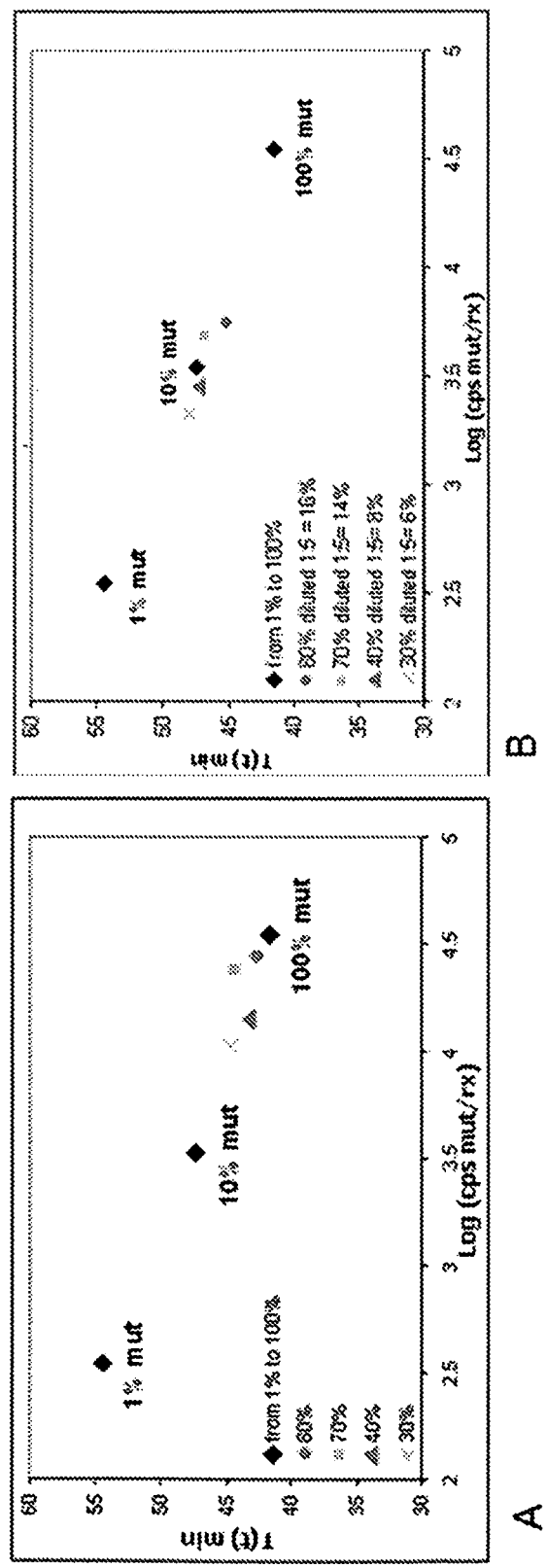

FIG. 13. Principle of the Estimation of Mutant JAK2 Allelic Copies in a Nucleic Acid Sample.

To estimate whether the amount of JAK2 allelic copies in a nucleic acid sample is higher or lower than 50%, the modified LAMP with mutant-specific stem-loop primer and PNA is performed on undiluted samples and samples diluted 1:5. If a sample contains more than 50% mutant JAK2 allelic copies, the threshold amplification minute of the target sequence is comprised between the (min)t of the calibrator 100% and the calibrator 10% for both the undiluted (Panel A) and diluted (Panel B) samples. If a sample contains less than 50% mutant JAK2 allelic copies, the threshold amplification minute of the target sequence is comprised between the t(min) of calibrator 100% and the calibrator 10% for the undiluted samples (Panel A), and between the min(t) of the calibrator 10% and the calibrator 1% for the diluted samples (Panel B).

Figure 14:
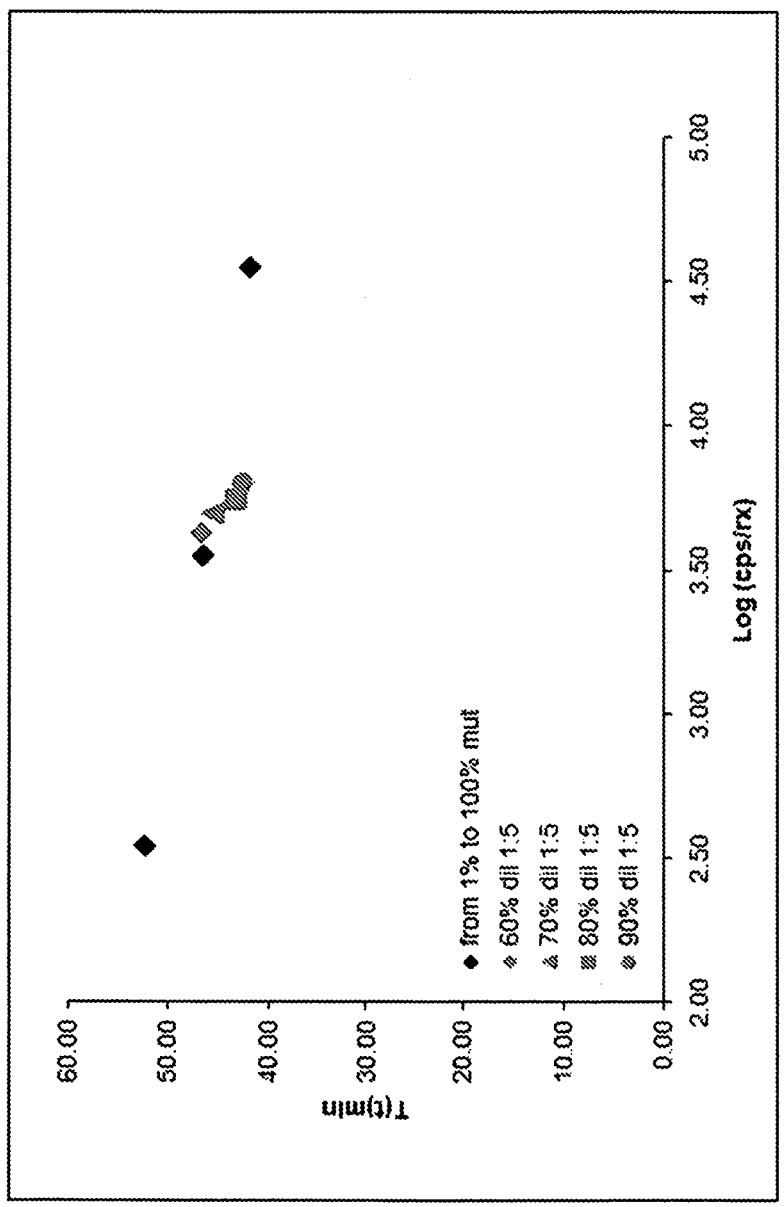

FIG. 14. Estimation of Mutant JAK2 Allelic Copies in Nucleic Acid Samples Containing More than 50% Mutated Target Sequences Four nucleic acid samples containing more than 50% mutant JAK2 plasmid in wild-type background (respectively 60%, 70%, 80% and 90%) were diluted 1:5 and analyzed using the "LAMP stem-loop primer with PNA" assay, together with three calibrators consisting of 100%, 10% and 1% JAK2 mutant plasmids in wild-type background. For all the four samples, the threshold amplification minute was comprised between the min(t) of the calibrator 100% and the min(t) of calibrator 10%.

Figure 15:
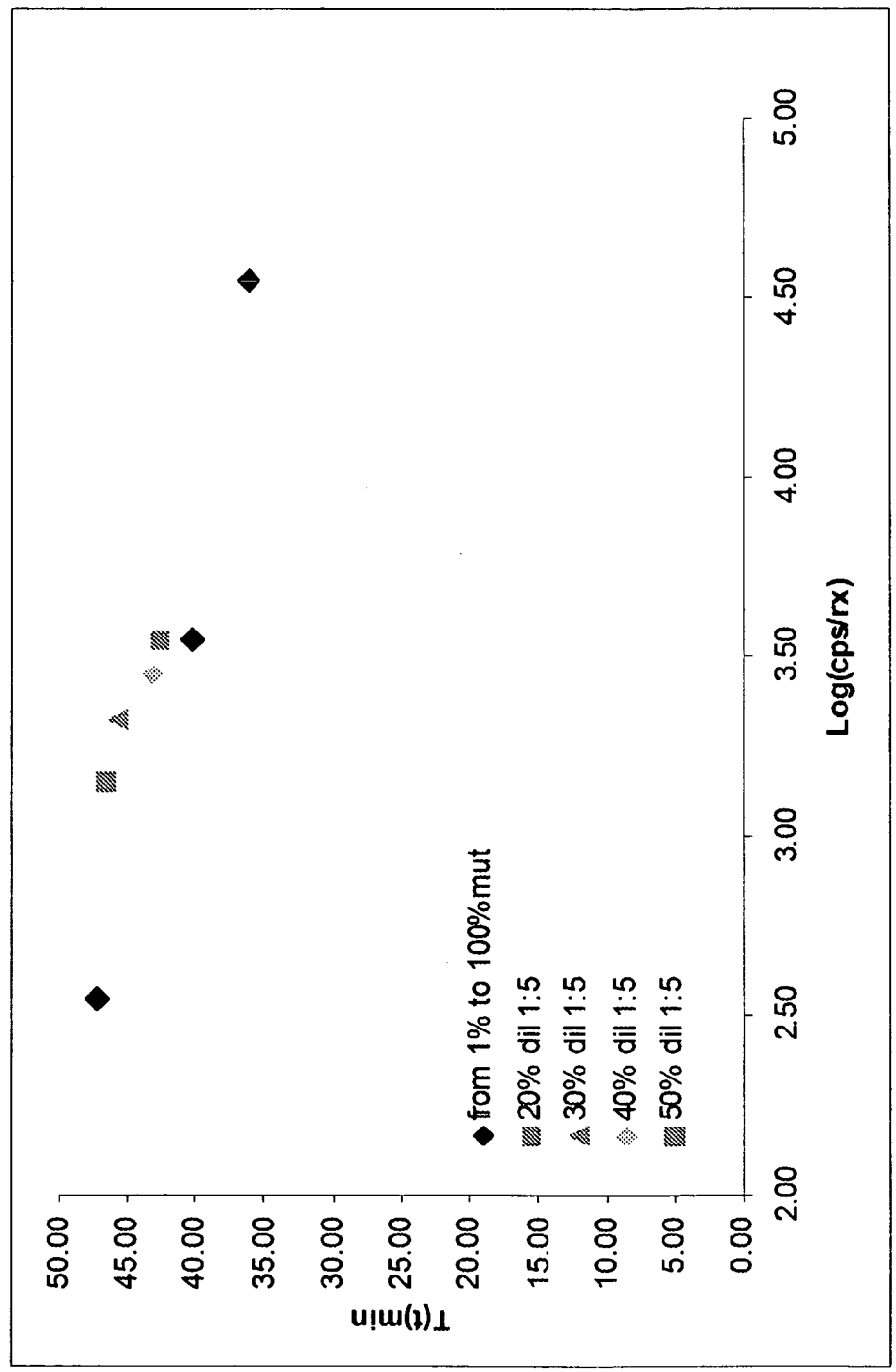

FIG. 15. Estimation of Mutant JAK2 Allelic Copies in Nucleic Acid Samples Containing Less than 50% Mutated Target Sequences Four nucleic acid samples containing 50% or less mutant JAK2 plasmid in wild-type background (respectively 40%, 30% and 20%) were diluted 1:5 and analyzed using the "LAMP stem-loop primer with PNA" assay, together with three calibrators consisting of 100%, 10% and 1% JAK2 mutant plasmids in wild-type background. The amplification of the 50% sample diluted 1:5 occurred at the same threshold minute of the 10% calibrator sample. For the remaining three samples, the threshold amplification minute was comprised between the min(t) of the calibrator 10% and the min(t) of calibrator 1%.

The following examples are provided by way of illustration only and are not intended to limit the scope of the present invention as defined by the appended claims.

Example 1

Materials, Methods and Results of the JAK2-Modified-LAMP "Dumb-Bell Strategy"

Reagents

JAK2 plasmids were provided by the supplier GeneArt (Regensburg, Germany) and contained the wild-type or the mutant JAK2 sequence. In details:
- JAK2 plasmid which Insert corresponds to the sequence 93249-93731 of SEQ ID NO:2, including a G base at nucleotide 93526, referred to as "wt plasmid";
- JAK2 plasmid which Insert corresponds to the sequence 93249-93731 of SEQ ID NO:2, including a T base at nucleotide 93526, referred to as "mut plasmid". Primers: synthesized by the supplier Eurofins MWG Operon (Ebersberg, Germany) referred to as "primers":

```
                                          (SEQ ID NO. 10)
GA211 (F3)    5' GTCAAACAACAATTCTTTGTACT 3';

(SEQ ID NO. 11)
GA212 (B3)    5' AGCTGTGATCCTGAAACTG 3'

(SEQ ID NO. 12)
GA216 (FIP)   5' AATATACTCCATAATTTAAAACCAAAT
                 GCTTTCTTTCTTTGAAGCAGCAAGT 3'

(SEQ ID NO. 13)
GA220 (BIP)   5' TTTTGTGGAGACGAGAGTAAGTAAAACT
                 ACATAAACAAAAACAGATGCTCTGA 3'

(SEQ ID NO. 14)
GA221 (LF)    5' GTGAGAAAGCTTGCTCATCAT 3'

(SEQ ID NO. 15)
GA222 (LB)    5' AGGCTTTCTAATGCCTTTC 3'
```

Reaction buffer: 100 mM; Tris-HCl pH 8.8, 50 mM KCl, 40 mM MgSO4, 50 mM (NH4)2SO4, 0.5% Tween, 5% DMSO "buffer 5×"

dNTPs mix 25 mM (Fermentas), "dNTPs"

Bst Large Fragment polymerase 8 U/ul (New England Biolabs), "Polymerase" Sterile apyrogen water (SALF Spa), "ddw"

Procedure

Sample Preparation

Prepare reaction mix as follows: 0.2 μM outer primers (F3 and B3), 1.6 μM inner primers (FIP and BIP), 0.8 uM loop primers (LF and LB), 1× buffer solution, 1.4 mM dNTPs mix, 8 U Bst Polymerase. Final volume of the reaction mix must be ⅘ of the total reaction volume (i.e. 20 μl reaction mix+5 μl sample). Always keep reagents on ice. Prepare the mix for at least 17 samples, comprising 3 negative control (7e3 cps/ul wild-type plasmid), 12 positive control (3 samples 7e3 cps/ul mutant plasmid, 3 samples 7e2 cps/ul mutant plasmid, 3 samples 7e1 cps/ul mutant plasmid, 3 samples 7e0 cps/ul mutant plasmid), 1 no-target control.

TABLE 1

| | sample mix composition | | | | | |
|---|---|---|---|---|---|---|
| Sample tube | 1-3 | 4-6 | 7-9 | 10-12 | 13-15 | 16-19 |
| Target to be add (5 μl) | Wt plasmid 7e3 cps/μl | Mut plasmid 7e3 cps/μl | Mut plasmid 7e2 cps/μl | Mut plasmid 7e1 cps/μl | Mut plasmid 7e0 cps/μl | |
| GA 211 100 μM | 0.05 | 0.05 | 0.05 | 0.05 | 0.05 | 0.05 |
| GA 212 100 μM | 0.05 | 0.05 | 0.05 | 0.05 | 0.05 | 0.05 |
| GA 221 100 μM | 0.2 | 0.2 | 0.2 | 0.2 | 0.2 | 0.2 |
| GA 221 100 μM | 0.2 | 0.2 | 0.2 | 0.2 | 0.2 | 0.2 |
| GA 216 100 μM | 0.4 | 0.4 | 0.4 | 0.4 | 0.4 | 0.4 |
| GA 220 100 μM | 0.4 | 0.4 | 0.4 | 0.4 | 0.4 | 0.4 |
| Buffer LAMP 5x | 2.5 | 2.5 | 2.5 | 2.5 | 2.5 | 2.5 |
| Bst Polymerase 8 U/μl | 1 | 1 | 1 | 1 | 1 | 1 |
| dNTPs 25 mM | 1.4 | 1.4 | 1.4 | 1.4 | 1.4 | 1.4 |
| Ddw to 20 μl | 13.18 | 13.18 | 13.18 | 13.18 | 13.18 | 13.18 |

Dispense 20 μl of reaction mix in the strip. Keep the strips on ice. Always keep the reaction mix on ice from now on.

Prepare serial dilutions of the target ("target dilutions") from shipped solution (WT plasmid and MUT plasmid). Shipped solution is a $7*10^{10}$ copies/μl. Dilute initially the mutant plasmid to a $7*10^4$ copies/μl in Tris 10 mM, then dilute serially to 7e3 cps/μl, 7e2 cps/μl, 7e1 cps/μl and 7e0 cps/μl in Tris 10 mM. Dilute the WT plasmid to $7*10^3$ copies/μl in Tris 10 mM.

Add 5 μl of target dilutions to the strips, in triplicate. Add 5 μl of the target dilutions starting from the less concentrated to the highest concentrated sample. Close all the tubes.

Reaction

The reaction follows the method scheme of FIGS. 1 and 2.

Program the turbidimeter (Teramecs) for incubation at constant temperature and real time monitoring of turbidity, in order to obtain a constant reaction temperature of 66° C. for 1 hour.

Put the strips in the instrument immediately before the beginning of the programs. Start the program.

Data Analysis

Analyze the variation of absorbance in terms of a.u. (arbitrary units of absorbance) to find the threshold time for each sample analyzed. The threshold time is the minute at which the sample absorbance, after baseline subtraction, reaches the arbitrary unit value representing the threshold (in this case 0.1 a.u.). The threshold time reached by each samples is correlated with its Log of DNA copies/μl.

Results

The "LAMP JAK2 Dumb-bell" strategy is based on the Eiken LAMP method for SNP detection (described in EP 1231281, 20, 21, 22.

In the present assay set-up illustrated in FIG. 2, the F1c and B1c oligonucleotides contained in the FIP and BIP inner primers are complementary to non-overlapping sequences of the JAK2 gene which ends and starts respectively one base upstream and one base downstream the nucleotide of interest at, position 1849 from the start codon in the JAK2 coding sequence. Furthermore, the 5' end base of the FIP and BIP primers is specific for the mutated T nucleotide in the JAK2 sequence and both inner primers have a mismatched base at the third base from the 3' end. When the reaction contains the wild-type target allele and a dumb-bell structure is formed, the mutant specific, F1c and B1c sequences do not anneal at the 3' end blocking any further amplification. Differently, if the mutant target allele is present in solution, the mutant specific F1c and B1c sequences hybridize perfectly to the complementary nucleic acid target region and are extended by the DNA polymerase.

As shown in FIG. 6, decreasing mutant plasmid concentrations were detected by the LAMP assay ranging from 7e3 cps/μl to 7e0 cps/μl (35 copies tot mutant plasmid). At low concentrations of the target nucleic acid sequence, this LAMP assay set-up could not discriminate between mutant and wild-type plasmids which are indeed amplified at a concentration of 7e3 cps/μl. Since a selectivity value lower than 1% is required in order to overcome the limitations of the assay methods previously described in literature, no clear advantage was gained with the present approach.

Example 2

Materials, Methods and Results of the JAK2-Modified-LAMP "Allele Specific Loop Primer Extension" Strategy Reagents JAK2 plasmids were synthesized by the supplier GeneArt (Regensburg, Germany) to contain the wild-type or the mutant JAK2 sequence. In details:

JAK2 plasmid which Insert corresponds to the sequence 93249-93731 of SEQ ID NO:2, including a G base at nucleotide 93526, referred to as "wt plasmid";

JAK2 plasmid which Insert corresponds to the sequence 93249-93731 of SEQ ID NO:2, including a T base at nucleotide 93526, referred to as "mut plasmid". Primers: synthesized by Eurofins MWG Operon, referred to as "primers":

```
                                              (SEQ ID NO. 16)
JAKR5 (F3)    5' TCTATAGTCATGCTGAAAGTAGGAG 3'

(SEQ ID NO. 17)
JAKR2 (B3)    5' AAGGCATTAGAAAGCCTGTAGT 3'

(SEQ ID NO. 18)
JAKR7 (FIP)   5' ACAAAGAATTGTTGTTTGACTGTTGTCCA
                 TTGCATCTTTATTATGGCAGAGAGAA 3'

(SEQ ID NO. 19)
JAKR8 (BIP)   5' AGTCTTTCTTTGAAGCAGCAAGTATGAT
                 GTTACTTACTCTCGTCTCCACAGA 3'

(SEQ ID NO. 20)
JAKR9 (LB)    5' AGCATTTGGTTTTAAATTATGGAGTAGGTT 3'.
```

The underlined base corresponds to a mismatched nucleotide; the bold base corresponds to the mutated nucleotide at position 1849 from the ATG initiation codon of the JAK2 coding sequence.

Reaction buffer: 100 mM Tris-HCl pH 8.8, 50 mM KCl, 40 mM MgSO4, 50 mM (NH4)2SO4, 0.5% Tween, "buffer 5×"

dNTPs mix 25 mM (Fermentas), "dNTPs"

Bst Large Fragment polymerase 8 U/ul (New England Biolabs), "Polymerase"

Sterile apyrogen water (SALF Spa), "ddw"

Procedure

Sample Preparation

Stock the primers in aliquots. It is better to store stock solutions at −20° C., while working dilutions should be stored at 4° C.

Prepare reaction mix as follows: 0.2 μM outer primers (F3 and B3), 1.6 μM inner primers (FIP and BIP), 0.8 uM loop primer (LB), 1× buffer solution, 1.4 mM dNTPs mix, 8 U Bst Polymerase. Final volume of the reaction mix must be 4/5 of the total reaction volume (i.e. 20 μl reaction mix+5 μl sample). Always keep reagents on ice. Prepare the mix for at least 14 samples, comprising 3 negative controls (7e3 cps/ul wild-type plasmid), 9 positive control (3 samples 7e3 cps/ul mutant plasmid, 3 samples 7e2 cps/ul mutant plasmid, 3 samples 7e1 cps/ul mutant plasmid) 1 no-target control.

TABLE 2

| Sample tube | sample mix composition | | | | | |
|---|---|---|---|---|---|---|
| | 1-3 | 4-6 | 7-9 | 10-12 | 13-15 | 16-19 |
| Target to be add (5 μl) | Wt plasmid 7e3 cps/μl | Mut plasmid 7e3 cps/μl | Mut plasmid 7e2 cps/μl | Mut plasmid 7e1 cps/μl | Mut plasmid 7e0 cps/μl | |
| JAKR5 100 μM | 0.05 | 0.05 | 0.05 | 0.05 | 0.05 | 0.05 |
| JAKR2 100 μM | 0.05 | 0.05 | 0.05 | 0.05 | 0.05 | 0.05 |
| JAKR7 100 μM | 0.4 | 0.4 | 0.4 | 0.4 | 0.4 | 0.4 |
| JAKR8 100 μM | 0.4 | 0.4 | 0.4 | 0.4 | 0.4 | 0.4 |
| JAKR9 100 μM | 0.2 | 0.2 | 0.2 | 0.2 | 0.2 | 0.2 |
| Buffer LAMP 10x | 2.5 | 2.5 | 2.5 | 2.5 | 2.5 | 2.5 |
| Bst Polymerase 8 U/μl | 1 | 1 | 1 | 1 | 1 | 1 |
| dNTPs 25 mM | 1.4 | 1.4 | 1.4 | 1.4 | 1.4 | 1.4 |
| Ddw to 20 μl | 14 | 14 | 14 | 14 | 14 | 14 |

Dispense 20 μl of reaction mix in the strip. Keep the strips on ice. Always keep the reaction mix on ice from now on.

Prepare serial dilutions of the target ("target dilutions") from shipped solution (WT plasmid and MUT plasmid). Shipped solution is a $7*10^{10}$ copies/μl. Dilute initially the mutant plasmid to a $7*10^4$ copies/μl in Tris 10 mM, then dilute serially to 7e3 cps/μl, 7e2 cps/μl, 7e1 cps/μl in Tris 10 mM. Dilute the WT plasmid to $7*10^3$ copies/μl in Tris 10 mM. Add 5 μl of target dilutions to the strips, in triplicate. Add 5 μl of the target dilutions starting from the less concentrated to the highest concentrated sample. Close all the tubes.

Reaction

The reaction follows the method scheme of FIG. 3.

Program the turbidimeter (Teramecs) for incubation at constant temperature and real time monitoring of turbidity in order to obtain a constant reaction temperature of 65° C. for 1 hour.

Put the strips in the instrument immediately before the beginning of the programs. Start the program.

Data Analysis

Analyze the variation of absorbance in terms of a.u. to find the threshold time for each sample analyzed. The threshold time is the minute at which the sample absorbance, after baseline subtraction, reaches the arbitrary unit value representing the threshold (in this case 0.1 a.u.). The threshold time reached by each samples is correlated with its Log of DNA copies/μl.

Results

The present approach consists in the selective amplification of a mutant sequence by using a mutant-specific loop primer (FIG. 3). We designed a universal (mutant insensitive) set of primers including the F3, B3, FIP and BIP oligonucleotides to obtain a dumb-bell structure presenting the putative mutation in the loop region comprised between B2 and B1c. In addition, we designed a loop primer presenting the last base at the 3' end complementary to the mutated nucleotide T at position 1849 of the JAK2 coding sequence and a mismatched base in the third base from the 3' end. If the reaction contains the WT target sequence, the 3' end of the mutant-specific loop primer does not anneal to the complementary nucleotide thus resulting in no amplification. Differently, if JAK2 mutant sequences are present in solution, the mutant-specific loop primer hybridizes perfectly to the complementary sequence and is extended by the DNA polymerase.

Assay evaluation was performed on mutant plasmid samples at concentrations ranging from 7e3 cps/μl to 7e1 cps/μl (35000 and 350 copies tot mutant plasmid) and on a WT sample containing 7e3 plasmid cps/μl, all tested samples in triplicate. With the present method unspecific amplification was detected for the WT plasmid sample at 7e3 cps/µl and mutant and wild-type samples at 7e1 cps/µl concentrations could not be discriminated. Since a selectivity value lower than 1% is required in order to overcome the limitations of the assay methods previously described in literature, no clear advantage was gained with the present approach (FIG. 7).

Example 3

Materials, Methods and Results of the JAK2-Modified-LAMP "Stem-Loop Primer Strategy"

Reagents

JAK2 plasmids were synthesized by the supplier GeneArt (Regensburg, Germany) to contain the wild-type or the mutant JAK2 sequence. In details:
- JAK2 plasmid which Insert corresponds to the sequence 93249-93731 of SEQ ID NO:2, including a G base at nucleotide 93526, referred to as "wt plasmid";
- JAK2 plasmid which Insert corresponds to the sequence 93249-93731 of SEQ ID NO:2, including a T base at nucleotide 93526, referred to as "mut plasmid".

Primers: synthesized by Eurofins MWG Operon, referred to as "primers":

```
                                         (SEQ ID NO. 3)
GA231 (F3)    5' GCATCTTTATTATGGCAGAGAG 3'

(SEQ ID NO. 4)
GA232 (B3)    5' TGCTCTGAGAAAGGCATTA 3'

(SEQ ID NO. 5)
GA233 (FIP)   5' GCTGCTTCAAAGAAAGACTAAGGA
                 AATGGACAACAGTCAAACAAC 3'

(SEQ ID NO. 6)
GA234 (BIP)   5' GCTTTCTCACAAGCATTTGGTTTTA
                 AATTAGCCTGTAGTTTTACTTACTCTC 3'

(SEQ ID NO. 7)
GA236 (LB)    5' GTCTCCACTGGAGTATGTTTCTGTGGAGAC 3'
``` the underlined base corresponds to the wild-type nucleotide at position 1849 from the ATG initiation codon in the JAK2 coding sequence (GeneBank accession no NM_004972).

ddC stands for not-extensible dideoxy-citosine.

GA236 (LB) 5' GTCTCCACTGGAGTATGTTTCTGTG-GAGAC 3' (SEQ ID NO:8)

the underlined base corresponds to the mutated nucleotide at position 1849 from the ATG initiation codon in the JAK2 coding sequence (GeneBank accession no NM_004972).

Reaction buffer: 100 mM Tris-HCl pH 8.8, 50 mM KCl, 40 mM MgSO$_4$, 50 mM (NH$_4$)$_2$SO$_4$, 0.5% Tween, "buffer 5×"

dNTPs mix 25 mM (Fermentas), "dNTPs"

Bst Large Fragment polymerase 8 U/ul (New England Biolabs), "Polymerase"

Sterile apyrogen water (SALF Spa), "ddw"

Procedure

Sample Preparation

Stock the primers in aliquots. It is better to store stock solutions at −20° C., while working dilutions should be stored at 4° C.

Prepare reaction mix as follows: 0.2 µM outer primers (F3 and B3), 1.6 µM inner primers (FIP and BIP), 0.8 uM both self-annealed loop primers (not-extensible LF and LB), 1× buffer solution, 1.4 mM dNTPs mix, 8 U Bst Polymerase. Final volume of the reaction mix must be ⅘ of the total reaction volume (i.e. 20 µl reaction mix+5 µl sample). Always keep reagents on ice. Prepare the mix for at least 26 samples, comprising 3 negative controls (100% wild-type plasmid, 7e3 cps/µl), 21 positive control (3 samples 100% mutant plasmid (7e3 cps/µl), 3 samples 75% mutant plasmid diluted in WT plasmid, 3 samples 50% mutant plasmid diluted in WT plasmid, 3 samples 25% mutant plasmid diluted in WT plasmid, 3 samples 10% mutant plasmid diluted in WT plasmid, 3 samples 5% mutant plasmid diluted in WT plasmid, 3 samples 1% mutant plasmid diluted in WT plasmid), and one no target control.

TABLE 3 sample mix composition

| Sample tube | 1-3 | 4-6 | 7-9 | 10-12 | 13-15 |
|---|---|---|---|---|---|
| Target to be add (5 µl) | Wt plasmid 7e3 cps/µl | Mut plasmid 7e3 cps/µl | Mut plasmid 5.25e3 cps/µl, WT plasmid 1.75e3 cps/µl | Mut plasmid 3.5e3 cps/µl WT plasmid 3.5e3 cps/µl | Mut plasmid 1.75e3 cps/µl WT plasmid 5.25e3 cps/µl |
| GA231 100 µM | 0.05 | 0.05 | 0.05 | 0.05 | 0.05 |
| GA232 100 µM | 0.05 | 0.05 | 0.05 | 0.05 | 0.05 |
| GA233 100 µM | 0.4 | 0.4 | 0.4 | 0.4 | 0.4 |
| GA234 100 µM | 0.4 | 0.4 | 0.4 | 0.4 | 0.4 |
| GA235 100 µM | 0.2 | 0.2 | 0.2 | 0.2 | 0.2 |
| GA236 100 µM | 0.2 | 0.2 | 0.2 | 0.2 | 0.2 |
| Buffer LAMP 10x | 2.5 | 2.5 | 2.5 | 2.5 | 2.5 |
| Bst Polymerase 8 U/µl | 1 | 1 | 1 | 1 | 1 |
| dNTPs 25 mM | 1.4 | 1.4 | 1.4 | 1.4 | 1.4 |
| Ddw to 20 µl | 13.8 | 13.8 | 13.8 | 13.8 | 13.8 |

Dispense 20 µl of reaction mix in the strip. Keep the strips on ice. Always keep the reaction mix on ice from now on.

Prepare serial dilutions of the target ("target dilutions") from shipped solution (WI plasmid and MUT plasmid). Shipped solution is a 7*10$^{10}$ copies/µl. Dilute initially the mutant plasmid to a 7*10$^4$ copies/µl in Tris 10 mM, then dilute serially the mutant plasmid in WT plasmid to obtain the following concentrations of mutant sequences in wild-type background: 75%, 50%, 25%, 10%, 5%, 1% (total amount per tube, 7e3 cps/µl).

Add 5 µl of target dilutions to the strips, in triplicate. Add 5 µl of the target dilutions starting from the less concentrated to the highest concentrated sample. Close all the tubes.

Reaction

The reaction follows the method scheme of FIG. 4.

Program the turbidimeter (Teramecs) for incubation at constant temperature and real time monitoring of turbidity, in order to obtain a constant reaction temperature of 65° C. for 1 hour.

Put the strips in the instrument immediately before the beginning of the programs. Start the program.

Data Analysis

Analyze the variation of absorbance in terms of a.u. to find the threshold time for each sample analyzed. The threshold time is the minute at which the sample absorbance, after baseline subtraction, reaches the arbitrary unit value representing the threshold (in this case 0.1 a.u.). The threshold time reached by each samples is correlated with its Log of DNA copies/µl.

Results

The present approach consists in the selective amplification of a mutant sequence based on a particular loop primer design resulting in selective hybridization of such loop primer to the dumb-bell formed from the mutant sequence (FIG. 4). We designed a universal (mutant insensitive) set of primers including the F3, B3, FIP and BIP oligonucleotides to obtain a dumb-bell structure presenting the putative mutation in the loop region comprised between B1 and B2. No major differences were detected when performing such experiments on alternative sequences containing the putative mutated nucleotide in the loop region within B2 or between B2 and B1c. We included in the primer set a particular loop primer presenting a 8-bases sequence region at its 5' end complementary to its own sequence at the 3' end. Consequently, this special loop primer forms an intra-molecular hairpin structure which is in equilibrium with its open form at the reaction temperature (65° C.).

When the mutated JAK2 sequence is present in the sample, such modified loop primer breaks its internal structure to hybridize to the complementary target sequence, according to the thermodynamic equilibrium (Tm between primer and specific target=65° C.). The loop primer hybridized to the specific mutated target is then extended by the polymerase and the amplification can further proceed. As additional feature, the loop primer specific for the JAK2 G→T mutation presents a Tm with the wild-type target sequence (59° C.) lower than the intra-molecular hairpin structure (65° C.). Thus, in a sample containing the JAK2 WT sequence, such difference in Tm values results in auto-sequestration of the modified loop primer that prefers to fold in the hairpin structure rather than to form a duplex with the unspecific target, since the intramolecular forces are higher than the intermolecular ones.

To limit the competition of this loop primer for the wild-type sequences likely to be present in large excess in the clinical sample, we included in the reaction set-up a second loop primer with analogous structure and containing a nucleotide sequence complementary to the JAK2 wild-type sequence, i.e. with G base at position 1849 from the start codon (GeneBank accession no NM_004972).

The 3' end of this "competitor" loop primer is made not extensible by a modification (3' dideoxy). The task of this competitor is to "silence" the WT sequence thus enabling the specific mutant primer to find its target.

When the "competitor" primer recognizes the complementary wild-type sequence, it breaks its intramolecular structure to hybridize to the WT target, according to the higher affinity (Tm of the duplex formed by the WT target and the WT modified loop primer=67° C.). The loop primer hybridized to the WT target is not extensible, resulting in no amplification of the wild-type sequences. Since the reaction is conducted at constant temperature, the WT-specific stem-loop primer stays attached to the wild-type sequences thus preventing the unspecific hybridization of the MUT loop primer.

In contrast to the mutant-specific loop primer, the "competitor" primer presents a Tm with the mutant target sequence (62° C.) lower than the intra-molecular hairpin structure formed with itself (65° C.). Thus the higher intramolecular forces compared to the intermolecular ones cause the auto-sequestration of the modified stem-loop primer that prefers to fold in the hairpin structure rather than to form a duplex with the mutant target sequence.

The selectivity of the present assay was evaluated by performing the target sequence amplification on serial dilutions of mutant plasmid in wild-type background (FIG. 8). The achieved selectivity is significantly less than 1% (350 copies tot mutant plasmid in 34650 copies of WT plasmid) indicating a higher performance than the assays previously described in literature.

Assay linearity is detected between 100% mutant plasmid (35000 cps) and 1% mutant in 99% wild-type plasmids (350 copies tot mutant plasmid in 34650 copies of WT plasmid) thus allowing the detection and quantification of low percentage of mutant sequences in large amount of WT plasmids. Therefore, a significant improvement has been achieved with such implemented LAMP approach.

Example 4

Materials, Methods and Results of the JAK2-Modified-LAMP "Stem-Loop Primer Strategy with PNA"

Reagents

JAK2 plasmids were synthesized by the supplier GeneArt (Regensburg, Germany) to contain the wild-type or the mutant JAK2 sequence. In details:

JAK2 plasmid which Insert corresponds to the sequence 93249-93731 of SEQ ID NO:2, including a G base at nucleotide 93526, referred to as "wt plasmid";

JAK2 plasmid which Insert corresponds to the sequence 93249-93731 of SEQ ID NO:2, including a T base at nucleotide 93526, referred to as "mut plasmid". Primers: synthesized by Eurofins MWG Operon, referred to as "primers":

GA231 (F3) 5' GCATCTTTATTATGGCAGAGAG 3' (SEQ ID NO:3)

GA232 (B3) 5' TGCTCTGAGAAAGGCATTA 3' (SEQ ID NO:4)

GA233 (FIP) 5' GCTGCTTCAAAGAAAGACTAAG-GAAATGGACAACAGTCAAACAAC 3' (SEQ ID NO:5)

GA234 (BIP) 5'GCTTTCTCACAAGCATTTGGTTT-TAAATTAGCCTGTAGTTTTACTTACTCTC 3' (SEQ ID NO:6)

GA236 (LB) 5' GTCTCCACTGGAGTATGT$\underline{T}$TCTGTGGAGAC 3' (SEQ ID NO:8)

The underlined base corresponds to the mutated nucleotide at position 1849 from the ATG initiation codon in the JAK2 coding sequence (GeneBank accession no NM_004972).

PNA: synthesized by Eurogentec, referred to as "PNA" GM43 $^{NH2}$GAGTATG$\underline{T}$GTCTGTGGA$^{COOH}$ (SEQ ID NO:9.)

The underlined base corresponds to the wild-type nucleotide at position 1849 from the ATG initiation codon in the JAK2 coding sequence (GeneBank accession no NM_004972).

Reaction buffer: 100 mM Tris-HCl pH 8.8, 50 mM KCl, 40 mM MgSO4, 50 mM (NH4)2SO4, 0.5% Tween, "buffer 5×"

dNTPs mix 25 mM (Fermentas), "dNTPs"

Bst Large Fragment polymerase 8 U/μl (New England Biolabs), "Polymerase"

Sterile apyrogen water (SALF Spa), "ddw"

Procedure

Sample Preparation

Stock the primers in aliquots. It is better to store stock solutions at −20° C., while working dilutions should be stored at 4° C.

Prepare reaction mix as follows: 0.2 μM outer primers (F3 and B3), 1.6 μM inner primers (FIP and BIP), 0.8 uM self-annealed loop primer specific for mutant JAK2 (LB), 0.8 uM PNA, 1× buffer solution, 1.4 mM dNTPs mix, 8 U Bst Polymerase. Final volume of the reaction mix must be ⅘ of the total reaction volume (i.e. 20 μl reaction mix+5 μl sample). Always keep reagents on ice. Prepare the mix for at least 23 samples, comprising 3 negative controls (100% wild-type plasmid, 7e4 cps/μl), 18 positive control (3 samples 100% mutant plasmid, 3 samples 1% mutant plasmid diluted in WT plasmid, 3 samples 0.5% mutant plasmid diluted in WT plasmid, 3 samples 0.1% mutant plasmid diluted in WT plasmid, 3 samples 0.05% mutant plasmid diluted in WT plasmid, 3 samples 0.01% mutant plasmid diluted in WT plasmid (total amount of DNA 7e4 cps/μl)), and one no target control.

TABLE 4 sample mix composition

| Sample tube | 1-3 | 4-6 | 7-9 | 10-12 | 13-15 | 16-19 |
|---|---|---|---|---|---|---|
| Target to be add (5 μl) | Wt plasmid 7e4 cps/μl | Mut plasmid 7e4 cps/μl | Mut plasmid 7e3 cps/μl, WT plasmid 6.93e4 cps/μl | Mut plasmid 3.5e2 cps/μl, WT plasmid 6.65e4 cps/μl | Mut plasmid 7e1 cps/μl, WT plasmid 6.993e4 cps/μl | Mut plasmid 3.5e1 cps/μl, WT plasmid 6.9965e4 cps/μl |
| GA231 100 μM | 0.05 | 0.05 | 0.05 | 0.05 | 0.05 | 0.05 |
| GA232 100 μM | 0.05 | 0.05 | 0.05 | 0.05 | 0.05 | 0.05 |
| GA233 100 μM | 0.4 | 0.4 | 0.4 | 0.4 | 0.4 | 0.4 |
| GA234 100 μM | 0.4 | 0.4 | 0.4 | 0.4 | 0.4 | 0.4 |
| PNA 100 μM | 0.2 | 0.2 | 0.2 | 0.2 | 0.2 | 0.2 |
| GA236 100 μM | 0.2 | 0.2 | 0.2 | 0.2 | 0.2 | 0.2 |
| Buffer LAMP 10x | 2.5 | 2.5 | 2.5 | 2.5 | 2.5 | 2.5 |
| Bst Polymerase 8 U/μl | 1 | 1 | 1 | 1 | 1 | 1 |
| dNTPs 25 mM | 1.4 | 1.4 | 1.4 | 1.4 | 1.4 | 1.4 |
| Ddw to 20 μl | 13.8 | 13.8 | 13.8 | 13.8 | 13.8 | 13.8 |

Dispense 20 μl of reaction mix in the strip. Keep the strips on ice. Always keep the reaction mix on ice from now on.

Prepare serial dilutions of the target ("target dilutions") from shipped solution (WT plasmid and MUT plasmid). Shipped solution is a $7*10^{10}$ copies/μl. Dilute initially the mutant plasmid to a $7*10^4$ copies/μl in Tris 10 mM, then dilute serially the mutant plasmid in WT plasmid to obtain the following concentrations of mutant sequences in wild-type background: 1%, 0.5%, 0.1%, 0.05%, 0.01% (total amount per tube, 7e4 cps/μl).

Add 5 μl of target dilutions to the strips, in triplicate. Add 5 μl of the target dilutions starting from the less concentrated to the highest concentrated sample. Close all the tubes.

Reaction

The reaction follows the method scheme of FIG. 5.

Program the turbidimeter (Teramecs) for incubation at constant temperature and real time monitoring of turbidity in order to obtain a constant reaction temperature of 65° C. for 1 hour.

Put the strips in the instrument immediately before the beginning of the programs. Start the program.

Data Analysis

Analyze the variation of absorbance in terms of a.u. to find the threshold time for each sample analyzed. The threshold time is the minute at which the sample absorbance, after baseline subtraction, reaches the arbitrary unit value representing the threshold (in this case 0.1 a.u.): The threshold time reached by each samples is correlated with its Log of DNA copies/μl.

Results

This approach consists in the selective amplification of a mutant sequence based on a particular loop primer design resulting in selective hybridization of such loop primer to the dumb-bell formed from the mutant sequence (FIG. 5). We designed a universal (mutant insensitive) set of primers including the F3, B3, FIP and BIP oligonucleotides to obtain a dumb-bell presenting the putative mutated nucleotide in the loop region comprised between B1 and B2. No major differences were detected when performing such experiments on alternative sequences containing the putative mutated nucleotide in the loop region within B2 or between B2 and B1c. We included in the primer set a particular loop primer presenting a 8-bases sequence region at its 5' end complementary to its own sequence at the 3' end. Consequently, this special loop primer forms an intra-molecular hairpin structure which is in equilibrium with its open form at the reaction temperature (65° C.).

When the mutated JAK2 sequence is present in the sample, such modified loop primer breaks its internal structure to hybridize to the complementary target sequence, according to the thermodynamic equilibrium (Tm between primer and specific target=65° C.). The loop primer hybridized to the specific mutated target is then extended by the polymerase and the amplification can further proceed. As additional feature, the loop primer specific for the JAK2 G→T mutation presents a Tm with the wild-type target sequence (59° C.) lower than the intra-molecular hairpin structure (65° C.). Thus, in a sample containing the JAK2 WT sequence, such difference in Tm values results in auto-sequestration of the modified loop primer that prefers to fold in the hairpin structure rather than to form a duplex with the unspecific target, since the intramolecular forces are higher than the intermolecular ones.

To further increase the discrimination capability of the LAMP system based on selective stem-loop primer, we added to the reaction mix a Peptide Nucleic Acid (PNA).

PNAs are non-extensible and not-displaceable oligonucleotides where the ribose-phosphate backbone is replaced by (2-minoethyl)-glycine units linked by amide bonds. Each base pairing DNA/PNA contributes to the stability of the duplex structure more than a regular base pairing DNA/DNA. Therefore a single mismatch in a PNA/DNA duplex results in a significant difference in Tm. A PNA probe fully complementary to the WT sequence of the JAK2 gene prevents the hybridization and extension of the mutant-specific stem-loop primer, suppressing the unspecific amplification of the wild-type sequence. In presence of a single mismatch, the PNA does not inhibit loop primer hybridization, which leads to amplification. Therefore PNA can be used to selectively block the WT sequence present in the sample.

The PNA is designed to be complementary to the loop region comprised between B2 and B1c presenting the wild-type G nucleotide. It forms a stable duplex only with the WT complementary sequence (Tm 65.7° C.), preventing the hybridization and extension of the mutant-specific stem-loop primer and therefore suppressing the amplification of the wild-type sequence. The PNA does not hybridize to the mutated JAK2 sequence because of the lower affinity (Tm=56° C.).

The efficiency of the PNA as a wild-type amplification clamp was assessed by comparing the performance of amplification reactions carried out with and without the PNA on 7e3 cps/ul wild-type and mutant plasmid samples (FIG. 9). Amplification curve analysis revealed that the presence of the PNA leaded to a one-hour delay in the unspecific amplification of the WT plasmid by the mutant-specific stem-loop primer and to 5 minutes delay in the specific amplification of the mutant plasmid. Conversely, in the absence of PNA the non-specific amplification of the WT plasmid by the the mutant-specific stem-loop primer occurred with only 5 minutes delay compared to the specific mutated target sequence. The observed delay in wild-type amplification is explained by the formation of a stable duplex between the PNA and the WT complementary sequence thus preventing the unspecific hybridization and extension of the mutant-specific stem-loop primer.

To determine the selectivity of this LAMP assay format, amplification reactions were performed on serial dilutions of mutant plasmid in wild-type background (FIG. 10). Since the achieved selectivity is less than 0.01% (35 copies tot mutant plasmid in 34965 copies of WT plasmid), the present approach shows higher selectivity than the assays described in the prior art, about 3 Logs higher in respect to direct sequencing, RFLP and pyrosequencing and about 2 Logs in respect to ARMS, Real-Time techniques and DNA-melting curve analysis.

In summary, the present LAMP assay format represents a significant improvement in respect to the strategies previously described in this document and detection methods illustrated in literature: i) the unspecific amplification of the WT sample (350000 cps WT plasmid) is delayed of about one-hour, ii) the specific amplification of the mutant target is detected down to 0.01% mutant sequences in wild-type (35 copies tot mutant plasmid in 349965 copies of WT plasmid) iii) assay selectivity is about 2 Logs higher than the selectivity of other approaches described in literature, iv) assay linearity is down to 0.1% mutant sequences (350 copies tot mutant plasmid in 349650 copies of WT plasmid), thus enabling the detection and quantification of low percentage of mutant alleles in a large excess of wild-type DNA.

Example 5

LAMP "Stem-Loop Primer with PNA" on Clinical Samples: Comparison with ARMs

A total of 29 samples of DNA extracted from patients at Ospedali Riuniti di Bergamo were analyzed using the JAK2 LAMP "stem-loop primer with PNA" strategy, as, described in the EXAMPLE 4. The obtained results were compared with the data obtained at the Hospital using the ARMs technology. The ARMS exploits the fact that oligonucleotide primers must be perfectly annealed at their 3' ends for a DNA polymerase to extend these primers during PCR. By designing oligonucleotide primers that match at the 3' end the specific JAK2 point mutation, ARMS can distinguish between wild-type and mutant alleles.

As shown in Table 5, the LAMP assay detected as positive all the samples previously diagnosed as such by ARMS. Out of 15 samples resulted negative by ARMS, 11 were diagnosed as negative by LAMP and 4 as low positive. To exclude that these 4 discordant samples were false positive in the LAMP assay and to confirm that the mutation diagnosis was due to the higher selectivity of the implemented LAMP method, we tested the discordant samples using a third assay. Such assay was based on the amplification of the JAK2 region of interest by PCR in presence of the PNA molecule complementary to the wild-type target with the purpose to enrich the mutated base, if present, by suppression of the wild-type sequence amplification via PNA clamping. If a 20% sample enrichment of the mutant allele is achieved, the altered sequence can be detected by a direct-sequencing approach. The primers (GA231 forward and GA232 reverse) and the PNA were as previously described (Example 4). The amplification was performed in 1× reaction buffer containing 2.5 mM $MgCl_2$, 200 μM dNTPs, 500 nM forward and reverse primers, 1.5M PNA and 0.025 U Taq Gold in a final volume of 45 μl. A volume of 5 μl target sequence (20 ng/μl) was added to the reaction mix and the solution was incubated in a thermocycler, following a thermal program consisting in 10 min at 95° C. followed by 35 cycles of 30 sec at 94° C., 40 sec at 62° C. cycles, 30 sec at 58° C. and 30 sec at 72° C. and finishing with 10 min at 72° C. for the final extension. The four discordant clinical samples, one no-target control sample and a positive and negative controls containing respectively the mutant and wild-type plasmid target were tested in duplicate. After the reaction, the amplification products were separated on an agarose gel and visualized using EtBr. No amplification was detected for the no-target control; a weak band was visible on the agarose gel for the negative control and a strong band for the positive control. The PCR products of the four clinical samples were subsequently analyzed via automatic-sequencing, all showing a double peak in position 1849 from the ATG initiation codon (GeneBank accession no NM_004972), corresponding respectively to the Guanine (wild-type) base and the Thymine (mutated) base. These results confirmed that the four discordant samples were correctly diagnosed as carrying the G→T base substitution by LAMP, while ARMS detected them as false negative.

TABLE 5

| sample | ARMs | LAMP self-annealed loop primer with PNA |
|---|---|---|
| PIGI | − | + (low) |
| PEVI | − | − |
| ACGI | + | + |
| BEMA | + | + |
| BILU | + | + |
| PAAN | − | + (low) |
| BOMA | − | − |
| OLIN | − | − |
| PALO | + | + |
| BOED | + | + |
| SAGE | + | + |
| BAGI | + | + |
| FEGI | + | + |
| BEAL | + | + |
| TALU | + | + |
| CAPI | + | + |
| SAGI | + | + |
| SAVGI | + | + |
| PECA | + | + |
| SCLU | − | − |
| BILU2 | − | + (low) |
| NAGI | − | − |
| MAST | − | − |
| COSA | − | − |
| GUAL | − | − |
| COCL | − | − |
| PEMG | − | − |
| SABA | − | + (low) |
| ANPI | − | − |

Example 6

Fluorescent JAK2-Modified-LAMP "Stem-Loop Primer Strategy"

Reagents

JAK2 plasmids were synthesized by the supplier GeneArt (Regensburg, Germany) to contain the wild-type or the mutant JAK2 sequence. In details:

JAK2 plasmid which Insert corresponds to the sequence 93249-93731 of SEQ ID NO:2, including a G base at nucleotide 93526, referred to as "wt plasmid";

JAK2 plasmid which Insert corresponds to the sequence 93249-93731 of SEQ ID NO:2, including a T base at nucleotide 93526, referred to as "mut plasmid". Primers: synthesized by Eurofins MWG Operon, referred to as "primers":

GA231 (F3) 5' GCATCTTTATTATGGCAGAGAG 3' (SEQ ID NO:3)

GA232 (B3) 5' TGCTCTGAGAAAGGCATTA 3' (SEQ ID NO:4)

GA233 (FIP) 5' GCTGCTTCAAAGAAAGACTAAG-GAAATGGACAACAGTCAAACAAC 3' (SEQ ID NO:5)

GA234 (BIP) 5'GCTTTCTCACAAGCATTTGGTTT-TAAATTAGCCTGTAGTTTTACTTACTCTC 3' (SEQ ID NO:6)

GA236 (LB) 5'TAMRA-TGTCTCCACTGGAGTATGT<u>T</u>TCTGTGGAGAC 3' (SEQ ID NO:8)

The underlined base corresponds to the mutated nucleotide at position 1849 from the ATG initiation codon of the JAK2 coding sequence (GeneBank accession no NM_004972). The Thymine base in bold at the 5' end has not a complementary base in the target sequence. It has been added to separate the fluorophore from the downstream Guanine base, which has a quenching effect.

GA235 (LF) 5'-5'GTCTCCACTGGAGTATGT<u>G</u>TCTGTGGAGAddC3' (SEQ ID NO:7)

The underlined base corresponds to the wild-type nucleotide in position 1849 from the ATG initiation codon of the JAK2 coding sequence (GeneBank accession no NM_004972); ddC stands for not-extensible dideoxy-citosine.

Reaction buffer: 100 mM Tris-HCl pH 8.8, 50 mM KCl, 40 mM MgSO4, 50 mM (NH4)2SO4, 0.5% Tween, "buffer 5×"

dNTPs mix 25 mM (Fermentas), "dNTPs"

Bst Large Fragment polymerase 8 U/μl (New England Biolabs), "Polymerase"

Sterile apyrogen water (SALF Spa), "ddw"

Procedure

Sample Preparation

Stock the primers in aliquots. It is better to store stock solutions at −20° C., while working dilutions should be stored at 4° C.

Prepare reaction mix as follows: 0.2 μM outer primers (F3 and B3), 1.6 μM inner primers (FIP and BIP), 0.8 μM fluorescent self-annealed loop primer specific for mutant JAK2 (LB), 0.8 μM self annealed not-extensible loop primer for wild-type JAK2 (LF), 1× buffer solution, 1.4 mM dNTPs mix, 8 U Bst Polymerase. Final volume of the reaction mix must be ⅘ of the total reaction volume (i.e. 20 μl reaction mix+5 μl sample). Always keep reagents on ice. Prepare the mix for at least 23 samples, comprising 3 negative controls (100% wild-type plasmid, 7e3 cps/μl), 18 positive control (3 samples 100% mutant plasmid, 3 samples 1% mutant plasmid diluted in WT plasmid, 3 samples 0.5% mutant plasmid diluted in WT plasmid, 3 samples 0.1% mutant plasmid diluted in WT plasmid, 3 samples 0.05% mutant plasmid diluted in WT plasmid, 3 samples 0.01% mutant plasmid diluted in WT plasmid, total amount of DNA 7e3 cps/μl), and one no target control.

TABLE 6

| | sample mix composition | | | | | |
|---|---|---|---|---|---|---|
| Sample tube | 1-3 | 4-6 | 7-9 | 10-12 | 13-15 | 16-19 |
| Target to be add (5 μl) | Wt plasmid 7e3 cps/μl | Mut plasmid 7e3 cps/μl | Mut plasmid 7e1 cps/μl, WT plasmid 6.93e3 cps/μl | Mut plasmid 3.5e1 cps/μl, WT plasmid 6.965e3 cps/μl | Mut plasmid 7e0 cps/μl, WT plasmid 6.993e3 cps/μl | MUT plasmid 3.5e0 cps/μl, WT plasmid 6.996e3 cps/μl |
| GA231 100 μM | 0.05 | 0.05 | 0.05 | 0.05 | 0.05 | 0.05 |
| GA232 100 μM | 0.05 | 0.05 | 0.05 | 0.05 | 0.05 | 0.05 |
| GA233 100 μM | 0.4 | 0.4 | 0.4 | 0.4 | 0.4 | 0.4 |
| GA234 100 μM | 0.4 | 0.4 | 0.4 | 0.4 | 0.4 | 0.4 |
| GA235 100 μM | 0.2 | 0.2 | 0.2 | 0.2 | 0.2 | 0.2 |
| GA236 100 μM | 0.2 | 0.2 | 0.2 | 0.2 | 0.2 | 0.2 |
| Buffer LAMP 10x | 2.5 | 2.5 | 2.5 | 2.5 | 2.5 | 2.5 |
| Bst Polymerase 8 U/μl | 1 | 1 | 1 | 1 | 1 | 1 |
| dNTPs 25 mM | 1.4 | 1.4 | 1.4 | 1.4 | 1.4 | 1.4 |
| Ddw to 20 μl | 13.8 | 13.8 | 13.8 | 13.8 | 13.8 | 13.8 |

Dispense 20 μl of reaction mix in the strip. Keep the strips on ice. Always keep the reaction mix on ice from now on.

Prepare serial dilutions of the target ("target dilutions") from shipped solution (WT plasmid and MUT plasmid). Shipped solution is a $7*10^{10}$ copies/μl. Dilute initially the mutant plasmid to a $7*10^4$ copies/μl in Tris 10 mM, then dilute serially the mutant plasmid in WT plasmid to obtain the following concentrations of mutant sequences in wild-type background: 1%, 0.5%, 0.1%, 0.05%, 0.01% (total amount per tube, 7e3 Cps/μl).

Add 5 μl of target dilutions to the strips, in triplicate. Add 5 μl of the target dilutions starting from the lowest to the highest concentrated sample. Close all the tubes.

Reaction

The reaction follows the method scheme of FIG. 4.

Program the real time instrument for incubation at constant temperature in order to obtain a constant reaction temperature of 65° C. for 1 hour. Program the real time instrument in order to obtain a fluorescence reading per minute.

Put the strips in the instrument immediately before the beginning of the programs. Start the program.

Data Analysis

The fluorescent self-annealed loop primer in reaction produces a fluorescent signal once it is excited by an appropriated wavelength-light emission. When the LAMP reaction proceeds, the fluorescent self-annealed loop primer hybridizes to the complementary target sequence being consequently incorporated in the amplification products. The fluorescent self-annealed loop primer is designed to be complementary to a sequence containing at least one Guanine nucleotide close to the 5' end. The Guanine base can absorb the wavelength emitted by the fluorophore (TAMRA in our case), causing the quenching of the fluorescent signal. In this case the detection of target sequence amplification during the LAMP reaction is based on measuring the decrease of fluorescence signal in order to find a threshold time for each sample under analysis. The threshold time is the minute at which the reaction fluorescence signal reaches 50% of quenching. For each sample, the threshold time is correlated with the Log of DNA copies/μl.

Results

The present approach consists in the selective amplification of a mutant sequence based on a particular loop primer design resulting in selective hybridization of such loop primer to the dumb-bell formed from the mutant sequence (FIG. 4). We designed a universal (mutant insensitive) set of primers including the F3, B3, FIP and BIP oligonucleotides to obtain a dumb-bell structure presenting the putative mutation in the loop region comprised between B1 and B2. No major differences were detected when performing such experiments on alternative sequences containing the putative mutated nucleotide in the loop region within B2 or between B2 and B1c. We included in the primer set a particular loop primer presenting a 8-bases sequence region at its 5' end complementary to its own sequence at the 3' end. Consequently, this special loop primer forms an intra-molecular hairpin structure which is in equilibrium with its open form at the reaction temperature (65° C.).

When the mutated JAK2 sequence is present in the sample, such modified loop primer breaks its internal structure to hybridize to the complementary target sequence, according to the thermodynamic equilibrium (Tm between primer and specific target=65° C.). The loop primer hybridized to the specific mutated target is then extended by the polymerase and the amplification can further proceed. As additional feature, the loop primer specific for the JAK2 G→T mutation presents a Tm with the wild-type target sequence (59° C.) lower than the intra-molecular hairpin structure (65° C.). Thus, in a sample containing the JAK2 WT sequence, such difference in Tm values results in auto-sequestration of the mutant-specific stem-loop primer that prefers to fold in the hairpin structure rather than to form a duplex with the unspecific target, since the intramolecular forces are higher than the intermolecular ones.

To limit the competition of this loop primer for the wild-type sequences likely to be present in large excess in the clinical sample, we included in the reaction set-up a second loop primer with analogous structure and containing a nucleotide sequence complementary to the JAK2 wild-type sequence, i.e. with G base at position 1849 from the start codon (GeneBank accession no NM_004972).

The 3' end of this "competitor" loop primer is made not extensible by a modification (3' dideoxy). The task of this competitor is to "silence" the wild-type sequence thus enabling the specific mutant primer to find its target.

When the "competitor" primer recognizes the specific wild-type sequence, it breaks its intramolecular structure to hybridize to the WT target, according to the higher affinity (Tm of the duplex formed by the WT target and the WT-specific stem-loop primer=67° C.). The stem-loop primer hybridized to the WT target is not extensible, resulting in no amplification of the wild-type sequences. Since the reaction is conducted at constant temperature, the WT-specific stem-loop primer stays attached to the wild-type allelic sequences thus preventing the unspecific hybridization of the MUT loop primer. In contrast to the mutant-specific stem-loop primer, the "competitor" primer presents a Tm with the mutant target sequence (62° C.) lower than the intra-molecular hairpin structure formed with itself (65° C.). Thus the higher intramolecular forces compared to the intermolecular ones cause the auto-sequestration of the modified loop primer that prefers to fold in the hairpin structure rather than to form a duplex with the mutant target sequence.

To follow the reaction on a real-time instrument, we labeled the 5' end of the mutant-specific stem-loop primer with a FAM dye. To avoid the binding of the fluorophore to the Guanine base present at the 5' end of the modified loop primer, which has a quenching effect, we added a Thymine base to the extremity of the oligonucleotide. The modified-labeled primer, when present in solution, emits a fluorescent signal if excited at the appropriate wavelength light. When the LAMP reaction starts and proceeds, the fluorescent stem-loop primer is incorporated in the amplification products. The Guanine bases present in the complementary nucleotide sequence can absorb the wavelength emitted by the fluorophore, causing a detectable quenching of the fluorescent signal in real-time. Therefore, the accumulation of amplification products can be monitored throughout the LAMP reaction by measuring the decrease in fluorescence signal caused by this "quenching effect".

Example 7

Control LAMP Reaction

Reagents

JAK2 plasmids were synthesized by the supplier GeneArt (Regensburg, Germany) to contain the wild-type or the mutant JAK2 sequence. In details:

JAK2 plasmid which Insert corresponds to the sequence 93249-93731 of SEQ ID NO:2, including a G base at nucleotide 93526, referred to as "wt plasmid";

JAK2 plasmid which Insert corresponds to the sequence 93249-93731 of SEQ ID NO:2, including a T base at nucleotide 93526, referred to as "mut plasmid". Primers: synthesized by Eurofins MWG Operon, referred to as "primers":

GA231 (F3) 5' GCATCTTTATTATGGCAGAGAG 3' (SEQ ID NO:3)

GA232 (B3) 5' TGCTCTGAGAAAGGCATTA 3'(SEQ ID NO:4)

GA233 (FIP) 5' GCTGCTTCAAAGAAAGACTAAG-GAAATGGACAACAGTCAAACAAC 3' (SEQ ID NO:5)

GA234 (BIP) 5'GCTTTCTCACAAGCATTTGGTTT-TAAATTAGCCTGTAGTTTTACTTACTCTC 3' (SEQ ID NO:6)

Reaction buffer: 100 mM Tris-HCl pH 8.8, 50 mM KCl, 40 mM MgSO4, 50 mM (NH4)2SO4, 0.5% Tween, "buffer 5×"

dNTPs mix 25 mM (Fermentas), "dNTPs"

Bst Large Fragment polymerase 8 U/µl (New England Biolabs), "Polymerase"

Sterile apyrogen water (SALF Spa), "ddw"

Procedure

Sample Preparation

Stock the primers in aliquots. It is better to store stock solutions at −20° C., while working dilutions should be stored at 4° C.

Prepare reaction mix as follows: 0.2 µM outer primers (F3 and B3), 1.6 µM inner primers (FIP and BIP), 1× buffer solution, 1.4 mM dNTPs mix, 8 U Bst Polymerase. Final volume of the reaction mix must be ⅘ of the total reaction volume (i.e. 20 µl reaction mix+5 µl sample). Always keep reagents on ice. Prepare the mix for at least 23 samples, comprising 3 negative controls (100% wild-type plasmid, 7e3 cps/µl), 9 positive control (3 samples 100% mutant plasmid, 3 samples 10% mutant plasmid diluted in WT plasmid, 3 samples 1% mutant plasmid diluted in WT Plasmid) and One No Target control.

TABLE 7 sample mix composition

| Sample tube | 1-3 | 4-6 | 7-9 | 10-12 |
|---|---|---|---|---|
| Target to be added (5 µl) | WT plasmid 7e3 cps/µl | MUT plasmid 7e3 cps/µl | MUT plasmid 7e2 cps/µl, WT plasmid 6.3e2 cps/µl | MUT plasmid 7e1 cps/µl, WT plasmid 6.93e2 cps/µl |
| GA231 100 µM | 0.05 | 0.05 | 0.05 | 0.05 |
| GA232 100 µM | 0.05 | 0.05 | 0.05 | 0.05 |
| GA233 100 µM | 0.4 | 0.4 | 0.4 | 0.4 |
| GA234 100 µM | 0.4 | 0.4 | 0.4 | 0.4 |
| Buffer LAMP 10x | 2.5 | 2.5 | 2.5 | 2.5 |
| Bst Polymerase 8 U/µl | 1 | 1 | 1 | 1 |
| dNTPs 25 mM | 1.4 | 1.4 | 1.4 | 1.4 |
| Ddw to 20 µl | 13.8 | 13.8 | 13.8 | 13.8 |

Dispense 20 µl of reaction mix in the strip. Keep the strips on ice. Always keep the reaction mix on ice from now on.

Prepare serial dilutions of the target ("target dilutions") from shipped solution (WT plasmid and MUT plasmid). Shipped solution is a $7*10^{10}$ copies/µl. Dilute initially the mutant plasmid to a $7*10^4$ copies/µl in Tris 10 mM, then dilute serially the mutant plasmid in WT plasmid to obtain the following concentrations of mutant sequences in wild-type background: 10%, 1% (total amount per tube, 7e3 cps/µl).

Add 5 µl of target dilutions to the strips, in triplicate. Add 5 µl of the target dilutions starting from the lowest to the highest concentrated sample. Close all the tubes.

Reaction

The reaction follows the method scheme of FIG. 11.

Program the turbidimeter (Teramecs) for incubation at constant temperature and real time monitoring of turbidity in order to obtain a constant reaction temperature of 65° C. for 1 hour.

Put the strips in the instrument immediately before the beginning of the programs. Start the program.

Data Analysis

Analyze the variation of absorbance in terms of a.u. to find the threshold time for each sample analyzed. The threshold time is the minute at which the sample absorbance, after baseline subtraction, reaches the arbitrary unit value representing the threshold (in this case 0.1 a.u.). The threshold time reached by each samples is correlated with its Log of DNA copies/µl.

Results

The present approach consists in a mutant-insensitive amplification of the JAK2 gene sequence by using the F3, B3, FIP and BIP primers (FIG. 11). We employed the same primer set described in the "EXAMPLE 4", excluding the PNA and the mutant-specific stem-loop primer from the reaction mixture. The detection of target sequence amplification in the "LAMP control assay" is indicative of different quality parameters such as the correct base matching of primers to template, the efficient extension conditions and the absence of inhibitors in the reaction solution. Conversely, the absence or delay of nucleic acid sample amplification in the "LAMP control assay" highlights problems in the reaction set-up (i.e. buffer composition, temperature, primers quality, . . . ) or the presence of an inhibitor in the reaction mixture.

To evaluate such assay control method, a clinical sample panel was analyzed in duplicate using both the LAMP assay specific for detecting the G→T mutation (EXAMPLE 4) and the "LAMP control assay". When the target nucleic acid sequence is amplified in both assays, a validated result is obtained and the sample is considered bearing the V617F mutation. When the target nucleic acid sequence is amplified by the "LAMP control assay" and not by the "JAK2-modified-LAMP Stem-loop primer strategy with PNA", again a validated result is obtained and the sample is diagnosed as a wild-type JAK2 sample. In the case of no target sequence amplification in the "LAMP control assay", the analysis is to be considered not valid.

The evaluation of the "LAMP control assay" was performed on DNA plasmid samples containing respectively 7 e3 cps/µl wild-type and mutant plasmid and on samples containing 10% and 1% mutant plasmid in wild-type background, 35000 total copies (FIG. 12). All tested nucleic acid samples showed comparable amplification efficiency thus indicating the absence of reaction inhibitors.

Example 8

Estimation of the Amount of Mutant JAK2 Sequences in a Sample Using the "LAMP Stem-Loop Primer with PNA" Assay Reagents JAK2 plasmids were synthesized by the supplier GeneArt (Regensburg, Germany) to contain the wild-type or the mutant JAK2 sequence. In details:

JAK2 plasmid which Insert corresponds to the sequence 93249-93731 of SEQ ID NO:2, including a G base at nucleotide 93526, referred to as "wt plasmid";

JAK2 plasmid which Insert corresponds to the sequence 93249-93731 of SEQ ID NO:2, including a T base at nucleotide 93526, referred to as "mut plasmid".

Primers: synthesized by Eurofins MWG Operon, referred to as "primers":

GA231 (F3) 5' GCATCTTTATTATGGCAGAGAG 3' (SEQ ID NO:3)

GA232 (B3) 5' TGCTCTGAGAAAGGCATTA 3' (SEQ ID NO:4)

GA233 (FIP) 5' GCTGCTTCAAAGAAAGACTAAG-GAAATGGACAACAGTCAAACAAC 3' (SEQ ID NO:5)

GA234 (BIP) 5'GCTTTCTCACAAGCATTTGGTTT-TAAATTAGCCTGTAGTTTTACTTACTCTC 3' (SEQ ID NO:6)

GA236 (LB) 5' GTCTCCACTGGAGTATGT T̲TCTGTGGAGAC 3' (SEQ ID NO:8)

The underlined base corresponds to the mutated nucleotide at position 1849 from the ATG initiation codon in JAK2 coding sequence (GeneBank accession no NM_004972).

PNA: Eurogentec, referred to as "PNA" GM43 $^{NH2}$GAGTATG T̲GTCTGTGGA$^{COOH}$ (SEQ ID NO:9)

The underlined base corresponds to the wild-type nucleotide at position 1849 from the ATG initiation codon in the JAK2 coding sequence (GeneBank accession no NM_004972).

Reaction buffer: 100 mM Tris-HCl pH 8.8, 50 mM KCl, 40 mM MgSO4, 50 mM (NH4)2SO4, 0.5% Tween, "buffer 5×"

dNTPs mix 25 mM (Fermentas), "dNTPs"

Bst Large Fragment polymerase 8 U/µl (New England Biolabs), "Polymerase"

Sterile apyrogen water (SALF Spa), "ddw"

Procedure

Sample Preparation

Stock the primers in aliquots. It is better to store stock solutions at −20° C., while working dilutions should be stored at 4° C.

Prepare reaction mix as follows: 0.2 µM outer primers (F3 and B3), 1.6 µM inner primers (FIP and BIP), 0.8 uM self-annealed loop primer specific for mutant JAK2 (LB), 0.8 uM PNA, 1× buffer solution, 1.4 mM dNTPs mix, 8 U Bst Polymerase. Final volume of the reaction mix must be 4/5 of the total reaction volume (i.e. 20 μl reaction mix+5 μl sample). Always keep reagents on ice. Prepare the mix for at least 23 samples, including 3 negative controls (100% wild-type plasmid, 7e3 cps/μl), 9 positive calibrator controls (3 samples 100% mutant plasmid, 3 samples 10% mutant plasmid diluted in WT plasmid, 3 samples 1% mutant plasmid diluted in WT plasmid) and one no target control.

TABLE 8 sample mix composition

| Sample tube | 1-3 | 4-6 | 7-9 | 10-12 |
|---|---|---|---|---|
| Target to be added (5 μl) | WT plasmid 7e3 cps/μl | MUT plasmid 7e3 cps/μl | MUT plasmid 7e2cps/μl WT plasmid 6.3e3 cps/μl | MUT plasmid 7e1 cps/μl, WT plasmid 6.93e3 cps/μl |
| GA231 100 μM | 0.05 | 0.05 | 0.05 | 0.05 |
| GA232 100 μM | 0.05 | 0.05 | 0.05 | 0.05 |
| GA233 100 μM | 0.4 | 0.4 | 0.4 | 0.4 |
| GA234 100 μM | 0.4 | 0.4 | 0.4 | 0.4 |
| PNA 100 μM | 0.2 | 0.2 | 0.2 | 0.2 |
| GA236 100 μM | 0.2 | 0.2 | 0.2 | 0.2 |
| Buffer LAMP 10x | 2.5 | 2.5 | 2.5 | 2.5 |
| Bst Polymerase 8 U/μl | 1 | 1 | 1 | 1 |
| dNTPs 25 mM | 1.4 | 1.4 | 1.4 | 1.4 |
| Ddw to 20 μl | 13.8 | 13.8 | 13.8 | 13.8 |

Dispense 20 μl of reaction mix in the strip. Keep the strips on ice. Always keep the reaction mix on ice from now on.

Prepare serial dilutions of the target ("target dilutions") from shipped solution (WT plasmid and MUT plasmid). Shipped solution is a $7*10^{10}$ copies/μl. Dilute initially the mutant plasmid to a $7*10^4$ copies/μl in Tris 10 mM, then dilute serially the mutant plasmid in WT plasmid to obtain the following concentrations of mutant sequences in wild-type background: 10%, 1% (total amount per tube, 7e3 cps/μl).

Add 5 μl of target dilutions to the strips, in triplicate. Add 5 μl of the target dilutions starting from the less concentrated to the highest concentrated sample. Close all the tubes.

Reaction

The reaction follows the method scheme of FIG. 5.

Program the turbidimeter (Teramecs) for incubation at constant temperature and real time monitoring of turbidity in order to obtain a constant reaction temperature of 65° C. for 1 hour.

Put the strips in the instrument immediately before the beginning of the programs. Start the program.

Data Analysis

Analyze the variation of absorbance in terms of a.u. to find the threshold time for each sample analyzed. The threshold time is the minute at which the sample absorbance, after baseline subtraction, reaches the arbitrary unit value representing the threshold (in this case 0.1 a.u.). The threshold time reached by each samples is correlated with its Log of DNA copies/μl.

Results

A subset of patients are homozygous for the JAK2 V617F allele[1]. The mechanism of homozygosity results from mitotic recombination and duplication of the mutant allele, known as acquired uniparental disomy[1]. The heterozygosity or homozygosity of the JAK2 mutant allele is correlated with the prognosis, thus resulting in the importance of determining whether the amount of JAK2 mutant allelic copies in the sample is higher or lower than 50%.

According to the present approach, the unknown samples are analyzed as undiluted and 1:5 diluted using the "LAMP stem-loop primer with PNA" assay previously described in EXAMPLE 4. In addition, the assay set-up includes three calibrator samples containing respectively 100%, 10% and 1% mutant JAK2 plasmid copies in wild-type background. If the amount of mutant JAK2 target sequence in the nucleic acid sample is higher than 50%, real-time amplification of said target sequence is detected at a time between the amplification threshold minutes of the 100% calibrator and the 10% calibrator both in case of undiluted samples (FIG. 13, Panel A) and samples diluted 1:5 (FIG. 13, Panel B). A different amplification performance is detected for nucleic acid samples containing less than 50% mutant JAK2 sequence amount since target amplicons in the undiluted samples are detected earlier than in the calibrator 10% (FIG. 13, Panel A) while the amplification threshold minute in the corresponding samples 1:5 diluted is measured at a time between the min(t) of the calibrator 10% and the min(t) of calibrator 1% (FIG. 13, Panel B).

The present approach was tested by performing the "LAMP stem-loop primer with PNA" reaction on control samples (7 e3 cps/μl wild-type plasmid, 7 e2 cps/μl mutant plasmid in 6.3e3 cps/μl wild-type plasmid, 7 e1 cps/μl mutant plasmid in 6.93e3 cps/μl wild-type plasmid), on four samples consisting in mixtures of mutant JAK2 plasmid in wild-type background in proportions higher than 50% (respectively 60%, 70%, 80%, 90%) and on four samples consisting in mixtures of mutant JAK2 plasmid in wild-type background in proportion of 50% or less than 50% (respectively 40%, 30%, 20%). Except for the controls, all the samples were analyzed as undiluted (5 μl of the 7e3 cps/μl for each reaction) and diluted 1:5 in Tris-HCl 10 mM.

For the test samples containing more than 50% mutant JAK2 allelic copies and diluted 1:5, the target sequence amplification was detected after the amplification of the corresponding sequence in the 100% calibrator and before 10% calibrator (FIG. 14). For the test samples presenting 50% amount of mutant JAK2 allelic copies and diluted 1:5, the target sequence amplification was registered at the same threshold minute as for the 10% calibrator sample (FIG. 15).

For the test samples containing less than 50% mutant JAK2 allelic copies and diluted 1:5, the target sequence amplification was detected at an intermediate threshold minute between the amplification time of calibrators 10% and 1% (FIG. 15).

Therefore, using the present approach it is possible to estimate whether the amount of JAK2 mutant allelic copies in a nucleic acid sample is higher or lower than 50%. Such an information is clinically very relevant since it provides indication about the "heterozygosity or homozygosity" in a sample which in turn is correlated to the disease prognosis.

REFERENCES

1. Levine, R. L. et al. Activating mutation in the tyrosine kinase JAK2 in polycythemia vera, essential thrombocythemia, and myeloid metaplasia with myelofibrosis. *Cancer Cell* 7, 387-397 (2005).
2. James, C. et al. A unique clonal JAK2 mutation leading to constitutive signalling causes polycythaemia vera. *Nature* 434, 1144-1148 (2005).
3. Baxter, E. J. et al. Acquired mutation of the tyrosine kinase JAK2 in human myeloproliferative disorders. *Lancet* 365, 1054-1061 (2005).
4. Kralovics, R. et al. A gain of function mutation of JAK2 in myeloproliferative disorders. N. Engl. J. Med. 352, 1779-1790 (2005).

5. Nelson M E, Steensma DP: JAK2 V617F in myeloid disorders: what do we know now, and where are we headed? Leuk Lymphoma 2006, 47:177-194
6. James C, Ugo V, Le Couedic J-P, Staerk J, Delhommeau F, Lacout C, Garcon L, Raslova H, Berger R, Bennaceur-Griscelli A, Villeval J L, Constantinescu S N, Casadevall N, Vainchenker W: A unique clonal JAK2 mutation leading to constitutive signalling causes polycythaemia vera. Nature 2005, 434:1144-1148
7. De Keersmaecker K, Cools J: Chronic myeloproliferative disorders: a tyrosine kinase tale: Leukemia 2005, 20:200-205
8. Kaushansky K: On the molecular origins of the chronic myeloproliferative disorders: it all makes sense. Blood 2005, 105:4187-4190
9. Baxter E J, Scott L M, Campbell P J, East C, Fourouclas N, Swanton S, Vassiliou G S, Bench A J, Boyd E M, Curtin N, Scott M A, Erber W N, Green A R: Acquired mutation of the tyrosine kinase JAK2 in human myeloproliferative disorders. The Lancet 2005, 365:1054-1061
10. Smith T A, Whelan J, Parry P J: Detection of single-base mutations in a mixed population of cells: a comparison of SSCP and direct sequencing. Genet Anal Tech Appl 1992, 9:143-145
11. James C, Delhommeau F, Marzac C, Teyssandier I, Couedic J P, Giraudier S, Roy L, Saulnier P, Lacroix L, Maury S, Tulliez M, Vainchenker W, Ugo V, Casadevall N: Detection of JAK2 V617F as a irst intention diagnostic test for erythrocytosis. Leukemia 2006, 20:350-353
12. Newton C R, Graham A, Heptinstall L E, Powell S J, Summers C, Kalsheker N, Smith J C, Markham A F: Analysis of any point mutation in DNA: the amplification refractory mutation system (ARMS). Nucleic Acids Res 1989, 17:2503-2516
13. Jones A V, Kreil S, Zoi K, Waghorn K, Curtis C, Zhang L, Score J, Seear R, Chase A J, Grand F H, White H, Zoi C, Loukopoulos D, Terpos E, Vervessou E C, Schultheis B, Emig M, Ernst T, Lengfelder E, Hehlmann R, Hochhaus A, Oscier D, Silver R T, Reiter A, Cross N C: Widespread occurrence of the JAK2 V617F mutation in chronic myeloproliferative disorders. Blood 2005, 106:2162-2168
14. James C, Delhommeau F, Marzac C, Teyssandier I, Couedic J P, Giraudier S, Roy L, Saulnier P, Lacroix L, Maury S, Tulliez M, Vainchenker W, Ugo V, Casadevall N: Detection of JAK2 V617F as a first intention diagnostic test for erythrocytosis. Leukemia 2006, 20:350-353
15. Baxter E J, Scott L M, Campbell P J, East C, Fourouclas N, Swanton S, Vassiliou G S, Bench A J, Boyd E M, Curtin N, Scott M A, Erber W N, Green A R: Acquired mutation of the tyrosine kinase JAK2 in human myeloproliferative disorders. The Lancet 2005, 365:1054-1061
16. Antonioli E, Guglielmelli P, Pancrazzi A, Bogani C, Verrucci M, Ponziani V, Longo G, Bosi A, Vannucchi A M: Clinical implications of the JAK2 V617F mutation in essential thrombocythemia. Leukemia 2005, 19:1847-1849
17. Jelinek J, Oki Y, Gharibyan V, Bueso-Ramos C, Prchal J T, Verstovsek S, Beran M, Estey E, Kantarjian H M, Issa J P: JAK2 mutation 1849G_T is rare in acute leukemias but can be found in CMML, Philadelphia chromosome-negative CML, and megakaryocytic leukemia. Blood 2005, 106: 3370-3373
18. Jones A V: Widespread occurence of the JAK2 V617F mutation in chronic myeloproliferative disorders. Blood 2005, 106: 2162-2168.
19. Steensma D: JAK2 V617F in myeloid disorders: molecular diagnostic techniques and their clinical utility. Journal of Molecular Diagnostics 2006, 8:397-411.
20. Iwasaki M. et al. Genome Letters 2003, 2:119-126.
21. Fukuta S. et al. J Appl Genet 2006, 47:303-308.
22. Ikeda S. et al. Pathol. Intern. 2007, 57: 594-599.

The invention claimed is:

1. A set of primers for detecting, by loop mediated isothermal amplification, the presence of a point mutation in a target nucleic acid molecule in a background of wild type nucleic acid molecules, the set of primers comprising:
  i. a first outer primer F3 and a second outer primer B3;
  ii. a first inner primer FIP and a second inner primer BIP, wherein FIP comprises a 3' nucleic acid sequence F2 and a 5' nucleic acid sequence F1c and BIP comprises a 3' nucleic acid sequence B2 and a 5' nucleic acid sequence B1c, wherein F1c is able to recognize and hybridize to a region of the target nucleic acid molecule designated as F1 and wherein B1c is able to recognize and hybridize to a region of the target nucleic acid molecule designated as B1, and wherein F1 and B1 are different regions located on opposite strands of the target nucleic acid molecule,
  wherein F2 is complementary to a region of the target nucleic acid molecule designated as F2c and B2 is complementary to a region of the target nucleic acid molecule designated as B2c, wherein F2c and B2c are non-overlapping regions located on opposite strands of the target nucleic acid molecule,
  wherein either B2c is downstream of the point mutation or F2c is upstream of the point mutation, and wherein
  if B2c is downstream of the point mutation, then said point mutation is located in the F2c sequence or between the F2c sequence and the F1c sequence, or
  if F2c is upstream of the point mutation, then said point mutation is located in the B2c sequence or between the B2c sequence and the B1c sequence;
    iii. a stem-loop mutant extensible primer comprising:
      a central loop sequence complementary to a region of a target nucleic acid molecule comprising the point mutation, and
      a 5' end sequence and a 3' end sequence which are complementary to each other such as to form a stem upon intramolecular hybridization,
    the hybridization affinity of the central loop sequence to the region of the target nucleic acid molecule comprising the point mutation being higher than the intramolecular hybridization affinity of the 5' sequence to the 3' sequence, and
    a non-extensible moiety capable of selectively hybridizing to the wild type nucleic acid molecules and of blocking amplification thereof.

2. The set of primers of claim 1, wherein each of the 5' end sequence and the 3' end sequence of the stem-loop mutant extensible primer is at least 3 nucleotides in length.

3. The set of primers of claim 1, further comprising a non extensible moiety capable of hybridizing to the wild type nucleic acid molecules.

4. The set of primers of claim 3, wherein the non extensible moiety is a Peptide Nucleic Acid (PNA).

5. The set of primers of claim 4, wherein the PNA is at least 10 bases in length.

6. The set of primers of claim 1, wherein the nonextensible moiety is a stem-loop 3' end modified wild type non-extensible primer, comprising:
  a central loop sequence complementary to a region of the wild type nucleic acid molecules comprising the nucleic acid position of the point mutation to be detected;
  a 5' end sequence and a 3' end sequence which are complementary to each other such as to form a stem upon intramolecular hybridization,
the hybridization affinity of the central loop sequence to the region of the wild type nucleic acid molecules comprising the nucleic acid position of the point mutation to be detected being higher than the intramolecular hybridization affinity of the 5' end sequence to the 3' end sequence.

7. The set of primers of claim 1, wherein the first outer primer F3 comprises SEQ ID NO:3, the second outer primer B3 comprises SEQ ID NO:4, the first inner primer FIP comprises SEQ ID NO:5, the second inner primer BIP comprises SEQ ID NO:6 and the stem-loop mutant extensible primer comprises SEQ ID NO:8.

8. The set of primers of claim 7, further comprising a non extensible moiety which is a PNA comprising the following base sequence:

```
                                               (SEQ ID NO: 9)
NH2-GAGTATGTGTCTGTGGA-COOH.
```

9. A kit for detecting, by loop mediated isothermal amplification, the presence of a point mutation in a target nucleic acid molecule, the kit comprising the set of primers of claim 1 and a DNA polymerase having strand displacement activity.

10. The kit of claim 9, wherein the DNA polymerase is selected from the group consisting of Bst large fragment polymerase, Bca (exo-), Vent, Vent (exo-), Deep Vent, Deep Vent (exo-), (I)29 phage, MS-2 phage, Z-Taq, KOD, Klenow fragment and any combination thereof.

11. The kit of claim 9, further comprising one or more calibrators, wherein said one or more calibrators comprise a predetermined percentage of wild type nucleic acid molecules.

* * * * *

```
                         SEQUENCE LISTING

<160> NUMBER OF SEQ ID NOS: 20

<210> SEQ ID NO 1
<211> LENGTH: 5285
<212> TYPE: DNA
<213> ORGANISM: Homo sapiens

<400> SEQUENCE: 1
ctgcaggaag gagagaggaa gaggagcaga aggggggcagc agcggacgcc gctaacggcc        60
tccctcggcg ctgacaggct gggccggcgc ccggctcgct tgggtgttcg cgtcgccact       120
tcggcttctc ggccggtcgg gccccctcggc ccgggcttgc ggcgcgcgtc ggggctgagg       180
gctgctgcgg cgcagggaga ggcctggtcc tcgctgccga gggatgtgag tgggagctga       240
gcccacactg gagggcccccc gagggcccag cctgagggtc gttcagagcc gtgcccgtcc       300
cggggcttcg cagaccttga cccgccgggt aggagccgcc cctgcgggct cgaggcgcg        360 ctctggtcgc ccgatctgtg tagccggttt cagaagcagg caacaggaac aagatgtgaa       420
ctgtttctct tctgcagaaa aagaggctct tcctcctcct cccgcgacgg caaatgttct       480 gaaaagact ctgcatggga atggcctgcc ttacgatgac agaaatggag ggaacatcca        540
cctcttctat atatcagaat ggtgatattt ctggaaatgc caattctatg aagcaaatag       600
atccagttct tcaggtgtat ctttaccatt cccttgggaa atctgaggca gattatctga       660
cctttccatc tgggagtat gttgcagaag aaatctgtat tgctgcttct aaagcttgtg        720
```

```
gtatcacacc tgtgtatcat aatatgtttg ctttaatgag tgaaacagaa aggatctggt      780
atccacccaa ccatgtcttc catatagatg agtcaaccag gcataatgta ctctacagaa      840
taagatttta ctttcctcgt tggtattgca gtggcagcaa cagagcctat cggcatggaa      900
tatctcgagg tgctgaagct cctcttcttg atgactttgt catgtcttac ctctttgctc      960
agtggcggca tgattttgtg cacggatgga taaaagtacc tgtgactcat gaaacacagg     1020
aagaatgtct tgggatggca gtgttagata tgatgagaat agccaaagaa acgatcaaa      1080 ccccactggc catctataac tctatcagct acaagacatt cttaccaaaa tgtattcgag     1140
caaagatcca agactatcat attttgacaa ggaagcgaat aaggtacaga tttcgcagat     1200
ttattcagca attcagccaa tgcaaagcca ctgccagaaa cttgaaactt aagtatctta     1260
taaatctgga aactctgcag tctgccttct cacagagaaa atttgaagta aaagaacctg     1320
gaagtggtcc ttcaggtgag gagattttg caaccattat aataactgga aacggtggaa      1380
ttcagtggtc aagagggaaa cataaagaaa gtgagacact gacagaacag gatttacagt     1440
tatattgcga ttttcctaat attattgatg tcagtattaa gcaagcaaac caagagggtt     1500
caaatgaaag ccgagttgta actatccata agcaagatgg taaaaatctg gaaattgaac     1560
ttagctcatt aagggaagct ttgtctttcg tgtcattaat tgatggatat tatagattaa     1620
ctgcagatgc acatcattac ctctgtaaag aagtagcacc tccagccgtg cttgaaaata     1680
tacaaagcaa ctgtcatggc ccaatttcga tggattttgc cattagtaaa ctgaagaaag     1740
caggtaatca gactggactg tatgtacttc gatgcagtcc taaggacttt aataaatatt     1800
ttttgacttt tgctgtcgag cgagaaaatg tcattgaata taaacactgt ttgattacaa     1860
aaaatgagaa tgaagagtac aacctcagtg ggacaaagaa gaacttcagc agtcttaaag     1920
atcttttgaa ttgttaccag atggaaactg ttcgctcaga caatataatt ttccagttta     1980
ctaaatgctg tcccccaaag ccaaaagata atcaaaccct tctagtcttc agaacgaatg     2040
gtgtttctga tgtaccaacc tcaccaacat tacagaggcc tactcatatg aaccaaatgg     2100
tgtttcacaa aatcagaaat gaagatttga tatttaatga aagccttggc caaggcactt     2160
ttacaaagat ttttaaaggc gtacgaagag aagtaggaga ctacggtcaa ctgcatgaaa     2220
cagaagttct tttaaaagtt ctggataaag cacacagaaa ctattcagag tcttttctttg     2280 aagcagcaag tatgatgagc aagctttctc acaagcattt ggttttaaat tatgagtat      2340 gtgtctgtgg agacgagaat attctggttc aggagtttgt aaaatttgga tcactagata     2400
catatctgaa aaagaataaa aattgtataa atatattatg gaaacttgaa gttgctaaac     2460
agttggcatg ggccatgcat tttctagaag aaaacaccct tattcatggg aatgtatgtg     2520
ccaaaaatat tctgcttatc agagaagaag acaggaagac aggaaatcct cctttcatca     2580
aacttagtga tcctggcatt agtattacag ttttgccaaa ggacattctt caggagagaa     2640
taccatgggt accacctgaa tgcattgaaa atcctaaaaa tttaaatttg gcaacagaca     2700
aatggagttt tggtaccact ttgtgggaaa tctgcagtgg aggagataaa cctctaagtg     2760
ctctggattc tcaaagaaag ctacaatttt atgaagatag gcatcagctt cctgcaccaa     2820
agtgggcaga attagcaaac cttataaata attgtatgga ttatgaacca gatttcaggc     2880 cttcttttcag agccatcata cgagatctta acagtttgtt tactccagat tatgaactat     2940
taacagaaaa tgcatgttta ccaaatatga ggataggtgc cctggggttt tctggtgcct     3000
ttgaagaccg ggatcctaca cagtttgaag agagacattt gaaatttcta cagcaacttg     3060
gcaagggtaa ttttgggagt gtggagatgt gccggtatga ccctctacag gacaacactg     3120
```

```
gggaggtggt cgctgtaaaa aagcttcagc atagtactga agagcaccta agagactttg    3180
aaagggaaat tgaaatcctg aaatccctac agcatgacaa cattgtaaag tacaagggag    3240
tgtgctacag tgctggtcgg cgtaatctaa aattaattat ggaatattta ccatatggaa    3300
gtttacgaga ctatcttcaa aaacataaag aacggataga tcacataaaa cttctgcagt    3360
acacatctca gatatgcaag ggtatggagt atcttggtac aaaaaggtat atccacaggg    3420
atctggcaac gagaaatata ttggtggaga acgagaacag agttaaaatt ggagattttg    3480
ggttaaccaa agtcttgcca caagacaaag aatactataa agtaaaagaa cctggtgaaa    3540
gtcccatatt ctggtatgct ccagaatcac tgacagagag caagtttct gtggcctcag     3600 atgtttggag ctttggagtg gttctgtatg aacttttcac atacattgag aagagtaaaa    3660
gtccaccagc ggaatttatg cgtatgattg gcaatgacaa acaaggacag atgatcgtgt    3720
tccatttgat agaacttttg aagaataatg gaagattacc aagaccagat ggatgcccag    3780
atgagatcta tatgatcatg acagaatgct ggaacaataa tgtaaatcaa cgcccctcct    3840
ttagggatct agctcttcga gtggatcaaa taagggataa catggctgga tgaaagaaat    3900
gaccttcatt ctgagaccaa agtagattta cagaacaaag ttttatattt cacattgctg    3960
tggactatta ttacatatat cattattata taaatcatga tgctagccag caaagatgtg    4020
aaaatatctg ctcaaaactt tcaaagttta gtaagttttt cttcatgagg ccaccagtaa    4080
aagacattaa tgagaattcc ttagcaagga ttttgtaaga agtttcttaa acattgtcag    4140
ttaacatcac tcttgtctgg caaaagaaaa aaaatagact ttttcaactc agcttttga    4200 gacctgaaaa aattattatg taaattttgc aatgttaaag atgcacagaa tatgtatgta    4260 tagttttac cacagtggat gtataatacc ttggcatctt gtgtgatgtt ttacacacat     4320
gagggctggt gttcattaat actgttttct aattttttcca tagttaatct ataattaatt   4380
acttcactat acaaacaaat taagatgttc agataattga ataagtacct ttgtgtcctt    4440
gttcatttat atcgctggcc agcattataa gcaggtgtat acttttagct tgtagttcca    4500
tgtactgtaa atatttttca cataaaggga acaaatgtct agtttattt gtataggaaa     4560 tttccctgac cctaaataat acattttgaa atgaaacaag cttacaaaga tataatctat    4620
tttattatgg tttccttgt atctatttgt ggtgaatgtg ttttttaaat ggaactatct      4680 ccaaatttt ctaagactac tatgaacagt tttcttttaa aattttgaga ttaagaatgc      4740
caggaatatt gtcatccttt gagctgctga ctgccaataa cattcttcga tctctgggat    4800
ttatgctcat gaactaaatt taagcttaag ccataaaata gattagattg ttttttaaaa    4860
atggatagct cattaagaag tgcagcaggt taagaatttt ttcctaaaga ctgtatattt    4920
gaggggtttc agaattttgc attgcagtca tagaagagat ttatttcctt tttagagggg    4980
aaatgaggta aataagtaaa aaagtatgct tgttaatttt attcaagaat gccagtagaa    5040
aattcataac gtgtatcttt aagaaaaatg agcatacatc ttaaatcttt tcaattaagt    5100
ataagggttt gttcgttgtt gtcatttgtt atagtgctac tccactttag acaccatagc    5160
taaaataaaa tatggtgggt tttgtgtgtg tgtgtgtgtg tgtgtgtgtg tgtgtgtgtg    5220
tgttatttat acaaaactta aaatacttgc tgttttgatt aaaagaaaa tagtttctta     5280 cttta                                                                5285

<210> SEQ ID NO 2
<211> LENGTH: 149939
<212> TYPE: DNA
```

<213> ORGANISM: Homo sapiens

<400> SEQUENCE: 2

| | | | | | |
|---|---|---|---|---|---|
| atgattgaag | atagacttcc | acactttgtg | ggtgaatcat | acattttttt | taaatataca | 60 |
| ttttccctgt | tgtaatttga | cagagtattt | ttctctctca | tcagcttact | atgatgtctc | 120 |
| ccttactcct | ggttatttca | gttgtgagta | cgctgacact | actagatcta | acttaagtca | 180 |
| aaaggagaaa | tttgtcataa | ggaagtattt | tcaagataga | aaatgcatga | agttttggtg | 240 |
| gaccttataa | gaaagaggga | actgaaaagc | tatggggaca | catactgcgc | acattctctc | 300 |
| tctcttctct | tctgtggcat | tcttctctcc | tatagcaaat | cagctttctg | tgcaagaatg | 360 |
| aagatggtaa | cctcatagtg | gcagccttaa | ctttagagca | tgggtaacct | catttcaagt | 420 |
| gaacagaaaa | gtctgatttg | ctgtttttga | atcccaactc | caaattcccc | aggagtgaga | 480 |
| ctctgatggc | tcagcttggt | ccaatcaagg | ggttgtggga | agcagggtgt | cacaaactag | 540 |
| aacgtaggtg | ccagaggctg | gctactctgg | gtgaagagga | cagttctcag | caaagaggac | 600 |
| agaatcctta | gtctaaatta | ggactcagga | attaagtctc | tgagtctctg | taaactaaca | 660 |
| attatgctag | ggatttatt | ttattttta | ttttatttta | ttttattttt | tgagatggga | 720 |
| gtcttgctct | gttgcccagg | ctggagtgca | gtagcatgat | ctcggctcac | tgcaacctcc | 780 |
| acctcccagg | ttcaagtgaa | tctcctgccg | cagcctcctg | agtagctggg | actataggca | 840 |
| catgccacca | tgcctggcta | attttttgta | tttttagtag | agacagggtt | tcaccatgtt | 900 |
| agccaggaga | tcttgatctc | ctgaccttgt | gatccaccca | cgctggactc | ccaaagtgct | 960 |
| gggattacag | gtgtgagcca | ctgcgcctgg | ccgaaatttt | gttttaaga | gtgaatgctg | 1020 |
| gcatgaatcc | tttcacacac | acaaaaaatg | ttttcgtga | ataggcaact | atatgtctaa | 1080 |
| cagttttaag | ttaaatttt | taaaagtagc | acatagttat | aatggtcatt | ttacatattt | 1140 |
| tgccaaataa | ttatcctcac | ttgaaagagg | ttattaattc | ttggcttaca | aagggaaaac | 1200 |
| tgttttggtt | ttcaagcacc | aaagtttaat | acatccagtt | atctcaaggg | aatgagggat | 1260 |
| ctgttcactg | gcaatatctt | ttttgttttc | cttttctttt | tgtgattgaa | agtaaggata | 1320 |
| agggaactga | tgtagagaca | aggacatgct | gaagtaccga | ggaggtattg | gaaaatttct | 1380 |
| ttgccatagc | caaccaaatt | ttggaataaa | tggtactaaa | atatctggat | gatttgtagt | 1440 |
| aaaaaaaaca | ttgcttgctt | gtctgtctac | ttgattaata | ccccttgcct | ttgtcttttg | 1500 |
| gcttataatc | ctacatttgg | aataaataag | cctctttcca | tattttattc | ctttctgcct | 1560 |
| tcaggaaagt | acatcttccc | tgttttggaa | agaaacaaac | taactcctgg | acttctcccc | 1620 |
| agcccttcgt | ttgagcctgt | ttcccttttcc | aaggactttc | ctgcatcttt | ttttgtgctc | 1680 |
| acatttatgt | ccctccttaa | gaatgatgtt | ttcagtctca | tcatttaatg | atatagttct | 1740 |
| gtttttttaaa | attcaaatgg | agatcttcac | atttatctct | attacaactc | agcccttatc | 1800 |
| ctaccagccc | acacagtcct | gtgtagtgca | ataaactgtg | acaaatactt | caatcttcct | 1860 |
| aataaaattc | aacaaatttc | ttatacctcc | cagcttggtt | atatctgtaa | attggtcctg | 1920 |
| ccacagatat | aatagacatt | tgataactgt | gctaagggtt | ttaaaatact | ttttcaccta | 1980 |
| atcttcaaaa | tctctctaca | ggggagatta | ttatcctcat | tatactgatg | aggaaacaga | 2040 |
| ggcttagaaa | atctaaataa | actttcctgg | caaaagctgt | gattgaaaga | aacctgggtg | 2100 |
| gtctggactc | ttaaagcgta | agttcttaaa | cccttggcca | tggattttca | accgtggctt | 2160 |
| tatgtcaaac | cacctaaaaa | tgttaaaaag | ttatagaagc | caatgcgcca | tctcacactt | 2220 |
| actgaggcag | tcttgttggg | gtgggggggaa | ggtttgggca | tagcagtcaa | gaatcactgc | 2280 |

```
tgccatgctg gccaacactg gaaggacaaa acctcaagac actacacaca gccccacagt    2340
caacaactag ctgttaagtt ttcccattag atcttgccac aaagttttga atctaaatgt    2400
gttaccttac agctcatatt tcttgtttct tcatattgta tgaatgtttt gaaagacttg    2460
gtcaaattcc ttggaattct tttcatcatt atcaaagaat aagggaaatt tcctgaaatg    2520
tttgccttga gtagcaaatt tctagtgatg ccactaccag gaatcacata aagagctcaa    2580
aagttctgtt aatacagagt gaaaaaagct caacattcca ggttagcatt gacttaaaat    2640
catgtcttag tgatgaggga ggctttcact ttctgaatga caggaggcaa gttgcttcat    2700
cttcctatgt ggggagacag aagatttctc aattctatag gcttatgaat aatataccc    2760 ttgtccacct tgtcttccat acccacatct ctaatattaa gaaataacc tgctccccca    2820 caaaatatc ctcaatattc accacttcca aatggcttct ccctgcaatt caccaatttc    2880
aaatggcttc tccctgcaaa caggctgtgg acagtaagag ataccatgcc tagttacata    2940
agtatatcac tgcaaaatat agaaacatca cttataatga aagtaatact gtttcagagt    3000
tctaaaacaa gcattttctt cccctcacaa aatatcacat ttccatttcc acagttgtga    3060
tgcttttcat ttacccatga cgttaagctc atctttagct cttcttcatt atgtgggtct    3120
gtgttctagc ttttacctca gtagcagttt tgttgcag gaaaaaagga actcttttgg    3180
tagtcactgt ttgtaattgc ggccttgata ttctaagcca ttgagtcaca attaataatt    3240
agaaattctt actaactttg cccatatatt acctatgaag cagtagccgt aggaatgcaa    3300
ttttcctgta aatccctccc tcttatacag ctctagttca ttatttaaaa gattcagggt    3360
gaattcaagt aatttcctat gctgctatca tttgcttaaa gacctttgc aatgggtctt    3420 atgtaagaag aaatgcagga gttgctttgg tgaggtttat ttaaagaaac cattaagtgc    3480
aagacagacc tgaagagcag catcagttgt gtatgggaa acaggagcta tgaatgcgtc    3540
acttcattta ggttgacaga aagagggcta atacttgaaa aaaatcccta cacgatctgg    3600
tgccaggcta cttctttggc ctcacctctt accactgccc cctccttccg tgtcctccag    3660
ccacagtgac ctctttcctg atccttgaac ttgccaaaca cttttccctt caaggtctt    3720 tgccttcagg agtccctctg cctgaaattc ttttcccaga tagtcatggg actggttcat    3780
tctcatcctt cagatctctg ctcaaatgtc acttattcta ggaaatcgtt cctggccacc    3840
gtaaaatagc acacccctc ctcactttct actccttttc tttgttatta tgtatatggc    3900
agcagaaaac tatgcatttt cttagtggca attacacacc ccgcacatta tgcatttaaa    3960
gcgttgtttg ttgttttgtc gcttccatca gaatacaatc cagtagggca aggagtgtgt    4020
ggggtcgtgt tcacctggta tctctgggga cctacagccc ggcacctagt agacactcag    4080
taaatatttg aatgaatgaa tgaggccctt tggcagccgg gaagcccgtc acagccgttg    4140
tctccaccct ctcccgggct acaccaggcc acgccggtaa agttgtttct cctctaggag    4200
aaacattcgc taggccttgt tgccaacccg caggcggctg ggcgcttcat cccacccctca    4260 cccctttcca gccaaggtgg ctgatgggag tcaggctctc gagggcgcat tgccacgaaa    4320
cagcgtgtgt gagcgcgttg tccccggccc ccggcgccac ttcccctcgg cctagcagcc    4380
tggactgggg aaggacgggt ctgctgtacc cgggaggtg aaggaaaagc cgaaagcgga    4440
gaagtgtgcg ggaggggagt ctccgcgcgg aggcagcccg gcctcctcca gtgcaggctg    4500
cgcgctgggg agccagccag ggtgagtcac tcccggccgc ttcctggag gcggcggcc    4560 acacacacac ccgcccatct agtgagggcc gggcccagcg ctggcgccta gctccagccg    4620
```

```
ggcaccagcg tttcgcgagg cgccgccgcc ttaacttcct tgcgcgctca cgcccagggg    4680
ccgtcccagg aatctccacg cgcgctcgcc ggcttcccga gaggcagctg ccctgcgtgg    4740
cccgcgcctg ccggtcccgc gaccagcacc gagcggcgca cgcgcactgc aggacgcgcg    4800
tccggctctc ccccagcctc tatccggccc ggtctcctgc cattcgggga gactgcaggc    4860
caaccgggag gctgagttcg aagctagcag ggcggcgaag ccagtgtcgc ccgcggcgtt    4920
gagaagacgg tgtggccccg gagagggtgg agacaactgt gacgggcttc ccggctgccc    4980
gaagtgggag tggtgtgggg ctgcaggaag gagagaggaa gaggagcaga aggggcagc    5040 agcggacgcc gctaacggcc tccctcggcg ctgacaggct gggccggcgc ccggctcgct    5100
tgggtgttcg cgtcgccact tcggcttctc ggccggtcgg gccctcggc ccgggcttgc    5160 ggcgcgcgtc ggggctgagg gctgctgcgg cgcaggaga ggcctggtcc tcgctgccga    5220
gggatgtgag tgggagctga gcccacactg gagggccccc gagggcccag cctggaggtc    5280
gttcagagcc gtgcccgtcc cggggcttcg cagaccttga cccgccgggt aggagccgcc    5340
cctgcgggct cgagggcgcg ctctggtcgc ccgatctgtg tagccggtgg gtgttatctc    5400
tgcctggctt ctgggtgggg ggcagcagct gtctctccac ccccttccta cctttggtc    5460 ccgcctgccc cctgctagtg gcagcaaact tctgagccag aaaaatcttc ctctttaaga    5520
cgacacctag aacgagtctt gctggtgata tttgcttcca tttgtgtctt ataattccct    5580
cgctcccgcc tccttattcc ttttttaaaat tttctagaca cttaaacagc ctagaaaaag    5640
catttgtttc ccctggattt atgtggtagt agttaactgc tgcttctgtt tttaggtttc    5700
agaagcaggc aacaggaaca agatgtgaac tgtttctctt ctgcagaaaa agaggctctt    5760
cctcctcctc ccgcgacggt gggtgtgctg tcctttatcg ctgcagtaaa ggcgaaggtg    5820 tctgagctg ggagtgcgtg cgtagggaag gttggaagcg tgtgaagaga ggcagggctc    5880
attgttgctt actcttctga aaatgtcagt gctaaacttt taatgttgat ctgggagagt    5940
aattttgggg tgttttgttg ttcgtcttgg atccttaag aaacattttt ttgttggctt    6000
tacacataac gtgactttgc agagaaacga aaaacgttgt ccattaccct ttcttcttaa    6060
gcagccagag attcttaatc ctttaaagag gagtatttcc aagcaataag agatagcttt    6120
tgggagaaca cgttagctat tcttgctggg gtttctgcta ccacattgaa tgtttcctca    6180
tggttttatc tgcctaagct tgctgtgtcg gttgaattta cccagtttgt tttccagtaa    6240
ttactaatct gttaggagaa actccatttc tctgaatgaa agggtaggag cggctgagta    6300
tggagaagga aactggaagt gggaataagg gaaatgattg cttttggttt cataataagt    6360
ttgtacagtg agttgttggg ctactgcaaa taaagatttt gtatcccttc tccagaatgc    6420
ttgggaccaa aagtgttttg gatttttttt aaaaattttg gaatgtttgc atatacaaaa    6480
tcagacatct tgaggatggg acccaagtgt aaatacgaaa ttcgtttgtt tcatatagac    6540
cttattcaca cagccactaa gtcatttgca atattttaa tacgtctgtg catgaaacaa    6600
agtttgtatt aagtacctat gcggggaatt ttccccttgt agcatcatgt tggtgctcaa    6660
aatgtttcag attttgcagc ttttcagata agggatgatc agcttgtatt tgatataac    6720 acccagaaca tttgaagatg aataatcaat ttttggcctc ccttccccca tccgcctcac    6780
cttataccac tttaagtgtg agaattattt gcttgtacat gcatttgtct gttggtgtgt    6840
aacgtatgta cagactggat gtatccagca cttgccttaa tagtacatgt atttacctga    6900
ataggaaagc tgcagtactt gctggccaga agagcacacc atgcttgttt ttgctctaac    6960
tgaatatcct gtatttgcaa tttatagcag ttttagggac tcattaggga attttgtgtg    7020
```

```
tgtgtgcctt tggtgatttg agacaggtgt ctcagatatg ggaagggaat atgacattgt    7080
ttctctttca cctggctatt actgaaaggt gggatgcttt tgaggcagaa taggaaagtg    7140
cattggcttt ggagtgagat ctggatttga atcctggtgt tcttgccact taagagttgc    7200
attatttacg gctggtcatg gtggctcacg cctgtaatcc cagcactttg ggaggctgag    7260
gaaggaggat cacttgaggt gaggagcttg agaccagcct ggccaacatg gtgaaacccc    7320
atctctacta aaatacaaa aattagccgg gcgtggtggt gcacacctgt aatcccagct    7380
actcgggagg gtgaggcagg agaattgctt gaacctggga agtggtggtt gcagtgagcc    7440
gagatctcac cactgcactc caggctgggc aacacagcaa gactctgtct aaaaaaaaaa    7500 aaaaaagaa agaaaaaaag agttatatta tttacgactc ttttagcttc actttcttat    7560
aagattgttg tgagaagtga gtaagacaca tgcaaagtgg taaactgcct ggctgtcata    7620
aaagtcttgg ctactatcac ggctgggagg caaaggagat tcagagaagg gcagaatgac    7680
tgcataaggt gatctgcctg taactcgtgt ttcctccttt ctagtataaa gagataaagg    7740
acttcaaggt cttaaactgg tgagggagta ttacagcctt tgtatggaaa ggtttgactt    7800
tgtgtctctg cttaaacccc cattgtgttg cccctaccaa ttattgtgct gcccccttgt    7860
ggttaactgt gctaagacct ttcttttgct cttctcccat tacatttccc acccttcccc    7920 actcccttt agacccctcc tcttagctcc cagtttccca aactgtgtgc caaggtgccc    7980
agagcacctc aggcttgaac ttgtgttttg agttggttca tggtttcaat attagatacc    8040
tacacccgtt tctacaatgt catgtctttg taaagatgta ttttcagagg ttgctccgat    8100
aaaaagcaac tactacatga aaatgaatgt agaacaggaa atgacagtgt ggtattgtcc    8160
aatttgattc taaggtttga taagttctac agtgctctac actaagttgt aaggacataa    8220
ctactaagta agttgttcaa acctatttct tttggcctgg gggtgtcgtg aaaaatttgc    8280
taagactcag agctccctga atgggtttgg aaacctctgc cttagctttt agtttgctt    8340 tctgataaaa ttattgatat aaagctagta ccagctgatc atggcttaat atatttcctc    8400
tcctatgtaa tatgtttata acttctgccc agttctttca ttttaaaact aatcctattg    8460
ctaacttgtt gtactagtca cttcctggtt tttcctgtac tggtcttctg cttctacttc    8520
tgttcatctc cttaaactcc gaatgcccca agtgaaagtt accattttct accccttaat    8580
tttcttctaa tcatgtaggc tttaaattag gcatcatctt taaactactt ctttcattta    8640
cctcttattc ccattcaaaa tgtccatatt tcctttcttt ctcatatctc tgctttccct    8700
cctttactgt gtgaatccca ggacacattt cctgagccta gaatattgaa agtcatttga    8760
acttctgaga attcagtgtc ccttccttct gtttatcctc aatagagatt ccactctaat    8820 actcctatt atagcattcc cttgccccaa aaccttcagt ggcttaccat tttctactta    8880
ttaaattttc ctgacttta agatagtcta ttatcaatcc ctgccctatt tatttagtct    8940
tttgtctaag gatctctagt ccttaagctt gtaagctgat ttccacactt tctaataata    9000
agctatgctt cttctatcct ttaattttg cccatgttct ccatccctct ttttttcct     9060 ctatttctgt agctctttag tcttagaaca ttttcacatg gtttaattat atgccatgct    9120
ttagttgttt gatagttatt tccctagtgt tagccatatc ttttcaagtt gattgtgtat    9180
tctttgagga gcagtacctt agattaaaaa aaaaccacaa cacacagtgg agagcacatg    9240
ggcagcattc aagaaataca tgttgattgt gtgataagga actgtagtca ccaaacaaat    9300
atttgttaat acttgcaatg taaaaggtac ttggctgtat tcaaaagaga aataaagaaa    9360
```

```
tataaaatag gctcctttcc ctaaggactt acagtataat tgggcagata agctaaataa   9420
taaaagttac agatatttaa gaccacttga gttgagcaga gattttgcat aataggaagg   9480
aactggtaga gggggtaagc aaaggcaaaa tatgtatata tgtatgatat gttcagagag   9540
cagtacataa ataacttgac tgaaatgaag atttgtgtga aagagtagta agaaattgtg   9600
ttaaaaatgt agttggaatt tgattatgga tgtctttaaa tgctaggatg agaagaatgt   9660
actttgacct gtagatatgg agaagcttta aaagttttga attgagaaag agttgctga    9720
aataagtatt ttaggaaaat caaagcagca ccagtgctag gtctcatatg aattggaaag   9780
agaatggtag aaagaggtag gaaaataatt gagccctgaa gtaatgagga cttagaaata   9840
agtcagattg cagagatgtc acaagacatt attatggatt ggataagaag ggagaatgga   9900
ggggagaaga gtgattaaag attaccttac cttgaaggtt tgcttttcag tgacggagga   9960
aatcaaagag tgttgactct ccaagacatc ttagaacatc taagtctata tgttttgtat  10020
attaggactc agaccagaga gatttaaaaa tgtgtccaaa gttactcagc tagttaatga  10080
caaagaaact gccgtttgat taatggcagt tactaacaaa aatagttatg gcagtgttag  10140
tagctggtag aggggatgta gacagttgag cgtatattgt ggatatgttg agtttgcggt  10200
ggccgtggga tgggcaagtg aaaattgata gcatacagtg ggacatatga ctagaatttg  10260
ttagcgaagt taaggctggt gctgtggtac ttaagagaaa agagtgggat tgcccataat  10320
tagcgggtgg gtgaaaggag aggaatgggt aaggagaca agaaaaaaa cagtatgaga    10380
ggcaaattag tggataggtt aggaggcgga atgatcaaca tgttgatcat tggcaagaaa  10440
tgagaagaat cagatccaaa aaaggtctt aaaaagatgt attcgtgttt ttcctaataa    10500
gaaatctata aaaacagaag aaaattgctt atactttccc tacgtggaaa taaccactgt  10560
taatattttg ttctctccgg tttaacaaaa gacctttgga tttgacagtt gggtgatcag  10620
tggagacttt tccaaagctc tccatcacta ggactaagga tgagaatttt aggcataata  10680
aaacctagga gatattttc aacagattgt cattcgtctg tatcgtctta tatatcacac    10740
tgtccaggta ctattcttcc tgtgtgcatt ggttctgtgt tttttctga atgatagaag    10800
gttagacaag ccatctctgg gtgctttgt gctggtaaaa tttgaataaa gtgataaaat    10860
atttgtttct aaaaggaagg agaaattctt ggtcgataac ttataaatct gagggttgaa  10920
tgattgatga aattagggt actggaagaa acaaagagaa gcattattta ttttgaagct    10980
tttctgtata gttacaaagg gttaactagg ttagaatggt ccatgggctg tttactttgc  11040
ttgcatgttt attttgatct tcccaagaac attcttctgt tcatcttttt agtatgttat  11100
tggaaacaga gtactcatta gttcttacta agtggtttta gtttaataaa ttatgattat  11160
gaaataaaat gctattaggt aatatttta taatataaag ggccatgtga tgtgagtaag   11220
tgcactgttt tggaaatcag gggataaggg actgaccctg ctctcagcat ggtatatgat  11280
ttcaggcaac tcacgtaatc agtgagtctt gtctattgag ggaatggact aaatcttttc   11340
tagaaaattt aaaaggtgg gatcacatgg taaaatgtgt ataagtttta aaaggaaat     11400
ggtttaccaa tgtttatgac aaaaaccagc aaactctttc ccaccccccc accccacatc   11460
tccttttcta gtctctaatt cctgtacacc aggcaaccac ctgtcctctg tactttgccg  11520
ttttcacctt tataatgaat gaattgttta gcatcccctc taaagcctct ccattcagtt  11580
gtgtagaaga gctcatcccc tttgccttca agggctttac cattatattt ctctcctctt  11640
tttcttgcct tctcaattct tccctctact ggattatttc catcagcatt actctgattg  11700
ctattgctgt gtaacagaaa ctacccaaaa cttagtgatt taaaacaact actttattag  11760
```

```
gctcacagat accatgggtc agtaattgag acagggcaca ccagggatga ctttgttttt    11820
gctccacaat ggctactagg acatgagttg ggaagaattg ccagccaggg gtgacttgaa    11880
ggcaaaggac tggaatcatc tggaggtgtc ttcactcaca tgatgggtag ttgatgctgg    11940
ctcttgactg ggatgttagc tgggctgtta actggagcat gtacatgtgg cctggatttc    12000
ctcacaatat ggtggcttca gggtggtcac ctttcatagt ggtgagtaga gaattaaaag    12060
tgagtgtgtc tcagcataaa tctttttatga tttagccttg gtagctgcac agtataactt   12120
ctgccatgtc ctactggttg taagggtcag aagcctgtcc agatttgatg ggggagtggc    12180
aagttcacac tgcagaagaa aaacatgtga gatgggaaat agtgttatgg ccatcttttgg   12240 acaattatta atactattgc catagtttgc cattttgcca aacttcacat ccctcctgta    12300
tctgaaatac acgcaaaata cactgagctt ctcctcaaag gtccctaatt cacatcccat    12360
catgacagta actcagagtc cagtatctca tcatataaat caggtccagg tacagaatag    12420
ttttcttggg tatggttaat tggatatggt tcttcttgaa ctgaggaccc atgaagagac    12480
agtttatatg tccccctgcat actttacaaa atggaaaagg cacaggttat ctgcagtaga   12540
cattcctcct caagaagcat gcaaggtagg cacagtctgt agcaattctg caacctcact    12600
gggcacatgt tgccagttcc ttgattaggt ctcagtcctg cttcctggaa gtcattctta    12660
ataggacata ggcttcttct gttttttgggt ttaccttctg aattatttat ctcccccacc   12720
cctgcaccca acccatataa attgctttgt atttgtaaga gtagctttct gagcttgctt    12780
cctgcctgta gtgctccaga gtccaaaggc ccccttttat atagcaactg tcccttttcat   12840 tccaagctaa tacaactcct ttaaaaactt tgtggacttc ctgtgtgtaa gtttataatc    12900
tgtactgcca tacccacaaa tctcttttga gaggaactct ttcctcccct aagctctgtg    12960
tgagtctgct gtgggacaac acccttaaga tccttagata atatttcgtc tgaaaggatc    13020
tatgaggtac tgatttagat cttaagaaag gatcttataa tcacactcta gattggatct    13080
ttgctctgag gcccttttta tttgacactt tgctggctga aaagattgtt ctgagtccat    13140
tacatctcct tgaaattcta ctcaaaaaat gaatagctta ttctttagtt catctctctg    13200
ttctctcaat tataagggca gctagaagaa gccaaattgc tttaacttcc tgctgagaat    13260
ctccttaatt cattaggtca ggtatgtatt ttattttcca tgttaatgta ggtgacagtt    13320 ttgctaaaact ttgccctagt atgtaacaag ggtgtcctct tattcagctt tcactatcat   13380
ttctctcact ttgcttgaag tcctcactga cagtctcctt gagggctctt aggctcccat    13440
gaagtttcct caagacccctt tacatgtgtg aacacaaagg gtccttatct gttcctggct   13500
atatagcagg tccttgaata actgtcatttt cttcataacg ttgataagaa aaaaatggat   13560
tcctggctgg ggccactgtt tgtgtggagt ttggacattc tccccacgtc tgtgtgggtt    13620
tttccgggtg ctccaatttc ctcccacatt ccaaagatgc atatgttagt ggatcggtgt    13680
gtctaaatgg tctcagactg agtgatcatg tatggatgag tgtgccttgc agtgggtgat    13740
gtcctgtcta gggttggttc ccaccttgtg ccttgagttg ctaggatagg ctctagccac    13800
tcgtgactga actgaattgg gttaataatt atcctacttg ttttttattag tctttcttaa   13860 atgtgtgtat agctcacatt tatttcagtg tttaataatc agagtgtttg gaatctttac    13920
ttagaagttt gatgatgttt ttgtggccat aaatatgcca taggaacttc cttatctcaa    13980
ttagcctatg gaaaaatgga ttttgttaca cattgtttca cttaaagtca cagttttccaa   14040 gaacctattg aagacagtga ggattaactg tactagaact gtttcctaac ccactggttc    14100
```

```
ttatcagaat tacctaaagg acttattgaa acacaaattg ccgctgggcc ccaccccccag   14160 agtttgtttc attagctctg gagtgggact tgaggatttg catctgtgag ttcccaggtg   14220
atctgataat gttgatctgg ggcctagatt gtgagaatta ctgatttaaa ccagggattg   14280
gcaagatttt tctattaagg atcataaata aaatatttta gactttgtgg gcaagattgt   14340
ttctcttgca cctactcaat tccgcctttg tggtgcaaaa gcagttatag acaatacgta   14400
aatgaacaga cgtggctcat ggctgtgttc tcataaagct ttatttacat aacaggcagc   14460
tggctaaatt tggtatgtgt gaactgtgct ctgccaattc ccaatttaaa tcattacttg   14520
actccacatc tcttcaagct atggccccat ttttcactcc cctttggaac aaaactctct   14580
gagagttgtc tgtatttgtc tctttttatt ctttcataaa aaaattatct atttttttgaa   14640 cacatttaaa tgtcttagaa ttcaaaaagt agtaaatatc tttgtacatt tgtcagggcg   14700
tgtgtgtgtg tgtgactata actaaagatt aagtagaaga ggagttgctg attcaaaagt   14760
ggtatatgtt actaagttca acaaatattg ccaaattgac atagaaatac caagttatgc   14820
ttttctacac ctttactaac attgtgtttt cagatgactt gattgttgcc aacttgagac   14880
gtgaaaaata gaatctcatt ataattttaa tttgcttttt attctccttt tttagggaac   14940
tcttcactca tatcttggcc cactttctat tggatttgtg gtccttttac tttgctttgt   15000
gggagctctt atactaagga agatagcttt gagtttgcga aatgagttgt tttccctagg   15060
ttgtctcttt atcttttttga ttctgtagat agtgtgattt tgttgttgtg catctaggta   15120
ggttccttct aaccctgaaa ttatattttg agattctccc ttgttttctt gttccatctg   15180
gaatttatac tgatgcaaga tataagatgg gacgcaactt ttttcccccta gatggttgtc   15240 cagtttcaat actatttgtc agataatcct tcttttctct gctgctgtga aatgctggtg   15300
ttttaaattg tgtatgtagt tggatctatt tctggacttt gtttcattct aaaaatggct   15360
cctctgaaac catattgtga gttcttgggt agtgaacatt tctatttatt tgtttccaag   15420
tcctgtataa tatttattag catatgggag gcattcaagt acttgaaaat aaaatgaata   15480
aatcaagcat ttaggaatag aagcagatct ttttgccaat tattcatttt agttattcta   15540
tttaattctc tatttctgat tttaaacttg aatttaacct tggttttcca ttttagtttt   15600
accttttttt taaacttttat tgtgaagtat taagttattt tttgtactta ctgaatgggc   15660
atttgctaac ttatgtgtct gctcttatta gtctatttttt ggcctcaaat tgttaaaaat   15720
tcacagtata gttttatttg tatcaaattt gctactgagg gaagcttgtc atttcataat   15780
ggcaatccat aggataggtc aagtcatttg agattggaac cattaaggat aagttcattt   15840
aacattgaat tattagatct gtggttaatt ggccaggtta gagaagacag aattacaggg   15900
aagtctggat tttacaactt attattttag agggtcaaat ttagaataat atttttaagc   15960
tttttaagta gaagtatatg gatcacctga ggtcaggagt tcaccaccag cctgactaac   16020
atggtgaaac cctgtctcta ctaaatacaa aaaatagcc aggtgtggtg gtgcatgcct   16080
gtaatctgag ctacttggga ggctgagaca ggagaatcgc ttgtacctgg gaggcagagg   16140
ttgcagtgag ctgagatcgt gccattgcac tctagcctgg gcaacaagag tgaaactctg   16200
tctcaaaaaa taaataaata aataaataaa aataaataca taaatagaag tatactattc   16260
tgattctctt atttatatgt ataatttatt tttttaaata catgaggtat tgtagatttt   16320 ttggttttttt tgaggagggg cgggggtgat gtgaaatata gttttcattg catcagatct   16380
tcagttgtaa tgatattgct ggaatccacc atttaggacc ctgtcttgtt aaaaaaaaat   16440
tatccttgcc ttcaccccta cccctcccctg ccacagactt ttaaaggtaa gtattctgcg   16500
```

```
ataattggat tatatttact attatgaaaa tttaaaatta ttagaagtaa aatgaaatat   16560
acctccattg tagtaagttt gattcacagt gcctctggtt atggtggtca gtaaaagtaa   16620
cactgtatta ggaacagtct tcatggtggg agttctctcc ttttactctt ctgttagttt   16680
gttctttttt tttttttttt tttttgagat ggtttcactg tcactcaggc tggaggacag   16740
tggctcgatc acggctcact gcagccttgc cttccctggg gtccagtgat cctcctacct   16800
cagcctcctg agtagctggc actgcaggcg agtgccacta ggcctggcta attttatat   16860
ttttttttgt agagatgggg tttcaccgtg tcactcagtc tggtcttgaa ctcctgggct   16920
ccagcaatct ttctgcatca gcctcccaaa gtgctgggat tatggttctg gagccaccgc   16980
gcatggcctg ttagtctgtt cttgcattgc tataaagaaa tacctgaggc tgagtaattt   17040
ataaagaaaa gagatttaat tggctcatgg ttctgcaggc ttacaagcat ggggctgaca   17100
tttgctcagc ttctggggag tcctccggga gcttttactc atggtcaaaa gctaagaggg   17160
agcaggaata tcacatttca agagctggag caaaagagaa tgtggggaag gtgcacacac   17220
ttttaaacag ccaaatcttg caagaactca gtatcttcag gacagcacca aggggatgt    17280
tgctaaacca ttcatgagaa atccacccccc atgatcaagt cacctcccac caggcctcac   17340
ctccaacatt ggggattaca gtgcaacaca tgaaatttaa aggggacaac atccaaactg   17400
tatcaacctt gctgtacccc tcagcctcat tttataggca acaattgaat atattggttt   17460
tataaaggtt tgatatggaa agattcatta ggagtggatt ttaggacttg gggaatgact   17520
cagagaagaa aatagtgcat gatagtataa gtctatctga ttgatgagta actggaaatc   17580
cttccaaaac ataatgcttc agtgtctgca gaattgtttc atttccatgt ttatgtattt   17640
cttattgttt ccttgtttat ccataggtgc ttaattttt tttaatctga atgcattatg    17700
ataatcttta aataattatt tcagaggaat atctgaaata ttcagtgttc ttctagcatg   17760
gcagtatttt aaaaatcatt atgagcttaa attcatactg atttaaacaa cttctagatt   17820
tttttgaata tcaatagcag agggtagttt taaatatttc acgagcagaa ttaattaaat   17880
ttcctgtgca atttatttt ttatagacaa actcgtcact tcttaaaatc ttttaaaaat    17940
gtcttggtaa tacaggcttg gaatatgatg gtattgaaat gagatcttaa gggaaaaaaa   18000
actccaacgg gtttttttgt tgttgttgtt gagatggagt cttgctctgt cacccaggct   18060
ggagtgcagt ggcattatct cagctcactg caacttctgc ctcccagatt caagcaattc   18120
tcctacctca gcctcccgag taactgggat tataggcgcg caccaccacg cccagctaat   18180
ttttgtattt ttagtagaga cggggtttca ccatgttggt caggctggtc tcgaactcct   18240
gacctcgtga tccgcccgcc ttggcctccc aaagtgctgg gattacaggc atgagccacc   18300
atgcccggcc aaaaactcca acttttagag gcctatttac agcacttgtc ccatatttgt   18360
tcacactttt tctgtatgtg tgttgtgaat tataaatctg gcttttccta caaatgtggc   18420
ttttcctgtg tagtcatcat taagcatgat tctaagaagt agctcaaaat ctcctaagac   18480
caaaaccac aaaaaacaaa aaaaaaaca acaaaaaacc aaaccagaa aagggataca     18540
ttttgcagaa taatttatat tttcttctct tcatggcatc agtttctca ggagttcttt     18600
ttttgagatg gagtctccct ctgtcaccca ggctgtagtg cagtggtgcg atctgcaagc   18660
tccgcctccc gggttcacgc cattctcctg cctcagcctc cggagtagct gggactacag   18720
gtgcccgcca ccacgcccgg ctattttttt ttttgtattt tcagtagaga cggggtttca   18780
ccgtgttagc caggatggtc tcgatctcct gaccttgtga tccacctgcc tcggcctccc   18840
```

```
aaagtgctgg gattacaggc gtgagccacc gcacccgggc tcaggaggtc ttttaagctt    18900
ttgcctgtca tgtgtgtact tctgacgctg gcccaaggta aaatgattac atttgacttc    18960
ggtagccctt aaatgtatgg ctgttcttaa tcttttctaa agcctaaaag ttgaattagt    19020
attcatctta gatttcttgt ttcttaagtg aaagaatcat gacattgtat aaaatatct    19080 tatttgcatg tattttatat actgttttaa taggcagtag tagtatacaa gctttgacca    19140
aatgtctctt catataaaaa attcaagtga ataaaaacag tcatttaaaa atgacattag    19200 tcaaggggc aaaaaagatt acaaatgctt attgtgattg acagaacttg cttaacatat    19260
tagggttctc tagaaggaca gaactaatag gatatatata tgagtttatt aaatattaac    19320
ttaaatgatc acaaggtccc acaataggct gtctgcaagc ttgaggagca aggagagcca    19380
gttcaagtct caaaactgaa gaacttggag tctgatgttc aagggcagga agcgtcttgg    19440
ctaatccacc catcttggcc tcccaaagtg ctaggattac aggcgtgagc ccccgtgcct    19500
ggtgtacatc attttttaata tctttatagt attctgttgg ctaagttgcc acaatttatc    19560 agacccttt aatgtcatta attttttccc aatatttaga cttgtttcat agaattatta    19620
gatatgcatg ctactactcc tgtccttttt caaaggacaa ttattagata ttcttgtttt    19680
cctcatatct ttgccaacac tgggtattgg cattcttctt gtttaccagt cagctaagga    19740
agctaaggaa gaaacaatat ctcattttta tgtacttttc tctgattctt aattatgttg    19800
accatgtttt catttctttt gtgaaatgcc tatttatgtt catttcata ttaaattgta    19860 agagttactt gtataaatat attaaacctt tgtagtatat attttttctg tttttttta    19920 aagttttgat tatagtgttt ataatatgca gtcaaattta cccatctttt atttcctcta    19980
tcatttttca cttagatgtg gggtttagaa aggaggtaca taatgtgaca gagttttgg    20040 tatagaaata actgacatag ttagatataa aacataccaa ggaaatagtc ggaaatgtcc    20100
aatttcgaat gtgtaaggag accagtaaga aaatcatgaa gaacagctaa cagcagtaat    20160
ttttaaaagg gtatttacaa acacttgaaa atgtttatgt agtttaaagg aatgattcaa    20220
atataaagag aagcgtaaca taaaaatgaa ataaaggcat atatatagtc attgtgtaga    20280
tggttttcta gtaacagtta taccaagttt gaaatgattt ttaggctttg ttatgccaac    20340
ttttaggagt tttctttta aacttttga gcttatgttt catcatggcc aattttata    20400 aattttccct tatatgctcaa aacattttt tagtggaagg ttttaatacg tctgtaattt    20460
ctccggtgtc ttaaaaataa ttagtttgtg gagctctttg tgtattggag ataccatctt    20520
cttgtttgat atatttgtat atgtattaag taagaactgg ataaagaagg tggttgggat    20580
atgtataaat atcaggtaag aacttgataa cgtattggtt ggtttgcata tgaaaagttg    20640
ccctcactgt caggttcttt cctgtttcta ggaattggct agccctggaa ggactgcccc    20700
ttccagggtc agcaaattcc caagatagca aagcatcaaa aatacagaat aaaaagacat    20760
gcttagtaga gtatatagaa atacaattgg ttttgtttat tttgtgatgt atcctgtgat    20820
actggtaaat tcatttataa gttctagtaa tttttttggta gaatcctcag catttttgat    20880
aaatacaatc atgtctgcaa ataaaaagtt ttatttcttt catttcaatc tctatgtctt    20940
ttatttcatt ttcttaccag attgcattag gtagaacctc cagtgttgaa tagaaatggt    21000
ggtggtgagc atcctttcct tgttcctgat tttatggaga aagcattcaa tatgtaatca    21060
ttaagtaata gaaggttgtt tgtagatgat ctttatttta ttgaggaaat tcccttcttt    21120
ttctaattta tttccagaaa ttttatcatg aattggtgtt gacttttgtc aaatgctttt    21180
cctgcaacaa ttgggacgat cttatggttt tgctccatta ttctgttaat gaggtaaatt    21240
```

```
gcattgattc attttcaaat gtcaaagcaa ccagtatgac tggaataaaa cccacttggt    21300
gatggtgttc tgaccttttt atatgctcct ggttctatgt tctattattt tgttatgttc    21360
atgagaaaca tttgcctgta attttttttt tttttatga tgtgttttg ccaggttttg     21420 gtattaggat aattctggcc acataaaatg atttggaaat tatttctgcc cctctgtttt    21480
ctgtaagagt ttatacagaa ttggtactat ttttccttaa atagttgac agactttccc     21540 agggaagtca ctttggccaa gagttttctt tgtgggtatg ttttaatga agaattcaat     21600 ttattgaaga gatatgatac tattcaaggt ttctgtttct tcctatgtca gttttggtaa    21660
tttttgtctt tcaaggaatt tgttcatcaa atctaacttg ttaaagtcat ggcatgaag     21720 ttgctcctat cttttatat ccacttactg tttataaaat ctgtagcgat atcctgcttt     21780
ttttacatca tatggggcac atattggtaa tatgtgttct tttctgtttg taaattgatc    21840
atcttagagg tttatcaact ttttaaatct tttctaaaaa caaagttttg gtttgattga    21900
ttttctttat tgttttatat attattaatt tttgttcttt attctttctt cactctctgg    21960
ttttgttttc tagctaccta ggaagcttac ataattaatt tcatatcttt cttcttttcc    22020
atcataagca tttatagcta tacattctct ctaaccacta ttttagctgt attccccaa     22080 attttattgt ttattatcat tcaggtgaaa ataatttctg atttccctt taatttcttc     22140 ttcgaacctg ggattattta gaactatgtt aattttgcaa tactgggaga ttttctagat    22200
agttttttga tattttattc taattcaatt ttgctatggc caagaatata attcatatta    22260
attcagtctt ttcaaatgtt tgagaattgg tttatggacc aacctatggt ataacttagt    22320
gaatgttctg tgagcacttg aaaaggatgt atgttctgca gttgttgggc attgtgttct    22380
gtaaatgtca gttatattta gttggttgat gtttaggtct tcattatttt tactgattaa    22440
aaaaattttt tttgttaatt cctgagaaat gagtattgaa attttagtg taatagttgt     22500 tttatttccc tctttacatt tttgcttcat gtaattggaa actattattg tgtgcatata    22560
tatttaagaa gagtaattta taaatcttct atgattagtg tttttatgtt ctgcttacaa    22620
gaggtcacat tggtctgttt tccatcttaa attaatattt gtgtaccgta tgaagtagat    22680
agaagttaag gttatttttt gccccatatg aataaccagt tgactaagcc acatgttttg    22740
aaatgaccaa tatttcttca ctgaaatgca atggcacatc tgttccaaat taggtaactg    22800
tatgtgagta tgttttttg gactctattc tgttccattt gtctatttgt tcattttgt     22860 gctaatacca atctgcttgt tctatcttta tgataaatct tgatgtctga taatataaat    22920
ctttagtttg ctcttcaaga ttgttttggc tattgtaaat cctttgtttt tcacagactt    22980
taggatcaac ttgtaaattt ccacaaaaac tgctaggatt ttaattggaa gtgggttgaa    23040
tctatagatt aatttggaaa agaaccgaca tctgaaccat actgagtttt tctgtattct    23100
tatatcagca tggtctatcc ctctcttatt tagctagcat ttatttttg tagaaatgtt     23160 ttacagtttt tattgcacag tttttacaga tatttccata gatgtattcc taggtatttg    23220
attttttgtt actattgtaa atgatactat ttttaaatgt tcatttaaaa aattgtttgc    23280
ttctgacata cagaaatgca gttgattttt atatattggt cttgcatctt gtgactttgc    23340
taaattcact cagtgattgg tagattcttt taaatttcct acatatacag acatgtcctc    23400
tatgaatact gacaattta cttatccttt ctaatcatca taactttat ttagttttct      23460 tgccttattg cactagccac aatgtccact atggtattga atagaaatca tgatttaga    23520 catgattgtt acgttttga actctagaag aacaagatca atattttacc attaggtata    23580
```

```
ttgttttttt actgttaccc tttatcagag tgaggaagtt tgcttttatt cctagtttga    23640
gattttaaaa tcatgaacat tggtaaaatt ttattaggag tagtttctgc atctattgaa    23700
atgatcatat ggtgtgtttt ctcattgtgc taataatgta aaatatattg actatttaaa   23760
aaatttttt ctaaattaca taaaaattgt atatatggtg tacaacatga cattttgtta    23820
tatgtataca ttgcagaatg gcaaaatcag tctaattaac atatgtatca cctcacatac   23880
ttatcttttg tggtgagaac acttaaaatc tactcttagc aattttcaag tatacgatat   23940
attgttattg gtaatcacca tgatgtacaa tagatctctt cagtttactc ctcctatcta   24000
acagaaattt cgtatccttt gaccaacgtc tcccattcct cctaatggga ccctcagcct    24060
ctggtaactg ctgttctact tactctctgc ttctatgatt tctactttt tagattctat    24120
ggatcagtga gatcatacag ttttgtcttt ctgtgcctag ctttatttca cttaatataa   24180
tgtcttccag gttcatccat gttgttgtaa atgacaagat tttcttcttt ttttaaggct   24240
gaattatatt ctattgtgta catatgctgt attttcttta tcagttcatc tgttgatgga   24300
cacttaggtt gattctttat cttggctatt aagaataatg ctgcaatgag catgggagtg   24360
tagatattgc tttgacatat tattttagt tccaataccc agaagtggga ttgctaaatc    24420
atatggtagt tccattttaa ttttttgagg aacctccatt cattttccat agtgactgta   24480
aaaatttaca ttttcccacc aagagtatac aagagtttct ttttctccac acactcacca   24540
atgcttgtta tccttatatc tttttgataa ggctcattgt aacaggcatg aggtgagatc   24600
tcactatggt tttaatttgc atttagtgat gttgaacgtt ttttcatgaa catgttggcc   24660
atttacatat tgtctttttt ttttttttt gagacagagt cttgctctgt tgcctaggct   24720
gaagtgcagt ggtgtgatca tagctcactg cagccttgac ctcccaagcg caagtgatcc   24780
tcctccttca gcctcttgag tagttgggac tgcaggcatg tgccagcatg cctggctaat   24840
ttttttttt tttttttttt tttttttttt tttttttttt ttttttttag gtacagggtc   24900
tcactgtgtt gcccaggctg gtcttgaact cctggtctca gtaatcctc ccaccttggc    24960
ctcccaaagt tttgggatta cagggttgag ccactgcacc cagtctgtat tgtccttga    25020
ggaatatctg ttccggtcct ttgcccattt ttaaatcagg ttatttgttt tcttgctttt   25080
gagttgtttg catttcttat ctattttgga tattaactcc ttatcatatg gatggcttga   25140
aaatattttc tcctgtttta taggttgtcc cttcactctg ttaattgttt cccttgctgt   25200
gtacaagtttt ttaaatctgg tataatgatt gatttctaaa tgttaacttt gcactcctgg   25260
gggtaaattc atttggtcaa gatgtattct tttaaagtgt tattggattt aatttgctag   25320
tattttgttt agcattttt tccaaatatg tttatgagag agattccagt gtaattttt    25380
tccttttcat gtccttacat attttggtat catgtttata ctctcatttt aagaatgtgg   25440
gtaagtgttt tttattttct atttcctgag agagtttgta taagctcaat gtttcttcct   25500
cagacatttg gaaaaattta ccagcaaagt cactgggcat tacattttct atgtggaaaa   25560
gttttaaatg gtatattctg agggctctgt tctgttccat tgatctatat ctctgttttg   25620
ctaccagtac catgctgttt tggttactgt agccttgtag tatagtttga agtcaggtag   25680
cgtgatgcct ccagctttgt tcttttggct taggattgac ctggcgatgc aggctctttt   25740
ttggttccat atgaaccttta aagtagtttt ttccaattct gtgaagaaag tcattggtag   25800
cttgatgggg atggcattga atctataaat gaccttgggc agtatggcca ttttcacgat   25860
attgattctt cctacccatg agcatggaat gttcttccat ttgttgtat cctctttat    25920
ttcattgagc agtggtttgt agttctcctt gaagaggtcc ttcacatccc ttgtaagttg   25980
```

```
gattcctagg tatttttattc tctttgaagc aattgtgaac gggagttcac tcatgatttg   26040
gctctctgtg tgttattggt gtataagaat gcttgtgatt tttgtacatt gattttgtat   26100
gctgagactt tgctgaagtt gcttatcagc ttaaggagat tttgggctga dacaatgggg   26160
ttttctagat atacaatcat ggtatattca attttttaaat tactgtattt gtttgttctc   26220
atattgctat aaagagctat ctgagactgg gtagttttta aagaaaagtt gtttaattga   26280
ctcatggttc cataggctgt acacaaggca tggctgggaa ggcctcagga aatttacaat   26340
catggtagaa ggtgaagggg aaaaaagtac atcttcatac agcaacagga aagagacagc   26400
aaaggacgac atgctgcaaa aatttaaata accagatctc atgcaaactc actcactatc   26460
atgagactag caaagcgtaa atccatccca tgacccagtc acctctcacc aggccactcc   26520
tctaacactg aagatcataa ttcaacatga gatttgggtg gggacacaga accaaaccat   26580
atcaattata tatagaatta ttcaaatttt atatttcttc ttgtgctagt ttaggtaaat   26640
tgttttaaaa ggaacttcat ttgttttttaa attggagaat attcctgttg tcttttacat   26700
gtttcaatat tgtaagctct ggtaataatg tctactttt aattcccgat attgataatt   26760
tatgttttat cttctttttt tcttgatcag tctttctagt gttttatcaa ttttaatgct   26820
tttaaaaagc caacgtttta ctttgctttt ctttatttta tttttatttt tctctgattt   26880
ctgctcttaa gtactttcat ttttatggtt tttggcttaa tttgttgcaa cttcttgaaa   26940
tgaaaattta tttaataaca ttgttcagcc tttcttctcg tcttgtgtat gaatttaaga   27000
ttatgaatat cttagtatac acttttactg cgtttttactc attttcatta ttgattcaaa   27060
gtatttttaa agttattctt tgtaccatgg gttctatgaa aatatattga ttaatttaca   27120
aatatatgcg ggtttctagt tatttttctg tatatgctgt ggtacttttg tcagtggtta   27180
tattttccat aagagatttt taatttaggt gccattggca aatttccatt aattcaaatg   27240
cagaacttca catttttcaa tgcatacgtg agttttttt gttgaggtat taagaatagc   27300
ataaatttat aaaatattaa gtaatcattg aatgcaaaat atgtcctatt ttgcaactta   27360 atatacttt attaggttga cgctaaagta attgcgtttt ttactcatac tttaatggca   27420
aaaaccacaa ttacttttgc accagtctaa taatgagaat tattattatt attatattgt   27480 ctttttttt tttggagtgg agtctcactc tgtcacccag gctgaactgc agtggtgtga   27540
tatctgagcc ttggctcact gcaatctctg cctcccaggt tcaagcaatt ctcctatctc   27600
agcctcccaa gtagctggga ttacaggcac gtgccaccac gcctggctaa ttttttgtgtt   27660 ttcactggag aacagggtct cactacattg gcctggctgg cctggaattc ctgacctcaa   27720 atgatcccc cgcctcggcc tcccaaagtg ctgggattac aggcatgagc caccgcgcct   27780
ggccctaata atgagaattc ttatcaaact gtttacacag aataacatga gtgggtaatg   27840
gtgaagctga gtttcacatt tttatgcgat attcttcagt gttgctattt gttcagtact   27900
tttaagaatt atataaattt tttatagtct atacataaag tcaatattat gggtcccaaa   27960
tatataaaat gtttgcttgt tccattgttt atgttttgaa tacaaattat attttgtatg   28020
atttcattaa taatttgttg agaatttat ggcctaacat gtggtctact ttctaaaata   28080
ttccagcttc atttgaaaag gatatgcatt cttcagttgt taggtgttg cttttgattg   28140 cttgtatttc tcagtcaaat gtaggaagtg gagattaaga aaagggctgg cacttttggt   28200
gattgaggag gagaaagtat gagatagttg tcttggatag tggaagagta aatgttctaa   28260
agaaatataa aatgatagtt gagcagcact aagggcccat ttgagtatga atctaaagag   28320
```

```
ggaccaatct gaatgcatgt gttttcatca gtgattttta tatgtgtggg taaaagctct   28380
gagtagacag agataaactg aactctttta gagtttcttt gttatctttg gtgtttggat   28440
cctttgcttt gatttgtatc ggtacagttt ttaaaaaatt aaatgttatc tcctctcagc   28500 agatctttt aacatgaacc cagcatcttt aacaccaata aaatttcttc tattattttt   28560
cttccctgtg ttttcattcg tcctccatct agagcttctc tttagaattg tactccctgg   28620
attgatcctc ttatttctta cttttatgct cataatattt ttttctttct gtctgtctct   28680
ttctctttct gagtctagga cctgggagtt tgtcttgact gtcttccaaa ttatgagttt   28740
gatcctttga gtcgtattat tcaactcttt cactgaattg tcatctatct ctttttcttt   28800
aatgtataga gaatttatta tgcacagcca cttgcaaact ttaacaagta tgattagagc   28860
agcattttct ataacagcaa cacataagtt ggaacaacac aaatcttaaa ataactggaa   28920
tggatgagca aattgggtgg tccgaggctc agacatcagc aggtgttaaa cacctgtggg   28980
aaaggagaga acgatccatt tatttatttc tataggaaat gcaaagagg caaaattaag   29040 aaaaatactg cttcatgata aagaataaag ccgtgaagaa tatccacaaa attgtgtata   29100
gtggctacat ctgatacaga atggaaacag ccaggataga gcagcacagg aacactatga   29160
aatgcccagg ctgtcttcat tactagtcag gattttttt tttaattttg taaactttat   29220
ttattctctg ctccttttc ataatctagt gatgctttat gttttcaaaa tattcttaaa   29280
tctctctgag aataccgaga aagattttaa accaagttat cttccctgca ttatctgttt   29340
cttctggggt cagttgtttt ctggtccatt ttggtcttac tcttttattc ctacaacccc   29400
tgccccatcc ccatcctaac tgtaataatc cttgataatc attgcatatt tatgcttttt   29460
atgtgtgtgc agacaactgt tttttatgctt atagatgcct tcctctgtgt attttttttc   29520
ttcagttaaa atttttttt tttgcagtca cagtcttgct ctgttcccca ggctggagtg   29580
aagtggtgcc aacctagctc actgcaggct caaactcata agcttaagcc gtcctcccat   29640
ttcagcctcc caagtagcta gtactacagg tgcacactac atgctggcta attttttagat   29700 ttctttttg tagagacagg gtctcgcaat gttgccgggg ctagtcttga gctccaggct   29760
caaacgatcc tctcgccttg gacttccaaa ttgctgggat tggaggcatg agccatcgca   29820
cctagcctat gtatgtttta aatagagtct atttcctcta ctctgtcatt ctagtcctat   29880
ctacttttga tcttcctgga attactgtaa atttctgatt tgctgatagc accttttctt   29940
atttgtcgga gccgccatga attcgtttat ataaactttt aatttactc cttttagcta   30000 ctgttgttac ctgttttact tttatatcta ttttaagccc taccatacac cgttattatt   30060
catgctttaa acaattgtca gttgtctttt tttttttag acggagtctc gctctgtcgc   30120
ccaggctgga gtgcagtaaa catgacctcc gttgcaacct ctgccttcgg ggttcaagca   30180
attctcctgc ctcagcctcc cgtgtagctg ggattacagg cgtgtaccac tatgcccggc   30240
taatttttat attttagta cagacagggt ttcaccatgt tggccaggtt ggtctcgaac   30300
tcctgacctc aggtgattca cccgcctcgg cctcccaaat gctgggatta caggcgtggg   30360
ccaccacgcc tggctgtcag ttgcctttta atacatttaa taaatggaag aagaataata   30420
ttataattaa tcacatattt actattttg agctcttcat tcctttctgt aaacctgagt   30480
ttacatgtaa tatttccttt aatccacatg attttcttta tcagttcttg agtgtgagtt   30540
tgttggtgat gtactctctc agcatccatt tatctgaaaa catatttgtt ttgccttgaa   30600
ttttgaaaat tcttattttt tataatacaa cagatccagt agtatgagaa ttattttca   30660 ggattgtaga attctgggtt gacagctttc cccctctccc taccagtact tgtcttctg   30720
```

```
gcctccatta cttctgaagc gatgtcagtt ctatttcttg tcttggttct cctgtatgta   30780
tgtgactgct tttaagatta tcttttttgtc tttggttttt agcagtttgg ctataatgtg   30840
acttaagtat ggatttgtat agattggatt cagatgaact ttttggatcg gtggtttgat   30900 tttttaaac aaacttggaa aacatttagc cagtattttt tcaagtattt cctctgttcc   30960
acttatatgt atcagacttt gttactcttg ttgttcagtg gtgtgatcac ggctttctgc   31020
agcctcaaac tcctgagcgc aagtaatcct cctacctcag cctcccaagt agctgggact   31080
acgggcacag agcaccatgc ccagcaaatt aaaaaaaaat ttttttgtag agatggggtc   31140
ttgctatgtt gccagggcta gtcttgaact cctggactca agcaatcctc ctgccttggc   31200
ctcccaaaat gttgggatta aaggcatgag ccatgactcc tggcctagat ttcttgatat   31260
tgtagagttt acatatggct tctttatctt catgcattat attaatttt tactgtaaat   31320 tctattacat atgtatcata gtaaacaaag tctttaaaat aaattctaat atttgggtct   31380
gctttgggtc catttctatt atatatattc ttcttttcat gtttaataag ttcagctga   31440 ctattgtaca ttgtgggtga tacagtgtag aaactccgga tgatgtggat ttcaatcttt   31500
ctctgaagta atgagttttg ttctagcagg cagttaaatt tactagcaga ccaacttgat   31560
cctgcggagg cttggtttta ggctttgttg ggacaggtct atttcagttt tgccattact   31620
tctggtaagt ggctcttatt cttcaagtgt ggcttttctg gcgtttcagt ggaaagcctg   31680
agatatttac cagttccctc taacactaaa tcctgactct ccaggaccag atagctgttg   31740
aaatctcttc ccagttcttt cagatttcta gctattgcct gtccctgggc ttcgattttc   31800
atcctatgga tgggaattca ggagtcaggc cccactgact cccatttttcc tgagatttct   31860 gccctcaatt tttggctttt ctagcagctc caaacttcat tctctgatac tttcacccag   31920
taagactgca gcttttttaca agagctctgt cccctcctct ggccctgcc tgtacacaac   31980 agactgtgta tgtagttgtc tcaggatgga agaagagtaa gtatgggcct cattcagtgt   32040 attcccctttc tttcaagggt catatccccc cgatttgtat ctgcttttgt ttctttgaca   32100
atgccttcaa atggtgtttt tataaatata tattttttaaa aagtttataa ttgtcgtcat   32160
caggaacatt agtgtagtat aaactactct ctcattatca aaaatctgta tgttaaaaat   32220
tacttaaaat tgttgttatt tatcatttcc ttggtgtttg gggcagaagg gaatgcacat   32280
gatttttctg aacttctcat taagggaggc aacccagcct tggtctggag atcccgaaat   32340
tataccgtat gtataataaa ataattattt tgttattttt atgagcatag cattaataaa   32400
ttaaatattt agtaagattt gtatctcagg attttctac ctgctaagaa tagatcgttt   32460
gacaaggcag atgaggttct ttgttgaatt ataaggtatt gaagcctata atttagtagt   32520
ggaaagagca catagcaaga gttgtatgat gaggttggag aggtaagcag caaacagata   32580
atggaatttt agtctaaaca ttcgtaaaat atgagggtgg ctcctgtggg agattaggtt   32640
attgggaggc aaagtagact tagggaaaat agttaggagg acattgcaat agttcaggag   32700
agaaataata gctgtttagt gtatgatggt agttgtggaa aaaaaagcca atggatggat   32760
ttgaaatata gtttggaagt aaaactatca gtacatattg atggactgga tataggggtg   32820
aaaaaagaga agaataaagg ttgaccaaat tctttattat ctcaaagtat gaaagcttgt   32880
taagacctct tttctgtttg tattttcttt cttgctcaat aagaaaacaa cccaaagcac   32940 ttttttttcta ataacttata tcttcttctt tgtgataaa aaaaaatagg agtggtcttt   33000
agagtacaat acaaaattct tttacatttc acctcaccat atttaggttt accaaagtag   33060
```

```
tataggaata attgtaggaa aaacatagta tatctacttg gactataaaa tttggtata    33120 ctaaagaaag taaatcaaaa tggttatatc ttgcaataga atgcaaaatc acatggatat   33180
taaaggtaaa catttaaatg tattttatat tcttggcttc ttcttcagac cactccattg   33240
ccttttggga catttctgtg gaaaagttga gaagcactga cctatctgaa ccttccaatc   33300
cagccaaact tgtctctact ttgttccagg aacatgctgt gtacattcct ctttccatgt   33360
tttgcatgct tttctccctg ccaataatgc cctgttttc attacttgtc aaaattctat    33420 tttccttta aggtccagcc tatgttttaa ttgttgtgtg aaacttctaa aacctttctt    33480
tgttttaaat aattatgatc attttcttct tgtcattttg tagcacttaa ttttaaaat    33540 ttattttgta cttagatgat gtgtaattta ctataaatca tagattttta agaattggga   33600
ggaacagcgg aaatttaatt aagtaattt attatacaag tgaggaagct gagattcatt   33660
tgtcatgtaa gtagtttgca ataagaaagg atgaaactta tttttaggtc tcttggctcc   33720
caggttagta atttttctaa tctactgcat tacttcttca tgtatattta ttgatctgaa   33780
aagttgtgtc tcttagaatt atgtagtata tgagtaaagt ttgaaaatat gaactttaa    33840 aatgtgatat ttgaggtact ggttttgag tgtatgtgta cagttgatta aaatttatta    33900 taactttat ttactctttc tttttttt tttttttc gtagagacag gttctcacta        33960
tgttgcccag gctggacttg aactcctgag ctaaagtgat cctctcacct tggcttccca   34020
gagtgcaggg attacaggtg tgagccactg tacccagcct cttattact ctttattcaa    34080 cagatttgtt aatcaacaca tgttgaccag acttaattac agcttttata tactcttcat   34140
ttattcaaca actttcatgt gtcagagagt atcctaggca ctgagtgcag tagtaaataa   34200
tacattaagg ttcttacctt caagaaactt tcattctagt ggtacaagac aatgagcaaa   34260
atcataatct aatctatggt gggaaaatat cagaacagct gtggccactt gagtggttgg   34320
agcagggact gatggagaag gagcatggaa gaactttctg ggatgctgat aatttcttag   34380
ggctttgggt tacataggta tatgcagtgt ccaaacttat tgactggtac acttaagatt   34440
tgtgcatttg attgtatta ggagggaaaa tcctgtaaaa ctagaataga tgtaacttat    34500
atgagagtta taaatgacaa tatgttaaac acccatgaaa ctaccaccca ccccaggaac   34560
tagaatgttg ccagcaattt gcacctacat atgtgtttct ccctagctat tctcctgtct   34620
atcttgcaga agtaaccatt gtgtattgta ttttgggatt aacatttcct tgatttttta   34680 tttttttt gcgggggcgg ggggagattt gtttaacaca tgtatatgcc taaacaatgt    34740
actattcagt tttgcttgtt tttgaaattt agaaaaacgg tatttacag cttcagtttt    34800 tctataattt actgcttttg caacattgta ttttaagat ttatccatgt tgcataaagc    34860
tatagttcat ttattttaac aactgaggaa cagattctgt agtataaatg cacaaaagta   34920
tttacctatt ttcctgatag tttgggttgt ttgcagtttt tgccattgga agctgaggcg   34980
caatgaatat tcttgtaatg tgtctcttgg tgtaaatatg catgaagttt gtaactagac   35040
gtagaattgt agcagttctc agaacgtggt ctctagagga tgcctgggta tcctaaaaac   35100
ctattcaagg gtttaatgaa attaaaatga ttttcataat aatgccaaga tgttaaatgt   35160 cttttcatt gagttgacat atgcacaaat ggtacagaag taatagtgag ttaaacggct    35220
ggcaccttag cacaaatcaa agcagtaatg ctggttgtag ttgtgatcat tgtattcttt   35280
ttctttttct ttctttttt tttttttga gacaaggtct cactttgtta ctcaggttgg    35340
agtgcagtgg catgagcaca atcactgctc actgcgcct cggtcctg gctcaagtg       35400 atcctattgt tttcttctc gtcatgtact tccaggaaaa gaaaaaagcc aattcgagtc   35460
```

```
acttattctt tgattctttt ttcgtagcaa agcatcaatg cattttctaa atgattgaat   35520
tcatttaaat tcgggaaaca tttactgagt gcctatggaa ttctgggata tgagtgtatg   35580
tttaaggcag tgtgatttcc agttaccatc ctttctgttc taaacacgat tgtgtcatat   35640
taaaatataa aaagagtaaa aaatatcctg aataaaaata gatcaagctg tacatatata   35700
tagattataa gtgcaaaata ctgagtgtgg ttaaagccta tgctatgctt gctgggtttc   35760
ctgtacagaa gtaggcattg gagacagttt tgctcttgtg gtacaacatg gatgactaga   35820
ggcaggtcca ggatgttact tttactgcca gccgtcgctt ccctccaaat agactattgg   35880
aaggggaacc tcccgccaaa cgctgcctac tgctatagtg ttggataagt tgcaagctta   35940
ggaagatgag atgacatgat ttaggaactt caggatgaag tgaagtatct cctgccttgt   36000
gactgactgg atctgcatcg tatcagatac ctcctcaagg caggaatttt aacctgctgt   36060
tataagacct ggttctatat atggatagcc caggtaggct aagttgtggc agccacagat   36120
tgttagatga ggagggacac cacagactgt gtatgtgtgt gtgttgaggg caaggtgagg   36180
tgaggaatgg tgcaatgagc ctgcaaacca aattgcaaaa tatatgaaga aatgtagtgc   36240
taagaaaaat agtcaacaaa attaaaaatt gaaaatgaa ttttttcctg ataaaatta   36300
aaaatgtaag taaacctcta attgaagtgt aacacacaaa caggaaagta tgctactcat   36360
aaatgcacag cttaacaaat tttcataaag tgaacacacc tttgttaacc actacttaga   36420
tcaagaaata gagtatcacc tgaattactg gcaggaggca ccccagaggt ctccctgtac   36480
ctcctgccag ttattctcca tgccctccca ctatcccaac cctgccaagc taaccattat   36540
cctaactttt tttcaccatg agaaagaaat ggaaggatat ggaagtgagc ttgagaggcc   36600
tccatggtca gtgaacagtt ctgctaaaat aatttagagg gaataacaaa gaagtagcat   36660
ttgacggcat agtagctgag aatttcctag aatagaaaaa agacatgaat ctttagatta   36720
aaagtatgta gtcattttg atcaagataa agaagaatct acatcaaaac cttttccaaaa   36780
atattgcaga acattgctgc taatgcaaac aagttttaaa ctacttgagg gaaagccatg   36840
acatgtagga gtgatagcag acttcatatt tatgttaata gataccacaa aacaatgcag   36900
taatatcttt aaagttctgg ggaaagaaaa ttataaatag gattttgaga gtgagggcaa   36960
catatttttt tcaaagacta caacttaaaa acccacagag ccccactgaa aggtctacta   37020
aaagatacat ttcagcagga aaaagtgagt cctgaaggaa gacccaaaac aatgatgagc   37080
acaaaacaat ccaaagtcag tggtgggcac aaactgataa aattctagca aatttactcc   37140
ttaatgctaa gaacttcgtt taaattaact ttctatcttt tcagaaaacc aactcttaga   37200
tttgttaatc ttttccatca tttttatagt ttctatgtca tttatttctg ctgtgaactt   37260
cattttttcc ttccttctgt tagctttggg ctttgttctt cttttctag ttccttgagg   37320
tgtaatgtaa tgttgtttga catctttctt cctttttgat gtaggtattt attgctataa   37380
acttccctct tataactgct tttgctgcat ttaatactga ctataataag atacgatgta   37440
atagatttca aggaattatg tatttttgaa taaattaatt ctttaaagtt gcatatccag   37500
ttgcagatga acttcaaaaa tcttgcagtt ttatatctgt tacagtaatt gccaggtttt   37560
gttgttgttg ttttgataca ttagaagttc tagaattgtt atatcctctt gatgaattaa   37620
tcccttatc attctagaat taccttgtct ctttactgtt tgtgacttaa agtctgttgt   37680
atctgatata cctttgcatg gaatatcttt ttctatccct ttactttcag tctatgtgta   37740
tctttaaagg tgagatgagg ttttgtaagt ggcatgtagt tgggtcatgt tttttagtcc   37800
```

```
atttagccat tctctatctt ttaagtggaa agtttaatct atttacattc aagtttattc    37860
ttgatatgtg aaggcttatt cctgtcattt tattaattga tttctggttg ttctgtaggt    37920
cctttgttct tttctttctc tcatattgtt tagcattgtg gtttgttggt tttctatagt    37980
gataacattt gaatcctttc ttgtctgtgt gtgtttgctt taccagtggg tttgatactt    38040
tcgtcatctg ttttttcataa tggtagtaat tgtccttttt gtttgtttgt ttgtttcttt    38100
tttgagacag ggttttgctc ttgttctgtc ctccaggctg gagtgcagtg gtgtgatcat    38160
ggctcactgc agcctcgacc tccatggtct caggtgatcc ttctgcctca gcctctcagg    38220
tagctgggac tacagaaacc tgccaccatg cctggctaat tcttttgtat ttttcgtaga    38280
catggggttt tgccatgttg tccaggctgc tcttgaactc ctgggctcaa gcagtctgcc    38340
tgcctcagcc acccaaagtg ctaggattac aggcttgagc cactgtgcct ggcctgacat    38400
tgttctttga cttccatatg tagaactccc tcaagcattt cttgtaggtc tggtctagta    38460
gtgttgaatt cctcagcttt tgcttgcctc agaaaaacta ttttttcctt gcttaatgaa    38520
ggataatttt gctgggtata gtatccttga cttgcaggtt ttttctttc agcactttc    38580 atatatcgtt ccattctctt cctggcctgt aatgattctg ctgagaaatc tgctgttagt    38640
ctgatggagc ttcccttaga agtgactaga ctcttttttc ttgctgtttt tagaattctc    38700
tctttgtctt tgacaagctg ttgtctctga caacagttct ctctttgtct ttgacaaact    38760
gttgacagtt tgactctaat gtgttgtgga gaacctgttg gaattttgtc ttttttgggga    38820 tctctgagct tctgtatctg aatgtctaaa tctcttgata tacttgggta gttttcagct    38880
attatttcat taaccaggtt ttctattcct tttgtatttt cattgtcttc tagaatactg    38940
aaaattctaa tattagtttg ctttatggta tcccatatgt catgcaggct ttgttcattc    39000
tttttctttt attttgtct aatgggggtta tttcagaaga cctgtcttca agttcagaaa    39060
ttctttcttc gtagatgctc tagaatgtat ttttatttc attaaatgaa ttcttcagtt    39120
tcagggtttc ttgttttctt tttaaatgat atctctctct ttggtaaatt tctcattgat    39180
atcctgagtt gttttctgg tttctttgta ttgtttatct gtatgcgttt gtatctccct    39240
gagcttcttt aatatcatta ttttttaatc tttttctggc atttcatgaa tttctttgc    39300 attggaatct tttggtagaa aattattttg atcctttgga gatgtcatat ttccctatgt    39360
tcccatgttt cttgtgacct tacttctttg atatccacac atctggtgta atcatcactt    39420 ccatttttt gaatttgctt tcatagggta ggactttttc ctgaagattt gactggggtg    39480
tttgttggcc agggcacttt gggtttgaat ctgggtgcat gcagtagtgt agtctctgta    39540
agattttttt tcctttgtaa acagcatcag tggtgtctgt gatttcctca gtggcatagt    39600
gtgtggttgt ggaggctgtg gtgaactttt gctggggatg gtgacaccag ctggactgat    39660
cctcagtcct cagttgtggc agcagttgga caaccatgcc tgtacattag ccccagggtg    39720
gcttacatta gtaatggtgt tagtgggtcc aggcagtcca atttttgggt ctccaggtga    39780
cttgtttggg taccaggagt ggcagtgatg ggctgggcag ctgagtgggt ccacaggccc    39840
ctgggcagtg agcatggcat gggttatgtc agtagcagtg gtaggagaac ctctggctgt    39900
ccagttgtct gtgcttatgt cggcagtgac ggcgattggc tggtaggca agtcctaaaa    39960 cctgcaggtg gcaagtgtga gtgggaacca gctgtgtggg tagtggcagg ttgggtgggc    40020
cacatcctca gaccccaggg tggaatgctc agttgacact ggacgtggac aaactggtgc    40080
gatcccaagg cccccagata acatgcttgg atacgtggga gtggggtgct gagctgggca    40140
gggtgagagt atcctcaggc cctccagtgg tgttagcagg tgctgtttgt ggtgggcagg    40200
```

```
agcaggatga tttccaattt cctggtggaa tgttcaggtg ggggcagcag tggctgtgct   40260
gtgccctgat gctggggagg gtgcagttgc tgtcagtggg agcagttgta gggagttggc   40320
taaggagtgt gcactgcagc tgcaggtgga ggctgtagat gtgatgaagc tgtactcagg   40380
gtgcatgcaa atttgcattt tgacacctag cggcagcagc ctgcaatggt ggcagctgta   40440
ggtggtagag cttgtcctca gggcacatac caatatatgg cagcccttct gctgggagca   40500
gtggggttat tgccaatggc ttgtgctttg gtcccagagg cggcagccag caatggaggt   40560
gactgtcggt ggaggatgtc agtggggctc taggggtgtg gatatgcagg ggctgttggg   40620
ctccagggta ggaggcattc tggtgtgggt tgggctttaa aaatggcacc gtgctgtagc   40680
tgcttaggac tcaggggtgt gttggaccag cataagctcc ctctctaaag caatgtcatt   40740
gtgcagtctc caggcagctc cctatgttac tcccagggcc catgaaagtt gacgggctct   40800
cttgtgtctg ggattgcagg agtttgcagt gaaaatgtgg gccactggga gtctctcact   40860
tactctttcc ccacattgtg caggctctct aggcttctgg ctgatcctgg ctgagcaggc   40920
tgccccactt ccctctcctt ccttgcatta ggtgttttct atcacttctc tgttgaattt   40980
ccgtgttctc tcttagatga cctattcaaa gtgtgattat ctactcgcta ttttggttct   41040
tctttgtgga gcaggtgagt accagataac tctagtcaac cttctggacc cctcttcccc   41100
caatttgaga tctcttcttc tgttgtctgt aactgagttt aatgcttgtt tgttcatgtt   41160
aggattttat atcatcgtcc tcaattaggt tgttaactgg aatttataa tctttgtcca   41220 caggaagttt aaaatgtatg atttcttgca ttgtgctttg tatgtagtaa tacacgatat   41280
ttatccagtt aatggatttg acagccattg ctgtcaagga gcagtccttc tttgtgtatg   41340
aagggtgcct tatcaatatt atttccattt gtaactttat ttatttatgt attcattttt   41400
gagacagggt cttgctgtgt cacccagact ggagtgcggt ggagtgcgga ggtttgctgc   41460
agcctcatcc tcccaggttc aagcaattct tccgctccac tcccagagta gctaggacta   41520
caagtgcgtg ctgccacgcc cagctaattt ttttcttttg tatgttttg tagagatgag   41580 gtttcaccat gttgctgagg cttgtctcca acttctgggc tcaagctatc tgcccgcctc   41640
ggccccgcaa agtgctagga ttacaggtgt gagacactgc gcccagccca tttgtaactt   41700
tattgttttc tcttacaggc aaatgttctg aaaaagactc tgcatgggaa tggcctgcct   41760
tacgatgaca gaaatggagg gaacatccac ctcttctata tatcagaatg gtgatatttc   41820
tggaaatgcc aattctatga agcaaataga tccagttctt caggtgtatc tttaccattc   41880
ccttgggaaa tctgaggcag attatctgac cttttccatct ggggagtatg ttgcagaaga   41940
aatctgtatt gctgcttcta aagcttgtgg taagtattaa aaaacagcat tttccttttt   42000
atgcatggat tgttttaatt atgctatgct aatactaggt acatgcataa tatatatttt   42060
tattttttta atgcttgtat ggctggcgtg tgtgttttca catgcataga aaatgaaagt   42120
gttactggag tacaatttat ggtgaatctg ccttgggcta ggtatcaaaa caattgatg   42180 cccataaatg tttgctgact attctttata attacatata aggtggttaa aaaatcctgt   42240
catgggctat ctcatgacat aaggtaatat taaagctaga tcctgagagc aacatgaaag   42300
caaaaaatta atgttttgaa atatgtattt gatttaaaat cttgattaaa tggctgacaa   42360
accatcattt tcttctagtt agcttctgaa gacctctgcc aatctttcct catatatatt   42420
tcttatgtct ttggtgtatc ttgaaatcat ttttactctt gagacctgat tatattatct   42480
atggaccaaa actgtgaacc agagaactct ttctatagag ctaacacatt ttactagacc   42540
```

```
actgaggtta ctatagagcc tactatcatg gtatctcatt tttaaatgtt cttttaatag    42600
aaagactagt tgacactatt ttgaagaata gtcgtatgat tttatttgta gaggcaaatt    42660
aaatgtctaa tatagtattt ataagaatgt atgattacat caatttattc tcttatttaa    42720
gatcagtata ggtcagaata accattaact gtaagttgga ggaagctagg tacatttcaa    42780
gttccttcta gctattttga aaaatacaat acattgttgt taactatagt caccctactc    42840
ttctatcaaa catttgaact tgttccttct gtctgtattt ttgtgcccat taaccaacat    42900
ctcttcattt ccctcttccc acccatataa ccttgccagt ctctgctacc aatccactct    42960
accttcatgt gatcaacttt ttagctccca catatgaatg agaacttgtt atatttgtct    43020
ttcagttcct ggcttatttc actcgacata atgaccttca gttccatcca tgttgctgtg    43080
aatgacatga ttacattctt ttttacgatg ccactgggcc ccaggggagt acgcattctg    43140
ttgtgagctg ggcttcaaaa tatcaccttg ctgtagctgc ttaggactcg gggggagcgt    43200
gggacccagt gtgaacttcc tcactggaat aggaaatgct tttgtgctgt ctctgggcag    43260
ccctctatgt gaattttttg tcctgcaagg ggctagggtc tctcctgtga ctaaaattcc    43320
aggggttcac agtaggaatg tggaccattg ggcatctcta acttaacctt tccctgtgtg    43380
gagtctctcc tagcttcttg ccaatcccgg ctgggcaggc tgtcttgttt cgtctccttc    43440
cttgcttttc tgttgaatac cagtgttcct cttggataat ctactcaaag tgtgattata    43500
tactcatggt tttagttttt agtggggaag tggatatgag agacctctgg tcagttatct    43560
tgactatatt gtaaagtctg tatttttgt tgtgtgtagt ctctgaaatc tctgatcctt    43620
tagcttatag taagattta gcttgtaaga ttttttagc ttttaagatt ttttagcttg    43680
taagatattt tttagctagt aagattttag cttgtaagat ttttagcttg ggccgggcac    43740
ggtggcttac acctgtaatc ccagcacttt gggaggctga ggcaggcaga tcacaagatc    43800
aggagatcga gatcatcctg gctaatatgg tgaaaccctca tctctgctaa aaatacaaaa    43860
aattagccag gtgtggtggt gggcacctgt agtcccagct acttgggagg ctgaggtggg    43920
agaatggcat gaacccagga ggcggagctt gcagtgagcc gagattcgcg cactgcactc    43980
cagcctgggc gacagagcga gactccatct caaaaaaaaa tttttttttg gcttgtaaga    44040 ttcatttta gcatgtaaga ttttgctttta gcttgtaaga ttttttttg acagatttta    44100 ttgaattcct agggccaaaa gaaataata gaaaagaaca aaaaactctt tcagtctttg    44160
cagattggct ctgtgttggg gctctcattc agtgtttacc cagtccattt acaactctgc    44220
cttagccttc ccttcctgct tgtgctgact ctaaagaaca gcttgaggtg aaagcttagg    44280 gtctttcct ctaagttctg ttccttgggc atgcatatgg cttttctact ctccaataca    44340
tagaaatgct tttcagtgct gtcatttccc aaataaactc tcctctgtca tctctgtttt    44400
ggttttcagt gtgtttattg tttgcctcaa ctttagacct ctgccccaga tagcaacagc    44460
ttgttcattt gcaatgtttt caatgaatat cttctgtgaa gctgcttttc tgccctgaga    44520
aagtcctgaa ttaagtggaa cataggtgtg ctctttgcat catttcttca gtcagtcccc    44580
agtcagggca aaagagagaa aaacagtttt ttgagattaa ggttggctct gttcactcca    44640
gagccaggga ccagagtttc acactggag caccaattgc catcttcaag actttgctta    44700
actaggggga gtggagccgg ggctggtggg caggacatgg gcgtagtggg tggttaaggg    44760
aaagtaaaaa tgctgcacaa cttttcctgcc attttttaagt ggctgttttc ttgattcagc    44820
atttatctga ttgctgcata tctttgccta ttttctgtag tttatatgaa gttcattctg    44880
acagttttta ctcatttttt ttttcctgtt tctgggagaa ggataggtcc ttggaactac    44940
```

```
ctactccacc attttcactg atgttactct tttacttttc taatcatgga agtaaagttt    45000
aagatttttc tatctatatt ggtgagatta cccttggtat cgtagtcaaa ctaaattcac    45060
aaaatgtgtc aatttctctg ttcgctcttg gtctattctc tgtgatagta tacttaagat    45120
ggaattgtct ttcatgtttg gttgaactca aatataaatc ttgtctgggc ctgatggtgg    45180 tttttttcttt cttcattgtt attttgttat tcttcttcct tcccttcttc tgtctctttc   45240
ttgctccttc tttcttttct tcttcttttg tttaagtgga tagagtttgt ttcctttttt    45300 ttttttttgag actgagtctt gctctgttgc ccaggctgga gtgcagcagc atgattatgg   45360
cacactgcca cctccgcctt ccaagttcaa gtgattcatt tccctcagcc tcctgactag    45420
ctggactaca ggcacccacc accacaccca gctaattttt gtatttttgg tagagacggg    45480
gtttgccatg ttggccaagc ttatctcaaa ctcctgactt caggtgatcc acctgcctcg    45540
gcctctcaaa gtgtgtgagc cactgcaccc agccagaatc tatttcttta atggttatag    45600
ttctgttgaa gttttaaatt aatgaatctt tttaaagtta catttcaca aaaattgtcc     45660 atctgtctat attttcaagt ttattggcat aatgttgttc tagcactctt tgtcttcata    45720
acttataatt atgcttttta aaagttctta gtgtttatct gtgcctcttt ttttcttatt    45780
atccttgaca aagatctatt ttgcaaagaa tcatctttta ttttgttact tctccctatt    45840 ggattttat catgtccatc tctaaccttt ctttgggatt actctattgt cttctactat     45900
attgagttag atacttagat catttgctct tattttctaa tataagcaga taaagctaca    45960
atttttcctc ttgagtttca ccttagttgt attccacaat ttttagtaca tgatattggt    46020
aatcattatt cattataaat gcctcccaat gtatttttcc tttgacttct gagttatttg    46080
gaagttattt gtaaataaaa gaatgaatgc aagtatactg tttaaaagtt gctgctaaat    46140
aatgttatta taaataactt accgaaatta ttacacatct gtaagtagac ggtcgtgtta    46200
ataatttaaa ttaagaattt aagtcttct tgtcagtttg tcatttgtgc cgtttctatc     46260
tacagtggaa aatagtgaaa acataactag aataaaatac ttttgtgttc tgtgagcctt    46320
atgttttaaa tataggat taaaaaaatt ttacatattc atttctgatt taattgaagt      46380
gtggttagag aacatggtat gaatggttat tctgtggaac ttctaaagac ttgttttgag    46440
ttcacgtgat tgttgtgttt gtgcttgtgt gtgtacgtgt atgcgtatgt gtgaatgttc    46500
tatatatgct tgaaaatagc ttgtattatt tacttgtgtg gtttaggtat tctcttggtt    46560
ttttagttca gtggctttca accatttgtt gatgtacctt ctaaaatatc ttttaagaaa    46620
ttacatatgc actcacattt taagttgata tttaaaattt ttcattgtaa attaaaatag    46680
cccaaaggac ataattatta atgtattgtg taaaacttga cacattgttc ttttaagagt    46740
attcatgact tctaaatatt tttgtgattt gatacctatt aattaaaaca actccttctg    46800
tgcaaccaca tgcaagcatg gattttatt atacctccag ttcagggaaa cttgaaaatt     46860
tgaaccaacc tttctataga ggacaactga agaaaccaga tgaaatgttt taaaaatatc    46920
tgcttgaaag agtctcagca gttatatttt aaaatactga cacacctcgg agatattgtg    46980
ggtttggttc cagactatcg cagtgaagca aatattgcaa taaagcaaat cacatgaagt    47040
tttaggtttc ccagtgcata taaaagttat gtttaaatta ttctgtagtc tgttaagtat    47100
gcaataatat tatgtccaaa aaagtacata ccttaattta aaaatacttt attgtcaaaa    47160
agcactcata atcatctgag ccttcagtga gtcataatct ttttgttagt ggagagtctt    47220
gccttgatgt tgatggctac tgactgacca gggtggtggc tgctgaaggt tgggtggcta    47280
```

| | |
|---|---|
| tggcaatatc ttaaaataag acaatgaagg ttgctgcatc agtggactct tcctttcgtg | 47340 |
| aaagatgtct ctgtagtatg caatgctatt tgatagcatt ttacccgcag tagaacttct | 47400 |
| ttgaaaatag gaagttgatt cactcaaacc ctgccactgc tttgattaag ttgatgtagt | 47460 |
| attataaatc ctttgttgtc atttcaacaa tattcacagc atcttcacca ggaatagatt | 47520 |
| ccatctcaag aaaccacttt ctttgctcat ccataaaaag caattcctta tatgtccaag | 47580 |
| ttttatcgtg agattacagc aattcagtca cgtcttcaag ctccacttct aattttagtt | 47640 |
| ctcttgttac ttctaccaca tctgcagtga cttccttcac tgaagattaa atccctcaaa | 47700 |
| gatacccatg agagccagaa tcagcttctt ccaaactcct gttaatgttg acattttgac | 47760 |
| ctcctctcat gaactacaaa tgttttcat dacgtctaga atggtgaact ctttccataa | 47820 |
| gttttttat ttactttgct tagatctgtg agaggaaaca ctgtgacagc cataaccttta | 47880 |
| ctaaatgtgt ttcccaaata ataagatttg aaagtcaaat tgctccttat ccatgggctg | 47940 |
| cagaatggat gttgtgttag caggcatgaa acaacatga aattcaatgt acatcttcat | 48000 |
| cagagctctt gggtgaccag gtgcattgtc aatgagtaat aatacttgga caggaatctt | 48060 |
| tttttctgag ctttaggtct caacggtggc ttaaaatatt cagtaaacca cgctatatac | 48120 |
| agatgtgcta tcttctaggc tttgttgtcc catttataga gcacaggcag ggtaattgag | 48180 |
| catagttctt aatggccata gattttcaga atggtcaata agcattggct tcaactaaaa | 48240 |
| gtcacttgtt gcattagctc ctcagaagag agtcattcag ttctttgaaa ctttgaaggc | 48300 |
| aagcactgac ttcttctag ctatgaaact actcctagat ggtatcttct tccaatagaa | 48360 |
| ggctgttttg tctacactga aaatctattg tttatcagtg atctttgtta gatctttgga | 48420 |
| taacttgctg catcctctcc atcaacactt gctgcttcac cttgcacttt tatgttaggg | 48480 |
| acatggtttc ttttcttaaa cctcatgaac cagcctctac tagcttcttg cttttcttct | 48540 |
| gcagcttcct cacctctctc agccttcaca ggtttgaaga caattagggc cttgctctgg | 48600 |
| tttagggttt ggcttgaggg aatattgtgg ctggtttgat cttctatcta gaccactcaa | 48660 |
| acttttgtca catcatcaat aaggctgttt tgctctctta tcatttatgt atttactgca | 48720 |
| gtcgcatttt taatttcatt caaaaacttt ttctttgcat tcagaacttg attgactggt | 48780 |
| gcaggaggcc tggcttttag cctctcttgg cttttaataa taccttcctc acttagttta | 48840 |
| attatttcta gcttttgatt taaagtgaga gatatgaaac tctttaatat atgaaactct | 48900 |
| tcctttccct tgaatgccta gaggccattg taggattatt aattggccta atttccatat | 48960 |
| tgttgtgtct cagggaatag agaggcctaa ggagagggag agacacagga atggctgttg | 49020 |
| ctggagcggt cagaacacac acagcatttg ttgcttatgt ttgtcatctt atatgggcac | 49080 |
| ggttcatagc ggccccaaat gattacaatt gtaatgtcaa agatcactga tcacagatca | 49140 |
| tcataactga tataataata aaaaagtttg aagtattgca agaattacca aaatgtgaca | 49200 |
| tagggacaca aagtgagcac gtgctgttgg aaaaatggtg ctgacagact tactagattc | 49260 |
| acacttgctc taaatcctta ttttgtaaag aaaaaaaccc cacaatatct gcaaagtaca | 49320 |
| ataatgcagg gtgcactaaa atgaagtatg tttgtataaa aaaagattgt gattaataat | 49380 |
| tcagttgtag gggttggtat atcaaaagat ttcgactgct attacatttt gttccgattt | 49440 |
| taagagttgt tactttagct tcatttcaaa ttataggtgc tatgtaaaaa tattctgttg | 49500 |
| tgtacccttta ataattcctt tctctgcttc ttttctaggt atcacacctg tgtatcataa | 49560 |
| tatgtttgct ttaatgagtg aaacagaaag gatctgtgat ccacccaacc atgtcttcca | 49620 |
| tatagatgag tcaaccaggc ataatgtact ctacagaata aggtactttc ttcagtaaag | 49680 |

```
taactcactt aatgctaaaa ggcaaaatgg gagaaattat caaatatttt ttaattgcaa    49740
ggtacttaat accagatacc tgaaccaatt agttagcact catttaagat ttcatttaag    49800
attctattct gtttctccat cagagaaact gtttatacat gttgtgtaag tagaatactc    49860
tgagaataaa gctgttttgg tgggatgcca cttaactcct tatgattata attaaataag    49920
taaacaaaat cacagtggcc tttattaaca aaatcctaaa tgtttgggat attgctggtt    49980
tgtgcagcgt tttgtgcaat agaatgcaat ttcacatctt atctttataa agaacttttt    50040
aaaaagttga cgtgaagaaa agagactttt cccagtgtgt atttgcagcc tcaaattgta    50100
agttaattta tataatttat ggtaatgtgt aatgcctatt tagagaaatc tagaagtatt    50160
tttttgctcg aaaggatgaa acaaagatac gtttgatttg tgtctcacaa atacctgtga    50220
tttttctaag catttatata catatatata taattcatca taacttcatg aggtgttaag    50280
atttccacat taaagataaa gaatttggag cactgagaag taatattact caaatttatt    50340
catggtcaca caggtaggaa ttgggagtca ggttcaaatc caagcctggt ttgcttcata    50400
agcttgcctc ttaatcacct catgtgtact tcattaaaga gataatgtat atataatatt    50460
tattattgtg cctatcactt ggtgctctct caataaattt tagtattgtt ttgcttcttt    50520
ctcttcccct attctatata aaaatatgca gttggatgtg tttgcattta ctgatgtcta    50580
atgtataatt tgcactgagt tcaaaaaaat attttttata taattattga aaagacaatt    50640
ggtgaaaaaa ataaatgttc aaagaaataa tagatgtaca aaaatcaaca gcattcttat    50700
atgcaagcaa ccagttatat aatagataaa gaagatccta tgcagtgtag ctacaaaaac    50760
ccttaactaa ccaggaatgg tcttaataag aaaaaacaga agacagtata ggaaaattag    50820
aaagttattt gaagaaatatg aagaattagg acataacatt ggaatgggga gatgaatat    50880
tacaaagatc aatttctctt atgctatatc cttagctcta agccaatcaa aatcctaaca    50940
aaggcatttt acggaatttg acacattact atgtaaattg agaattatta aataagatag    51000
ccatgagaaa gaagacttac ctggcaattg taaaatattt tgtcccagga gatattttca    51060
cattatatga aactacaaaa tggtatctat tattaaagcc acataattaa attcagaatc    51120
ataaactaaa taatgagaat gatggggcca gtatatcttg aaagtactcc ttcatacata    51180
tagaaacata ataatatgaa gaaatctttt catattaacg tggaagggag agattagtca    51240
acaaatggtg gtagaatagt tgattagctg tttgaataaa attttagctt cttactttat    51300
aatgtatatc agataaatta tagattgatt aaagatcaga ttgatatgta aatagaaatg    51360
taaagaaaat caaactataa aagtctgaat tggaactgaa ttcaagtcct tgggaaaata    51420
ccatttaagt tgcaaaacaa tagaaaaaat catatgggaa tgactgcaat tgtcaactat    51480
aaaaattttc aaatgtctga aggtttcctc ttaaaatgaa aaggcaggag ggtggagcca    51540
agatgactga ataggaacag gtccagtcta cagctcccag catgggcgat gcagaagacg    51600
ggtgatttct gcatttccaa ctgaggtgta ccgggttcgt ctcactgggg agtgtaggaa    51660
agtgagtgta ggacagtggg tgcagcacac tgagcatgag ccgaagcagg gcgaggcatc    51720
gccacacccg ggaagcgcaa agggtcaggg aattcccttt cctagtcaaa gaaaggggtg    51780
acagacggca cctggaaaat cgggtcactc ccactctaat actgcgctat tctaacggta    51840
ttagcaaatg gcacatatcc cgcgcctggc tcagagggtc ctacgcccac ggagcctcgc    51900
tcattgctag cacagcagtc tgagatcaaa ctgcaaggtg gcagcgaggc tgggggaggg    51960
gcgcccgcca ttgccgaggg ttgagtaggt aaacaaagca gccaggaagc tcaaactggg    52020
```

```
tggagcccac cacagctcaa ggaggcctgc cggcctctgt agactccacc tctgggggca    52080
gggcatagcc aaacaaaagg cagcagaatc ctttgcagac ttaaatgtcc ctgtctgaca    52140
gctttgaaga gtagtggttc tcccagaatg cagctggaga tctgagaacg gacagactgc    52200
ctcatcaagt gggtccctga accccgagta gcctaactgg gaggcacccc caagtagggg    52260
gagactgaca cctcacatgg ccgggtactc ctctgagaca aaacttccag aggaacagtc    52320
aggcagcaac atttgctgct caccaatatc cgctgttctg cagccactgc tgctggtacc    52380
caggcaaaca gggtctggag tggacctcca gcaaactcca acagacctgc agcagagggt    52440
cctgactgtc agaaggaaaa ctaacaaaca gaaatgacat ccacaccaaa accccatctg    52500
tatgtcacca tcatcaaaga caaaggtag ataaaaccac aaagatgggg aaaaaacaga    52560
gcagaaaaac tggaaactct aaaaatgaga gcacctctcc tcctccaaag gaacgcagct    52620
ccttaccagc aacggaacaa agccggatgg agaatgactt tgacaagttg agagaagaag    52680
gcttcagacg atcaaactac tccaagctaa aggaggaagt ttgaactcat ggcaaagaag    52740
ttaaaaacct tgaaaaaaaa ttagacaaat ggctaactag aataaccaat gcagagaagt    52800
ccttaaagga cctgatggag ctgaaaacca aggcacgaga actacgtgat gaatgcacaa    52860
gcctcagtag ccgattcaat caataggaag aaagggtatc agagatgaa gatgaaatga    52920 atgaaatgaa gtgagaagag aagtttagag aaaaaggaat aaaaggaaac aaacaaagcc    52980
ttcaagaaat atgggactat gtgaaaagac caaatctacg tctcattggt gtacctgatg    53040
gggagaatgg aaccaagttg gaaaacactc tgcaggatat tatccaggag aacttcccta    53100
atctagcgag gcaggcaaac attcaaattc aggaaataga gagaacgcca caagatact    53160 ccttgagaag agcaactcca acacacataa ttgtcagatt caccaaagtt gaaatgaagg    53220
aaaaaatgtt aagggcagcc agagagaaag gttgggtaac ccacaaaggg aagcccatca    53280
gactaacagc agatctcttg gcagaaactc tacaagccag aagagagtgg gggccaatat    53340
tcaacattct taaagaaaag aattttcaac ccagaatgtc atatccagcc aaactaagct    53400
tcatatgtga aggagaaata aaatccttta cagacaagca aatgctgaga gattttgtca    53460
ccaccaggcc tgccctaaaa gagctcctga aggaagcact aaacatagaa aggaacaact    53520
ggtaccagcc actgcaaaaa cacgccaaat tgtaaagacc atcgaggcta ggaagaaact    53580
gcatcaacta atgagcaaaa taaccaggta acgtcataaa gaccggatca aattcaccca    53640
taacaatatt aaccttaaac gtaaatgggc taaatgctcc aattaaaaga cacagactgg    53700
taaactggat aaagagtcaa gacccatcag tgtgctgtat tcaggaaacc catctcacgt    53760
gcagagacac acataggctc aaaataaagg gatggaggaa catctaccaa gcaaacggaa    53820
aacaaaaaaa ggcagggatt gcaatcctag tctcggataa aacagacttt aaaccaacaa    53880
agatcaaaag aaacaaagaa ggccattaca taatggtaaa gggatcaact caacaaaaag    53940
agctaactgt cctaaatata tatgcaccca atacaggagc acccagattc ataaagcaag    54000
tccttagaga cctacaaaga gacttagact tccacacaat aataatggga gactttaaca    54060
ccccactgtc aacattagac agatcaacaa gacagaaagt taacaaggat atccaggaat    54120
tgaattcagc tctggaccaa gcagacctaa tagacatcta cagaactctc accccaaat    54180 caacagaata tatattttca gcaccacacc acacctattc caaaattgac cacatagttg    54240
gaagtaaagc actcctcagc aagtgtaaaa gaacagaaat tataacaaac tgtctctcag    54300
accacagtgc aatcaaacta gaactcagga ttaagaaact cactcaaaac cactcaacta    54360
catggaaact gaacaacctg ctcctgaatg actactgggt acataacgaa atgacggcag    54420
```

```
aaataaagat gttctttgaa accaacgaga acaaagacac aacataccag aatctctggg   54480
acacattcaa agcagtgtgt agagggaaat ttatagcact aaaggcccac aagagaaagc   54540
aggaaagatc caattgacac cctaacatca caattaaaag aactagaaaa ccaagagcaa   54600
acacattcaa aagctagcag aaggcaagaa ataactgaga tcagagcaga actgaaggac   54660
atagagagac aaaaaaccct tcaaaaaaat caatgaatgc tggagctggt gttttgaaaa   54720
gatcaacaaa attgatagac tgctagcaag aataataaga aaagagagaa gaatcaaata   54780
catgcaataa aaaatgataa aggggatatc aacccgatcc cacagaaata caaactacca   54840
tcagagaata ctataaacac ctctacatga ataaactaga aaatctagaa taaatggata   54900
aattcctgga cacatacacc ctcccaagac taaaccagaa agaagttgaa tctctgcata   54960
gaccaataac aggctctgaa attgaggcaa taattaatag tttaccaacc aaaaaaagtc   55020
caggaccaga tggattcaca gctgaattct accagaggtg caaagaggag ctggtaccat   55080
tccttctgaa actattccaa tcaatagaat aagagggaat cctccctaac tcattttatg   55140
aggccagcat catcctgata ccaaagcctg gcagagacac aaccaaaaag gagaatttta   55200
taccaatatc cttgatgaac attgatgcaa aaatcctcaa caaaatactg gcaaaccgaa   55260
tccagcagca catcaaaaag cttatccacc atgatcaagt gggcttcatg cctgggatgc   55320
aaggctggtt caacatatgc aaatcaataa acgtaatcca gcatataaac agaactaacg   55380
gcaaaaacca tatgattatc tcagaggcag aaaaggtctt tggcaaaatt caacaaccct   55440
tcatgctaaa aactctcaat aaattaggta ttgatgggac gtgtctcaaa ataataagag   55500
ctatctatga cataccgaca gccaatatca tactgaatgg acagaaactg gaagcattcc   55560
ctttgaaaac tggcacaaga cagggatgcc ctctctcacc actcctattc aacatagtgt   55620
tggaagttct ggccagggca gtcaggctgg agaaggaaat aaaggttatt tgattaggaa   55680
aagaggaagt caaattgtcc ctgtttgcag atgacatgat tgtatatctg gaaaacccca   55740
tcgtctcagc ccaaaatctc cttaagctga taagcaactt cagcaaagtc tcagcataca   55800
aaatcaatgt gcaaaaatca caagcgttct tacccaccaa taacagacaa acagagagcc   55860
aaatcatgag tgaactccca ttcacaattg cttcaaagag aatacctagg aatccaactt   55920
acaagggatg tgaaggacct cttcaaggag aactacaaac cactgctcaa tgaagtaaaa   55980
gaggatacaa acaaatggaa gaacattcca tgctcatggg taggaagaat caatattgtg   56040
aaaatggcca tactgcccaa agtcctttat ggattcaatg ccatccccat caagctacag   56100
atgactttct tcacagaatt ggaaaaaact actttaaagt tcatatggaa ccaaaaaaga   56160
gcccacattg ccaagtcaat cctaagccaa agaacaaag ctggaggcat cacgctacct   56220
gacttcaaac tatactacaa ggctacagta accaaaacag catggtactg gtatcaaaac   56280
agagatatag accaatggaa agaaataatg ctacctatct acaaccatct gatctttgac   56340
aaacctgaca aaacaagaa atggggaaag gattccctat ttaataaatg gtgctggaa   56400 aactggctag ccatgtgtag aaagctgaaa ctggatccct tccttacacc ttatacaaaa   56460
attaattcaa gatggattaa agacttaaat gttagaccta aaaccataaa acccctagaa   56520
gaaaacctag gcaataccat tcaggacata agcatgggca aggacttcat gtctaaaaca   56580
ccaaaagcaa tggcaacaaa agccagaatt gacaaatggg atctcattaa accaaagagc   56640
ttctgcacag caaaagaaac taccatcaga gtgaacaggc aacctacaga atgggagaac   56700 attttttgtaa tctactcatc tgataaaggg ctaatatcca gaatatacaa tgaactctaa   56760
```

```
caaatttaca agaaaacaac aacccccatca aaaagtgggc gaaggatacg aacagacact    56820
tcttgaaaga agacatttat gcagccaaaa gacatgaaaa aatgctcatc accactggcc    56880
atcagagaaa tgcaaatcaa aaccacaaag agataccatc tcacaccagt tagaatggcg    56940
atcattaaaa agtcaggaaa caacaggtgc tggagaggat gtggagaaat aggaacattt    57000
ttacactgtt ggtgggactg taaactagtt caaccattgt ggaagtcagt gtggcgattc    57060
ctcagggatc tagaactaga aataccattt gacccagcca tcccattact gggtatatac    57120
ccaaaggatt ataaatcatg ctgctataaa gacacatgca cacgtatgtt tattgcggca    57180
ctattcacaa taacaaagac ttggaaccaa gctagatgtc caacaatgat agactggatt    57240
aagaaaatgt ggcacatata caccatggaa tactgtgcag ccatgaaaaa tgatgagttc    57300
atgtcctttg tagggacatg gatgaagctg gaaaccatca ttctcagcaa actatcgcaa    57360
ggacaaaaaa ccaaacactg catgttctca ctcttaggtg ggaattgaac aatgagaaca    57420
catggacaca ggaatggaac atcacatacc ggggcctgtt ctgggtgggg ggatggagg     57480
agggatagca ttaggaaata tacctaatgt taaatgacga gttactgggt gcagcacacc    57540
aacatggcac atgtatacat atgtaactaa cctgcatgtt gtgcacatgt accctaaaac    57600
ttaaagtata atagaaaaaa atgaaaaggc aaattgtaaa gatagtttca acaaatcaaa    57660
taaacataag gttagtattc ttgtaagtat gaaatttaaa acagtgtatc catttaacaa    57720
ttacttaatg tacatgaata tatagcgtca ctagttatga gaataatgaa cgagattgct    57780
tgctttagca catagttaca actattcatt attcttataa ctagtgatgc tgagaatttt    57840
ttgaaaaggc cattaatgat ttgttcttct tttgttaaat atttcttcat gtacattaaa    57900
taattgttta atggatacag tgttttttaat gccaacaaat tagaggatca agatgaaatg    57960
gacaaattcc tagaaagaca caagttatag gaactgctaa aagaaagaac agaaagtttg    58020
aataggtcta tgacaaataa agaaatcaaa ttagcaattt ttataaaagc ccaggcccaa    58080
gtggcttcac ttgtgaattc tatcacacat taaaaaaatt attactagtt attcacaaaa    58140
aatagaaaag gaaggaggat ttctgagctc tttctgtgag ttcagtatta ccctgataac    58200
aaattcagac aaagatgtct agaagaaaag aaaactacag accaatgttg taggtagaaa    58260
atcaacaaaa tacttgcaaa ccgaatccag caatacagct tgaatatgtc ttatctgaaa    58320
tgcttgggac cagaagtgtt ttggatttta gatttttttt ttttttttg gattttagaa    58380
tatttgcaga gtatacgctg gttgaacata cctaatataa aaatctaaag tctgaaatgc    58440
tctgatgaat atttcttttg cacatcaggt tagcgctcta aaggttttga attttggagc    58500
atttcggatt tcagattttc aggttaggaa tgctcagttt gtttataaaa agatgaaata    58560
ctatgaccag gtgggattta tcccaggaaa tacaaggcta gtgtaacttc caaaaatcaa    58620
tcaatgtaat acaccacatt aatagaataa atgaccaaaa ccacatgatc atcccaagag    58680
acacagaaaa agtatttgat aaaatccagc atcccatcat tataaaaaaa ctcaacacaa    58740
taggaatggc aaggaacttc ctcaatttgt taaagggcat ctgtaaaaaa ttcaaaagta    58800
atgtcatact tattagtgaa agactgaatg ccttttccct atgatcagga atgagatgag    58860
gatagctact tttaccactt tgatttaaca ctatactgta gattcagggt agggaaatta    58920
ggcaagaaaa agaaataaaa ggcatttata ttggaaaata agaagtaaaa ttgtagtcat    58980
cccgctgtat ccatgggttt cacatccatg gattaaacca actgcagatt gaaaatactt    59040
ggaaaaaaag ttgtgcttac actgaacatg tacagacttt tcttgtcat tactccctaa     59100
agaatacggt ataacaacta tttacataac atttacattg tattaggtat tataaatagt    59160
```

```
ctagagattt taaagtatac tgaaggatgt gcacaggtta tatgcaaata ctatgccttt    59220
gtatatcagg aacatgagta tttgcagatt ttggtatgtg tgggaggttc tggaactagt    59280
actgcataga taccaaagga tgattgtgta ttcacagatt acatgatctt gcatattaaa    59340
aatcctaagg aattaataaa aaaactatta gaactaataa atgagctcag gtcagttgca    59400
gaatagaaga tcaatatata aaaatcagtt gtatttctat acagagacaa agaacaatcc    59460
aaaaatgaaa ttaaaaaaat ttcattaaca atagcataac aaattttag gaataaactt     59520
aaagaagtgt aaaatgtata cactgagaaa tataaaacat cattgaaaga aattaaggaa    59580
acacctaaat aaatggaaag atatctcata gaggacttca tattttaag atggcaatac     59640
tccttaattg atctgtatgt tcaatgcaat cctactgaa ttcctaaatg tctttattgc      59700
agaaattgac aggttaatca taaatttata taaaaagcaa agggacttag catagctaaa    59760
acaatcttga aacaatacaa agtttgaaga cttatacttc ctaattacaa aatttattac    59820
aaaaggactg taatcaagac aatgtgatac taaaggatga atatacagat taatggaaag    59880
gaattgacag tctcaatata atttctcaca ttgatggtga ttgattttg atcagggtgc      59940
caagacaatt catgggcata gaatagtctt ttaaactaac agtgcgggga caactggata    60000
tccacatgta aactaatgaa gtaagacaat ctacttcaca ctatatacaa aaaaaaaag     60060
cttaaagtgg atcataggcc tatatatgag agctaaactt attaaaactc caagaagaaa    60120
cacagaagtc tttgtgtact tagattaggc agtggtttct tagatatgac accaaaagct    60180
caagtgacaa agaaaaaata gttaagttag gctttatcaa agttaaaaac atctgtgtgt    60240
caaagcacac tatcaaaaat gcgaaaagac cacccacaaa tgggttccac aaaatggaag    60300
caaatgtttg ggaatcatat atctgataat tgtcttatct ccagaatata aagaattct     60360
tacagctcaa caagacaatg acaacttaat ttaaaaagta ggcaagggac ttggatagac    60420
attttttccaa ataagatata caaatggcca aaaagcatgt aaaaagatgc ccaacaggtg    60480
ggcccctgag cgggcgtccg ggaccgtggt gtgccaggcg ccttccgccc ttaacatgcg    60540
gtggctggcc caggcggtgc aggagctgga gcggggcccg agtggggcgc cagagcccca    60600
gcgcgagcag gagaggggcc ggagcgcgga tccgcgccgc gctgctgaag cctggccggc    60660
cacccagacg ctgccggcag cctggccatg gcggagccaa ggaaagaatc tctatacaaa    60720
caaatatgtg gctatcaaat tggagctgat caagttccgg accccgcagc tgcacctggg    60780
taccggttct acaagcagct cagcgccata gagggcgtcc ctcaggtcta ctacctacta    60840
cagcctggag gacctgttcg accttcacgc ccaagacggt gctcctgatc gccatccggc    60900
tgatcacgcg catggattat gtgcacacca agaacctcat ttaccaggac gtgaagcccg    60960
agaacttcct ggtggggcgc ccggggacca agcggcagca cgccatccac atcatcgacc    61020
tcgggctggc caaggggtac actggtctca ggaccaagaa gcacatcccg tgcagccagc    61080
acaagagctt gacaggtacg gcgtgctaca tgagcatcaa catgcacctg gcaaggagc     61140
agagccactg caacaacctg gaggtgctgg gccacatgtt catgtacttc ctgtgcagca    61200
gcctcccctg gcaggggctc aaggctgaca cgatcatgag cggtacagaa gatcggggac    61260
acatagcgcg ccacgcccat cgaagtgctc tgcgagaact tcccagagga gatggctacg    61320
tacctgcact acgtgcggcg cctggacttt gagaagcccg actgtgacta catgcggcgc    61380
ctggactttg agaagctcga ctacgactac ctgcggaagc tctccagcta cctcttcgac    61440
cgaagcggct tcgtgttcga ctctgagtac gaggggctcg ggaagcccct tggcgacccc    61500
```

```
atcagcagtg tccacaccga cctgccctcc cagcctcagc ttcgggacaa agatcagccg   61560
cacagcaaaa accaggcgct gaactccacc aatggggagc tgaacgcgga cgaccccatg   61620
gccggccact ccagcgccca tcagggcgcc tgcagagatg gaggtgggcg atgaaacgaa   61680
atgctgctgt ttcttccccc tgaatcttct ccgtgcggcc ccttggggag cgagcttgtg   61740
tgagggcctt ggggcccacc cacagcggcc cagggccaga cgctggctgg aagccaggac   61800
acagactgca gggtcttggc cggcggcccc atccccggga cgaggggtca cttccttcac   61860
gtaagactgg ccaaaatttc tttttttttt ttttttttt ttttgagacg gagtctcgct   61920
ttgtcgccca ggccggactg cggactgcag tggcgcaatc tcggctcact gcaagctccg   61980
cctcccgggt tccgccatt ctcctgcctc agcctcccaa gtagctggga ctacaggcgc   62040
ccgccaccgc gcccggctaa ttttttgtat tttagtaga cggggttt caccttgtta   62100 gccaggatgg tctcgatctc ctgacctcat gatccacccg cctcggcctc ccaaagtgct   62160
gggattacag gcgtgagcca ccgcgcccgg ccaagactgg ccaaaatttc tacacctgtg   62220
tctagtcctc ccctccaaga gcattaacta tttaaaacaa ggaataaagg aaaaaaaaga   62280 aaggcccct ccaccccac ccctccatta ctttgctgaa gtgagtagtg ggatcctgga   62340
ggcccccagg gctgaggccc agccagctgc ccccgttagc gtcataaagt ccagcttgtc   62400
tccctcatcc aaaggccgtt ttctcagtgg gagggcaggc ctggcctgga ggggtgctgt   62460
ggggccatct tgcccaggcc cacctgggag ggacacaggc attgctgcca ggggtgaggc   62520
tgtgccccag gcctcccaa aactaaaggg gaacggaggg gtggggccgc ggctgaagcc   62580
agccccgcaa ccaaaatgct gcaccaaagc tcggtcgcca caggcacggc caccgcagcc   62640
tttcacagcc tggccccggc gaggggcagg tgggccctgc taggagggtg cttctcgagg   62700
cacctgttcc ccgaggctgt gctccgaccc tcagaagctg aggggggtgg gccggctggc   62760
gtcgcgcggc tcggcccctg ggccctgctg tgtggaggcg cgcgggctcg tggcttcctg   62820
tctctgtgct ccgccccctg gcaagcagcc gcagacaaaa tgccttaaag ccccgaccc   62880 agccccgcag gtgtatgtgc agggggggtct gcgggcggcc ctggactggc tggcggactc   62940
ccagcgggtc agcttgaggc agtgcccagg gcggtggccg tgagtctggt ttttgcttta   63000
ccaagtgtac ggaaatggcg tttacgtttc tctgatgctc ttttgaagcc atacaactta   63060
ggggctttaa aaaaaaaag gaaaaatgaa accctccgaa aaaagatgc ccaacatcat   63120 tggtcattag agaaatacaa atcaaaacca cgatgggata ataataggtc tacaaggatg   63180
gcaaaaatca gaaagacaaa caataacaag tgttagagaa tttggactaa tttggatgca   63240
gtatattgct gttgggaatg taaagtggtg ctgctacttt ggaaaacagt ttggccattc   63300
cttaaagggg taaacaaaga gttaccatat gactcagcaa ttctacttct agatatatat   63360
gcaatagaaa tgaaaacata tccacaaaaa cttgtacatg actcttcata ctagcgttat   63420
tcacaataga aaataatag aaacaaaccc aaatgtctgt caggcgatga atggatacag   63480
aaaaagtggt atattcatac aatgaaatat taatttggca ataaaaggaa atgaagtaat   63540
gatacatgct ctaatgtgga tgaaccttga aaacattatg ctgagtgaaa gaaggcagac   63600
agaaaggcca catgttctaa aattagattg tgatattgt acaatgctat gaataaacta   63660
aaaacattga attttacact ttaagtgggt ggactttatg gtatgtgaat tatatctcaa   63720
taaaggtgtt actaaaagac aatatagagt gttctttgtt tctctgaagg acaagttttt   63780
aacttccatt tctccaaata agcaattatt tgttttata ccaaattagc attttcgat   63840 tccctactga tgttactgga ttaagctatg ttttaactt tttgttaatt tctacatttt   63900
```

```
ttgtttccta ctattgcttc tacattttgt gcactgaagg aggtagtata ttgattttac   63960
acttacattt cttgtacttt ctgcctatat tagtgttatc cacatatcct tttgtctcac   64020
atttatattt aatactgtta gctgtgtttt ctaagtatgg gataatacct ttcagtatgc   64080
tgtaggtgac tatatataga tagtacgttt gtatttgaac tatttggaag ctgaccaaat   64140
gtttttatta tcttgtagat tttactttcc tcgttggtat tgcagtggca gcaacagagc   64200
ctatcggcat ggaatatctc gaggtgctga agctcctctt cttgatgact tgtcatgtc    64260 ttacctcttt gctcaggtat gattatatta tcttacttgt acatgagtta aatgataaat   64320
atcttgctgt ttaataagtc acttaatcag gaaaaacttt acatatggga aaattgcagt   64380
tctgtcttgc acagcaggtg cagagaagta acaaaattga gtcttttagc actagttttt   64440
aatcccatgg tttatggata atagaatcta ttttataaag ttttttttgga ctgatccttt   64500 tgaatttctt tctttttttag gactttagat cattttaagg atttcgcaaa gtatagactg   64560
aggtttacaa catgattcat gtagacatac gtggctaaaa tattagtaac atttctttat   64620 ggttttaaa aaaattttg gacaatttca ggcttacaca atggacaatg aactgtagag    64680
aaagtaggtt acataaaaaa atgagctctg atagtttgtt tagctgttta taggaaggtg   64740
actggatgtt gatacttagt ctaagagcta tattcaagtt atttgttcac taatacagtt   64800
atgtcaaatt tttgtattgt gttggtattt cataatgctt tcttctctat taccttgatt   64860
taaacagtaa ttgaaatatt ttgtcattaa ataacttgtt tttatgtgct gctagactag   64920
taggaataga aattaaagga agaaaatata ttagtgctct tgggtaaaaa taggcacttg   64980
gtatccccaa ggtatcagga gttctaaatc agatttgcta atattgtagg aaacaagccc   65040
acagatcctc atggctcgca tttctgagag gaagcctagt aagcctagtt cagtttatga   65100
acaacaaaag gaaaaacatt tctctattgg ggtatgagac caacaaactt tatttttatt   65160
gtggtaagag atatataata aaaatgacca ttttaaccat tttaagtgta cagttcagtt   65220
gtattaagta caaatacatt gctgtacaac catcaccacc atccatctcc agaacatttt   65280
tcatcttccc aaatgaaaac ttcataccca ttaaataata actctgtatt tcccactccc   65340
aatggccttt tgcaatcacc attctacttt ctgaatataa atctgccttt tctatgtacc   65400
tcatacaaat ggagttatat agcatttgtc cttttttgac tggcttattt cacttagcat   65460
aatgtctgtc aggttcatcc atgttgtagc atgtgccaga atttctttcc tttttaaggc   65520
tgaataatat tccattgcat atgtatactg cattttattt gttcattcat ctgttgatgg   65580
atacttgggt tgctgctgtg aacatgggta aacaaatatt tccttgagtc cctgttttca   65640
gttcttttca atatataccc agaaatggaa tcgctggatc atatggtaaa tttataattt   65700

tttttgagga actgctacat tgтттttctgt agtggctgca ctatttttca gtcctaccag   65760
cagtgcacaa gtgttccaat ttctcaacat cctcaacaat gctttgctttgtttgataat   65820 agccatctct atgggtttga ggtggtatca tt gtgatttt gatgcatact tctctaacaa   65880
ccagtgatca tgagcatctt tcatatgct tgttggccat ctgtttatct tctttgcaga    65940
gatgttgctt gттggcтаттт гтттатсттcттттgсаgаg atgtctactg аагтccтттg   66000

cccattttta aatcaggttg tttgtttgtt gttatattat agaaattatt attctggatc   66060

ттаасccтт атаагатаса тgатттgтаg атаgтттттc ccatt ctcta ggttgccttt   66120

tcatt ctgtt gcттgтcттт тgатggacaa аагтттаааа тттggcтgтa тт ctaatt ta   66180

tctattt ttt gtttcctatg tttttggtgt catatccaag aaaatcatt gc сааатcсаат   66240
```

```
gttatgaacc tttctttctg ttttcttgta agagttttat cattttagct cttacattta   66300
ggcattgggt ccattttgag ttaattttttg tctatcgtga aggtaagggc ccaacttctt   66360
ttgcttgtga atatccagtt ttcctagcac catttgttga aagactgtct tttctccatt   66420
gaatggtctt ggcacctttg ttgaaaatca tttgaccacc aacctacttt tttatacagc   66480
tcctttatct gtatagccat tatgaaaaga gaggggaatg gagagaggct tctaagaata   66540
gccttttgaa aacaggatat tatgaggtta caactttctg ttgcttttac gggtatatta   66600
tttcacctgt gctgcagagc tagtatattt tgggggtagg ctagttaagt cccatttata   66660
agccaagttt tcccaaacta ttcattcagc tactttagcc taatattaat actgcaatgt   66720
ctagtatttt tgatctagaa aaattttggg tgatttcaga atactcaatt ttatccttct   66780
aggaaggatt gtcttatcta gcatggcaag gtaattccac catataattc taaattatgt   66840
ctagatagta ccacaagcaa ttttctattt tttaatgttt ttacttctct aaatttgtgc   66900
ccagaaaata tgatagtatt tagattactc taagattgta ctgttatcat tttatattat   66960
atgcatgttg tagactatat atagcaaatg tgaccagtgg cattaccaga gtgtaagaat   67020
atcttgacat cttaaaataa ccaaaaaata gataagccac tgaactgtct ttaaagttct   67080
taagacagta cctgtaggaa gacagatttg gaaaggtaa gcaaataaaa atcaaaagta   67140
agatggccct tttaaaattca gtttcctctg ggaattaatt gcctttatat catcaaatat   67200
ggctgctaag caaataaact gctgacatgt gaacaacttt taattaattc atatctattc   67260
aacaacaatt ggatgtttac ctcatgttct tggcatcatt tctgattttg tgactgtgac   67320 tgtttttat ttccctggct aatgaagatg taaatttctt aagttcaaat tttgtcagct   67380
actcaaatga gaaaaggttt tcttcttat tttattttt tatagagatt gaactcctgg   67440
gctccagtga ttgtcttgct tcagcctgtc agcctcctga gtagctaggt acaggtgtgt   67500
gccactatgc ctggctaatt ttttagttt tggttttgtg gagatggggt ctcgctctat   67560
tgtccaggct ggtttcaaac acctggcttc aaatgatcct cctacctcag cctcccaaag   67620
tgctgggagt acgagtgtga gccaccacac ctggcctgaa attttcagt agttctaatt   67680 aaatgaaatt tctgagggta catactataa tatttaagga atagtattta ttatgttttg   67740
gcatttgaga ctcttccatt tgtaacttttt ctctagtgaa tagtttatta tgtttttagt   67800
attgccatca ctcattttttc atatatttat tgtcttctga tcatgacttc catagaattt   67860
ccacatgagc agaatttgtt atctaccagt tcttttcttt tctttcttt tttttgagat   67920 ggagtctccc actgttgcct gggctggagt gcaatggcgt gatctcggct cactgcaacc   67980
tctgcctccc aggttcaagt gattctcctg actcagcctc cctagtagct gggattacag   68040
gtgcctgcca ctacgcccgg ctaattttttt gtatttttag tagagatggg gtttcactat   68100
gttggccagg ctggtctcga actcctgacc ttgtcatctg cctgccttgg ccttctaaag   68160
tgctgggatt acaggtgtga gccactgcac ccagcccatc tactagttct atagggaacc   68220
aaggcaggct attaaaaaga atctaccaag tcattgatca tcttctactt aaacagtata   68280
acttacttgc ctgttctcaa aagtgtggtg aaataagtgt ttaaaattga gcaaaaatct   68340
gtctcctacc ctgaattaat tttgtattag caacgtttag gcctttgttt tgggtgatac   68400
tgattatttg atggtgtggt tcttaatagt ttattttctt atatgaaaat atcttctata   68460
ttttattaat agaaaagcaa atatacttttt aaatatgttt cttttaataa aattagttta   68520
aaaaggttcc agtaaagctt taatttcatg agacaagtta ttcatcaag agaagagaaa   68580 tacagatgta gagtatagag ggcccttgtc cggtttaaaa ccttgattcg cattgttatt   68640
```

```
ttaggtaata tggctcttac ctttttttct acaaagaaaa ttggtattat gtttagaata    68700
tttgtacttc tgctttcttt ttctttctcc cattacatgt tcagtcagat ttatctgtat    68760
tcctaaatcc tccaggtcaa aatcgtagaa cctctgtgtt tctctcttct tcattcttta    68820
gacaatatat agttaataaa gttatcagcc ttttttcaga atcttttagt atcttctgtt    68880
tcctggatca gatccttatt atttcgtatc tgagccatac accagcctct taaagagcct    68940 ccgtaaaatac actttatttt cttcaagcac ttctatcatt gctactactc tgccaatgga    69000
agagacatga tgaaaacaga tctccatagt ttctaggatc aggtcattca agggtacctg    69060
cagtcggacc ccaacttact tttctaagtt ttaatccaca ttatttcttc acataaactt    69120
caggccctaa tcaaattagt ttatgcatct gaacatatct ggtgcttttg tgtgtgtgtc    69180
attccttcta tttctttacc ctgttttgtg tccatcatac atttctttat ttttaaacac    69240
actgtgaagt ttcaaatctt ccatgaaacc ctccttgatt actccagctg aatataatct    69300
taactttctc caagttcctg aaggagcttt tgtgtggtgc ttcctatatc atgtctggtg    69360
ttataattat ttgcttctgt ttcgcttcta agctaaattt tggtcccctt gatgactgag    69420
accacatctt atacagtcat gtgtcactta cttatgggga tatattctga gaaatatgtc    69480
gttaggcaat tttattgttc tgtgaatatc atgtattgta cttatacaaa cctatatgtt    69540
atagcctagt atatgcctag tctgtatggt atagcctatt attgctctag gctacaaact    69600
tatatagcat gttgctgtac tgaatattgt aggcacttgt aacacaacgg taagtatttg    69660
tgtagttaaa catatctaaa cataaaaaag atacagtaaa aatgcagtat tacaatctta    69720
tggaaccatc gttatatatg tggtctgcca ttgaccaaaa cattgttatg gggcacatgg    69780
ctatttcttt gtatccaaca ccacttgtag tatgatactt ccaacataat tggagttcag    69840
tatatattta actcagtaat atctacttta atttaggtaa tttttatgta gaagatataa    69900
tttgaagata tatttaatga aataggttga tgttatatgt actctgtaat tgggaaccca    69960
gtgtaaatca gtttccattt gcaaatgaac ttttattaaa attgtatcgc aaaatgaatg    70020
aaaattaaag gaggaattta tgccatttat ttatttatta atcattttag agactgggtc    70080
ttggtctgtt acccagacta gggtgcagtg gtgtgatcat agctgaagag atcctcctac    70140
ctcagccccc caagtagctg ggactgcagg tatgtgccac catgcctgga taattttaa    70200 attttttgtg gagatgagat cttgccatgt tgcccaggct ggtctcaaac tcctgggctc    70260
aagtgatctt catgccttgg cctcccaaag ttctgggatt acaggcatga gccactgagc    70320
ctggccaatt tgtatcttgt aaatgcatat gttctgaaaa ttatgattaa aatataatca    70380
tagattaaaa catgataatg aaacttacga tgagatattt ccttcaaatt tttggtttta    70440
gtggcggcat gattttgtgc acggatggat aaaagtacct gtgactcatg aaacacagga    70500
agaatgtctt gggatggcag tgttagatat gatgagaata gccaaagaaa acgatcaaac    70560
cccactggcc atctataact ctatcaggta attttctttt gcaaatcctt acacataagt    70620
gtgagtagag attttatata attcgtatat attttctgtg tttacccatg cctttttgatt    70680 ttgtaatact agttaagtac tccttatcta aaatgcttgg aatcagaaat gcttcagatt    70740
ttggatattt ccagattttg gaatattggc attgaactta ccagttgagc accctaatc    70800 caaaatgctc taatgagcat ttcctttgaa catcatgttg acgttcaaaa agttctggat    70860
tttggaacat ttcgtatttc agatatttgc aagaggata gtcaacctat aataaaaat    70920 catatgggta agttttatat cttgggagta aaacacactt tgtaaggtga aattatttaa    70980
```

```
agagttgtac tacaggaaat atcataggta ttaaatatct attatttgat ttcatttatt    71040
ctgagaaggc tagggaagtt cagaggaaca gaagaaacac ctggaggcat acttttttgat   71100 agaagatcct ccagttggct atataaatga cctgaataag tatttcccaa atggtggtgt   71160
atattttatt tgcattagac tcacgtgggg gagcctgtta aaatcaaaga tttctgggtc   71220
ctaatccaag agatttggat tcagtaaatc tgagttgaag cccacaaata tgaatttta   71280 cagatgctct agggtattct tatacaaatg gtccaaactc tgcattcttc aaattattct   71340
tctgcatatt gaacttgaca atcatggcta atataaaact gcttttaaa aaggtatata   71400 taagaatggt ttaagtttga aggcaaatat gtattttata tattacatac ttcccagatt   71460
aaaaatttga gtacatcatg agtgtggtta aagcttcctt ttttgaaatt gttctcccaa   71520
taactggctt cagtcatttc tttgccatgt catcaaaaca gttacatacc caatttgcag   71580
agtatcaatt tctgtatttc tctctttggt tttaaatatt cttgttttac tttcagatgt   71640
ctgttaggtc ttaacctaag ggtgtaggcc atagggtata atttttaggaa ctcagaaatc   71700 tagaagattc caaagcccaa aggaaaaaaa aaacacattc attcattcaa cagctactta   71760
ttgaatactt gctgtatgcc aggctatagt agaacatagt tggaggaaga gtatcttaga   71820
tgtcgttaca tagaaactga aggaattcag gggaacacag ttgaagaaca gaagctttga   71880
cccattgaag atgaatgtta taaatatgaa gccatctcta gacttaagct atcgtggaat   71940
atttctgctt tggaaaccat gctgtcatcc aaagtcttgg cacaatcttt ctatgtagat   72000
tgtagtttct tccagtttga gaatcatgtc atctattgct cttatcccta cattatttag   72060
tctagtgtcc taaacctaat gactatttag taactattta tctgattctt ttaactcatg   72120
ctcttagcca ggatataaac acagatgcaa aatgctgcat cattttttt tactgcttta   72180 cttttaaaaat agtgtagata ttaaacattc atataagatt ccatgatatt ttaaaagagt   72240
ttattgagat aatttacaaa tcataaatct cacccatttta aaatatacaa tttaatattt   72300
tgtattatat tcacagggtt gtataaagat gaccagaatc taattttaga acatttgcat   72360
cctttctgaa agaaaccca tgcccattag cattcagtcc tcatcccact ttccccccagc   72420 ctctggaaac cacttatctt tttgtttgcg tggattttcc tgtctcaaac atttcatata   72480
aatagaatca tgcaaaatgt ggtgtggcat ttttttttgtc tggcttcttt cacttaatat   72540
gatgtttcca aggttcattc atgttgtaga atgtatcagt acttcatttc ttttattgc   72600 tgaatcattt cattatatag atataccaca ttttgcttat tgttcttca cttgatgaaa   72660 atgtgggctg cttccatgtt ttggctattg tgactaatgt ggctatgaac agttgtatat   72720
gagtaatttt gtggatgtat ttttttcatt ttttcttgtg catatattta ggagtggaat   72780
tcctggaaca tatggtaact gtttaacttt ttgaggaact gcttaacttt tcaaaagcag   72840
ctgtgccaca ttacattcac actagcagta catgaagagt tccaactctt tccgcacttg   72900
tttctgtctg tattttatcc atcctagtgg gtggaagtgc tgtctcattc tagttttgat   72960
gttcatttct ctaatgacta ctgatgtttg gcatcttttc atgtactttt tggccatttg   73020
tatgccttct gtagagaagt gtctatttga attcattgct catttttttaa ttgggttatt   73080 tgtctttttaa ttattgagtt tagaaaattc tttttatatt ctggatacaa gtctccacat   73140
ataatcatat ttatgatttg ccattatttc ctcccattct gtgtattgtt attttacttt   73200
cctgaaggta tcatttgtag cacaaaagtt ttaattttga agtagtctaa tttgccccat   73260
ttttctttgt gtcttgtgcc atgtggaaat gtggttttag caacatggat gtctttcttg   73320
gttttagcaa gagcagtttc tcttgaaata atggaacaga agccaaactg gaatgagttg   73380
```

```
agggataaat ggaaggcaag aaaatggaaa tggctatgta catgctttca aaaagaggcc   73440
agataggctg tggccagaag gaaatgtggg attaagagat tttacatttt atacgggacg   73500
gacattaatt tagcaagtcc tttgtgcctg tggattctac atctaatatg ccacagaatg   73560
aggtccagaa aggcttcctg gattagatgg tacttgagcc ttgtcgaatg agtaactaga   73620
taggagatgg atgattggaa gaaagattag catatattac ggcatggaaa attatttaat   73680
ggtacttcag aaataaaatg ttccttagaa gcacagaaat aaattacctt ctttagaata   73740
ttgtacatag agatgaatgt acagaaaagt cagaatattt ctaaatggaa ttgttttgat   73800
cacaaaggaa ttattaggag ttgaagctgg cctaacaaaa taatatacag aagtatgttt   73860
gcataatgaa aatggcttcc aacaaaatgt aacaatttcc aaaattcagg taaatgttgg   73920
agcacagcat cataggaaat atttgtagca cagttcaata tatgccaaaa tattatctta   73980
taaaccatta actctggtat gtgaaataga gaaaggaat ttttagagat tcttattaac   74040
tagactgagg attcatttca ttaggggaag aagattaaca tcttcttttg taaacattga   74100
tgataactta gagtgtgtgg atatatttat atcatcaaac aaaatcttaa agttttatac   74160
tgtatggatg ggggttatgt caacttacgc cacttggcca ctgtgttgta aggcctactt   74220
aatcatggaa aaaggtggta acttcttttt caattttag atttatcttc caattttgt    74280 tttgttttgt ttttctgtat gtgctttttt atccctagct acaagacatt cttaccaaaa   74340
tgtattcgag caaagatcca agactatcat attttgacaa ggaagcgaat aaggtacaga   74400
tttcgcagat ttattcagca attcagccaa tgcaaagcca ctgccagaaa cttgaaactt   74460
aagtatctta taaatctgga aactctgcag tctgccttct acacagagaa atttgaagta   74520
aaagaacctg gaagtggtcc ttcaggtgag gagattttg caaccattat aataactgga   74580
aacggtggaa ttcagtggtc aagagggaaa cataaagaaa gtgagacact gacagaacag   74640
gtaatcctta atgatatgtt cttgttcttt gttattttaa gtacaatgga aataaaaaca   74700
aagtaatttt aatcatttgc aacatggtat tgcacttctc ccatttgata gaagtggaag   74760
tttttaatag cgtgaaccta tcaaggtcat ataattcttt gcctactatt cttaaatggt   74820
tttttcattt aatttttat gacaaaataa ttaccaatga ctatattata gtttcagaaa   74880
gatgtcaaat tctaaaagtg attttaaagg agttttgcct ttcactacta gtgataacag   74940
aaggcataat tataaaactt gttaactaga aaagattgat attaattgat tttatgataa   75000
tatatacctg ctaaataatg aatttatttt aggtttgcat tgcaagtttt gaatttgtta   75060
atatccgtgt tgttcataga ttgttactag agatttagag ggatcatttt ttaatttttc   75120
atctttggta gtcacatttc cagttttctg gcagtggttt ctactaatgt taattgaatt   75180
gaagagtgcc atagcacatt ttagattcct ggcatcattt aatgccctca ttttaagtc    75240 aagcaagata cagcatagtc ttagggttag attgatagag taaatcacgt ttaatgctta   75300
tctattgtta tcaataccttt tttattttta aagaatttgg aaagaatgtt gtcttcttaa   75360
gtcttgtttt aaaatggctc tgtaaattct acccgttttt aattttacat gcttttaatt   75420
ataggattta cagttatatt gcgattttcc taatatattt gatgtcagta ttaagcaagc   75480
aaaccaagag ggttcaaatg aaagccgagt tgtaactatc cataagcaag atggtaaaaa   75540
tctggtaagt ttgctttatg attgaataat ggtttcattt tatagttctc agaaatgtgt   75600
attttagaat cttagtacca aaattatttt ctggtaggaa ttttgattgt agttttaaat   75660
ataactctaa acatcagttc agtaaacttt ttgataacat ctagcttttt gtattactat   75720
```

```
caacaccatc ttcctacaga gtttcttgta cattactgta cttttttttac tcatttttat   75780 gattagcaaa gcaccagtta ctttctcccc catccctact ctagattata ctagttctct   75840
gatgtaatgc tcacccctga ctaaaatatt ttatcaacag ggatgtatat gtgccagtta   75900
tactgcctaa ttaaaggaga aaaaataaat caatgatgtc tggaatttat ataacaaaat   75960
gtaaatcaat cccaggtcag ccccacccaa gctgtaggac atggttgatt ctaaaagatt   76020
aacgctttct cttttttaa atagcttcag aaatctaatt tattttaatg taaataggag    76080
aaatgaatta ttttatactt tgctcttaag tttctcattt atcttctctg tcttcttttt   76140
aactcagatg cttcttgacc cttcctggct taaactagtc ctattaatgt tatttgtcta   76200
tttatcttaa gtatttatat ggcttacctg tctggctgtt ccagggttat attaccaaaa   76260
ttgtaactaa cttgcaactc acttaattca gcatagtttt ctgttcttag ataaaaatat   76320
gatagtacac ctactgccta gtagactgtg agccttttga aggtaaggat catattttta   76380
tgtgtgtttg tacccctac accttgcaca gtactcaggg cctagtttag aaaaagcttg    76440
ataaatattt tatggatgca taaaaggatg attaacaatt atcaacctca atgtggatat   76500
ataataaatg tttctgggag agtttattga tcttaatgtg aacaaactgt agtaacccaa   76560
agaacttctc catgggactg tatttggact tggcttaatt ttaagtctgc aatacagaga   76620
agttaagtaa ctttccaagg gcacagtgtt agttaagtgg tagggctatt taaactcaaa   76680
tgcatgcttt gaaaacctaa gctcttaagt gtgacactaa cttctttgct aagtatccgt   76740
aaagctcctt aaaaatatta tactgacatt ttgttggaat tgtgcaacaa actgggaaga   76800
gttgacattt ctttctcata ttaaattttt tattttaggg atacattgta tttctccttg   76860
tatacaagta ttattttatg ttttttcagta attcttgatc atttttattca tattgataca   76920 tcatgtttct tgctgaattt tattcatgat atgttatgct tttctgttg tttattaaaa    76980 ttaatacttc ttctctgtgt attttcctac caaattattt atggatatag gaaagtaatt   77040
tttgcttatt attgcatttt cccagtgtat tatgtgttag taacatttg ttttttactgt   77100 catttttcctc ttcattctgg catttatttc tctttataat tttggtaaaa tatatataaa  77160
ataaaattta gcatcttaac cattttttaag tgtacagttt agtagtgtta agtatattca   77220
cttttgcatc caatttccag aactctttta tcttgcaaaa ttgaagtcta cacccattaa   77280
ataaaaactc accatttccc cctcttccca atccttgcaa ccagcattct actttctttt   77340
tttttttttt ttttttttgag atgagtcttg ccctgtcatc caggctggag cacaatggcg   77400
cgatcttggc tcactgtaac ctgtgcctcc tgggttcaag caattttcct gcctcagcct   77460
cccgatagct gggattacag gtgcacgcca ccatgcttgg ctaatttttt gtatctttag   77520
tagagacggg gtttcaccat gttggccagg ttggtcttga agtcctgacc tcatgatccg   77580
cctgcctcat cctcccaaag tgctgggatt acaggtgtga gccactgtgc ccagcccctc   77640
tactttctta ttctatgaat ttgactactc tagatacctc ataaaagcag gctgaaacaa   77700
tactgtcttt ttgtgacagg cttatttcag ttagtataat atactcaagg ttcatttgta   77760
ttacagcatg tatcaatttc cttcattttt aatatatgta tgtattctgt gtcatgtata   77820
taccacattt gttcattcat ccatcaatga atattcaggt cactttttta cttttttgaca   77880 attgtgagta atgctgctgt gaacatgggt gtacaaatat ctcttgaaaa ctctgctttc   77940
aattcctttg gatatatacc ttctattagt ccgttctcac actgctataa agatactacc   78000
tgggactgga taatttattt aaaaagaggg tttaattgac tcgcagttcg gcatggctgg   78060
cccaggaaac ttaaaatcat ggcagaaggt gaagggcaag gaagccatgt cttacatggc   78120
```

```
agcagaagag agacagtgtc caggggaaag tgccactttt aaaccatcag atctcatgag   78180
aactccctca ctatcatgag aacagcatgg gggaaacaac ccccatgatt cagtcacctc   78240
ccaccatgtc cctccctcga cacatgggga ttacaattaa agatgagagt tgggtgggga   78300
cgcagagcca aaccatgtca tacctagaag tagaattgct ggatcatatg gtaattctac   78360
ttgtaatttt ttagggagcc accatgctgt tttccatagc agcggcacca ttttacattc   78420
ctaccaggag tacattctcc acatgctcat caaaacttgt tattttctgt tttctgatag   78480
tagccatctg atgggtgtga agtagtatct cattgtgatt ttgattcaca tttccctaat   78540
gattagtgtt gctgagcgtc ttttcatata tgtattgcca tttgtatatc ttctttgaag   78600
aaatatatat tcaagtcctt tgctcatttt ttaatcaggt tttttttgct gaattataga   78660
aattatttat gtattctgga tattaatccc ttttcaaata tatgatttgc aaatattttc   78720
tcccattcca tagattgctt ttcactatgt tgcttgtgtc ctttgatgcg cagatgtttt   78780
aaagttttag ctagttcaac ttttgttgcc tattttctt tttactttgt tgagatataa   78840
catgaaccca gtaaagcaca ctaatcttac gtgtatagct caatgaattt ttacatattt   78900
gtacatcttt gtagccacac ccacctcaaa aaacagaata gttctcttac tcctagaagg   78960
tttccacatg catcttccca catattcacc tccacccta acttaagata cctatcatct   79020
accatcactt agttttatct attaataaag gttgtataaa tggaatgata ctgtatgtat   79080
tcttttaaaa tctagattct tttagttagt ataatgtttg gagattcatt tatgttgtta   79140
catgtgtcag ttcattcctt tttattgctg ggtagtattg aattgtttga ctgtacctca   79200
aattttaaat gtattctgtt gatggacatt tgggttgctt tcactttggg gattttaggg   79260
ataaatttac catgaacatt cttatacata ttttttggtg gacttatgca ctctttttt   79320 gtatatatat atcctagaga taggattatt gagtcatagt gatagcttta gtatactgcc   79380
aaacaatttt ttgtagttct atcagttcac tcttctttca gtaatgcatg aaaattacag   79440
ttgtctcata tccccatcaa ctcttaattt tgtcagtcta aaaatgtctt agtttgtctg   79500
gtggatgtgt actggtagct attgtagttt ttattttcat tgccctggtg agtaatgatg   79560
ttcaatactt tttcacttac ttattgttca tctgaatatc cttcttatga agtgcctgtg   79620
acagtctttt gcacattttt cattgacttg tccctttctg atcaatctgt agagtctcta   79680
tagattctaa gtcttttgta ggatgtttgt aaaacgtata tagacatacg tcagagatat   79740
ttctagttca gttctggacc actgcaataa agcaattttt gcaatgaagt gagtcacata   79800
aattttttgg tttctcagta catataaaag ttatgtttac actataatca agtctactaa   79860
gtgtgcaaca gcattatgtc ttaaaaatta atttaaaaca ctttattgct aaaaaatcct   79920
aatgataatc tgagcctcca gagagttata atctttctgc ttatgagggt attatttga   79980 tgttgatggc tgctgaccga tcagtgtggt ggctgcttaa ggttgggttg gccaaagcaa   80040
tttcttaaga taacaatgac atttactgca tcagtagact cttcatttcg ttaaagttgt   80100
ctctgtagca tgtgacattg tttggtaaca ttttaccac agtagaattt ctttagaaat   80160
gagtcagtcc tctcaaaccc tgccactgct ttatgtacta aactttattc taaatccttt   80220
gctgtctttt caacaacatt cacagcatct tcacccagga ctagattcca tctcaagaaa   80280 ccatttttt atgcataaga agcaacttat ctgtccaaat tttatcatga gattgtagca   80340
attcagtcac atcttcagct ctacttctaa ttctagttct cttgctattt ctaccacatc   80400
ctagtgactt cctccattga agtcgtgaac ccctcaaagt catccatgag ggttggaatc   80460
```

```
aacttcttcc aaattcctga taatgttaac actttgacct tcttccatga atcactgatg    80520
ttcttcctgg catcaagaat ggtgaatcct ttccataagt tttcctattt acccagctcc    80580
atcagatgaa tcactatcta tggcagctta gccttacaaa atgtatttct tagataataa    80640
gacttgaaag ttgaaattac tccttgaccc atgggctaca gaatggatgt tgtgtcacca    80700
ggtctgaaaa taacatgaat atccttgtac atctctgtca gagcgcttgg gtgaccaggt    80760
gcgttgtcaa tgagagtaat actttgaaag caatcttttt ttctgagcag atcttaacaa    80820
tgggcttaaa atagtcagta aaccatgcta taaacaatag atgtgctgtc atccaagcct    80880
tgttgttcca tttatagagc acaggcagag tagacttagc ataattcgca gagccctggg    80940
attttttggaa tggtaaatga gcgctggttt gaatttcaag tcaccaatgg cataggccct    81000
tagcaagagg gtcagcctat cctttgaagt ttgaaggcaa gcactgactt ctcctctcta    81060
gctgtggaag tcctagatgg catattcttc caacagaagg ctgttttgtt tacatttgaa    81120
aatctgtttg ttagtgtcac catcttcatc aatggtcctt actagatctt ctggataact    81180
tgctgtagct tccacatcag catttgctgc ttcaccttgc acttatgctg tgcacatggc    81240
ttcttttctt aaacctcatg aaccaacctc tgctagcttc caacttttct tctgcagctt    81300
cctcacctct ctcagccttc atagaattta agagcattag ggtcttgctc tagattaggc    81360
tttggcttaa gggaatgtta tggctggttt gatcttctat ctagaacttt ctctgtatca    81420
tcaataaggc tgttcacttt cttataattt atgtgctcac aggagtagca ctttcagttt    81480
ccctcaagga cttttccttt ggattcataa cttgcctttt tagtgcaaga ggcctagctt    81540
tcagcgtgtg ttggctttca gcatgccttc ctcactaagc ttaatcattt ctagcttttg    81600
atttaaagtg agagatgggt gaatcttcct ttcacttgaa tactcagtgg tcattgtagg    81660
attattaatt ggcctaattt cattattgtt gtgtctgagg gaatagggag gcctgaggag    81720
agggaaaaag aaagggaaat agctattcgg tggagcagtc agaacatata caaatttatc    81780
acttaagttc accatcttat ataggcccag tgtgtggtgc cccaaaacaa ttacagttga    81840
cccttggaca tcacaggttt gaattgtgtg ggtccactta tatgcaattt ttttcagcc    81900
aaacatggat ggaaaatata gtattcacag gatgcaaaac ctgcatatgt gtagggctga    81960
cattttgcat atatgggttc tgcagggctg atttcagaac ttgaatatgt tcagattttg    82020
gtatatgcag gggtcctgta actaatcccc cttgtattct gagggacaac tgtacaatag    82080
ttacatcaaa ggtcattgat cacaaatcac cgtaacaggt ataatagtaa taaagtttaa    82140
attttgtgaa aattaccaaa acatgacaca taggaagtaa gcatatgcta ttggaaaaat    82200
tgcactgata gacttgtact tgctccactt aagtttgtca gaaaccttcc atttgtaaaa    82260
aaaaaaaaaa aaaaaaaaaa aaaaaaaggt catatctgca aggagcaata aagggaagtg    82320
cagtaaaaca aaatgtgtct gtatatcaat aagagggata ctagttagtg aactgctagt    82380
tcaaagggta tgaatatta caactttgat agattattaa aatacttctc aaaaggtgtt    82440
tccaatgtat ctgtacacct gttttcttgt atcctttgcc aacactggat gttatcaatc    82500
ttttaatttt tctgccaaat caatgggcaa ataatgctg tcctgttata tttcatttcc    82560
ttaattagaa cctgagattg agcaatacct catgtgttta taggtcagct ttaatattta    82620
tacttctgtg gattgccttt tcatgtcctt tgactagttt tctttttta tttttaattg    82680
ttttatacgt tttattccca caatgtatgt taggtatatt cctttgttat acatgtttgt    82740
aatctccaag tcttttaatt ttgttaggga tacctttat agtacttgtt tttttggcta    82800
tttgtgttag ctaaatacct tttatagttc aaacatgtca catgcttgtc tctttattat    82860
```

```
aatttttggt tgaggactct attctgtgtt ctctttatga ttatgtaaat attgttcatt   82920
gctgggccaa gaaatatgct gtaatcacat tttcgttctt ataaacttt ttccaggagt   82980 taattattgc tttatgattt ttcctttgta tctagctttta ttttcatttt ctacaagaac  83040
tctgtaaagt agtggacttc tcaatacaaa atttcacata atcaaacctg tcatatatga   83100 tagcatttttt acttctttttc tggagaagta cctcttcgat cacagcatct tactttgtag  83160
tgtggactgg aagttttctg ggtacagcta ttattttgtc agctgtaatt tttggtcatt   83220
cctttcttat cctggtaact atgttttcat ctctcttata ttggatctga ttttctaaat   83280
ctcatgtttg ccctgttttt ctaggtacag cctctggtat ttgttggtat ctttaatgtg   83340
attgagacaa attagaaaat taatttagag aggatttttta catttttatg atattgaatt  83400
ttcctaccat ggttaatctt ctatatattt aaataaaaag ttgcataaga gtgttttgaa   83460 gttttttgtta attattgata ttgcatcctc tttgttacaa atgggctttt tttcattata  83520
taactgactt tttgtatgta aaatataat acgtctatat attttcccat gtaagtaaca    83580
tgctgcattt ttggctgact acatgttcac atatgtatta agatacaatc aggccgggca   83640
tggtgactca cgcgtgtaat cccagcactt tgggaggcca aggcgggcgg atcattaggt   83700
caggaatttg agaccagcct ggccaacatg ttgaaactct gtctctacta aaaatacaaa   83760
aattagccgg cgcgtcttggc gtgtgcctgt aatcccagct ttttgggaga ctgagacagg  83820
agaatcgctt gaacccagga ggcagaagtt gcagtgagcc aagatcgcgc cattgcactc   83880
cagcctgggc gacagagcaa gactctgact gggcggggggc cacaaaaaaa tcatagcata  83940
gctacatatc ctaacattttt agtttgtagc atgaatactt tagcagtatg taattggtat   84000
gtagggctga tgccgtggct cacgcctgta accccaacac tttgggagac tgaggtgggt   84060
ggatcacttg aggtcaggag ttggagacca gcctggccaa catggcgaga acctgtcttt   84120
actaaaaata caaaaattag ctgggcatgg cggcatatgc ctgtaatccc agctactcat   84180
gagggtgagg tgggtggatc gcttgagcct gggaggtgga ggttgcagtg agccaagatt   84240
gtgccagtgc acttcagcct gggcgatgga gcaagactct caaaaaaaaa aaaaagaaa    84300 aaaggaaatg ctcatgattt ctaatgtcaa cttttatatc atattaaata gatttctagc   84360
tgagataact ggtatattag tctaagaagg acattggaaa ataaagtaaa atgatggcta   84420
tagagtgaac tataactggg aaggtatgat aatctgtatt taggaggatc ttaaatatca   84480
gacatgagaa tttgtaattc atattgagta ctgagccata aaagatatga gcaatttaga   84540
agaaaattgt atttaacatg gaatgaagaa aattttcaat atttaacatg gagttgactt   84600
tctaaaaggt gctatttctt tttcttttct ctgcttagga aattgaactt agctcattaa   84660
gggaagcttt gtctttcgtg tcattaattg atggatatta tagattaact gcagatgcac   84720
atcattacct ctgtaaagaa gtagcacctc cagccgtgct tgaaaatata caaagcaact   84780
gtcatggccc aatttcgtga gtaatacaga cttaaaagta aattttttaga aaagtaaatg  84840 ctgtatttac aaagaagatt taacagagtg atacatgtat gtttagaaaa aataatttg    84900 acaagttttt tttaaacaaa aggctatttg caatcagatt acataataat tagaattatt   84960
tagtgtataa tttaccatct gtatcccaat ctataatatt tataagttgt acaagtttaa   85020
catttgttaa tcatgcctat gtgtgattca ctcctgcatg ttactaaaaa agaaagatct   85080
ccaatttatg ttttattaat tttaaaatac tgcaaggaag ccacagtgca aaatttgaaa   85140
attctttatg tttggatagt ccatctccctt ctactgaaag gttcaaacac aagatatata  85200
```

```
tgatgtccac atttctagac tagtgctatg tagaacttcc tgcagcgatg aaaatattct    85260
atatctgtgc tgtgtaacac agcagccact agctacatgt ggctgtttag catttgagat    85320
gtggctaatg caaccgagga actgaatttt aatttaattt taatttcttt acatttaaat    85380
agctacatgt ggctagtaac tatcacattg gctcacacag ttgtagatcc ttactttaat    85440
actgggtaaa gctagctatc atgcataaca tctatttagc ttaagtccta atgatctctt    85500
agctaggatg tggtttatgt tgacaacaga tttgaataac tcgagcaaag ggaaaatctg    85560
ggatcatgag catattatgt tctttgcatt taacctaccc ctaaatattt gagaaaatac    85620
atcttgggta atataaagag ttgatttagt ctatgcttaa tatttattta gtaatgaata    85680
ttgttgctat gaaaaagttg tactacttga actttatgtc tgtaatttac atgtttaata    85740
tttttaaaac tccttgcctt tattcatgta tccataaatt cattcaaaca ttctttttatt   85800 tatatttact gagtaactac tatgtgcaag cattggtttg tatattagaa atggtgat     85860 aagtgaaaca gaatgattct ttcttttgta tagattatat tttgcttttc tttcagggtg    85920
tgcagcttca gaaaacataa aaaattttaa aaaccagtag tctttgtcag ttgccatggt    85980
tcttctctta gactttgtta tcgtactgaa taataaaatc atgcattcag attttatgt    86040 cagtaactgc tatggtagta gagatataag tattttctga tatataatct ttatagttaa    86100
atgaaggttt ctgagagtat ggttttaaaa atattaactt tgtaatcagc aggcagaaaa    86160
atcaaatgaa caaattgttc tttgtgattt tgtcttataa atacctttta ttggttttta    86220
aagctatata attgtccctt gaagtggttt gaacttactg caaaatagct tggtactttg    86280 atttttcct ttgaaagatt attgctaaac atataaagta gaggagacaa ttctgacagt     86340
tttagatttg acttttgatt gttttagatg acacttggtc ataatattat ggtgcttgat    86400
atattattca aattgcttct tctttacctt taggatggat tttgccatta gtaaactgaa    86460
gaaagcaggt aatcagactg gactgtatgt acttcgatgc agtcctaagg acttta ataa   86520 atattttttg acttttgctg tcgaggttag tatgtcacac ttattagtgg taacacttta    86580
tttagttcat ttaatttcct ctccatattt atttaccata tttccttttt aatactgaga    86640
attatagctt tggatatgat aactagtata atgcttaatt tcctcagaga ttctgtacaa    86700
ataaacaagt tataattccc agggtttata taaaaatata aaataattta taatgtctat    86760 cttttttattt tgcatttatt ttattttctg atgttttggt gttaccagtg tgttaaaagg    86820
tatttcatca agtgtcttga tgtttctttg tttgcaaaac tggaaatctt tgccacatca    86880
tgtagaacaa aataaatcgg aagcaaattt tctgtttatt aacagtggtt gcagaattag    86940
aggaaacaga attagagaaa actaggtcaa taacaaacaa atagaaacat taaagcactt    87000
ttaactgatg attttctaat atttttaaga atagtggtct acaatgcatg tttcaacggt    87060
aaaactgcaa tgaaacccca ctgttaatac agatcatttt ggatctcatc tatgattata    87120
tactatcact tatgaggcaa tttcatggta taaatcctaa gaaactatag aagcttgcaa    87180
atttatcttg cttttttaaa acagagaaaa ataagaactt tgttattcaa ttatttttaat   87240 ttttataaaa tgcaacttat atttggcata tgtagagggt agattactta cagaagggag    87300
gttatgccat cactttacct ttgtgtaaaa ctggtaatct atcctaattt caaagtatcc    87360
tgttactata acagataata gtacattata ttcaagtatg aattcaaaaa aatatatata    87420
tatattttat gttcactgta tgtgccaagc ctaatgtgag agctatgtat tatagagttt    87480
atgctacagc cctaccttca ggaaacttat ctactggaca aacaaaaatt ttcaaatata    87540
caaaaaattc taaatcgaac attgtaatta tctagcatag gcaaatatag acagtaacag    87600
```

```
acaggtttac aattattaag aaagggcagc caggtgtggt ggctcacacc tgtaatacca    87660
gcactttagg aggccaaggc gggtggatca cgaggtcaag agattgagac catcctggcc    87720
aatgtggtga aatggtgaaa ccctgtctct accaaaatta caaaaattag ctgggcatgg    87780
tggtgcgcac ctgtagtccc agctactcgg gaggctgagg taggagaagc gcttgaaccc    87840
gggaggtgga ggttgcagtg agtcaagatt gtgccactgc actccagcct ggcgacagag    87900
cgagacacgg tctcaaaaaa aaacaacaac aaaaaaaaaa aaaacaaga aaggttattt    87960 ggcataggaa gaacctgatt gaccttgagg tattggtaga ttttatataa atgtttctga    88020
gtagaatgaa tatgtttata aaatgcacct taaaaatagg tgaacaagtt cataatatag    88080
tgcataagac aaatatttaa aaactgcaaa atattaaaaa tgtaatatta aagataatta    88140
tacaaataca atggtggtgc agtggaatgg ctgtatgttc acctttgctt gtgcaaagag    88200
gtgagcatta gagaggacct cttagaaaca gtggtacttg aactgagttt tgatgaatga    88260
ataaaggttc attgctcaga agaagtgggt atacattctt aggtagaaag atagcatgaa    88320
gaattatcaa ggcatgaagc agcatggcat ttgcttgaaa tgatttaagt catttaatat    88380
ggctggaacg taggttgtat gttggcagtg gcaggagctg agattggaga tggaggcaga    88440
aaccagctca tggaaggctc tatatgctac atttgtttta ggctttatct tataaatgat    88500
ggaaaactat taaggatggt attgttgcta ttaattatca ttgccttctt acatgctttt    88560
tcataaaatc aacttttaaa ccacttttgt aggctgagaa attgtaaatt gccctttga    88620 ggaactaagt acttctatca ctatactggc actacatcgg attcatggtt caaatgttta    88680
ttctgttgct tgttcttgtg atatcatttt gtcagaataa tcactgtgat gtccattgtg    88740
actatccctc cctttcttta taattaaact tatacagcga gaaatgtca ttgaatataa    88800 acactgtttg attacaaaaa atgagaatga agagtacaac ctcagtggga caaagaagaa    88860
cttcagcagt cttaaagatc ttttgaattg ttaccagatg gaaactgttc gctcagacaa    88920
tataattttc cagtttacta aatgctgtcc cccaaagcca aaggtaaga taattttcta    88980 gttattttta aattactggt catggattgt ttatgtggcg tgaagtatct tcagtacatt    89040
gatttcaaag gatatatgaa agaagcagct ctaaaagtta attttatctt attctattgt    89100
acaagcatca tcaaataaga ttgtttactt tggttttggt ggtctagaag tgacttgaag    89160
ttcaattatt ctaaaatgag attttaaaca taatgtgtgg tatgatgtca tttattgaac    89220
tggaagatct cactactaaa ttcttatgtt gttttaagta aaaattttca tatacttcga    89280
ggattttaat ttctgtattt taaaaataaa gacagtaaag ttggaaattc cttgaaataa    89340
tgagccttac tattaaaaat tattaaaatt cctgaaaaat tgtatgagtt aaggaagtta    89400
ctataatttt gaattaatga aataactggc aggaatacat caaaatccaa attacattag    89460
ttaaggaagt gattataatt ttgaatgtat gaagtaacta agaagaaata tcaaagttca    89520
atgagttgac ccctaaaata atttttctatt ataaaaaag aacaattagg agttattaag    89580
catttcttat acgtagaaca catttcattt tactcctctt tggagcaatt catactttca    89640
gtgtattttg aagtgatata tatgtatttt attttttcag ataaatcaaa ccttctagtc    89700
ttcagaacga atggtgtttc tgatgtacca acctcaccaa cattacagag gcctactcat    89760
atgaaccaaa tggtgtttca caaaatcaga aatgaagatt tgatatttgt aagtcattag    89820
atactcatta ctgtctttt tgtccttta aaacaacatc tgttttcttg atttacattc    89880
atgtgacatt ggaattattt tgttatatac aaatttagtt gtgatttaaa tatttttctt    89940
```

```
atgaaaaata tgccaacctt gtgttagatg ttagcaaaat taattatctt aattatccta    90000
agaatggaat cttaattttc tttttggaaa tttaaaaatg attcttcaca aatctcaaat    90060
taaaaattaa aaatctacaa agacctatat cgcaactccc aagttctcaa gaaagtaagg    90120
gaaattcaag gggttaaaaa taagaagaa actgagaaaa aaatccagcc atctctcagt     90180
gtccatgagg gattggttcc aggactaccc atggatacca aaatctgagg atacttaagt    90240
ggaacctgtg gatatgaaaa gttggccctc tatatacatg ggttttgcat cctatgaaca    90300
ctgtatttct ttttttaaat aactaattat tttttaaaat tatttattta tttattagag    90360
caggacttgc tgtgtcaccc aggctggaat gcagaaatac tatattttcc aactgagttt    90420
ccttgcagat gcagaacccg ccctgccagt acagagggcc cactggattt attgaaaaaa    90480
acccacatat aaatggacct gtgcagtcca aacccatgct gttcaagggg caactgtagt    90540
acataagatc tgataatctg gcagtcaggt ggtgagggtt gatgatcagc cacatttatc    90600
aagggggtta agatttaaga gcaatttaaa agggccaggt ctcagacctg tgcaaggcca    90660
cgagttaaaa gtgagactat ccctgagtaa aaccaggaca cttaagtaaa tacatcctca    90720
gtaaaacaat atatagaatg tgaaaaattc acccactagc aagcagagaa gaaaaggaat    90780
attgtcattt ttaactgcgc ttctggtgag gaaaaggagt ctctcctaag aatttgtcat    90840
cataagcttt ggaatttggg cttcattata ctacctacat agactgagaa atcctaaatt    90900
aaaagtggta ctctcctaat attgtgtggt gcttggaaga aacaaaaaaa tcttttcgga    90960
accacatact cttaacctag gcaacccata attcccacag ataaaagcat gcaaacaca    91020 agcttttaat agaaaattta gaaacataca aggaaataat gcaggattaa ttaagagtca    91080
gtagaccaac aaacatcaaa attagaactc caggaacttc ctatcacaga attttcagat    91140
acagactata aaatacatat acatgtttaa agatagaaaa ggaattgaaa ccacggaaa     91200 ataacaagac attgttttaa caaacaaaaa agatgtcagg aaaaaggcat agaaatgata    91260
aatatcctca ttgacattaa aacagaatat acaggatgaa aagtaaatta cttatagctg    91320
aagagagatg tagtgaacct caagacagat ctgaagaaat taagaatgca gcagttaggg    91380
agaaagaaat ggattatatg aaagagggat taagtggcat ggaaggcaaa atgagaaaga    91440
cccaactcat atctgagctc tataaggaga caatagatag aattagccag aatggtaaag    91500
acaagcatct tcatgtgagt aacaggaaac agagtggcca ggtaacttga ctaacattac    91560
aaatctaata aatagtagac cttggatttg aacacaagca gccttactgc agagtgcagg    91620 cttttcaacaa ttactttgta aagatatgca agaaatacta gtattagtag taatagctga    91680
tacttaatgc acatttacta tgtgtcatgg actgtgctaa gtgcttttat gtatttattc    91740
acttattgat cataacaatc ctatgggaaa atagttatta ttctcatttt tcagatgaag    91800
aaaccacgac agctgcagca cagagattaa atagcctgta caaggtcata caagtggtaa    91860
taagagaaag tcagatattc tgcctctgca gaccacattc tctagtgtgc tagtaggaaa    91920
ggcaaagaaa atgattccca tgtaagcaaa tgtaggtaaa cactgactct attttaaaa     91980 agtgacaatt atagcccatt caggagattt caaaaccgag tagagccaaa atacacttaa    92040
ttcattaatc cttgttttct gtctcttatt actatttaag gaagcagaat aaaagcatta    92100
atttggagtc ttaaatctgg atttagattc taaggaaaat acttgcttat ggatttaaaa    92160
aaattcttcc tcattgaatg tattttcttg ttcctacttc gttctccatc tttactcatt    92220 ctttttctttt acctttttct cttgaagaat gaaagccttg gccaaggcac ttttacaaag    92280
atttttaaag gcgtacgaag agaagtagga gactacggtc aactgcatga aacagaagtt    92340
```

```
cttttaaaag ttctggataa agcacacaga aactattcag aggtgtgtat gttctttata   92400
ttgttcatgt agtttatgct gtttaaagat gtgctctcat atgcatacaa cgtactcatg   92460
tgtgcagctt ttcaaaattg taattttaa atgtgtcaag gacttttctg aggatacatt    92520
cttgtggggc tatagaatta cagggtttga aaattaccgg attaaaaaaa ttaattccaa   92580
actaattatg tttagcatta tgttaggagt gttattacat ttctgcatat actgtggcct   92640
tgattttcaa acttggctcc ccagagcttt atgggttaca cagaggctcc tctacaatta   92700
catttatttg aaaaaaaaac aaaaaaccaa gtttcaaagg cactgtacta aggaacatgc   92760
ttagtgaaat ctagatgcct ctgggcatca tccagagatg ctagctggca gaccccgtgg   92820
ccagttgcca gagctctgaa catagcaaga tatgatactt acaatatctt aaagggtgtt   92880
ggtgttagaa gatgatgtga aaagttcaag ccaaagagtt gttctaatcc agaataccac   92940
agtattggtg attgtgattc actaatcata cccagggggtt ctagtcacag tttagttgaa  93000
ttagagtgat gttaaaacta tgctagtatc ctgacacaga tgtcgtgata ttttatctgc   93060
acattcttaa ttctttagca agtgttattt aaaggctaca tccatctacc tcagtttcct   93120
atatctatct ctgacatcta cctctagttg tacttctgtc ctctatttca ggtgttatgg   93180
gtcaagcctg tttgactggc attattcatg attcctgtac cactcttgct ctctctcact   93240
ttgatctcca tattccaggc ttacacaggg gtttcctcag aacgttgatg gcagttgcag   93300
gtccatataa agggaccaaa gcacattgta tcctcatcta tagtcatgct gaaagtagga   93360
gaaagtgcat ctttattatg gcagagagaa ttttctgaac tatttatgga caacagtcaa   93420
acaacaattc tttgtacttt ttttttttcct tagtctttct ttgaagcagc aagtatgatg   93480
agcaagcttt ctcacaagca tttggtttta aattatggag tatgtgtctg tggagacgag   93540
agtaagtaaa actacaggct ttctaatgcc tttctcagag catctgtttt tgtttatata   93600
gaaaattcag tttcaggatc acagctaggt gtcagtgtaa actataattt aacaggagtt   93660
aagtattttt gaaactgaaa acactgtagg actattcagt tatatcttgt gaaaaaggaa   93720
agcaatgaag ttaaaagtag aaggttacaa tgcccaaaca atagagtatt atagtaaaca   93780
aatgtctata aaacattttg tgttcatgat agcaaaagag attatggcag gttcaacata   93840
acattggaat aactggcctt ttcagtacaa acttatctgg aattatgaag acaaagcata   93900
taaatgatac acttaatttt taatggaact gacagaaatg attatgttga tatgatacta   93960
gatatatttt ttggctaaat ttaggtgttc acagaaacta ctaaaagtat aaatcgtacc   94020
ccatgcttta atactataca ggcatgcctc attttattgc accttgcttt attgtgcttc   94080
ttagatattg tattttttac atattgaagg tttacggcaa cccagtgtct agcaactctg   94140
tcagcaacat tttcccaaca gcatgtgctc atttcatgtc tctgtgtcat attttggtaa   94200
ttctagcaac atttcaaact ttaaaaaaat catatggtga tctgtgatca gtaatcttta   94260
atgctagtat tgtaattatt ctggggtgtc ccaaacagag agaatataag aaggcaaact   94320
tcatagatga atgcagtgtg tgctctgact gctccatcaa tgagccattc ctctgtctct   94380
ctccctctcc tggggcctcc ctattccctg agacaacaat attaaaatta ggccatttaa   94440
taatcacaca atggtctta aatgttcaag tgaaggaag attcacccgt ctctcacttt     94500
aaatggaaag ctagaaatga agcagcaaac gctgatgtgg aagctgcagc agttatccag   94560
aagatctagc aaagaccatt gatgaagatg gcttagagag gaaggcatgc tgaaagccaa   94620
gacaagctga aagctaggcc tcttgcacta aaaaggcaag ttatgaatcc aaaggaaaag   94680
```

```
tccttgaagg aaactgaaag tgctactcct gtgagcacat aaattacaag aaagtgaaac   94740
agtcttattg atgatacaga gaaagttcta gatagaagat caaaccagtc acaacattcc   94800
cttgagccaa agcccaatct agagcaagat cttaatgctc ttaaattcta tgaaggctga   94860
gagaggtgag gaagctgcag aagaaaagtt ggaagctagc agaggttggt tcatgaggtt   94920
taagaaaaga agccatgtgc acagcataag tgcaaggtga agcagcaaat gctgatgtgg   94980
aagctacagc aagttatcca gaagatctag caaggaccat tgatgaagat ggtgacacta   95040
acaaacagat tttcaaatgt aaacaaaaca gccttctgtt ggaagaatat gccatctagg   95100
acttccacag ctagagagga gaagtcagtg cttgccttca aagcttcgaa ggacaggctg   95160
accctcttgc taagggccaa tgccattggt gatttgaaat caaaccagc gctcatttac    95220 cattccaaaa atcccagggc tctgcgaatt atgctaagtc tactctgcct gtgctctata   95280
catggaacaa gaaagcctag atgacagcac atctgtttat agcatggttt attgactatt   95340
ttaagcccat tgttgagacc tgctcagaaa aaaagattgc tttcaaagta ttactgatca   95400
ttgacaatgc acctggtcac ccaagagctc tgatggagat gtacaaggat attcatgtta   95460
ttttcaggcc tggtgacaca acatccattc tgtagcccat ggatcaagga gttatttcaa   95520 cttttcaagtc ttattatcta agaaatacat tttgtaaggc taagctgcca tagatagtga  95580
ttcctctggt ggatctgggt aaagtaagta gaaaaactta tggaaaggat tcaccattct   95640
agatgccagg aatagcattc atggttcatg gaaggagatc aaaatggcag cattaatagg   95700
aatttggaaa aagttcattc taaccctcct ggatgacttt gagggatatg gtactttaat   95760
gaaggaagtc actgcagaga tggtggaaac agagaactaa gaagtggagc ttgaagatgt   95820
gactcaattg ctacaatctc acgataagcc ctgaaagaag gaggagttgc ttcttatgga   95880
taagcagaga aagtggtttc ttaagatgga atctactcct agtgatgatg ctgtgaacat   95940
tgtgaaatga caacaaaggg tttggaattt tacataaact tgattgatca agcagttgca   96000
gggtttgaga ggactgaccc tgtaaagttc tactgtgggt agaaggctat caaacagcat   96060
tgcatgctac agagaaatct ttcatgaaag gaagagtctg cagtgaattt cattgttgtc   96120
ttattttaag aaactgccac agctacctga actttaagca gccaccacca tgatcagtca   96180
gcagcgatta acatcaagca aaaagattac aactttctga aggctcagat tatcattagc   96240
accttttttg gcaataaagt attttttaaa agatatattc tttgtttttt ttaagatata   96300
acgctgttgc acactaaata gactccatta tagtgtatat acaagtttta tatgcattgg   96360
gataccaaga aattcatgac ttgctttatt atggtagtct aaaaccaaac tggtaatatc   96420
ttcgaggtat gcctttattt tagtgcctca caaagtttac attcaagaaa attgtttata   96480
taattcccta ttttccacta gtaatgcaga ttaaatacac atctacactt gtatgacatt   96540
ttttcatatc tttgaaaatt gataatcttc tcaaaagcag tggtttggaa cctgttatat   96600
ggaggtatct gagaggctcc tgtggaccat gaaggaatcc aggattgttt ttggaagcca   96660
acacttgttt ttctggcaaa atatgtttta tatattttt taaaaagtt ttaaagataa     96720 agcagcgcaa acatttctg tatttttgc agaattaaaa gattaaatgg agctagaact     96780
caaattctcc tttatgtcta tagtactata gacaattgtt agtaatttt gtgtgtagaa    96840 gaacttcagg aaggtttgaa tgtctaaaaa gttatgtgga agagaaattg agaaatttc    96900 atttatttt aaaaccagc cataattcag tactaatata taaggtgtg ctggtatatt      96960 atatattata catttatgtt atatataata atatataatt gttagactc ctactcttgc    97020 tgttgtaagt aaactaaaaa ccaaaaatat aatgctgtgt atccattaag ttttctttaa   97080
```

```
agttgtgagt tttgccaatt taatttcttt acctataatg gtcacatgta agtataaaga    97140
tttaaattac atatatttaa ttatatttat acttaagcct tattattatt acttatattt    97200
taatgcagat attctggttc aggagtttgt aaaatttgga tcactagata catatctgaa    97260
aaagaataaa aattgtataa atatattatg gaaacttgaa gttgctaaac agttggcatg    97320
ggccatgcat tttctagtaa gtagtacaac ctttttatca aaagatacta ttttatttta    97380
taaaacaata tacaaattat ctttacctgg aaacaaaaaa taaatctgta attggatgcc    97440
aattcatgta aaatagtctg tgttaggtga taaaaagaga ttactttagg catatgttta    97500
tgtatgtaaa atcacttttg aaaaaaaagt tttgtcatcc catcaatatc ttagaactac    97560
taatagacaa tctgtatgtt gtgtcttttg gatttagaaa attcaaccaa aaattatgca    97620
gaagtatgtg cttctgtatt tttgggccat tgtacattat ggtccatgag aaagcggtgt    97680
tgacagagaa gaataccagg gggactgcca gtcatcagac ccctcagggt gcacctatgt    97740
cctgctgcag aactgaagta gtatttctta atgtcagctc ccatccagaa acacaaacca    97800
tgtcagcctt agaactcatg tgaaatggca ttggtagttt taatttattc atttcatcac    97860
aagcatagat tattgtgtta tttaaaatgt aaaacaggaa gcataggagt cataaatttc    97920 ctttttctc aatgcatgcc tccaaattat tatactatca tgtatttttc ttctttaaat    97980 ctgtttggg ggcttgaaca tactaaatgc tccagtactt gtggactgat atttgaatat    98040
atgtgcgttt aactctaata ggaagaaaac acccttattc atgggaatgt atgtgccaaa    98100
aatattctgc ttatcagaga agaagacagg aagacaggaa atcctccttt catcaaactt    98160
agtgatcctg gcattagtat tacagttttg ccaaaggaca gtaagttcta gaaggattat    98220
atataatgtt actaagcttt acttgggcag tggtgtaaag ggcatgttgt taatttttcct    98280 tgaattccat ttaatttgta tgttcctgat taataataaa attatcactt ttagcaattt    98340
aaattgttag ttaaatctta gtctctattt ttctttctta taagcatata accatggact    98400
gtgaggtgat ttttttaaaaa cagttttaat ctctaattat gtatgaagga taggattta    98460 tccattttta gtatgaagtt ttgtaatatt ccttgagcca caagtaaaatt ttctaaatat    98520 tcttttcttc tcgtcactaa ataaaaattt agcctgagat tttaggattt ttttctatcc    98580
tctgtgaaga aattagttta attatccagc taattctgac ttttttaaaac cttaaaaaaa    98640 ctttgatttg tgtttgttca tctttactac ttaacacagt gggttaaaaa tacaaatttc    98700
agtcagatag ttgagagggg tttttttgggt ctagataatt ataactgaat tttgttatct    98760 tagataatttt ctctaattgg atgttctaaa tttagattct aaattgatca attttgtgc    98820 actgatgtgt cctatttaag ctaatagtac ttaaacttaa tgacttatct gacagtgaag    98880
acagtgataa ctgggcagta gtacaggagt agggagtatg gcagaaaatt cttacagggt    98940
cttacatctg gtatcctgga aaatttatc ctttggaatc ggaagtgaag atggaaaaaa    99000
atgtattcat atggtgaagg tatttgtcaa tcaatctatt tgtctgtctg tctatgtcag    99060
aataccagaa agtagggtta tattgcttct tcctttcttg aatacagtcc ttctggtgga    99120
atcaaagacc acagaaactt tacttgagaa attccgtgat ttgagcagag cccacctata    99180
tcaattccat atatctagaa tattttggtg caatttagcc ttccatctgc cataaatgct    99240
tgttggtcct tgggtttttt tttttatctg caagtgggaa ttgccatggc tattaaatca    99300
ttagaacatc tctgaatgat gtaacattac ctttactact tacgcattat gaagaaatac    99360
caaaaagtat catgggcaa ttttaggata aactatataa aaaaaaaaga tttggccagg    99420
```

```
tgcagtggct catgcctgta attccaatgc tttgggaggc tgattgcttc ctaaagcgct  99480
tgggtggatc acttaagccc aagaggtcaa agcatagtga gctgcaatcg tgccattgca  99540
ctctagcctg agtgacacag tgacaccctg tctcaaaaaa aaaattttt tttttgaag    99600 gtaaaactaa tggaaagagg ttgagaaaat ggtatgccag ttgagacact atggtttaat  99660
ggaaagatta gttgattcag aactcactgt acaggattct aattctgtct ctgctgctaa  99720
caaattgtgt ggctttgggc agattactca atcatatgtc tccatgttgt cattgttaaa  99780
gatgaaatat tgaattagat gatcttgaag gtcccttctg gttcttaagc ttatgcagtc  99840
atgtgcatgt gcacatccaa cccctccaaa ataaagaaaa taggcctgat tattcaaatg  99900
atttgaactt taaagctatt tacatataaa agattggttt acttgtgaat tatttaaccc  99960
tactctgttc gtatcattta aaagttcttc aggagagaat accatgggta ccacctgaat 100020
gcattgaaaa tcctaaaaat ttaaatttgg caacagacaa atggagtttt ggtaccactt 100080
tgtgggaaat ctgcagtgga ggagataaac ctctaagtgc tctggattct caaagagtaa 100140
gtttatatag actaagttag aattactcta tctctgaact ttcatatttc tttcacatga 100200
tttgtatttt ttagcccatc taattttaaa aagaaggttg gtgtggcatt acacaattta 100260
ttctcagttt gtggttcttt aattatagaa gctacaattt tatgaagata ggcatcagct 100320
tcctgcacca aagtgggcag aattagcaaa ccttataaat aattgtatgg attatgaacc 100380
agatttcagg ccttctttca gagccatcat acgagatctt aacagtttgt ttactccagg 100440
tatgtatttg aatgatctta ttgattttcc agctttctat ctttattgta tttaatgaat 100500
cattactaat ttttaattcc tttaaaacat tttcttgatg tcatttgggc cctcttaatt 100560
tcttatgttc atatggcttt tcatgcttta tacatattct aatctccttg actgagaatt 100620
attttcattt ttataaaaag acctttctt tttttttt tttttttg agatggagtc 100680 ttactctgtc gcccaggctg gagtgcagtg gcgcgatctc ggctcactgc aagctccacc 100740
tccaaggttc acgccattct cctgcctcag cctcctgagt agctgggact acaggcgccc 100800
gccaccacac ccggctaatt ttttgtattt ttagtagaga cggggtttca ccgtgttagc 100860
caggatggtc tcgatctcct gatcttgtga tccgcccgcc tcggcctccc aaagtgctgg 100920
gattacaggc ttgagccacc gctcccagcc aaaaagacct tttcttttcag taacctaatt 100980 ttagttttcc atttagtgag ttgtaaatta tagtatttt tttttgctta aattgacttt 101040
taaaaaacaa ttctctttaa catttctcat attttataat tgattgattc tctaaacatg 101100
agctgtattt gttttgcttt gttctctcct ttttcaaaat actgagctga atgcatgtg   101160 tttgacctat aggtgctttc taccccagta ctactcacct ttctcacaat aagtatcagt 101220
atattacctt actttatgaa tactaaaact tcttattttg gaaaacaaaa ttttatcctt 101280
tgcaaagtct ctcttgaagg cctgtcagat tatgggtaat gattaaaggc tcccattaat 101340
ataattgaaa ctatttgagt ttccctgtat catttagtat ttttaactca cgattatttt 101400
ggtcaacttg aatgtatatc agtttagtcc agagaatgtt atttgctaat ttaaggtgat 101460
aatattcttt atttctccag attatgaact attaacagaa aatgacatgt taccaaatat 101520
gaggataggc gccctgggt tttctggtgc ctttgaagac cgggatccta cacagtttga 101580
agagagacat ttgaaatttc tacagcaact tggcaaggta aattgtcaga atttttcaa  101640 atagagtata atcatttcat ttaggaaaaa cttaagagcg tttctaaagt tcactttcta 101700
caacatttta aggagtgctt gtagaaaaaa aaggtttggt tgtcagatgt tggagaaatg 101760
ctgtgttaaa taaacagcta tctttactga atgaagggg ccagccctc cacacctgtg  101820
```

```
ggtaattctc gtcaggtggg accagagact gagaaaagaa agaagacaca gagacaaaag   101880
tatagagaaa gaaaagtggg cccagggac cagtgctcag catatggagg acccgcacca   101940
acactggtct ctgagtttcc tcagtattta ttactgtttt cactatctca gcaagaggaa   102000
tgcggcagga gagcagggtg atagtgggga aaggtcagc aagaaaacat gtgaggaaag   102060
gaatctgtgt cacaaataag ttcaagggaa ggtactatgc ctggatgtgc acataggcca   102120
gatttatgct tctctccacc caaacatctc agtggagtaa agaataataa agcagcattg   102180
ctgccaacat gtctcgcctc ccgccacagg gcagttttc tcctatctca gaaatgaaca   102240
aatgtataat tgggttttat accgaggcat tcagttccca ggggcaggca ggagacagtg   102300
gccttcctct tttactaatc ctccccagca cagacccttc acggatgttg ggctggggga   102360
cggtcaggtc tttcccatcc cacgaggcca tatttcagac tatcacatgg ggagaaacct   102420
tggacattac ccggctttcc agggcagagg tccctgcggc tttccgcagt gcattgtgtc   102480
cctggtttat tgagactgga gaatggcgat gacttttacc aagcatactg cctgtacaca   102540
ttttgttaac aaggcacatc ctacacagcc ctagccttaa accttgattc catacaacac   102600 atattttttgt gagcttcagg ttggggcaaa gttacagatt aacagcatct cagggcaaag   102660
caattgttca gggtacagat caaaatggaa tttcttatgt cttccttttc tacatagaca   102720
cagtaacaca ctgatctctc tttcttttcc ctataactga gaacttttc agaggcttta   102780 acatgtaatg tgcatgaaca tcttcaagag gaagatgaat taggcagtat tattcaaatt   102840
gacttgacca agagactgtt ccttggtagc aggagttcat tgttaagtga ttcagtgaaa   102900
tacagaaagg aatacataag cttttctgcc tgcctttctg cctttagtta tctcagggag   102960
aattaatctt attgcttagg gtctaggatt ttgactgtgc catattcact agcagagact   103020
ctgtctatta aaacgtcaca cagtcatgta taacctacat attataagta agaccaggga   103080
atgctcagtt cttagtaggt ccaaccatag tggtaagctc tttctcgcat aagcttgcta   103140
ggataaggtt ctcactagta agtaccatgt tagtgttgtc tgttattatc agctattcct   103200
aaattcatat ttcctgaaa tatctccaga tgtcattgat tttcctcttt tctgggaact   103260
tatagcattt attgtttctt ttatacaact taatcacagt cttctgttgt ttattagatc   103320 ttggttttg tttgcttgcc ctttttttcc ttgacttaaa aaagttcct ttagatccca   103380 atagattact aggcacacaa ttttgtcata tattgtcaaa acaatggaat atatactggt   103440
atttaagaag tagacataac aaagaataca tcaaaagatc actaatttag attaacaaaa   103500
gggaaacagc agactaaatt ataaagttat cttttcaagt aattttttcta gttatgaaag   103560 tgatatactg cttatagaga aattggaaaa tattacaatg aagatacgtt ccatttgttg   103620
tagtctctgc acaactacac aatttctttc aatagtgaaa ccattctata tatacaattc   103680
tatatcttgc tatttttcat atatcaagat tttcccatta ttaatattct tttgagacat   103740 aatttttaagt gaatatacca taattttattt acaacattcc cctttattgt aattttgagt   103800
taatgttctt ttgctttta acatttttag tgttttccat agttccgtga gcttaaaatt   103860
cttttaaaca taagtaaatt gaagagactc taaggaaggc gttttcaaaa tacatgtaca   103920
atgaaatata tttcttagta atttagtttg taggaaatga aaggtaaatg gtgtaatcat   103980
tagtcagtca tagatatttt aatgtggata tttcctatct gtatttaaca ccataatttt   104040
actttcatct ttgtttgttt gaagtaattg atgtgttcag tggtttgtct agatatttgt   104100
actgccttac tgaaacaatc aaaatgccat tcctacaaaa atgattgcat gtcaccttc   104160
```

```
cattttataa aaattagcta ctgtatccct ttgttatcct tttcaattag tggtatggtg    104220
aaaatattcc aaagagggat atatatttaa aattattttc atatgtttta agccaagaga    104280
aataatggta tattttttta ttttttaaaa aatatttca tactgttgta aaaggagcca     104340
agaaactatt gtgaaatctt ttcttttgct atttgaaatc tagagtgttt tttgctttct    104400
tcctttatcc tcatgcccac atatacttat attcttttt aaattaattt taacatggat     104460
tatttgtgta atagccttac atgtggatat taacagtgta aacagtacca catataacca    104520
tcaagacacc tcaattagaa tttataggac tagaatgaca gattcagatg gtttaattac    104580
atttaaaaag ttttctgaaa aaacttttgc aataaaacaa attgcccatc aataagtttg    104640
atatctttta aaatgatttt tggttatctg cacatgaagc aaacaaagtg tattccacaa    104700
aattcttagg cacagtctga gatagctgcc agaaagaaca gaaagagttg tcatttatgt    104760
cttgtgagta caatttctga aagttgaatg agggcgtctc tttctgggga tgagaagttt    104820
actgctctct cttattgctt catggcagta ctgctgggca aggtaggttg tttgttttac    104880
accatcactc tgtaatacat actgtggagc tctgtctaca tctcccggca aactgaacca    104940
tctcatgatc atagcattca tttctgggaa ctgctgacag gcaaatagga caggaccagt    105000
ggctaacctg agattcacat cagctgatgt tggtttgcct atgttagaac atgaggtgaa    105060
gtcgaataca tcatctatta gctgaaaagc tattcctaca ttttttccgt actgataggt    105120
gatctcatgc accactgggt cggggcatcc tagaacagag actgctttac aactgttggc    105180
tatcaggctc gcagtattct tgaaggtctt ttcaaggtat tgtgcaaatc tctcatgctc    105240
attttctttt gacccgagct gaagaaattc accacacacc aaatcttcaa taactcgggt    105300
taaaatagat ataacagctg tatttccagt ttgtgcccca cctatagata ctacagaaag    105360
aattaaatct ccagcaagga cagccttctt ttcaccccag atcttgtgtg ttttccttt     105420 cgagaacgtg cattatcaat aacgtcatcg tgaacaagac tagcagtgtg gatcatttct    105480
gcaattaagg ctgtggcgcg ctggctagct tgcacatgtc gggagttatt atgatgaata    105540
ttacatgctc gggccattag taccacaata attgatcgaa aggcttttcc ttttacatca    105600
aagtagtact cagagatttc cttaagttct gttgttgata tgagcggttc ctttctaata    105660
ccctcataca gacctttcaa gtctctccaa ccgagtttga aaggatcggt gtatttctca    105720
ccactgtgtg ttttgctgta cggggttgtg tgatgaaact gtgatatact atatacatt     105780 ggacaggcag gtgttaaatg cttcacaaga ttaaaatagg gtatctgaga caagtcaagt    105840
cccttctgcc tatgagcctg cgcgggcatc ggcagcggcg cgcggccccg gcggcccgc     105900 aaggctcggg gagcggtctc cacgccgccg gtctccagca acagccgcgc cgccccgcc    105960 accagcgcga ggccacggtc ggagtctgaa agtcgcggta ggatggtggc tccgcctctg    106020
gcccgcgatc ctcctgccag gacctggagc ctgaaacctc ttatattctt tatatccttt    106080
accttctcgc ttcactccta gcggtttga aatcctcttt attccttttt cctccatggt    106140
gcagatatgg gattcagaga tcaggatctt agtgcgacta ctttgaaatt atcagcatca    106200
ttctcaatct tctctgaata tgattcttat tttcctctct tcccatcatt agctaacatc    106260
ttggtccaca ttccttgaat acttttagta ctcattgttt tctcatcacc ttacctcctg    106320
ccattatttt ggatgcccctt ccaatactta aaaaaaaaat tccttggctt ctctacccca   106380
aagttatgat tatgttaaat gagttccttt gaactctata atcccatgta ataaccttac    106440
ttagaaaatt tcctaccctg aaatctccct gtctgactat aactttatag cctttggctt    106500
ttttcaacat aaatgccttc tttttgatat ctttggtatt gctagtgtct ttcacacttt    106560
```

```
cttcttattg gaacgtaaat tggtgaccct ttctagagag cttctcatag agcagtttgt    106620
atcaagcgcg tttaaatgtt catatctttt aaactactttt cgctggtatc cacaattata   106680
tcaccccccc ttcccttgat tatctgcttc actttcccta ttatttccta gtacgggaac    106740
aatacaactt agcatttttta aattgtgctt ccatccctca aacactaaaa gaaaaaaatc   106800
agatataaat ctttattgtt ttcattgaaa attggtttcc aacattggtt aggcacttat    106860
gactcttact ggttgtatta gtctgttctc acgctgcaaa taaagacata cccgagactg    106920
ggtaatttat aaaggaaaga ggtttaattg actgacagtt acccatggct ggggaggcct    106980
caggaaactt acagtcatgg cagaaggcac ctcttcacag ggcagcagga gagagaatga    107040
gtgccagcag gagaaatgcc agatgcttac aaaaccatca gatctcatga aactatcac    107100
gagaacagca tggaggaaac cacccgcatg attcagttgc ctcccaccag gtccttccaa    107160
tgacatgtgg ggattatggg gtttacaatt caagatgaga tttgggtgag acaatgcca    107220
aaccatatca ctcccttact tgatttcttt cctggtccta tctcaaaccc ttctggtttt    107280
ctatcttaaa tctttctttt cgctgtattt ttcttcatct ccttcttcca taagaaaaat   107340
agaggcattc cgaattaaaa gtgagactga ttttttgccta tcaaagtgac aaggatttag   107400
aaaaagtata atgatcattg ttggcaggga tgtgataaaa tatacatttt cccactgctt    107460
attggaacat caaatggtaa ccactgccag acagcttcta atgcagtgtg tatcaagtcc    107520
ctttgaaatg ttcttatctt ttgaacagct aattaagtat ccttaataga gatgtacaca    107580
aatatttatt tataagaata ttattgcaat gacatgactg tatttaaaaa tttttcttag    107640
tgtacattta tgtttccaat gttaaaatta gtgcattcgt gtgacaatat acaataatta    107700
aaaattatta atttcaagga atatatagtg gcactagaaa ataaatttta tgaacacatt    107760
gttaagtaga ggggaagaag ataaaactta tttcctactt ttgttttcta aaatgtgttt    107820
tggaataatt tctcacaaca gcctcatgag atagacattt tattattctc cactttaagg    107880
atgaaaaacc tcatttttagg gagttctgaa ttgtccgcgg tcacagagag agcaagttgt    107940
ggatcaaatat tctagttcca atctgacttg agagtcctgg gtcttgagag tcctgggtct    108000
atccaccttta ttgtgtggcc ttctaaactg tgtaattaag agatttaact ttgagcctac   108060
atggtctagg ttttttaaaa aactgacttc aagtatataa ctgaaaatat agtcacttag    108120
aatcttgtaa ctcaagaact acattgtttt atcctgtaag aatgcaataa tatccaaaat    108180
acactaattt gattaatatc aaaaacctat actttattta aatgttatag caacttacca    108240
attctatgta cttaatgagt tttaggtaaa aagagtggat ttctttaaag acatcttcaa    108300
aaaaaaaaat gtagagtcat cccataggct aaaagtttct tacttcttaa tttgctttgg    108360
ctgctataac aaaataccat agactgggta gcttaaacat cagacattta tttctttgaa    108420
ttccagggcc tggaaagtct gagatcaaag ttctggcagg gattggtttc tagtgaggtt    108480
tcttcttggc ttgcagatgg ccatcttctt gctgtgtcct cacatgggag agagagattg    108540
ctctaatgtc tcttcctctt ataagggcac tagccttgtc acattagagt tccaccctta    108600
taacctaatt taacttttat cacctcctca caaggcccta tctccaaata cagtcatatt    108660
ggggggttaag gcttcattat ataaattttg ggtaaggggt cactgacatt tagcccataa    108720
cagacacatt ccatccagat cactgacagt gatagcaaaa ggtatttttgt aaaaaggaa    108780
aattcttcct ggaagttagt gacaaaagtt taggaatcct cagcatgtcc cttggcttat    108840
cttgacaatt aatgctcatc atttatttaa atgcttttttt gaagtaattt atatttcagc    108900
```

-continued

```
ctataattcc ttttgaagaa attaaattta cagatttact acccacctgt tgagatagta  108960
tttccttttc ttgttctaag agttccttaa tataagctta aagatagtct gctgctgggc  109020
atggtggctc atgcctgtaa tcccagcact ttgggaggcc gagttgggtg gatcaccagg  109080
tcaggagatc aagacaatcc tggctaacac agcgaaaccc tgtctctact aaatatacaa  109140
aaaattagct gggcgtattg gcgggcgcct gtattcccag ctactgggga ggctgaggca  109200
ggagaatggt gtgaacccag ggggcggagc ttgcagtgag ccgagatcgt gccactgcac  109260
tccaacctgg gtgacagagc gagacttcgt ctcaaaaaaa aaaaaaaaaa aaaaaaaaa  109320 agacagtctg ctaattccag ctactagaat tttctatata attataaaat ttatttgtaa  109380
tttgccttga aaacttggta tttccatcct aatgtgatgt gtcatttagg gtaattttgg  109440
gagtgtggag atgtgccggt atgaccctct acaggacaac actggggagg tggtcgctgt  109500
aaaaaagctt cagcatagta ctgaagagca cctaagagac tttgaaaggg aaattgaaat  109560
cctgaaatcc ctacagcatg acaacattgt aaagtacaag ggagtgtgct acagtgctgg  109620
taagctgccc attgaaacct attttaaatt caaggtatgt gtttggcatc ctgtgtaata  109680
taaatgtaca atgtcttaac gatctggact tatgccaatg cccagaggga gaggcattct  109740
ataatgacta gagattgtgt tggtgatca tagactataa ctataggaag tatttggcta  109800
gttggtaaaa cattcttttc acctcttgct taagcttacc aagaaagtat catttttaaa  109860
ggaattgttt ttgtttacat tttctataaa atattttg aattcaatgt tttttgttcg  109920
atatcaatga ggagaaagga agttttctca tcagtttatt ttggtttgcc tgaagagtta  109980
tagaaaactg aaacgcaaat agtttcaaag ctttttattca ttcaaaagtt tttgattcaa  110040
aaagactatg ttcttaacaa ctatatcacc tttaatgtat aataaagttt tgtcatctta  110100
gatttcatat atgtttaagt catttatgta tgatagtttt ctaatatta atcagtataa  110160 tatggcagag taaaacatta tttccacctt tatgttaaaa ggtcggcgta atctaaaatt  110220
aattatggaa tatttaccat atggaagttt acgagactac cttcaaaaac ataagaacg  110280 gatagatcac ataaaacttc tgcagtacac atctcagata tgcaaggtaa ctaatatcct  110340
gattatttgc tgtagatgaa gcaaccgtgt tgaagtagac attaggaaat catctagacg  110400
ttttcataga taataaaggg aatatatagg gttaagacca tttaaattgt ttatatttat  110460
aaaactagct gaaagaaaaa tgttttatcc atagggtatg gagtatcttg gtacaaaaag  110520
gtatatccac agggatctgg caacgagaaa tatattggtg gagaacgaga acagagttaa  110580
aattggagat tttgggttaa ccaaagtctt gccacaagac aaagaatact ataaagtaaa  110640
agaacctggt gaaagtccca tattctggtg agtatatttc agtatgataa atgaaatttt  110700
agagcacaga cttcaaactt tattgttgtt atttaatagt ttgccatttc tatatttaca  110760
gtaacagtga acatttaagt cttttaagtc ttacatttaa cttttttttt ttaggtctta  110820
tagtcatggt tatagtccac gtgggaaaat ggcatatgct ttatttctat taagtgttgt  110880
cttatttata gggattgtag gttttttcttc aaaactgtct cctatttatt gaggcttagg  110940
ggtaattatt agtggtgctg tgggttgtgg tattgtgttg aattttggtg gggctttcat  111000
ggggttaata gtcttttttta tttacttggg tggtataatg gttatttttg gttatactcc  111060
agtgatagct attgaggagt atcctgaaac atgagggcca agtactgata tttgagggc  111120 cttattatta ggattattaa tagagttgat actggtttgg tgaatagttg aatatgatgg  111180
ggtggtgatc acggttgatt ttaatagcat agggagttga tttaattttt gagggggagg  111240
ggttgattca tgaggatttt gtaggtgcag ctgccttgta taattatggg tgttggttgg  111300
```

```
tggttgctgg ttgatcattg ttagtatttt tgtcgcaatt gaaattactc agggtaatag   111360
attagataat taatagtaga gtttaggcct ttttggtcag atacagtaat ggaggctgaa   111420
gtttgggttc gtgaaatggt ttttggtata gacttttcta gtcaaactgg gtctagtaga   111480
agtgaagcta gattttggct tatgaatagg cttaagtcgg ggggctgaat ggtgaattgt   111540
agctgaataa aaacctagta tactggagaa gttaaatgtc tataatgggt actttaaggt   111600
tgttagttat gaaattaagc tctattgcta gtaagagacc tagggtggtt acacctaggg   111660
ctgtgagctt taggtggagt ggtatagttg tttgggggga tgaagtaggg ataatactgt   111720
tagtgatgag gaatccggcg aagatactgc cgattgctag gtgctgaact gagttaattc   111780
ggagaggatt atcattaata acaatcagaa ttgtaaaaca aggttgtcct attacagcac   111840
ctaaggttat aaagtaagca caagtaaata cataaaaacg ttaggtcaac gtgtagctca   111900
tgaggtggca agaaatgggc cacattttct accccagaaa atctcacgac aacctttatg   111960
aaatctaagg gctcaaggag gatttagcag taaaccaaga gtagagtgct tggttgaggt   112020
tgaataaggc cacgaagcac gcacacactg cctgtcaccc tccgcaaata tcattctaga   112080
aatattattt aaattctcta tacatgaata gaggagataa gtcgtaatat ggtaagtgta   112140
ctggaaagtg ctcttggaca aacaaagtgt cgcttaaccc aaagcatcca gcttacaccc   112200
ggaagatttc atcacaacct ggtcactttg agccaaccct agcccaaac ctcactaaaa    112260
atactattaa accatcgtaa tcaaaccatt taccttagac aaaagaatag gcaatagaaa   112320
ttcttatctt ggcacaatag atacagtacc gtaaggaaa gatgaaagaa ctgagcaaag    112380
acaagccctt ataccttctg cataaagtat taagtagaaa taactttaca cagagatagc   112440
caagtccccc gaaaccaaat gagctatgca agaatggctg aaagagcgta ctcacctacg   112500
tggcaaaata gtgggaagat tcatgagtag tggtgataag cctatcaagc ctgctgatag   112560
ctggttgtcc aagatagaat cttagttcag ctttaaactt acccacagaa ttacttaatg   112620
tccctgtaag tttaactgtt aatctaaaga gggacagctc tttagaccct aggaaccaac   112680
cttcctacag agagtacaaa ataacatcgc catagttggc ccaaaagcag ccaacaatta   112740
agaaagtgtt caagctcaac atccaagtat cttaaattct aatcactcta cggaactcct   112800
aacattacac tggtctaatc tattatttaa tagaagcaat aatgttaata taaataacat   112860
gaaaatattc tccaccgcat aagcttacat aagactggaa taacccactg actgacagtt   112920
aacagctaga tattttacaa taagcatcct attatttata ctgttaatcc aacacaggca   112980
tgctctaagg aaatattaca aaaagtaaaa ggaactcggc aaatcttacc ccacctgttt   113040
accaaaaaca tcacctctag cattaccagt attagaggca ctgcctgccc agtgacatat   113100
gttcaacgac caccatatcc tgaccttgca aaggtaacat aatcacttgt tccctaaata   113160
gggacttaga agaatggcca catgagggtt cagctgtcat gagggttcag ctgtctctta   113220
cgtttaatca gtagaatctg acctattggt gaagaggagc ttataagcaa ataagatgag   113280
aagacccat ggcactttaa ttcattaatg caaataaaaa ctcaaaaagc ctataggcct    113340
taacctacta tctctgcatt aaaaatttg gttggggtga cctcatagca tattcaacct    113400
ccgaacaacc taaactaaga ccacagtagt ctaagcgagt aatacacat tgacccaata    113460
atttgatcaa cagaacaagt taccctaggg ataacagtgc aatcctattc tatcatatca   113520
ataatagggt ttacgacctc gatgttggat caggacatcc taatggtgta gccgctatta   113580
agggttcatt tattcaatga ttaaagtcct atgtgatctg atttcagacc agagtaatcc   113640
```

```
aggttggttt ctatctgttt aacatttctc ctagtatgaa aggacaagag aaatacggcc 113700
cacttcataa agtgccctcc ccccataaat gatgctatct caatctagga aatcaccaca 113760
cacccaagaa cagggtttct taagatggcg gagcctggca atagcataaa acgtaaaact 113820
ttacaatcaa aggttcaact ccccttctta acaatatgcc tataattaac cttttcctac 113880
ttatattccc actctaattg ctatagcatt ccttacactt aacagttacg caaaggacct 113940
gataccgtag gccctgtgg actgcttcaa ccatttgctg acccaataaa acttttcacc 114000
agagaaccct tacgaccctc aacgtctact gttacccttt atatcattgc ctccaaccct 114060 ggcccttct atcaccctcc tcttctggac tccccttcct atacccatc ccctaattaa 114120 ttttaatata ggcctcttat ttattctagc cacatcaagc ctagcagtct attccattct 114180
atgatcagga taagcatcca attcaaatta tgtactgatc ggcacactac gagctgtggc 114240
ccagacaatt tcatatgaag tcaccctagc cattatcctg ctatcactac tactgctaag 114300
tggctcaact tatatgcatg catcacaatg ccagaattac tctgaccgct cctaccatca 114360
tgacccttag ccatattatg atttatttcc acactagcaa aaactaaccg agccccttt 114420 gacttaacag aaagagaatc agaactagtt tcaggcttca atgtcgaata tgctgcaagt 114480
tcatttgccc tcttctttat agcagaatat atgaatatta ttgtataaat gccctgacta 114540
ctactatttt tctaggagta ctacacacta tgtattcacc agaactctgt accataaatt 114600
tcattaccaa gaccctcctt ttaaccaccg ttttatgaa tccgaacagc atacctccaa 114660
ttccactaca accaactcat ataccttta tgaaaaaatt tcctaccact tacattagca 114720
ttctgcatat atctcaatgc ctttcctaat ttccagcatt ccaccccaaa cataggaaat 114780
atgtctgaca aaagaattac tttgatagag taaacaagag aggttaaaat cctcttattt 114840
ctggaactat aggaattgaa cctatccctg agactccaaa attctccatg ctacctatta 114900
aaccatatcc taaagtaagt tcagctaaat aagctattgg gcccattctc ctgaaaatgt 114960
tggttatacc cttcccatac taattaatcc attagctcaa cttattatct ctcttactat 115020
tttcacagga accctcatca caatgctacg ctcacactga tttcttatct gaacaggcct 115080
aggaataaat atagtagttc ttacccccat cttgattaaa aaacaaatc tccactctac 115140 agaagcagcc accaaatatt tcttacaca agcaactgca tctataattc tcatgatggg 115200
tatccttttc aacaacccgt cctccgggca atggacaata ataaacacta ctaatcaatt 115260
ttcatcctta ataataacag ccctagtaat aaagctagaa atagccccct ttcacttccg 115320
agtcccagaa gtaacccagg gaacttctct aatgtctggc atacttctcc tcacatgaca 115380
aaaactagcc cctatctcaa ttatatttca aattttccca tcaataaaca cgaccagtct 115440
cctatctatc acaatcctat ccattaacgt aagcggttga ggaggactta atcaaacaca 115500
attctgcaaa atcttaacct actcctcaat tactcatata ggttgaatga tcccagtact 115560
aacttataat ccaaacgtta ccattataaa tctgattgtt taccttattt taacaactac 115620
cacatttcta gcacttagcc taagtataag cactacaacc ctgtcactgt ctcacacttg 115680
aaacaaatta acatgattaa cacctatagt ttcactaatt ctactatccc taggagcttt 115740
acctccatta acaggatttc tgcctgaatg agtcatcatt caagaatttt caaaaaacaa 115800
tagtcttatt accccaacca ttatagctat cataacacta ctcaacctgt agttttatat 115860
atgcctaatt tactccatct caatgacaat attcccacca tccaataata cgaaaataaa 115920
atgacaattc aaaaacacaa aacccatatt actcctccct ccacttattt cttctacctt 115980
cctcttaccc atctctccac tgattctagt tataacttag aaatttaggt taaataagac 116040
```

```
cagggacctt caaaacccctt agtaaatgaa ttatacttaa tttctgtaac aaacccaagg  116100
actgcaaaac tctattctgc atcagttgaa cgcaaatcaa ccactttaat taagctaagt  116160
ccttgctaga tcggtggaat tcaaacccac aaaaatttag ttaacagcta aatacccctaa  116220 tcaactggct tcaatctact tctccctcca tgtgggggga gggtggtagg ccggagaagc  116280
cctggcagca ttgaagctgc tcctttgaat ttgcaattca acataaaaaa ttacctcagg  116340
gctggtaaaa agaggtcttg acctctgtct ttagatttac agtccaatgc ttactcagcc  116400 atttttacccct ttttttccact tatgttcatc aattgttgat tgttttcaac caatcacaaa  116460
gctatcggaa cactatacct gctgttcggc gcatgagtgg ggatagtggg tacctcctta  116520
agccttctaa tttgagcaga attaggtcaa ccaggaactc tgctaggaga tgaccagatc  116580
tataatgtta ttgttaccgc ccacgaattt gtcataatct tctttatggt catatcaatt  116640
ataattgggg gtttcggcaa ctaactagtc cctctgataa ttgctgcccc tgatatggca  116700
tttccacgga taaataataa tgagcttttt acttctcccc cactctttcc tactcctact  116760
tgcatcctca atagaagccg gtgctggaac tggctgaaca gtttatcccc ctttagctga  116820
aaacctaaca catgcaggat cctttgtggg tcttaccatc ttctcacttc acttggcagg  116880 tattctatttt taggagccat taactttatt actacaatta ttaacaaaaa gcccccagcc  116940
atatcccaat atcaaacacc cctttttcgtc caaccattcc tcattacagc aatcctactc  117000
ctttctctct cagtcctagc cgctggcatt accacaatat taactgaccg taacctcaac  117060
actacttttt gaccctgctg gtgggggtga tcctatctta tatcaacatt tattctgatt  117120
ctttggtcac cctgaagttt atatccttat tctatcaggc tttgggatga tctcccatgt  117180
cgtgacgtat tactctggaa aaaaggagcc atttgggtat atgggcatag tatgagccat  117240
aatatctatt ggcttcttag ggttttattgt atgagcacac catatatttta cagtaggaac  117300 agacatagac acagacacat gagcatactt cacctccgct accataatta ctgctatgcc  117360
tactggcatc aaggtctttta gctgattagc tacactgcgt ggtggtaaca tcaaatgatc  117420
tcccgcaatg ttctgagccc taggattcat ctttcttttc acagtaggag gtctaattgg  117480
cattgtacta gctaattcat cactagatat tattttacat gatacatact atgttgtagc  117540
tcatttccac tacgtcctat caccaggagc ggtgttcgcc atcataggag gctttaccac  117600
tggttccccc attctcaggt tatatgctta atcagaccta cgctaaaatt cacttcacca  117660
ttatattcat aggtgttaat ttaacctttt tcccacagca cttccttggc ctatccggta  117720
tgccgcaacg ttattccgat tatcctgatg catacaccgc atgaaatatt atctcatcct  117780
taggctcatt tatctcatta gcagcagtta tgctaacaat ttttataatc tgagaagcct  117840
ttgtttcgaa agaaaaact ataacaattg aacaaccatc tagtaattta gagtgactt  117900 atggctgtcc accaccttac cacacatttg aagagccaac ctacattaaa cccttaaatg  117960
aaaaagaaag gaattaactt ccagaaactg gtttcaagcc aatcaaaaac ctctgtgact  118020
ttctcgataa gatattagca aattcattac gtaactttgt caaagttaag ttataggcta  118080
aatcctatat gtcttaatgg ctcatccagt tcaattaggc cttcaagacg ctacatcccc  118140 tatcatgaa gaaccgctca ctttccgtga ccacgttctt ataattattt tcctaattag  118200
ttcctggttc tatacattat ttccgtaata ctcacaacaa aattaactca tattagcacc  118260
acagatgccc aagaaattga gactgtttga actatcttac ctgccattat cttaatttta  118320
aggcctctca tccctacgta ttctgtataa aacagatgaa gttaataatc cttcccttac  118380
```

```
tgtcaaagca attggtcatc aatgatattg aagctatgaa tatatagact atgaagaatt    118440
aagcttcaat tccttttttt tttttttgag acagagtctc gctctgtcgc ccaggctgca    118500
gtgcagtggt gtgatctcag ctcactgcaa gctctgcctc ccgggttcac gccattctcc    118560
tgcctcagcc tcccgagtag ctgggactac aggcgaccgc caccatgcct gggtaatttt    118620
tttgtatttt tagtagagac ggggtttcac catgttagcc aggatggtct tcatctcctg    118680
acgttgtgtt ccacccactt cagcctccca aagtgctggg attacaggcg tgtgagccac    118740
tgcgcccggc ttaagcttca attcttatat aaccccaaca ccagacttaa aaccaggaga    118800
acttcgactc cttgaagttg ataaccgaac aattctccca acagaaatac ccatccatat    118860
attaatctca tctgaagaca tcctgcactc atgaactatc cccttattag gcctcaaaac    118920
agatgcaatc cccagatgct taaatcaaac taccttaacc actgggcgac caggtcttta    118980
ctatggacag tgctcagaaa tttgtgaatc taaccagttt tatacctatt gtcctagaac    119040
taatcctctt aaaatatttc aaaacctgat ccacatctac actaaatat cactgtaaag     119100 ctattcagca tttacctttt aagttaaaga ttgacggagt ctacacctct ctgcagtgaa    119160
tgcctcaact agatacttcc acatgatcca ttattatcct gtcaataatc ataactttat    119220
tctccattat tcagttaaaa ttattaaatt tcatttatat tatccctaca ccaaaaataa    119280
tcaaaacaca aaaacacaag gcttcctgag aattaaaatg aacgaaatct attcatctct    119340
tttgctaccc ctacaattct aggcctacca gcagtagtat taatcattct gtttcccact    119400
gtttccaacc tctagtcatc aaattagtaa ccgattattt tctattcaac gatgattaat    119460
ccaacctgca ctaaaacaga taataattac ccataacatt aaaggacaaa cctgatccct    119520
tataataata tccctaatta tcttcactgc ctcaaccaac ctccttgggc ttctacccca    119580
ttcatttaca ccaactatcc aattatcaat aaacctgggt atagcaatcc ccctgtgagc    119640
aggcgcagta attacagtct tctgctttaa acgaaaaac tccttggctg cttttttacc     119700
acaaggcaca cctatgccac ttatccctat actagtaatc attgaaacca ttagcctatt    119760
tattcaacca atagcattag ctgtgcaatt aacagccaac attatagtca gtcatctact    119820
aatacattta attgcaggag acacactagt actattagct attagttttc ccacagcttc    119880
agttgctttt attattctaa tcctactgac tattctcaaa ttcgccatag accttattca    119940
ggcttatgtc ttcacactac tagtaagcct ttatctatat gacaacacat aatgaccac     120000 caaacacatg cttgccatat agtcaaaccc agccctgac cactaacaga agctctctca     120060
gctctactaa taacatctgg cctggccatg tgatttcact ttaattctac tactctttta    120120
accctaggcc tattaatcaa cacactaact gtataccaat gatgatgtga tattatctga    120180
gaaagtaaat ttcaaggcca ccatacaaca gttgtccaaa aaggcctcca atatggaata    120240 attctatttta ttatctgaga agtattcttc tttgctggtt tcttctgggc attctatcac   120300
tctagtctag ccccaatgcc agaattagga ggacactgac cccccaacag gcattttcc     120360 cctcaaacgc ttagaagtac ctttctgaat acatctgtat tatttgcatc aggagtttca    120420
gttacttcgg ctcatcacag cctgatagaa ggaaatcgaa agcaaataat tctagcacta    120480
tccatcacga ttaccttagg tatttacttc accctcctac aaatctcagt actttgaggc    120540 ccctttact atctctgatg ggatctatgg ctcaacattc tttacagcca caggctttca     120600
tggatttcat gttattactg gatcaacatt tctcactatc tgcttcctcc gccaattaaa    120660
atatcacttt acaagatgtc tgaataggaa tagctccagt ctgcagctcc cagcatgatc    120720
gacgcagaag atggtgattt ccgcatttcc aactgaggta cctggttcat ctcatcggga    120780
```

```
ctggttggac agggggtgca gcccacagag ggcaagttga agcagggcgg ggcatcacct 120840
cacccaggaa gcacaagggg tcagggatt tccctttccc agccaaggga agccatgaca 120900
gactgtacct ggaaaatcag gacacttttg cccaaatact gtgcttttcc aacagtctta 120960
ccaaatggca caccaggaga ttatatccca tgtctggctt ggcaggtccc acacccacgg 121020
agccctgctc actgctagca cagcagccta agatccaccc gtgaggcagc agcctggcag 121080 gcggagggc gtccgccatt gctgaggctt gagtaggtaa acaaagtggc cagggaagct 121140
cgaactgggt ggagcccacc acagctctgc aaggcctgct gcctttgtag accacacctc 121200
tgggggcagg gcatagctga aaaggcagca gaaacttctg cagacttaaa cgtccctgtc 121260
tgacagctct gaagagagca gtgtttctac cagcatggtg tttgagctct gacaatggac 121320
agactgcctc aggtggatcc ctgatgcttc tgtagcctaa gtgggagaca cctcccagta 121380
gaggccaact gacacctcat acaggtgggt gcctgtctgg gacgaagctt ccagaggaag 121440
gatcaggcag caacattggc tgttctgcaa tatttgctgt tctgcagcct ccactgcaga 121500
taccgaggca aacagagtct ggagtggacc tccagcaaac tccaagagac ctgcagctga 121560
gggacctgac tgttagaaag aaaactaaca aacagaaagg aatagcatca acatcaacaa 121620 aagggcatc cacaccaaaa ccccatctgt aggttaccag caccaaagac caaaagtaga 121680 taaaccaca aagatgggga gaaccagag cagaaaagct gaaaattcta aaaccagag 121740 ggcctcttct cctccaaagg attgcagctc cttgccagct ggatggagaa tgactttgac 121800
gagctgacag aagtaggctt cagaaggttg gtaataacaa acttctccaa gctaaaggag 121860
gatgttcaaa cccatcgcaa ggaagctaaa aaccttgaaa aaagattaga ccaatggcta 121920
actacaataa acagtgtaga gaagacctta aatgacctga tggagctgaa aaccatggca 121980
tgagaactac aggacgcatg cacaagcttc actagccgac ttgatcaagt ggaagaaagg 122040
gtatcagtga ttgaagatca aattaatgaa ataaagcgag aggagaagtt tagagaaaaa 122100
agagtaaaaa gcaacaagat aaagcctaca agaaatacag gactatgtga aaagaccaaa 122160
tctacatttg attgttgtac ctgaaagtga cggggagaat ggaaccaagc tggaaaacac 122220
tcttcaggat attatccagg agaacttccc cgacctacca aggcaggcca acattcaaat 122280
tcaggaaata cagagaactc cacaaagata ctcctcgaga agagcaaccc caagacacgt 122340
aattgtcata ttcaccaagg ttgaaatgaa ggaaaaaaat gttaagggca gccagagaga 122400
aatgtcgggt tgcccacaaa gggaagccca tcagactaac agcggatctc tcagcagaaa 122460
ctctacaagc cagaagagag tggaggccaa tattcaacat tcttagagaa aaagactttt 122520
caacccagaa tttcatatcc agccacacta gcttcataa gtgaaggaga ataaaatcc 122580 tttacagaca agcaaatgct gagagatttt gtcattacca ggcctgcctt acaagatctc 122640
ctgaaggaag cactaaacat ggaaaggaac aaccagtagc agccactgca aaacataccc 122700
aaattgtaaa gaccatcgat gataggaaga acagcatca actaacgggc aaaataacca 122760
gctaacatca taataacagg ttcaaattca cacataacaa tattaacctt aaatgtaaat 122820
gggatgaatg ccccaattaa aaaacacaaa ctggcaaatt ggataaagat tgaagaccca 122880
tcactgtgct gtattcagga gaccaatctc atgtgcagag aaacacatgg gctcaaaata 122940
aagggatgga ggaagatcta ccaagcaaag ggaaagcaaa aaaaaaaaaa aaaaaaaaa 123000 aaaaaaaaaa agcaggagtt gcaatcccgg tctctgaaaa aaaagacttt aagccaacaa 123060
agatcaaaag agacaaaaaa ggccattaca taatggtaaa aggatcaact gggcaagaag 123120
```

```
agctaactat actaaatata taggtaccca atacagcagc accaagattc ataaagcaag    123180
tccttagaga cctataaaga gacttagact cccacacaat aataatggga gactttaaca    123240
cctctctgtc aataatagac agatcaatga gacagaaggt taacaaggat atccaggaca    123300
tgaactcagc tctgcaccat gtgaacctaa tagacatcta cagaaccctc accccaaat    123360 caacagaata tacattcttc tcagcacgac atcacactta ttccaaaata gaccacatag    123420
aagtaaagca cttctcacca aacgtaaaag aacagatatc acaacaaact ggctctcaga    123480
gcacagtgca atcaaattag aactcaggac taagaaactc actcaaaacc gcacaacttc    123540
atggaaattg aacaacctgc tcctgaatga ctactgggta aataatgaaa tgaagacaga    123600
tataaagatg ttctttgaaa ccaacgagaa caaagacaca gcataccaga atctctggga    123660
catatttaag gcagtgtgta gagggaaatt tatagcacta aatgcccaca agagaaagca    123720
ggaaagagct aaaatcgaca ccttaacatc acaattaaaa gaactacaga agcaagagca    123780
aacaaattca aaagctagca gaaggcaaga ataactaag atcagagcag aactgaagga    123840
gatagagaca caactcttca aaaaatcaat gaatccagga gctggttttt caaaaagatc    123900
aacaaaatag atacactgct agcaagacta ataagaaga aaagagagaa gaatcaaata    123960
gagggaataa aaaatggtaa aggggatatc accaccgatc ccacagaaat acaaactacc    124020
atcagagaat actattaaca cctctacaca aataaactag aaaatctaga agaaatggat    124080
aaattcctgg acacatacac cctcccaaga ctaaaccagg aagaagttga atctctgaat    124140
agaccaataa caggctctga aattgaggca ataatagcct accaaccaaa aaaagtccag    124200
gaccagatgg actcacagcc gaattctcct agaggtacaa agaggagctg ataccattcc    124260
ttctgaaact attccaatca atggaaaaag agggaatcct ccctaactca ttttatgagg    124320
ccagcatcag cccgatacca aagcctagca gagacaccac aaaaaaataa ttttagacca    124380
atatccctga tgaacgtcga tgtgaaaatc ctcaataaaa tactggcaaa cccaatccag    124440
cagcacatcc aaaagcttat caaccacgat caagtcggct tcatccctag gatgcaaggc    124500
tggttcaaca tttgcaaatc aataaacgta atccataaca taaacagaac caatgacaaa    124560
aaccacatga ttatttcaat agatgcacaa aaggtctttg acaaaattct acagcccttc    124620
atgccaaaaa ctctcaataa actaggtatt gatggaatgt atctcaaaat aataagagct    124680
gtttatgaca aactcacagc caatatcata ctgaatgggc aaaaactgga agcattccct    124740
ttgaaaactg gcaaaagaca aggatgccct ctgtcaccat tcctattcaa cactgtgtta    124800
gaagttctgg ccagggcaat caggcaagag aaagaaataa agggtattca attaggaaaa    124860
gaggaagtca aattgtccct gtttgcagat gacacgactg tatatttaga aacttggtc    124920 atctcagccc caaatctcct taggctggta agcaacttca gcaaagtctc aggatacaaa    124980
atcaatgtgc aaaaatcaca agcattccta tacacccata acagacaaac atacagccaa    125040
atcatgagtg aactattcac aattgctaca aagagaataa aatacctggg aatccaactt    125100
acaagagatg cgaaggacct ctggacctct tcaggaaaa ctacaaacca ctgctcaatg    125160
aaatacaaga ggacacaaac aaatggaaga acattccatg ctcatggata ggaagaatca    125220
atatcgtgaa aatggcgata ctgcccaaag taatttatag attcaatgcc atccccatca    125280
agctaccaat gactttttc atagaactgg aaacaactac tttcaagttc atatggaacc    125340 aaaaagagc ctgcattgcc aagaccatcc taagccaaaa gaacaaagct ggaggcatca    125400
cactacgtaa cttcaaacta tactacaagg ctaccgtaac caaaacaaca tggtactgct    125460
acccaaacag agatagacca atggaacaga acagaggcct cagaaataac accacacatc    125520
```

```
tacaaccatc tgatctttga caaacctgac aaaaacaaga aatgggaaaa ggattcctta   125580
tttaataaat ggtgctggga aaactggcta gccatatgta gaaagctgaa actggatccc   125640
ttccttacac cttatagaaa aattaattca agatggatta aagacttaaa tgttagactt   125700
aaaaccataa aagccctaga agaaagccta ggcaatacca ttcaggacat aggtgtgggc   125760
aaggacttca tgatgaaaac gccagaaaca aaggcaacca agccaaaac agacagatgg    125820 gatctaattc aactaaacag ctgcacagca aaacaaacta ccattagagt ggacaggcaa   125880
cctacagaat gggagaaaat ttttgcaatc tacccatcag acaaagggct aatatccaaa   125940
atctacaaag aaatttacaa gaaaaaaaca accccatcaa aaagtgggca aaggatatga   126000
acagacactt ctcaaaagaa ggcatttatg cagccaacag acatataaaa aatgcttatc   126060
atcactggtc atcagagaaa tggaaatcaa aaccacaatg agataccatc tcatgccagt   126120
tagaatggtg atcattaaaa agacaggaaa caacagatgc tggagaagat gtggcgaaat   126180
aggaacactt tcacactgtt ggtgggagta gtgtaaacta gttcaaccac tgcagaagac   126240
agtgtggcga ctcctcaagg atctagaact agaaatacca tttgacccag ccatcccatt   126300
actgggtata cacccaaagg attataaatc atgctgctat aaagacacat gcccatgtat   126360
gtttactgtg gcactattca caatagcaaa gacttggaac caacccaaat gcccatcaat   126420
gatagactgg ataagaaaat atgccacaaa tatcccaagg aatactatgc agccataaac   126480
aagggtgagt tcatgtcctt tgcagggaca tggatgaagc tggaaaccat cattctcagc   126540
aaactagcgc aaggacagaa aagcaaacac tgcatgttct cactcatagg tgggagttga   126600
acaatgagaa cacttggaca catggcaggg aacatcacac aaaggggccc gggggaggga   126660
tagcattagg agaaatacct aatgtaaatg acgagttaat gggtgctgca atcaacatg    126720 gcacatgtat atctatgtaa caaacctgca cattgtgcac atgtacccta gaacttaaag   126780
tataataaaa atatatatac atcactttac atccaaccag cactttggct ttgaagccac   126840
tgcctgatgt tgacactttg tagatgtagt atgactattc ttatatgtct ctatctactg   126900
atgaggatcc tactctttta gtataaagag taccattgac ttccaatcaa ctagtttcga   126960
taatatctga aagatattaa ataacctgac actagcctta gtaaccgaca ccttactggc   127020
cctactacta ctactaatta cattttact tccacaaatt aatatttata tagataaatc    127080
cagcccctat gaaggcagat ttgacccaat aacctccaac tgcctcccct tttccataaa   127140
attcttccta gtagccaaca catttctcct cttagactta gaaatcgctc taatactacc   127200
cctgccatga gctattcaaa caaattacct aacaacaata atcaccacag cccttatact   127260
agttatcatt ttaatcctag gcttaattta caaagaact caaaagggt tagattgaat     127320 tgaattggta aatagtttaa gtcaaaagaa atgatttcga ttcattagat tataataaac   127380
catatttacc aaatgccctc tatttacatc aacattatat taccatatac catatcacta   127440
ctggtaaaat taatctatca aacccaccta atatcatccc tatgtgccta gaaggcataa   127500
tactgtcaat atttatcata attacccctta taactttaaa tatacatttt actctagcat   127560
ctataatacc cattatcctc ctagtatttg ctgcctgtga agccgcagtg ggccttgcct   127620
tattagtttc aatctccaac acatacggcc tagattacac acaaaatcta aatttacttc   127680
agtgctaaaa attattccga caattatgct gttaccaata atatgattct ctaaaaattc   127740
tataatctga attaacatga ccatccacag cctacttatc agcctcatca ccctattgtt   127800
ttttaaccaa ttcaacagta actcatccaa cttctcacta gttttctctt ctgatctgct   127860
```

```
gatgtcaccc ctcctaattt taacagccta ttacctttta taatcctagc aagccaatat    127920
taactgttca atgaatcacc cccacaaaaa agctctatat ttctatattg atttccctgc    127980
agatttttta aaattatagc attcacagcc acagaactaa ttatatttta tattttcttt    128040
gaagccacac taattcctac cctaattatt attatcaccc gctgagggaa ccaaccagaa    128100
cgcctcaatg caagctcata tttcctattg tacacactag tagggtccct tcctctactt    128160
gttacacttg tctacacttt aaatacttca gattctctaa atatgctagt aatgatattt    128220
actgaccaag aactgttagc ctccttatcc aataatctta tatgactagc atgtattatg    128280
gcctttatag taaaaataac tctattcgga cttcacctgt gactcccaaa agcccatgta    128340 gaagcccta ttgccggctc aacagtactt gcagcggtac tcctaaaact aggcggctgc    128400
ggtataatac ggcttaccct tatcctcagc cccctaacag aatatatagc ctacccttc     128460 ctcacactat ccctatgagg gatagttatg caagctcca tttgtctaca aaccgatgta     128520
aaatcagtta ttgcctactc ctctgtaagc catataccac ttgtcatcat agctctccta    128580
atccaaaccc cttgaagctt tacaggtgcc gtcacccta taattaccca tggagtcact    128640
tcatccctgt tattctgcct agcaaattcc aactacgagt gagtccaaaa cggaatcata    128700
tacttacctg aggccttcaa atactcctcc cactgatata gcctcatgat gacttctagc    128760
aaatctcact aatcttgcct taccccctacc attaatctag taagggaact ctctgtgatc   128820
atggcttcat tctcctgatc aaacatcact attatgctta caggacttaa tatactaatt    128880
acaaccctct actccctaca tgtaccaatc acaacacaat gagggacact tacatattac    128940
attaacagtt aaaccttcct ttacacgaga aaatacatta atatttatac atgttacacc    129000
tattcttcta ttatcctaaa tcctaaaatt attatgggct ttacatgctg tagctatagt    129060
ttaaccaaaa cattaaattg tggatctaat aatagaagcc tgcaacttct tatctaccaa    129120
gaaagtatgc aagaactgct aactcatgcc cccatgccta acaatatggc tttctcaact    129180
tttaaaggat tggagtcatc cgttggcctt aggaaccaaa acattggtg caactccaaa     129240 gaaaagtaac aaatatgtat ttttccacta ctataatagc cctaatcgcc ttaatcacac    129300
caattattac gttagtcaac ccctgcaaaa gaagattcat acccaaatta cataaaaata    129360
gccatcacat gcgccttcac cattagcctc atcccaacgt ttatatatac agaccaagaa    129420
gtcattatct caaactgaca ttgaatgaca atcccaactc ttaaactctc actaagcttt    129480
agactacttc tccataatat ttattctagt agcactattt gttacctgta gaattctcaa    129540
tatgatatat aaactcagac cctaacatta atcaattttt caaatatttt cctcatcaca    129600
gtattcttcc aatattccac caacaaactc tttcaactct ttatcggatg agaaggtata    129660
ggaatcatgt ctttcttact aactggctga caatatggcc gagcagatgc taatacagca    129720
gccctccaag cagtcctgca caatcgcatc ggcgacattg gttttatttt agttatagca    129780
tggttcctct tttcctccaa cacatgagag attcaacaag cattcattct aaaccctacc    129840
tctaatcccc ttccattaat tcgccttctc ttagcagcag caggaaagtc agctaaattc    129900
ggcctccatc cctgacttcc atccgccata gaaggcccaa ccccagcctc agccctgctc    129960
cactccagca ctatagttgt agcaggagtt ttcctgctca tccgcttcta ccctttaata    130020
gaaaataacc tctgaaccca aacctttaca ttatctccag gggctgttac caccttattt    130080
acagcaatct gcgctctaac acaaaatgat atttaaaaaa tcatagcatt ctccacctca    130140
agtcagctgg gccttacgat agtcacaatt ggcattaatc agccacatct agcattcctt    130200
cacatgtgca cccacacctt ttttaaagct atattattta tatgctcagg ctccatcatc    130260
```

```
cacaatctca atgatgaaca agatatttga aaaataggac tattcaagac tttacccttc   130320
acttcctctt cccttattat tggtagcctt gcacttacag atatgccttt cttcacaggc   130380
ttttactcta aagaccttat tatcgaaacc acaaatactg tcatatacca acgcctgagc   130440
cctttctatt actcttactg ccacctcctt aactgctggc tatagtaccc gtgttatttt   130500
ctttgctctg cggactggcc atgcaggagt ggtaagggcc cgggccacgc gcgacgcctg   130560
ggggccctgc tgcatcgccc gtttgttcgg ggaaggtggg gggacgctt  catgccgccg   130620 cgcccagcag ggtttccatg tctgagatgc ccgctctggc ccaagagaa  tgaaccagcc   130680 gcagaggatg gcatccgtgg acacggacaa ggagctcagt aacctggact tcagcatgat   130740
gttcccgctg cccgttgcca acgggaaggg ccggcccgcc tccctggccg ggcgcaatt   130800 cagaggttca ggtcttgaga actggcccag ctcaggctcc tggggcagcg gcgaccagaa   130860
cagctcctcc tttgacccca gctggacgtt cagcgaaggc gctcaacttg ctgagtcgca   130920
cggcagccac tctccattca cattcctggg accgggactc ggaggcaaga gcagctagcg   130980
cgggcctatt cctcctttgg tagagacgca ggcgtgcgca gcctgactca ggctggcttc   131040
ctgccgggca agctggccct cagcagcccc ggacccctgt cccctcagg  catgaagggg   131100 acctcccggt actaccccctc ctacgccagc agctctggcg acagaggcg  acagcggcc   131160 tggacacgca gcccacgaag gtcgggaagg tcccgcctgg tcttccatcc tcggcgtacc   131220
tgcccagctc aggtgaggag tacggtaggg atgccgccgc ctatccatcc gccaagacgc   131280
ccagcagcgc ctgtcccgcc cccttctaca tggcagatgg cagcctgcac ccctaagccg   131340
agctctggag ttccctgggc caggtgggct ttggccccat gctgggcggg ggctcatgcc   131400
cctcgtccct cccgcccagc agcggccctg tgggcagtgg cggaggcagc agcacgtttg   131460
gcggcctgca ccagcacgag cgcgtgggct accggctgca cggaggagaa gtgaacggtg   131520
ggcttccggc tgcatccacc ttctcccttgg cccccggagc cacgtaggcg gcgtctccag   131580
ccacacgcct gtcggcgggg ccgacaacct cctgggctcc cgagggacca cagccagcag   131640
ctctggggac gccctcggga aggcctggcc tcaatctact ctccggatca ctcaagcaat   131700
aacttgtggt ccagcccctc caccgccgtg ggctccccc  agggcctggg agggacgtcg   131760
cactagcctg gagcaggagt ccctggtgcc ttatcaccca gctacgacgg gggtctccac   131820
ggcctggaga gtaagataga agaccaccta cctgaacgag ggcatccacg tgctctgcag   131880
ccacgccatg ggcacggcta gcaacgtgca cacgctgcta cccggccacc gggcgctggc   131940
cttgggcttc gccggcccca tgctgctggt ggggcagca  cgcaggcctg gttggaggcg   132000
aacaccctga ggacggccct gcgggcagcg ccagcctcat gcacatccat gttgccctct   132060
ccagctagcc aggcgccctc cccgacctct cttggccttc cgactcctgc agtgggctag   132120
ggcgagcagg ccactgggga aatcaagcgg gaggaggagg atgaggagaa cacgtcggcg   132180
gctgaccact caagaggaga agaaggagct gaaggacccc cggaccgga  ccagcccaga   132240 caaggacgag gaggaagatg accttttccc cccagagcag aaggccgagt gggagaagca   132300
ggtggccaat aacgccaggg agcggctgcg ggtcccttaa gagggctctt aaggagctgg   132360
ggcgcatgtg gcaactgcac ctcaacagcg agaagcccca gaccaaactc cttatcctgc   132420
accaggccgt ctcggtcatc ctgaatttgg agcagcaagt gcgagagcgg aacctgaatc   132480
ccaaaacagc ctgtttgaaa cggcgagaag agaaggtgtc gcgcgtgttc ggaggccccc   132540
agatggtgct ttcagctgcc cacctgggct tgagtgaagc ccacaacccc gctgggcacg   132600
```

```
tgtgaaaggt acgcctccgt gggacgagcc acccgccctc agccccgtgg gctgggccca   132660
gaacgcccac ttgaggccct gggcttcatc cacatccaca cctcacacaa ctgttgtcag   132720
cattgagcca acaccgacct gatgaggctc agagtgatgg gggcaaggaa ggtgagtgat   132780
gggggtgagg aaggtgacgc tgggtccagg agctccctgg gaccccggct cacccctcac   132840
tgccctcgct cccctgccc ccgtatctca gccaccatgt caccctgtga cctgcccat    132900 ggaccctgaa actgcatctt ggccctgttg tctgggctgg caggagcttt tttttttttt   132960
tttttttttt tttttccagt aaacaaaacc tgaatgcaag caacaaaaca tacactttgt   133020
cagaaaagaa aaaatgcctt aactataaa atgtggagaa atcgtaacat atcacttgag    133080
ggagatgctg tggaaacttg gcttattctt caaaagccag cagcaaattg tgcctaagcg   133140 taatttttt taaggaaaat aaaaagaaca ttagttattt aaaaaaaaaa aaaaaaaaa     133200 aaaacccgg actgaccttg gccaggctgg atcagactgg cctagagtag acttcagagg    133260
gtgactcccc tggtgggctg gtctcagctg atcttgactg tcccgcctcc acacagggcc   133320
catccatctt ccccttgatc ccctgctgca aagacattgc ctctgatgcc acctccatga   133380
acctgggctg cctggccaca ggctacttcc tgaagtcagt gactgtgacc tgggacacag   133440
gctccctcaa caggagcgct gggaccttcc cagccaccac cctcacgccc tctggccatt   133500
acgccatcac cagccagctg actgcctcgg gtgcgtgggc caaacgctca cctgcagcgt   133560
ggcacacact ctgtggtccg cagaccaggt cagtaccttc agcatctact ccagggactt   133620
caccctcccc accgtgaaga tcttacagtc ctcctgtgat ggcagtggac acttaccccc   133680
gaccatccag ttcctgtgcc tcatctctgg gtacacccag gtgccatcag catcacctgg   133740
ctggaggatg ggcaggtcgt ggatgtgaac tggtccatcg cctctcccat actggaggat   133800
gagctggcct ccacacaaag caagctcacc ctcacccaga agcgctggct gcccgaccac   133860
acctacacct gccaggtcac ctatcaaggt aacacctttg aggacagtgc caagaagtgt   133920
gcagattcta acccgcaagg ggtgagcacc tacctgagcc ggtccagccc cttctacctg   133980
ttcatccgca agttgcccac aatcacctgt ctggtggtgg acctggcacc cagcaaggag   134040
aacgtgaagc tgacttggtc ccaggccagt gggaagtctg tggctcaggt catcctaagg   134100
caagagaagc agtgcaatgg cacgttcacc atcacgtcca ccctgctggt gggcaccaga   134160
gactggatca aggggggagac ctaccagtgc agggtgaccc acaccacct gcagtccacg   134220 accaagatca gcggcccatg tgctccccca caggtctacg tgtttgcaac gctagaagag   134280
ccgaggaacc aggacaagcg caccctcacc tgcctgatcc agaacttctg gcccaaggac   134340
atcttggtgc agtggctgta caacgaggtg cagctcccgg acacttggca cagcatgacg   134400 cagcccccgca aaaccaaggg ctctggcgtc ttagtcttca gctgcctgga ggttaccagg   134460
gctgaatggg aacagaaaaa cgagttcatc tgctctgtgg tccatgagac agcgactggc   134520
tcacagaccg tcaagtaact gttgtctgta aatcccatta aatgtcctcc tgccttcctc   134580
cccactaggg ctctgtccag ctgtgtggtg ggaagggctg ccagaccctt ctgtccactg   134640
ttgcaatgac cccaggaagc cacccccaat aaacagtgcc tgctcagaaa acaaacaaac   134700
aaacaaacaa acataaaaac cctagaggaa aacctaggca ataccattca ggacataggc   134760
atgggcaagg acttcatgac taaaacacca aaagcaatgg caacaaaagc caaatagac   134820 agatgggatc taattaaact aaacagctgc atagcaaaag aaactgatca gagtgaacag   134880
gctacctaca gaatgggaaa aatttttgc aatctagcca cctgacaaaa ggctaatatc   134940
aagaatctac aaagaactta aacaagttca caagaaaaaa acaaccccat caaaaagtgg   135000
```

```
gtaaaggata tgaacagaca cttctcaaaa gaagacattt atgtggccaa caaacatatg   135060
aaaaaaagct catcatcact ggtcatcaga gaaatgcaaa tcaaaaccag agtgaggtac   135120
catctcatgc cagttagaat ggcgatcatt aaaaagtcag gcaacaacag atgctgaaga   135180
ggatgtggaa aaacaggaat gcttttacat tgttgatggg agtgtaaatt agttcaacca   135240
ttgtggaaga cagtgtggca attcctccag gatccagagt tagaaatacc atttcactga   135300
gcaattccat tactgggtat atacccaaag gattataaat cattctacta taaagacaca   135360
tgcacatgta tgtttattgt ggcacttttc acaatagcaa agacttggaa ccaacccaaa   135420
tgcccatcaa tgatagactg gataaagaaa atgtgacaca tatacaccat ggaatactat   135480
gcagccataa acaaggatga gttcatgtcc tttgcaggga caaagatgaa gctagaaacc   135540
ataattctca gcaaacacag gaacagaaaa ccatacacca cttgttctcg ctgataagtg   135600
ggagttgaac aatgacaaca tatggacaca gggaggggaa catcacacac cagggcctgt   135660 tgtgggtgg agggctaggg gagggatagc tttaagagaa atacctaatg tagttgatgg   135720
gttgatgggt gcagcaaacc accatgacac gtgtatacct acgttaacaa acctgcacct   135780
tctgcacatg tatcccaaaa cttaaagtat aataaaattt aaaaaaaaaa cagtgaacat   135840
ttattgtagg cttacattgg gctaaatgca ttttatggat aatctcattt aatcctcata   135900
acaacccttg gagaacatgt atgattatta tctctatttt aagcatggag aactgaatag   135960
cttacccaag gtggcatgac tagtaaatca ctggaccagg atttaaaccc aaaaagtctg   136020
atcccagagt tcatgcttat aagccttcct aaccatgata atgctttaat ctggcattaa   136080
ttgttctcta atttgggtag gtttgaaatt tttcataata aatattaaaa atacttttg   136140 aggaaatgtc gtcatgataa acattagaac tgcgttcatc taattacttt tagggtatga   136200
gtgaaactaa aaagtaagac tcatctaaaa ataatcatct gttttggcca tatccccagt   136260
gatacatgaa tttaattgtt tttattgttt tcagaatgaa aaattaaaga ggttaaataa   136320
aattagctgg caatcaaaaa atattagtta tatgaagatt cagagatttg gttatactta   136380
atgaatacaa gctaataaat atttattaag actctactgt gctccaaata ctatacaggg   136440
aggtagggat atgaagatag gcttagcatc agaaaaggac tgtcccttag tagaaaggct   136500
gaactaaaag gaaaagtttg acgtgatagg caaattcaac tgacaggtcc actacccata   136560
gtcccttcaa gagctcataa ttaggaaaag tcatatgtat aatatggcac tttcaataat   136620
taagtgcaat aagtgtaagt gcaataatta aggtactggg aaaacataac agtacaaata   136680
attcagctga agatttatgt aagataacta agatgacatt tcaacgattg gttgaattga   136740
cctctccctc atgaatggga ttaaggccct tataagaggc ttcatgcagc atttggctcc   136800
tcttgccttt ccactttcat ccatgtgagg acacggcatt cctctcctct aaagatgtg   136860 gcaacaaggc tccccttgga agcagagagc agccctcacc acacacctga acctgccagc   136920
acctttatca tggactccca acctccagaa gtatgagaaa taaatttctg ttctttataa   136980
attatccatt gtcaggtact ctgttatagc agcatacatg gacgcccagt acatcatgtt   137040
aatgagttca gaccttcttt agtagacagt gcgtaaggtg ggaaattaga ggctttatcc   137100
aggggaataa catggtgaga ttcatatttt agaaagatag ctctactttt gttatagaac   137160
agcagttctg aaagtgtggg gactttaggg tgtctgtgaa gtaaaaaata ttttcataat   137220
aatggatgtt atttgctctt ttcactcatt ttttcataag tatagttttc cagaggcaat   137280
aagatatgtt ttctatttaa ccaaacattg aagagacttg caaaaatgta aaacaatgtg   137340
```

```
actcttatca aagtttatttt tggaaatagt tgttttccat aaaatacatt acttatgtta    137400
acaggtaatg gttttatctt aaataaatta ataaatattt ttatatttta ttagctttaa    137460
tatttaatat ggtaaatact ggtagatata actcacagaa acaaaagttt tttggcaacc    137520
tcagtaattt ttaagagtat acgaggaagc ctgagatcaa aagctttgag aactactgac    137580 agagggacg ttgtattaat gagaggctaa tagtagagag gcagctaatt agattttatg     137640
aggatctagg ccactggttt tcaaacccttt taagtatata tgctcactaa aagaatttag   137700
aaaaaccaca tcctcttaca cattttttaaa ttgatagcta attttttttct ttgtaagtag  137760 ttataatgta tttctaaaag tactgtaaat attgacattt aaataacagc tatgtcaatc    137820
ctttaaatgt gtccaactga atctaaatag tgcttgcagt gagcggagac ctcgccactg    137880
cactccagcc tgggcgacag agcgagactc catctcaaac aaacaaataa atagtgcagc    137940
aatttgatac ccacttatca cccacttaaa aagattatat gaatagactt ttattttttt    138000
gtacaaactt tgtatcattc cttttctct ttaaaatagt attcccactt cccttctcat     138060
tccaaatttt gcataatatg ttacactttg tatttggata atcttatgat cacctatttt    138120
ctttgtaacc aagatatgta tataagtaag ttgaaattaa ttaaaaattt tcctgtgacc    138180
aacaaacttg taactattca cattttttctt ctgggttatc attgaagtta ctaggataca   138240
gttttccaaa gcaatgtaaa taacaaattt ggataattgc tttaaaaatt ttattggtga   138300
atggaacaat ccctcccctc caattggttt gtatatcctc ggatgaatat tatttatttc    138360
tataatggga caagattaag cataaattct gtgttcattt tgcactttac agatgtaaac    138420
gctgagaaaa cttgttttgtg taagtgagtg gacaggaatg gaaggagttt tgttataata   138480
gtatcattca tttctatgac gccttctgag atatgcagga aaaaagtaca gtaatatacc    138540
attaaaaatt atctgttatt gggcagtttc atttgatcag atccattatg tttcaattttt   138600 attaaaagca gagaattaaa accacttgac tttcaaaaat gagtttacta accagtcatc    138660
aggttcatct gttttctcaa tttctgaaaa gtataccaaa aagcttttaa aattaattcc    138720
aactatatgt tacactttca cgtggatgta ccttgtttaa actaatacat tcagaaaagt    138780
ttgaaaaaac agactattat taatacatta ttattaacat atttttatcat gttttaaata   138840 tatgatttaa acacagcaaa cctctcagct acctcaaagg ttgagtagat tttgtgaaga    138900
atgtccttca tacaacccat ttggtaatgc caggcatcaa acaaatcact taatttctgg    138960
cagaaaaact cagacttcat ttttcaagtc actaaatata ttaataatat gtgattttttt   139020 taaaacctga gaaacaaatg acagaacaaa tgcatggagg tatgtttatt atgaagctaa    139080
tgaagcatat ccagaggtcc tccttccaag gttcctttct aattttaaat agaaaattat    139140
gcactttcat gtataatttt gtattctttg tcataatgaa agcctaaaaa aaaaaggctt    139200
caaattatat aagctttggg acctgtatct ctgcctatac atgtgaaaaa atcatgaggg    139260
cagtcaggat aagctgaaga tgatatatat atctggcata attaatttca tattatgaaa    139320
ataagataat ttctcattac ttaatttgca ataaataata cagagtaaaa tatggctaag    139380
attataactt atgaagtaag gtatatggta catggcatgg tcattccttc agtaaatgtg    139440 ttaggggag gtatgaagtg aattctgact ttggggaata attagaagca acttgtatga    139500
aaatcagaaa taacttatttt ttcctcatga tcaaaatttt catatgtact taatgaacac   139560
aaaaaatata tactgctaaa agcaaatcag gcagttagca tatagtttta ttttttatatt   139620 tgcaagtaga aaataaatat tttatacaat gaaatgaagt tcattaaatt ttatgtaaat    139680
attttagaat atgaattgat aaaataagtt tgagctaact tattgaataa taaacactgt   139740
```

```
cttagtccct ttatgctgct ataacagaat acctgaaaat ggataattta taaagaacag   139800
aaatttattt ctcacacttc tagaggttag gagtccatga aaaaagtgct ggcaggttca   139860
ggcgtctggt gagagctgct ctcttctttc caagatggag ccttgctgct tcctccttca   139920
gagaggagga acaccatgtc ctcacatgga caaaagtgga agggcgagag gggccaaatg   139980
ctgcatgaag cctctcataa gggccttaat cctattcatg agggagaagc cctcatggcg   140040
taatcatctc ttaaaggccc cacctgttaa taccatcaca ttaacaacac ctgaattttg   140100
gaggagacac atagcaaaca ctaaatctga agtctgaaag aactcaattt ttattcacag   140160
gattttgccc atgatatcat ttttttaaaa actcaatttc atttaaaaga aactttgtta   140220
tctatattgt ttttcttgtt cgaaaaggct cttttgtttt aagctaacaa tatggttgac   140280
ggtaataact gggggaaaaa gtgcctctgc ttaaatgttg taaaaaatcg gtgaaacagg   140340
attttggact cctggaggat cctttactct ttttactaca gaagtaccca ttggatgatc   140400
tttgtacatt attcttcacc ttgtgtgaag acctctgtgc tagtcatgag ataaggatgt   140460
gatgtaaact gtaacaatgg gttaggagac tgattggaga tatttctaag ctatactcta   140520
aagggactta gtgggtcatt agacactgga gtgaaagatg cgtcaaaaat aattaagatt   140580
ttcaaattga gcagctaaat agattgtgat gctatttatt gcataagaaa caaaataatc   140640
agcaagtttt ggaagagga tggaattctg tttgcctata gatctttaat gtggaaatgt    140700
tctaaaagtc tggagcacta acaaaggtc aaagatatgg ttataaattt gggagacttt    140760
agtatatagg tggatgatac tatctaaggg aaagtttta accaagagag gaataaatct    140820
gatgaagaga ccctgggaaa ccttcaattt agaagaggca gaatagtagt agtagtgttg   140880
ggaaagtata attgaaaaca aaatcttcca acccagaaaa cctttccaca aagatagaag   140940
gaaaacaatt ttatgattga gtaagcatta gagcaggatg tgatgtgtat cacaagcagt   141000
cccctaagag atttgcaaag acagaaggaa atctcaccct tttatatagc caacctgata   141060
taaccccttt cattcaagtt cttaggataa acattaacta gtcctcaagt aagaagactt   141120
gacagcacta tttgccacat acgtagttta ttctaaattc acttggtaat tggagtgact   141180
ttgctaattg gctttataca aaggaaaata cactttttcat atcttcatga caggaggtag   141240
ttttgcagct tggaaggagg ctcctgctga agttaggctt ctactcccac agaaactggg   141300
agtaagggtg ctatcttcct tgatgactga attcccaaga gatagttaca cgttcttgag   141360
aaagacattc atgggtcaca aaactggcaa gaggctttga agcaagagat ttttaaaaga   141420
tttacataca cttcaaaaag acaaagaatt tacaagtttt ctgaatgctc taagaacaaa   141480
gaaggaggag tctttcttct tattttcaac aagggggaatt aattttgttc tttttaaatt   141540
tgtatttacc cttacataag tgatagaaca gacagaaaaa aacagctgtg gaaatgtgcg   141600
ggaaattaca atgagtgcta tatgaaaacc agaggaagag catattttgc aaggagtgag   141660
ggaatagtgc tgtcttcaag aactttgcat tcccttgtg gaataaaact aacatacatt    141720
tgataataac ataactagat atgtaaaatt tgtaaagact aaatgtaaaa agaatatagc   141780
attaggatgt ttaattacgt agtatggact gccagtacta taggaattca gtggcctgag   141840
ggcaataaga cctggagtag gcagggaagg atttgtggag attaggaaac ttaaatggga   141900
ttttgaagga gagattaaat ctatgtaatt cacatttta atatcagtct aaaacacatc    141960
tctgtagctg tctctataat aaagataaac ttagcaatgg aaccatgata ctcacagtcc   142020
actaggccaa aacgttccct tggatagtgt taatgcttga gtgaacaatg acaccattgc   142080
```

```
tgtgactttt tcctttctgt attccttagt cacccctctt ctggttaaca ggttctttct 142140
tttatagctt taagtcttgc cttggaacca attttttct ccagcatatt tatatggatt 142200
catttaaagc ttaacttgca aagagcagct tattttcact tcttagaagg tactctgcag 142260
ttaaccttgg tgctgtctac agagacaaaa ataaatttct ttggatttta gttatctttc 142320
tatgtcagag attcccaaga ccatccccag gttgacgatt tgctaggaag actcacagga 142380
ctcagcatat atccatattc atggttatga ttcattatag ggaaataaca taaagcaaaa 142440
ttaggcactc tccgcctggc acatactaaa gttacatact cccagaagaa aagtagatgt 142500
cagcataaac cgtattgttt gtacaaacaa tctaggcata gtgagtcact cttatttagg 142560
gaattgtgga atccctcctg aaatctaagt tcacaggtgc caggcaaaaa ggccctttta 142620
atcatagaag cctcaggcct gctgtgataa ctcttttctc tacatgtttt tttttttaat 142680
ttatacaatg atttgcaggt aaaatcaaga gtccacatat caagtaactg tcttttaaat 142740
gttattcata tatttacagg tatgctccag aatcactgac agagagcaag ttttctgtgg 142800
cctcagatgt ttggagcttt ggagtggttc tgtatgaact tttcacatac attgagaaga 142860
gtaaaagtcc accagcggtc agtgtgcttt ttatttactt tcagttttt gtttgttcgt 142920 ttgatttta taaatttatg gggtacaagt acaattttgc tacatgcata cattgcatag 142980
tggtgaagtc agagctttta gggtatccac caccttaata acatacattg tatcccttaa 143040
ataatttctc agcatctact ccaccaatgg ctcacccttc caagtctcta ttgtctatca 143100
ttccacattc tacgttcatg tgtatacatt atatagctcc cgcttataag tgaaaacgtg 143160
gtatttgtct ttctatggct gatttgtttc acttaagata attacctcca tccatgttgc 143220
tacaaaagac ataatttcat tcgttgttat ggctgaatag tattccattt gtatgtata 143280 ccacattttc tttatccagt catccactga tggacactta ggttgattcc atgtcttgc 143340 ttttgtgaag aatgctgcaa taaacataca ggtggaggta tcttttgat acagtgattt 143400 cttgtccttt aggtagatac cccatagtgg gaatgctgga tcgaatggta gttctatatt 143460
taggtctctg agaaatcttt ataatgtttt ccatagaggt tgtacaaatg cacattctca 143520
ccaacagtgt ataagagttc ccttttctcc acacccttgc caacatctgt tattttttct 143580
ctctctcatt tttttttcca ttctgactgg agtcagacat atctcactgg ggtaatttt 143640 tctcttttt tttttgtca ttctgactgg aataaggcat atctcattgt gatttaatt 143700 tgcatttctc tggtgattag tgattagcat ttttcatat gcctcttgtc agtttgggtg 143760
tcttcttttg aaaatgtcta ttgatctcct ttgtccactt tttaacacga ttattagggg 143820
gttttggttg aattgcttga gttccttata aattctggat ggtagttcct tgtcagatac 143880
aaagtttgca aatattttct ccgattatgc aggttttctg ttcattctgt tgattattga 143940
ttttgctatg ctgaaatttt ttagcttaat aaagtctcat ttgtctattt ttggttttgt 144000
tgcctatgct tttgaggtct ttgccatgaa ttctttgttt acactcattt ccattaaagt 144060
tttctctagg tttttttct agtatttttc tagtttcaga tcttacattt aagtctgtaa 144120
tcgatcgagt taattttct atatggtgat aaatatgggt ccagtttcat tcttctgcat 144180
atggcaatcc aatttaccag caccatttat tgaaagggt gtccttccc atactgcgca 144240 aagcaatctg cagattcaat gcagttccta tcaaaatacc aatgtcattt gttcacagaa 144300
ttagaaaaaa caatcctaaa attcataggg aaccaaaaag agccctaata gcaaagcga 144360 ttctaagcaa aaagaacaaa gctggaagca tcacattact tgacctcaaa ttatattata 144420
aggctacagt aaccaaagca gcatggtact catataaaaa acaaacacat agatcaatgg 144480
```

```
aacagaatag aaaacccaga aataaagcca caaatttata gccaactgat ctttgacaaa 144540
atcaacaaga acatacattc aagttttttt ttaacatgag aaaggattta tccaaagaat 144600
agtaagccta ggactcactt tagagctttt attgcttatt tttaaggcaa tatcaaacaa 144660
aataatccca aacctattcc taaactagct tgaattttta aaaaggggat attgggaagc 144720
tagttagtac agtctcttaa tattacttttt attaaatcca gtaagctaat tcattctagg 144780
aattattgca taagttaaaa taaaccttcc aaagtaattt ttctcttggt catcatagaa 144840 tttttttttaa tatggaaaag tatgaaaaaa taaaaatcat ctctaatgca attactcaga 144900
gaagaccacc tcaatattgt ggtatgttac ctttcaggct tcattttgtg tataaaagta 144960
tatacaaaga agtatataaa acttttataa cttttataaa agttcactta tataaatata 145020
tattatttta taaaattaag gtcatactgt gcagtttgct ctccttctgt ttcatgaagt 145080
attacagcat gggtaattta ctgtattaga aaaatgtact gcaaatatgt tttctaattg 145140
ctgagtagca ttccatcata aggctatata tgtctgaaca atcattttcc attcttcagt 145200
cttttaagta acacttcagt gaacatagtg aacatcctca tgcataaata tttatattta 145260
tctctgataa ttatcttaga ataaaagtat aagtaaaagt tatgaactat tttaaaattt 145320
ttttaatttc aaaatgcttt ctagaaaagc tgtgccaaat tatatctcaa cagcaatgca 145380
tagggatgta catttcatca tttgccacta ttggttatta tattttatg tacttttgcc 145440 aagttgatag gggagaagtt atatatattt taatttccat ttcttttctt aatgtggttg 145500
actatatatt tgttgggtgt ttagggtggg tatgtatata tgtgaattat ctcttctgtg 145560
ctttgcctat ctttatattt gtaattttttt ttcccaattt ataagagctg tctatattga 145620
aaataagtaa atgatgttta agtatttttcc tagcttataa ttcagatttt aattttataa 145680
actttgacat atgaaagttt tctttgttgt atttatgctt attcattcat tttttcttat 145740
attctctttt atattcaact ttttatttca attgaaatgt aatatgataa aaatatgagt 145800
tttttaacaa caaaaaactc aaaggaaata tgttttttagt tcatgtgttt tgagccctcc 145860 tcagggggatt tgtgttgagt ttattacagc tatggaaatg gaattatag aagttccata 145920 tttaacagcc ttatgttttt gatcctaaaa gtagtttgtt ttgaaaaggt ttgaaaacat 145980
acaaaagcac acatatacta aatttttttcc cattgactgg aggaaattga gaaagaattt 146040
tgctacaaat taaatgtaca aaaaatattg aaagtgggtt tgttttagga atttatgcgt 146100
atgattggca atgacaaaca aggacagatg atcgtgttcc atttgataga acttttgaag 146160
aataatggaa gattaccaag accagatgga tgcccagatg aggtaacaat ttttttttaa 146220
tccagggtag tcatgcattt tcttttactt tttactcaag gacttcagtt cacttcctga 146280
aatttaatgt gcggagcttc cagataaaca gcataatcag atgactgtgg aacaaggcat 146340
ggttatgaca tgtgccctgt attgaaaatt aatgtcttcc accaattaaa agatggccct 146400
tagtgttcat ttaattttgg tttatttttct cctttacaga tctatatgat catgacagaa 146460
tgctggaaca ataatgtaaa tcaacgcccc tcctttaggg atctagctct tcgagtggat 146520
caaataaggg ataacatggc tggatgaaag aaatgacctt cattctgaga ccaaagtaga 146580
tttacagaac aaagttttat atttcacatt gctgtggact attattacat atatcattat 146640
tatataaatc atgatgctag ccagcaaaga tgtgaaaata tctgctcaaa actttcaaag 146700
tttagtaagt ttttcttcat gaggccacca gtaaaagaca ttaatgagaa ttccttagca 146760
aggattttgt aagaagtttc ttaaacattg tcagttaaca tcactcttgt ctggcaaaag 146820
```

```
aaaaaaaata gacttttca actcagctttt ttgagacctg aaaaaattat tatgtaaatt   146880
ttgcaatgtt aaagatgcac agaatatgta tgtatagttt ttaccacagt ggatgtataa   146940
taccttggca tcttgtgtga tgttttacac acatgagggc tggtgttcat taatactgtt   147000
ttctaatttt tccatagtta atctataatt aattacttca ctatacaaac aaattaagat   147060
gttcagataa ttgaataagt acctttgtgt ccttgttcat ttatatcgct ggccagcatt   147120
ataagcaggt gtatactttt agcttgtagt tccatgtact gtaaatattt ttcacataaa   147180
gggaacaaat gtctagtttt atttgtatag gaaatttccc tgaccctaaa taatacattt   147240
tgaaatgaaa caagcttaca aagatataat ctatttatt atggtttccc ttgtatctat   147300
ttgtggtgaa tgtgtttttt aaatggaact atctccaaat ttttctaaga ctactatgaa   147360
cagttttctt ttaaaatttt gagattaaga atgccaggaa tattgtcatc ctttgagctg   147420
ctgactgcca ataacattct tcgatctctg ggatttatgc tcatgaacta aatttaagct   147480
taagccataa aatagattag attgtttttt aaaaatggat agctcattaa gaagtgcagc   147540
aggttaagaa ttttttccta aagactgtat atttgagggg tttcagaatt ttgcattgca   147600
gtcatagaag agatttattt ccttttaga ggggaaatga ggtaaataag taaaaagta   147660 tgcttgttaa ttttattcaa gaatgccagt agaaaattca taacgtgtat ctttaagaaa   147720
aatgagcata catcttaaat cttttcaatt aagtataagg ggttgttcgt tgttgtcatt   147780
tgttatagtg ctactccact ttagacacca tagctaaaat aaaatatggt gggttttgtg   147840
tgtgtgtgtg tgtgtgtgtg tgtgtgtgtg tgtgttat ttatacaaaa cttaaaatac   147900
ttgctgtttt gattaaaaag aaaatagttt cttactttat ttttactggt atgttctact   147960
tttttgaaag ttgtactgaa gacttctgat tttgggttga agggaaggaa aaggaagaaa   148020
tgttttttac attcattatt atacttaaag cattttaaa gcattttaat agttctggat   148080
gcagaaatca tctaaaatga cagtgaatta ggttttaaaa agatttttaga ttttttgaa   148140 agtttaattt ttatttgtaa agactcctca aggatttgta tatgcaacac agtaaggaga   148200
tcttccattt tactaccttt caagtgaaaa atagcctatc atacaatatg cttgatttca   148260 gatttcata ctaaaactta actacatact taaaagtagg ttcttatcaa gggtctctaa   148320
cattgctttt taaaacaaga tgtgaactaa cttttcttaa acattttttt aaatgcttca   148380 tctttagtt ttatataaag aatcccacat gtacattctt gttttagaa tggggtgact   148440 accttattat aaaattccaa gtttccaaga gacttctttt cattgaggct tcgtaaagtt   148500
ttccattttg attctgacta cacataaaaa taagataacc ctgtagttat taagttggtt   148560
ctgtacaaga aacaggtaag taattattgt accagttaat gccaaaatat ttttcacgtt   148620
aatattcttc agaaacaagg gtaaaggtat tcttagaatt atgtaattct gtaactattc   148680
cagtatatta agttatacaa tctttatata aatgacttt tccatgggta cttgtttgga   148740
aaatagtcac tttttcacgc tatttatata tgctgccagt aacactataa tttgctatgg   148800
aagagtgttc ttttaaccta aggcttctag tttacagtca agtgtaattt tcatcacaac   148860
tataacttct ggtatttaaa ttttatttaa acagctacaa aagagttagc aaatacctac   148920
agttctgtat ctatagagcc aatcttgatg gtgggtgtgg cattatgtgc tcactttatt   148980
gagcctatgt taatttcttt agcatgctcc ccctaaattg aaatagtgat gtagtaaata   149040
ttcagaagcg atttttcttt tgcattttac ctaaccaagg aaacgggcca cacaccttgg   149100 tttagggat tgtgatagc ttaccttcca gtttttaaga aatgcttcct acaactgctg   149160
tcaaccactg tattgtcttt aatgaacact gttgtatccc atcctaattc ttgtactgaa   149220
```

-continued

```
attatttctc atgaaagttt ctctaatatt tctaatgaaa gtttctctaa tttgggggca    149280
taatgtacta agaatcagtt tgctgtatat tagaataaat agtaacagta agtcagcagg    149340
attatccaaa caaaagacta ggttttatga gataagcttg atttaagaaa aaaacaatta    149400
aagtatgaat atcagaaata ctgtgtgttt actctcagat tttagttggt tggatttaat    149460
atcaagataa ctagctgcta agcgtttcat aattctcaca gtgatattag atttcaaaat    149520
gacactgaga gaactgaaaa actacatcag tcaaattcat gtatgtatat catatagcct    149580 ttaactttt acattaatca gattcttagt aaaatgcaga ctgtatacct aaatattaaa    149640
atatttactt ttataatctt acctttatt tcaatataaa taaaattctt cttaggttaa    149700
aaaattaatt tcagttgtgt ttatgccaga tggcattgct tagttggtgc aagctctcaa    149760
tatgtttcat tctttttat agtctttcac atttataagg aaaagcctta tctccaactg    149820
aaacaccagt cttactacta cggttttaaa agttgttaat gatcattatc tattataagg    149880
cctttattta catagcaaat tgcttaacat tttattttga atataacaga ttttaaaa    149939
```

```
<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
gcatctttat tatggcagag ag                                                 22

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
tgctctgaga aaggcatta                                                     19

<210> SEQ ID NO 5
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 5
gctgcttcaa agaaagacta aggaaatgga caacagtcaa acaac                        45

<210> SEQ ID NO 6
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 6
gctttctcac aagcatttgg ttttaaatta gcctgtagtt ttacttactc tc                52

<210> SEQ ID NO 7
<211> LENGTH: 30
<212> TYPE: DNA
<213> ORGANISM: Artificial Sequence
<220> FEATURE:
```

```
<223> OTHER INFORMATION: synthetic oligonucleotide
<220> FEATURE:
<221> NAME/KEY: misc_feature
<222> LOCATION: (30)..(30)
<223> OTHER INFORMATION: not-extensible dideoxy-cytosine

<400> SEQUENCE: 7
gtctccactg gagtatgtgt ctgtggagac                                    30

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 8
gtctccactg gagtatgttt ctgtggagac                                    30

<210> SEQ ID NO 9
<211> LENGTH: 17
<212> TYPE: DNA
<213> ORGANISM: Artificial Sequence
<220> FEATURE:
<223> OTHER INFORMATION: Peptide Nucleic Acid (PNA)

<400> SEQUENCE: 9
gagtatgtgt ctgtgga                                                  17

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
gtcaaacaac aattctttgt act                                           23

<210> SEQ ID NO 11
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 11
agctgtgatc ctgaaactg                                                19

<210> SEQ ID NO 12
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 12
aatatactcc ataatttaaa accaaatgct ttctttcttt gaagcagcaa gt            52

<210> SEQ ID NO 13
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 13
```
ttttgtggag acgagagtaa gtaaaactac ataaacaaaa acagatgctc tga        53

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 14
gtgagaaagc ttgctcatca t        21

<210> SEQ ID NO 15
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 15
aggctttcta atgcctttc        19

<210> SEQ ID NO 16
<211> LENGTH: 25
<212> TYPE: DNA
<213> ORGANISM: Artificial Sequence
<220> FEATURE:
<223> OTHER INFORMATION: synthetic oligonucletide

<400> SEQUENCE: 16
tctatagtca tgctgaaagt aggag        25

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 17
aaggcattag aaagcctgta gt        22

<210> SEQ ID NO 18
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 18
acaaagaatt gttgtttgac tgttgtccat tgcatcttta ttatggcaga gagaa        55

<210> SEQ ID NO 19
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 19
agtcttcctt tgaagcagca agtatgatgt tacttactct cgtctccaca ga        52

<210> SEQ ID NO 20
<211> LENGTH: 30
<212> TYPE: DNA

```
<213> ORGANISM: Artificial Sequence
<220> FEATURE:
<223> OTHER INFORMATION: synthetic oligonucleotide

<400> SEQUENCE: 20
agcatttggt tttaaattat ggagtaggtt                                          30
```